US010533165B2

(12) United States Patent
Kolkman et al.

(10) Patent No.: US 10,533,165 B2
(45) Date of Patent: Jan. 14, 2020

(54) SERINE PROTEASES OF THE BACILLUS GIBSONII-CLADE

(71) Applicant: Danisco US Inc., Palo Alto, CA (US)

(72) Inventors: Marc Kolkman, Oegstgeest (NL); Rie Mejldal, Ostbirk (DK); Frits Goedegebuur, Vlaardingen (NL); Lilia Maria Babe, Emerald Hills, CA (US); Anja Hemmingsen Kellett-Smith, Arhuc (DK); Harm Mulder, Oegstgeest (NL); Richard R. Bott, Burlingame, CA (US); Miles Christopher Scotcher, Hayward, CA (US)

(73) Assignee: DANISCO US INC, Palo Alto, CA (US)

( * ) Notice: Subject to any disclaimer, the term of this patent is extended or adjusted under 35 U.S.C. 154(b) by 20 days.

(21) Appl. No.: 15/104,219

(22) PCT Filed: Dec. 12, 2014

(86) PCT No.: PCT/US2014/070107
§ 371 (c)(1),
(2) Date: Jun. 13, 2016

(87) PCT Pub. No.: WO2015/089447
PCT Pub. Date: Jun. 18, 2015

(65) Prior Publication Data
US 2016/0319266 A1 Nov. 3, 2016

Related U.S. Application Data

(60) Provisional application No. 61/915,737, filed on Dec. 13, 2013, provisional application No. 62/069,200, filed on Oct. 27, 2014.

(51) Int. Cl.
C12N 9/54 (2006.01)
A47L 15/00 (2006.01)
C11D 3/386 (2006.01)

(52) U.S. Cl.
CPC ............ C12N 9/54 (2013.01); A47L 15/0002 (2013.01); C11D 3/386 (2013.01); C12Y 304/21 (2013.01); A47L 2601/20 (2013.01)

(58) Field of Classification Search
CPC combination set(s) only.
See application file for complete search history.

(56) References Cited

U.S. PATENT DOCUMENTS

2005/0113273 A1 5/2005 Weber et al.
2014/0017763 A1 1/2014 Wieland et al.

FOREIGN PATENT DOCUMENTS

DE 102100005345 A1 9/2012

OTHER PUBLICATIONS

Deng et al., "Secretory Expression, Functional Characterization, and Molecular Genetic Analysis of Novel Halo-Solvent-Tolerant Protease from Bacillus gibsonii," J. Microbiol. Biotechnol., 2014, vol. 24, No. 2, pp. 197-208.
Database Geneseq [Online] Nov. 8, 2012 (Nov. 8, 2012), "Bacillus gibsonii protease variant GI2L/I21V/MI22L/A222S, SEQ ID: 6.", retrieved from EBI accession No. GSP:BAA09836 Database accession No. BAA09836.
Database Geneseq [Online] Oct. 15, 2003 (Oct. 15, 2003), "B gibsonii protease.", retrieved from EBI accession No. GSP:ABR63713 Database accession No. ABR63713.
Database UniProt [Online] Oct. 16, 2013 (Oct. 16, 2013), "SubName: Full=AprBG {EC0:0000313:EMBL:AGS78407.I}; EC=3.4.21.19 {EC0:0000313:EMBL:AGS78407.I}; Flags: Fragment;", XP002737457, retrieved from EBI accession No. UNIPROT:S5VEFO Database accession No. S5VEFO.
International Search Report and the Written Opinion—PCT/US2014/070107—dated Apr. 9, 2015.

Primary Examiner — Kagnew H Gebreyesus

(57) ABSTRACT

The present disclosure relates to serine proteases cloned from Bacillus gibsonii, and variants thereof. Compositions containing the serine proteases are suitable for use in cleaning fabrics and hard surfaces, as well as in a variety of industrial applications.

17 Claims, 18 Drawing Sheets

Specification includes a Sequence Listing.

```
                                            1                                                   50
      WO2007131657-CAS91385    (1) QQTVPWGITRVQAPAVHNRGVTGSGVRVAILDSGISQ-HSDLTIRGGASF
        WO03054184-CAE48421    (1) QQTVPWGITRVQAPAVHNRGVTGSGVRVAILDSGIST-HSDLTIRGGASF
      WO2008086916-CAV33594    (1) QQTVPWGITRVQAPAVHNRGVTGSGVRVAILDSGISQ-HSDLTIRGGASF
                    Bgi02446   (1) QQTVPWGITRVQAPAVHNRGITGSGVRVAILDSGISA-HSDLNIRGGASF
        WO03054185-CAE48424    (1) QQTVPWGITRVQAPTVHNRGITGSGVKVAILDTGIAQ-HSDLTIRGGASF
             US7642080-0004    (1) QQSVPWGITRVQAPAAINRGTNGSGVRAAVLDTGIST-HSDLTIRGGASF
             US7642080-0006    (1) QQSVPWGITRVQAPAAINRGTNGSGVRVAVLDTGIST-HSDLTIRGGASF
             US7642080-0002    (1) QQTVPWGIQRVQAPAVINRGINGSGVRVAVLDSGISS-HSDLSISGGVSF
             B_lentus_P29600   (1) AQSVPWGISRVQAPAAHNRGLTGSGVKVAVLDTGIST-HPDLNIRGGASF
         B_sp_Sendai_BAA06157  (1) NQVTPWGITRVQAPTAWTRGYTGIGVRVAVLDTGIST-HPDLNIRGGVSF
          Bacillus_sp_BAA05540 (1) SQTVPWGISFINTQQAHNRGIFGNGARVAVLDTGIAS-HPDLRIAGGASF
    B_amyloliquefaciens_CAA24990 (1) AQSVPYGVSQIKAPALHSQGYTGSNVKVAVIDSGIDSSHPDLKVAGGASM
    G_stearothermophilus_ABY25856 (1) AQSVPYGVSQIKAPALHSQGFTGSNVKVAVIDSGIDSSHPDLKVAGGASM
        B_atrophaeus_YP003972439 (1) AQSVPYGISQIKAPAVHSQGYTGSNVKVAVIDSGIDSSHPDLKVSGGASF
           B_subtilis_BAN09118  (1) AQSVPYGISQIKAPALHSQGYTGSNVKVAVIDSGIDSSHPDLNVRGGASF
           B_circulans_ADN04910 (1) AQTVPYGIPQIKAPAVHAQGYKGANVKVAVLDTGIHAAHPDLNVAGGASF
    B_stratosphericus_WP_007497196 (1) AQTVPYGIPQIKAPAVHAQGYKGANVKVAVLDTGIHAAHPDLNVAGGASF
       B_licheniformis_CAJ70731.1 (1) AQTVPYGIPLIKADKVQAQGFKGANVKVAVLDTGIQASHPDLNVVGGASF
            B_pumilus_ADK11996  (1) AQTVPYGIPQIKAPAVHAQGYKGANVKVAVLDTGIHAAHPDLNVAGGASF
          B_sp_sprD_AAC43581    (1) AQTVPYGVPHIKADVAHAQNVTGSGVKVAVLDTGIDASHEDLRVVGGASF
     Bacillus_sp_LG12sprC_AAC43580 (1) AQTVPWGIPHIKADKAHAAGVTGSGVKVAILDTGIDANHADLNVKGGASF
          Bacillus_sp_BAD11988  (1) AQTTPWGVTHINAHRAHSSGVTGSGVKVAILDTGIHASHPDLNVRGGASF
                                     * .*:*:   :::          *  ...:.*::*:**  :  * **  : **.*:
                     Consensus  (1) AQTVPWGI  I APAVH RG TGSGVKVAVLDTGI  HPDL  RGGASF 51                                                  100
      WO2007131657-CAS91385   (50) IPGEP-TTADLNGHGTHVAGTVAALNNSIGVIGVAPSADLYAVKVLGANG
        WO03054184-CAE48421   (50) VPGEP-TTADLNGHGTHVAGTVAALNNSIGVIGVAPSADLYAVKVLGANG
      WO2008086916-CAV33594   (50) VPGEP-TTEDLNGHGTHVAGTVAALNNSFGVIGVAPSADLYAVKVLGAGG
                    Bgi02446  (50) VPGEP-TTADLNGHGTHVAGTVAALNNSIGVIGVAPNAELYAVKVLGANG
        WO03054185-CAE48424   (50) VPGES-TTADLNGHGTHVAGTVAALNNSIGVIGVAPSADLYAVKVLGANG
             US7642080-0004   (50) VPGEP-NTSDLNGHGTHVAGTIAALNNSIGVVGVAPNADLYAVKVLGANG
             US7642080-0006   (50) VPGEP-NTSDLNGHGTHVAGTIAALNNSIGVVGVAPNADLYAVKVLGANG
             US7642080-0002   (50) VPGEP-TIADGNGHGTHVAGTIAALNNSIGVVGVAPNAQIYGVKVLGANG
             B_lentus_P29600  (50) VPGEP-STQDGNGHGTHVAGTIAALNNSIGVLGVAPSAELYAVKVLGASG
         B_sp_Sendai_BAA06157 (50) VPGEP-SYQDGNGHGTHVAGTIAALNNSIGVVGVAPNAELYAVKVLGANG
          Bacillus_sp_BAA05540 (50) ISSEP-SYHDNNGHGTHVAGTIAALNNSIGVLGVAPSADLYAVKVLDRNG
    B_amyloliquefaciens_CAA24990 (51) VPSETNPFQDNNSHGTHVAGTVAALNNSIGVLGVAPSASLYAVKVLGADG
    G_stearothermophilus_ABY25856 (51) VPSETNPFQDNNSHGTHVAGTVAALNNSVGVLGVAPSASLYAVKVLGADG
        B_atrophaeus_YP003972439 (51) VPSEPNPFQDNNSHGTHVAGTVAALNNSVGVLGVAPSASLYAVKVLSSSG
           B_subtilis_BAN09118  (51) VPSETNPYQDGSSHGTHVAGTVAALNNTIGVLGVAPSASLYAVKVLDSTG
           B_circulans_ADN04910 (51) VPSEPNATQDFQSHGTHVAGTIAALDNTIGVLGVAPSASLYAVKVLDRNG
    B_stratosphericus_WP_007497196 (51) VPSEPNATQDFQSHGTHVAGTIAALDNTIGVLGVAPSASLYAVKVLDRNG
       B_licheniformis_CAJ70731.1 (51) VAGEA-YNTDGNGHGTHVAGTVAALDNTTGVLGVAPSVSLYAVKVLNSSG
            B_pumilus_ADK11996  (51) VPSEPNATQDFQSHGTHVAGTIAALDNTIGVLGVAPSASLYAVKVLDRNG
          B_sp_sprD_AAC43581    (51) VSEEPDALTDGNGHGTHVAGTIAALNNNVGVLGVSYDVDLYAVKVLSAGG
     Bacillus_sp_LG12sprC_AAC43580 (51) VSGEPNALQDGNGHGTHVAGTVAALNNTTGVLGVAYNADLYAVKVLSASG
          Bacillus_sp_BAD11988  (51) ISGESNPYIDSNGHGTHVAGTVAALNNTVGVLGVAYNAELYAVKVLSASG
                                     :. *.      * ..*********:***:*. **:**: ...:*.****. *
                     Consensus (51) VPGEP   T D NGHGTHVAGTVAALNNSIGVLGVAPSA LYAVKVLGANG
```

FIG. 4A

```
                                      101                                            150
        WO2007131657-CAS91385   (99)  RGSVSGIAQGLEWAAANNMHIANMSLGADAPSSTLERAVNYATSQGVLVI
          WO03054184-CAE48421   (99)  RGSVSGIAQGLEWAAANNMHIANMSLGSDAPSITLERAVNYATSQGVLVI
        WO2008086916-CAV33594   (99)  RGSVSGIAQGLEWAAANNMHIANMSLGADAPSSTLERAVNYATSRGVLVI
                      Bgi02446 (99)  SGSVSGIAQGLEWAATNNMHIANMSLGSDFPSSTLERAVNYATSRDVLVI
          WO03054185-CAE48424   (99)  RGSVSGIAQGLEWAATNNMHIANMSLGSDAPSTTLERAVNYATSRGVLVI
               US7642080-0004   (99)  RGSIGGIAQGLEWAAANNMHIANLSLGSDAPSSTLEQAVNYATSRGVLVI
               US7642080-0006   (99)  RGSIGGIAQGLGWAAANNMHIANLSLGSDAPSSTLEQAVNYATSRGVLVI
               US7642080-0002   (99)  RGSVSGIAQGLEWAATNNMDIANLSLGSDAPSSTLEQAVNFATSRGVLVV
                B_lentus_P29600 (99)  SGSVSSIAQGLEWAGNNGMHVANLSLGSPSPSATLEQAVNSATSRGVLVV
          B_sp_Sendai_BAA06157  (99)  SGSVSSIAQGLQWTAQNNIHVANLSLGSPVGSQTLELAVNQATNAGVLVV
            Bacillus_sp_BAA05540 (99) SGSLASVAQGIEWAINNNMHIINMSLGSTSGSSTLELAVNRANNAGILLV
       B_amyloliquefaciens_CAA24990 (101) SGQYSWIINGIEWAIANNMDVINMSLGGPSGSAALKAAVDKAVASGVVVV
       G_stearothermophilus_ABY25856 (101) SGQYSWIINGIEWAIAYNMDVINMSLGGPSGSAALKAAVDKAVASGIVVV
           B_atrophaeus_YP003972439 (101) SGDYSWIINGIEWAISNNMDVINMSLGGPQGSTALKAVVDKAVSQGIVVV
              B_subtilis_BAN09118  (101) SGQYSWIINGIEWAISNNMDVINMSLGGPTGSTALKTVVDKAVASGIVVV
             B_circulans_ADN04910  (101) DGQYSWIISGIEWAVANNMDVINMSLGGPNGSTALKNAVDTANNRGVVVV
       B_stratosphericus_WP_007497196 (101) DGQYSWIISGIEWAVANNMDVINMSLGGPSGSTALKNAVDTANNRGVVVV
           B_licheniformis_CAJ70731.1 (100) SGSYSGIVSGIEWATTNGMDVINMSLGGASGSTAMKQAVDNAYARGVVVV
                B_pumilus_ADK11996  (101) DGQYSWIISGIEWANNMDVINMSLGGASGSTALKNAVDTANNRGVVVV
               B_sp_sprD_AAC43581   (101) SGTLAGIAQGIEWAIDNNMDVINMSLGGSTGSTTLKQASDNAYNSGIVVI
          Bacillus_sp_LG12sprC_AAC43580 (101) SGTLSGIAQGIEWSISNGMNVINMSLGGSSGSTALQQACNNAYNRGIVVI
              Bacillus_sp_BAD11988   (101) SGTLSGIAQGVEWSIANKMDVINMSLGGSSGSTALQRAVDNAYRNNIVVV
                                       *   .  :  .*: *:       :.: *:***.   *  ::: . : *   .::::
                      Consensus (101)  SGS SGIAQGIEWA ANNMDVINMSLGG  GS TLE AVN A   RGV VV 151                                            200
        WO2007131657-CAS91385   (149) AATGNNGSGS------VGYPARYANAMAVGATDQNNRRANFSQYGTGIDIV
          WO03054184-CAE48421   (149) AATGNNGSGS------VGYPARYANAMAVGATDQNNRRANFSQYGTGIDIV
        WO2008086916-CAV33594   (149) AATGNNGSGS------VGYPARYANAMAVGATDQNNRRANFSQYGTGIDIV
                      Bgi02446 (149) AATGNNGSGS------VGYPARYANAMAVGATDQNNRRANFSQYGTGIDIV
          WO03054185-CAE48424   (149) AATGNNGTGS------IGYPARYANAMAVGATDQNNRRANFSQYGTGIDIV
               US7642080-0004   (149) AASGNNGSGN------VGYPARYANAMAVGATDQNNNRANFSQYGAGLDIV
               US7642080-0006   (149) AASGNNGSGN------VGYPARYANAMAVGATDQNNNRANFSQYGAGLDIV
               US7642080-0002   (149) AASGNNGSGN------VGYPARYANAMAVGATDQNNNRANFSQYGAGLDIV
                B_lentus_P29600 (149) AASGNSGAGS------ISYPARYANAMAVGATDQNNNRASFSQYGAGLDIV
          B_sp_Sendai_BAA06157  (149) AATGNNGSGT------VSYPARYANALAVGATDQNNNRASFSQYGTGLNIV
            Bacillus_sp_BAA05540 (149) GAAGNTGRQG------VNYPARYSGVMAVAAVDQNGQRASFSTYGPEIEIS
       B_amyloliquefaciens_CAA24990 (151) AAAGNEG-TSGSSSTVGYPGKYPSVIAVGAVDSSNQRASFSSVGPELDVM
       G_stearothermophilus_ABY25856 (151) AAAGNEG-TSGSSSTVGYPGKYPSVIAVGAVNSSNQRASFSSVGSELDVM
           B_atrophaeus_YP003972439 (151) AAAGNSG-SSGSTSTVGYPAKYPSVIAVGAVDSNNQRASFSSAGSELDVM
              B_subtilis_BAN09118  (151) AAAGNEG-SSGSTSTVGYPAKYPSTIAVGAVNSSNQRASFSSAGSELDVM
             B_circulans_ADN04910  (151) AAAGNSG-STGSTSTVGYPAKYDSTIAVANVNSSNVRNSSSSAGPELDVS
       B_stratosphericus_WP_007497196 (151) AAAGNSG-STGSTSTVGYPAKYDSTIAVANVNSNNVRNSSSSAGPELDVS
           B_licheniformis_CAJ70731.1 (150) AAAGNSG-SSGNINTIGYPAKYDSVIAVGAVDSNSNRASFSSVGAELEVM
                B_pumilus_ADK11996  (151) AAAGNSG-SSGSRSTVGYPARYESTIAVANVNSNNVRNSSSSAGPELDVS
               B_sp_sprD_AAC43581   (151) AAAGNSGSVLGLVNTIGYPARYDSVIAVGAVDSNNNRASFSSVGSQLEVM
          Bacillus_sp_LG12sprC_AAC43580 (151) AAAGNSG-SSGNRNTMGYPARYSSVIAVGAVSSNNTRASFSSVGSELEVM
              Bacillus_sp_BAD11988   (151) AAAGNSG-AQGNRNTIGYPARYSSVIAVGAVDSNNNRASFSSVGSELEVM
                                       .*:** *           :.**.:*  ..:**. ..... * . *  *. :::
                      Consensus (151) AAAGN G  SG   TVGYPARY S IAVGAVD NN RASFSSYG ELD
```

FIG. 4B

```
                                           201                                                250
         WO2007131657-CAS91385     (194)  APGVNVQSTYPGNRYASLNGTSMATPHVAGAAALVKQRNPSWNATQIRNH
           WO03054184-CAE48421     (194)  APGVNVQSTYPGNRYASLNGTSMATPHVAGAAALVKQRYPSWNATQIRNH
         WO2008086916-CAV33594     (194)  APGVNVQSTYPGNRYASLNGTSMATPHVAGVAALVKQRNPSWNATQIRNH
                        Bgi02446  (194)  APGVNVQSTYPGNRYVSMNGTSMATPHVAGAAALVKQRYPSWNATQIRNH
           WO03054185-CAE48424     (194)  APGVGIQSTYLNNSYASMPGTSMATPHVAGVAALVKQKNPSWNATQIRNH
               US7642080-0004     (194)  APGVGIQSTYPGNRYASLNGTSMATPHVAGAAALVKQRYPSWSASQIRNH
               US7642080-0006     (194)  APGVGIQSTYPGNRYASLNGTSMATPHVAGAAALVKQRYPSWSASQIRNH
               US7642080-0002     (194)  APGVGVQSTYPGNRYVSMNGTSMASPHVAGAAALVKQRYPSWSNTQIRNH
              B_lentus_P29600     (194)  APGVNVQSTYPGSTYASLNGTSMATPHVAGAAALVKQKNPSWSNVQIRNH
          B_sp_Sendai_BAA06157     (194)  APGVGIQSTYPGNRYASLSGTSMATPHVAGVAALVKQKNPSWSNTQIRQH
            Bacillus_sp_BAA05540  (194)  APGVNVNSTYTGNRYVSLSGTSMATPHVAGVAALVKSRYPSYTNNQIRQR
     B_amyloliquefaciens_CAA24990  (200)  APGVSIQSTLPGNKYGAYNGTSMASPHVAGAAALILSKHPNWTNTQVRSS
       G_stearothermophilus_ABY25856 (200)  APGVSIQSTLPGNKYGAYNGTSMASPHVAGAAALILSKHPNWTNTQVRSS
          B_atrophaeus_YP003972439 (200)  APGVSIQSTLPGSSYGSYNGTSMASPHVAGAAALVLSKHPNWTNSQVRNS
             B_subtilis_BAN09118   (200)  APGVSIQSTLPGGTYGSYNGTSMATPHVAGAAALILSKHPTWSNAQVRDR
             B_circulans_ADN04910  (200)  APGTSILSTVPSRGYTSYTGTSMAGAAAALILSKNPNLSNSQVRQR
     B_stratosphericus_WP_007497196 (200) APGTSILSTVPSSGYTSYTGTSMASPHVAGAAALILSKYPNLSTSQVRQR
         B_licheniformis_CAJ70731.1 (199) APGAGVYSTYPTNTYATLNGTSMASPHVAGAAALILSKHPNLSASQVRNR
              B_pumilus_ADK11996   (200)  APGTSILSTVPSSGYTSYTGTSMASPHVAGAAALILSKNPNLTNSQVRQR
            B_sp_sprD_AAC43581    (201)  APGVAINSTLPGNQYGELNGTSMASPHVAGAAALLLAQNPNLTNVQVRER
     Bacillus_sp_LG12sprC_AAC43580 (200)  APGVNILSTTPGNNYASFNGTSMAAPHVAGAAALIKAKYPSMTNVQIRER
             Bacillus_sp_BAD11988  (200)  APGVSILSTVPGSSYASYNGTSMASPHVAGAAALLKAKYPNWSAAQIRNK
                                          ***. : **         *     *****:*****.***:   : *. .  *:*.
                     Consensus     (201)  APGV IQSTYPGN YAS NGTSMATPHVAGAAALVK K PSW N QIRN 251             276
         WO2007131657-CAS91385     (244)  LKNTATNLGNSSQFGSGLVNAEAATR    (SEQ ID NO:24)
           WO03054184-CAE48421     (244)  LKNTATNLGNSSQFGSGLVNAEAATR    (SEQ ID NO:25)
         WO2008086916-CAV33594     (244)  LKNTATNLGNSSQFGSGLVNAEAAIR    (SEQ ID NO:26)
                        Bgi02446  (244)  LKNTATNLGNSSQFGSGLVNAEAATR    (SEQ ID NO:4)
           WO03054185-CAE48424     (244)  LKNTATNLGNSSQFGSGLVNAEAATR    (SEQ ID NO:27)
               US7642080-0004     (244)  LKNTSTNLGSSTLYGSGLVNADAASR    (SEQ ID NO:28)
               US7642080-0006     (244)  LKNTSTNLGSSTLYGSGLVNADAASR    (SEQ ID NO:29)
               US7642080-0002     (244)  LKNTATNLGNTNQFGSGLVNADAATR    (SEQ ID NO:30)
              B_lentus_P29600     (244)  LKNTATSLGSTNLYGSGLVNAEAATR    (SEQ ID NO:31)
          B_sp_Sendai_BAA06157     (244)  LTSTATSLGNSNQFGSGLVNAEAATR    (SEQ ID NO:32)
            Bacillus_sp_BAA05540  (244)  INQTATYLGSPSLYGNGLVHAGRATQ    (SEQ ID NO:33)
     B_amyloliquefaciens_CAA24990  (250)  LENTTTKLGDSFYYGKGLINVQAAAQ    (SEQ ID NO:34)
       G_stearothermophilus_ABY25856 (250) LENTTTKLGDAFYYGKGLINVQAAAQ    (SEQ ID NO:35)
          B_atrophaeus_YP003972439 (250)  LESTATNLGNSFYYGKGLINVQAAAQ    (SEQ ID NO:36)
             B_subtilis_BAN09118   (250)  LESTATNLGSFYYGKGLINVQAAAQ     (SEQ ID NO:37)
             B_circulans_ADN04910  (250)  LENTATPLGNSFYYGKGLINVQAASN    (SEQ ID NO:38)
     B_stratosphericus_WP_007497196 (250) LENTATPLGNSFYYGKGLINVQAASN    (SEQ ID NO:39)
         B_licheniformis_CAJ70731.1 (249) LSSTATYLGSSFYYGKGLINVEAAAQ    (SEQ ID NO:40)
              B_pumilus_ADK11996   (250)  LENTATPLGDSFYYGKGLINVQAASN    (SEQ ID NO:41)
            B_sp_sprD_AAC43581    (251)  LRDTATNLGSAFNYGHGVINLERALQ    (SEQ ID NO:42)
     Bacillus_sp_LG12sprC_AAC43580 (250)  LKNTATNLGDPFFYGKGVINVESALQ    (SEQ ID NO:43)
             Bacillus_sp_BAD11988  (250)  LNSTTTYLGSSFYYGNGVINVERALQ    (SEQ ID NO:44)
                                          : .*:* **.. :* *::: * .
                     Consensus     (251)  L NTATNLG SF YG GL NA AA       (SEQ ID NO:45)
```

FIG. 4C

```
B_gibsonii_DSM9728    QQTVPWGITRVQAPAVHNRGVTGSSVRVAILDSGISTHSDLTIRGGASFVPGEPTTADLN
B_gibsonii_DSM9730    QQTVPWGITRVQAPAVHNRGVTGSSVRVAILDSGISTHSDLTIRGGASFVPGEPTTADLN
B_gibsonii_DSM9731    QQTVPWGITRVQAPAVHNRGITGSSVRVAILDSGISTHSDLTIRGGASFVPGEPTTADLN
B_gibsonii_DSM9729    QQTVPWGITRVQAPAVHNRGVTGSSVRVAILDSGISAHSDLNIRGGASFVPGEPTTADLN
Bgi02446              QQTVPWGITRVQAPAVHNRGVTGSSVRVAILDSGISAHSDLNIRGGASFVPGEPTTADLN
                      *******************:****************:***.*******************

B_gibsonii_DSM9728    GHGTHVAGTVAALNNSIGVIGVAPSADLYAVKVLGANGRGSVSGIAQGLEWAAANNMHIA
B_gibsonii_DSM9730    GHGTHVAGTVAALNNSIGVIGVAPSADLYAVKVLGANGRGSVSGIAQGLEWAAANNMHIA
B_gibsonii_DSM9731    GHGTHVAGTVAALNNSIGVIGVAPSADLYAVKVLGANGRGSVSGIAQGLEWAAANNMHIA
B_gibsonii_DSM9729    GHGTHVAGTVAALNNSIGVIGVAPNADLYAVKVLGANGSGSVSGIAQGLEWAATNNMHIA
Bgi02446              GHGTHVAGTVAALNNSIGVIGVAPNAELYAVKVLGANGSGSVSGIAQGLEWAATNNMHIA
                      ***********************.*:********** *************:*******

B_gibsonii_DSM9728    NMSLGSDAPSTTLERAVNYATSQGVLVIAATGNNGSGSVGYPARYANAMAVGATDQNNRR
B_gibsonii_DSM9730    NMSLGSDAPSTTLERAVNYATSQGVLVIAATGNNGSGSVGYPARYANAMAVGATDQNNRR
B_gibsonii_DSM9731    NMSLGSDAPSTTLERAVNYATSQGVLVIAATGNNGSGSVGYPARYANAMAVGATDQNNRR
B_gibsonii_DSM9729    NMSLGSDFPSSTLERAVNYATSRDVLVIAATGNNGSGSVGYPARYANAMAVGATDQNNRR
Bgi02446              NMSLGSDFPSSTLERAVNYATSRDVLVIAATGNNGSGSVGYPARYANAMAVGATDQNNRR
                      ******* **:**********:.:******************************

B_gibsonii_DSM9728    ANFSQYGTGIDIVAPGVNVQSTYPGNRYASLNGTSMATPHVAGAAALVKQRYPSWNATQI
B_gibsonii_DSM9730    ANFSQYGTGIDIVAPGVNVQSTYPGNRYVSMNGTSMATPHVAGAAALVKQRYPSWNATQI
B_gibsonii_DSM9731    ANFSQYGSGIDIVAPGVNVQSTYPGNRYVSMNGTSMATPHVAGAAALVKQRYPSWNATQI
B_gibsonii_DSM9729    ANFSQYGTGIDIVAPGVNVQSTYPGNRYVSMNGTSMATPHVAGAAALVKQRYPSWNATQI
Bgi02446              ANFSQYGTGIDIVAPGVNVQSTYPGNRYVSMNGTSMATPHVAGAAALVKQRYPSWNATQI
                      *******:********************.*:*****************************

B_gibsonii_DSM9728    RNHLKNTATNLGNSSQFGSGLVNAEAAATR    (SEQ ID NO:11)
B_gibsonii_DSM9730    RNHLKNTATNLGNSSQFGSGLVNAEAAATR    (SEQ ID NO:19)
B_gibsonii_DSM9731    RNHLKNTATNLGNSSQFGSGLVNAEAAATR    (SEQ ID NO:23)
B_gibsonii_DSM9729    RNHLKNTATNLGNSSQFGSGLVNAEAAATR    (SEQ ID NO:15)
Bgi02446              RNHLKNTATNLGNSSQFGSGLVNAEAAATR    (SEQ ID NO:4)
                      ******************************
```

FIG. 5

| Chain | | | | | | | | | | | | | | | |
|---|---|---|---|---|---|---|---|---|---|---|---|---|---|---|---|
| 1. SUNKA | AQTVPYGIPLIKADKVQAQGFKGANVKVAVLDTGQASHPDLNVVGGASFVAGE-AYNTDGNGIGTHVAGTVAAL |
| 2. 2ST1A | AQSVPYGVSQIKAPALHSQGYTGSNVKVAVIDSGIDSSHPDLKVAGGASMVPSETNPFQDNNSHGTHVAGTVAAL |
| 3. 1GC1A | AQSVPWGISRVQAPAAHNRGLTGSGVKVAVLDTGIS-THPDLNIRGGASFVPGEPS-TQDGNGHGTHVAGTIAAL |
| 4. BG46 | QQTVPWGITRVQAPAVHNRGITGSGVRVAILDSGS-AHSDLNIRGGASFVPGEPI-TADLNGHGTHVAGTVAAL |
| 5. DSM9728 | QQTVPWGITRVQAPAVHNRGVTGSGVRVAILDSGS-THSDLTIRGGASFVPGEPI-TADLNGHGTHVAGTVAAL |
| DSM9231 | QQTVPWGITRVQAPAVHNRGVTGSGVRVAILDSGS-THSDLTIRGGASFVPGEPI-TADLNGHGTHVAGTVAAL |

| Chain | | | | | | | | | | | | | | | |
|---|---|---|---|---|---|---|---|---|---|---|---|---|---|---|---|
| 1. SUNKA | DNTTGVLGVAPSVSLYAVKVLNSSGSGSYSGIVSGIEWATTNGMDVINMSLGGASGSTAMKQAVDNAYARGVVVV |
| 2. 2ST1A | NNSIGVLGVAPSASLYAVKVLGADGSGQYSWIINGIEWAIANNMDVINMSLGGPSGSAALKAAVDKAVASGVVVV |
| 3. 1GC1A | NNSIGVLGVAPSAELYAVKVLGASGSGSVSSIAQGLEWAGNNGMHVANLSLGSPSPSATLEQAVNSATSRGVLVV |
| 4. BG46 | NNSIGVIGVAPNAELYAVKVLGANGSGSVSGIAQGLEWAATNNMHIANMSLGSDFPSSTLERAVNYATSRDVLVI |
| 5. DSM9728 | NNSIGVIGVAPSADLYAVKVLGANGRGSVSGIAQGLEWAAAANNMHIANMSLGSDAPSTTLERAVNYATSQGVLVI |
| DSM9231 | NNSIGVIGVAPSADLYAVKVLGANGRGSVSGIAQGLEWAAAANNMHIANMSLGSDAPSTTLERAVNYATSQGVLVI |

FIG. 8A

| Chain |  |  |  |  |  |  |  |  |  |  |  |  |  |  |  |
|---|---|---|---|---|---|---|---|---|---|---|---|---|---|---|---|
|  | 151 | 155 | 160 | 165 | 170 | 175 | 180 | 185 | 190 | 195 | 200 | 205 | 210 | 215 | 220 | 225 |
| 3UN1_A | AAAGNSGSSGSTNTIGYPAKYDSVIAVGAVDSNSNRASFSSVGAELEVMAPGAGVYSTYPTNTYATLNGTSMASP |
| 2ST1_A | AAAGNEGTSGSSTVGYPGKYPSVIAVGAVDSSNQRASFSSVGPELDVMAPGVSIQSTLPGNKYGAYNGTSMASP |
| 1GC1_A | AASGNSGA----GSISYPARYANAMAVGATDQNNRASFSQYGAGLDIVAPGVNQSTYPGSTYASLNGTSMATP |
| EG46 | AATGNNGS----GSVGYPARYANAMAVGATDQNNRRANFSQYGTGIDIVAPGVNVQSTYPGVNRYVSMNGTSMATP |
| 5.DSM8728 | AATGNNGS----GSVGYPARYANAMAVGATDQNNRRANFSQYGTGIDIVAPGVNVQSTYPGNRYASLNGTSMATP |
| DSM9731 | AATGNNGS----GSVGYPARYANAMAVGATDQNNRRANFSQYGSGIDIVAPGVNVQSTYPGNRYVSMNGTSMATP |

| Chain |  |  |  |  |  |  |  |  |  |  |
|---|---|---|---|---|---|---|---|---|---|---|
|  | 226 | 230 | 235 | 240 | 245 | 250 | 255 | 260 | 265 | 270 | 275 |
| 3UN1_A | HVAGAAALILSKHPNLSASQVRNRLSSTATYLGSSFYYGKGLINVEAAAQ |
| 2ST1_A | HVAGAAALILSKHPNWTNTQVRSSLENTTTKLGDSFYYGKGLINVQAAAQ |
| 1GC1_A | HVAGAAALVKQKNPSWSNVQIRNHLKNTATSLGSTNLYGSGLVNAEAATR |
| BG46 | HVAGAAALVKQRYPSWNATQIRNHLKNTATNLGNSSQFGSGLVNAEAATR |
| 5.DSM8728 | HVAGAAALVKQRYPSWNATQIRNHLKNTATNLGNSSQFGSGLVNAEAATR |
| DSM9731 | HVAGAAALVKQRYPSWNATQIRNHLKNTATNLGNSSQFGSGLVNAEAATRX |

B. Gibsonii-clade Motif $D_{31}XGIXXHSDLXXXGGASXXXXXPTTADLNXHGTH_{64}$ or $D_{31}XGIXXHSDLXXXGGASXXXXXTTADLXXHGTH_{64}$

FIG. 8B

```
                    1                                                  50
BG1-B08     (1)  QQTVPWGITRVQAPAVHNRGITGSGVRVAILDSGISAHSDLNIRGGASFV
BG1-C05     (1)  QQTVPWGITRVQAPAVHNRGITGSGVRVAILDSGISAHSDLNIRGGASFV
BG2-B08     (1)  QQTVPWGITRVQAPAVHNRGITGSGVRVAILDSGISAHSDLNIRGGASFV
BG2-D10     (1)  QQTVPWGITRVQAPAVHNRGITGSGVRVAILDSGISAHSDLNIRGGASFV
BG2-G08     (1)  QQTVPWGITRVQAPAVHNRGITGSGVRVAILDSGISAHSDLNIRGGASFV
BG4-A09     (1)  QQTVPWGITRVQAPAVHNRGVTGSGVRVAVLDTGISAHSDLNIRGGASFV
BG4-D10     (1)  QQTVPWGITRVQAPAVHNRGFTGSGVRVAILDSGISTHSDLTIRGGASFV
BG5-E02     (1)  QQTVPWGISRVQAPAVHNRGITGSGVRVAILDSGISAHSDLNIRGGASFV
BG5-E05     (1)  QQTVPWGITRVQAPAVHNRGITGSGVRVAILDSGISAHSDLNIRGGASFV
BG5-F02     (1)  QQTVPWGITRVQAPAVHNRGITGSGVRVAILDSGISAHSDLNIRGGASFV
BG5-G10     (1)  QQTVPWGITRVQAPAVHNRGITGSGVRVAILDSGISAHSDLNIRGGASFV
BG6-A10     (1)  QQTVPWGITRVQAPAVHNRGITGSGVRVAILDSGISAHSDLNIRGGASFV
BG6-D08     (1)  QQSVPWGISRVQAPAVHNRGITGSGVRVAILDSGISAHSDLNIRGGASFV
BG8-B03     (1)  AQTVPWGITRVQAPAVHNRGITGSGVRVAILDSGISAHSDLTIRGGASFV
Bgi02446    (1)  QQTVPWGITRVQAPAVHNRGITGSGVRVAILDSGISAHSDLNIRGGASFV
DSM9728     (1)  QQTVPWGITRVQAPAVHNRGVTGSGVRVAILDSGISTHSDLTIRGGASFV
DSM9731     (1)  QQTVPWGITRVQAPAVHNRGVTGSGVRVAILDSGISTHSDLTIRGGASFV
Consensus   (1)  QQTVPWGITRVQAPAVHNRGITGSGVRVAILDSGISAHSDLNIRGGASFV
                   51                                                 100
BG1-B08    (51)  PGEPTTADLNGHGTHVAGTVAALNNSIGVIGVAPNAELYAVKVLGANGSG
BG1-C05    (51)  PGEPTTADLNGHGTHVAGTVAALNNSIGVIGVAPNAELYAVKVLGANGRG
BG2-B08    (51)  PGEPTTADLNGHGTHVAGTVAALNNSIGVIGVAPNAELYAVKVLGASGSG
BG2-D10    (51)  PGEPTTADLNGHGTHVAGTVAALNNSIGVIGVAPNAELYAVKVLGANGSG
BG2-G08    (51)  PGEPTTADLNGHGTHVAGTVAALNNSIGVIGVAPNAELYAVKVLGANGSG
BG4-A09    (51)  PGEPTTADLNGHGTHVAGTVAALNNSIGVIGVAPNAELYAVKVLGANGSG
BG4-D10    (51)  PGEPTTADLNGHGTHVAGTVAALNNSIGVLGVAPNAELYAVKVLGANGSG
BG5-E02    (51)  PGEPTTADLNGHGTHVAGTVAALNNSIGVIGVAPNAELYAVKVLGASGSG
BG5-E05    (51)  PGEPTTADLNGHGTHVAGTVAALNNSIGVIGVAPNAELYAVKVLGANGSG
BG5-F02    (51)  PGEPTTADLNGHGTHVAGTVAALNNSIGVIGVAPNAELYAVKVLGANGSG
BG5-G10    (51)  PGEPTTADLNGHGTHVAGTVAALNNSIGVIGVAPSADLYAVKVLGANGSG
BG6-A10    (51)  PGEPTTADLNGHGTHVAGTVAALNNSIGVIGVAPNAELYAVKVLGASGSG
BG6-D08    (51)  PGEPTTADLNGHGTHVAGTVAALNNSIGVIGVAPSADLYAVKVLGANGSG
BG8-B03    (51)  PGEPTTADLNGHGTHVAGTVAALNNSIGVIGVAPSADLYAVKVLGANGRG
Bgi02446   (51)  PGEPTTADLNGHGTHVAGTVAALNNSIGVIGVAPNAELYAVKVLGANGSG
DSM9728    (51)  PGEPTTADLNGHGTHVAGTVAALNNSIGVIGVAPSADLYAVKVLGANGRG
DSM9731    (51)  PGEPTTADLNGHGTHVAGTVAALNNSIGVIGVAPSADLYAVKVLGANGRG
Consensus  (51)  PGEPTTADLNGHGTHVAGTVAALNNSIGVIGVAPNAELYAVKVLGANGSG
```

FIG. 10A

```
             101                                              150
BG1-B08 (101) SVSGIAQGLEWAATNNMHIANMSLGSDFPSSTLERAVNYATSQGVLVIAA
BG1-C05 (101) SVSGIAQGLEWAATNNMHIANMSLGSDAPSTTLERAVNYATSRDVLVIAA
BG2-B08 (101) SISGIAQGLQWAATNNMHIANMSLGSDAPSTTLERAVNYATSRDVLVIAA
BG2-D10 (101) SVSGIAQGLEWAATNNMHIANMSLGSDAPSTTLERAVNYATSQGVLVIAA
BG2-G08 (101) SVSGIAQGLEWAATNNMHIANMSLGSDAPSTTLERAVNYATSAGVLVVAA
BG4-A09 (101) SVSGIAQGLEWAATNNIHIANMSLGTDAPSTTLERAVNYATSQGVLVIAA
BG4-D10 (101) SISGIAQGLEWAAANNMHIANMSLGTDAPSSTLERAVNYATSQGVLVIAA
BG5-E02 (101) SISGIAQGLEWAATNNMHIANMSLGSDAPSTTLERAVNYATSRDVLVIAA
BG5-E05 (101) SVSGIAQGLEWAATNNMHIANMSLGSDFPSSTLERAVNYATSRDVLVIAA
BG5-F02 (101) SVSGIAQGLEWAATNNMHIANMSLGSDFPSSTLERAVNYATSQGVLVIAA
BG5-G10 (101) SVSGIAQGLEWAATNNMHIANMSLGSDFPSSTLERAVNYATSRDVLVIAA
BG6-A10 (101) SVSGIAQGLEWAATNNMHIANMSLGSDFPSSTLERAVNYATSRDVLVIAA
BG6-D08 (101) SVSGIAQGLEWAAANNMHIANMSLGSDFPSSTLERAVNYATSRDVLVIAA
BG8-B03 (101) SVSGIAQGLEWAATNNMHIANMSLGSDAPSTTLERAVNYATSQGVLVIAA
Bgi02446 (101) SVSGIAQGLEWAATNNMHIANMSLGSDFPSSTLERAVNYATSRDVLVIAA
DSM9728 (101) SVSGIAQGLEWAAANNMHIANMSLGSDAPSTTLERAVNYATSQGVLVIAA
DSM9731 (101) SVSGIAQGLEWAAANNMHIANMSLGSDAPSTTLERAVNYATSQGVLVIAA
Consensus (101) SVSGIAQGLEWAATNNMHIANMSLGSDAPSTTLERAVNYATS GVLVIAA
             151                                              200
BG1-B08 (151) TGNNGSGSVGYPARYANAMAVGATDQNNRRANFSQYGTGIDIVAPGVNVQ
BG1-C05 (151) TGNNGSGSVGYPARYANAMAVGATDQNNRRANFSQYGTGIDIVAPGVNVQ
BG2-B08 (151) TGNNGSGSVGYPARYANAMAVGATDQNNRRANFSQYGTGIDIVAPGVNVQ
BG2-D10 (151) TGNNGSGSVGYPARYANAMAVGATDQNNRRANFSQYGTGIDIVAPGVNVQ
BG2-G08 (151) TGNNGSGSVGYPARYANAMAVGATDQNNRRANFSQYGTGIDIVAPGVNVQ
BG4-A09 (151) TGNNGSGTISYPARYANAMAVGATDQNNRASFSQYGAGLDIVAPGVNVQ
BG4-D10 (151) TGNNGSGTISYPARYANAMAVGATDQNNRRANFSQYGSGIDIVAPGVNVQ
BG5-E02 (151) TGNNGSGSVGYPARYANAMAVGATDQNNRRANFSQYGTGIDIVAPGVNVQ
BG5-E05 (151) TGNNGSGSVGYPARYANAMAVGATDQNNRRANFSQYGAGLDIVAPGVNVQ
BG5-F02 (151) TGNNGSGSVGYPARYANAMAVGATDQNNRRANFSQYGTGIDIVAPGVNVQ
BG5-G10 (151) TGNNGSGSVGYPARYANAMAVGATDQNNRRANFSQYGTGIDIVAPGVNVQ
BG6-A10 (151) TGNNGSGSVGYPARYANAMAVGATDQNNRRANFSQYGTGIDIVAPGVNVQ
BG6-D08 (151) TGNNGSGSVGYPARYANAMAVGATDQNNRRANFSQYGTGIDIVAPGVNVQ
BG8-B03 (151) TGNNGSGSVGYPARYANAMAVGATDQNNRASFSQYGAGLDIVAPGVNVQ
Bgi02446 (151) TGNNGSGSVGYPARYANAMAVGATDQNNRRANFSQYGTGIDIVAPGVNVQ
DSM9728 (151) TGNNGSGSVGYPARYANAMAVGATDQNNRRANFSQYGTGIDIVAPGVNVQ
DSM9731 (151) TGNNGSGSVGYPARYANAMAVGATDQNNRRANFSQYGSGIDIVAPGVNVQ
Consensus (151) TGNNGSGSVGYPARYANAMAVGATDQNNRRANFSQYGTGIDIVAPGVNVQ
```

FIG. 10B

```
              201                                                250
BG1-B08  (201) STYPGNRYVSMNGTSMATPHVAGAAALVKQRYPSWNATQIRNHLKNTATN
BG1-C05  (201) STYPGNRYVSMNGTSMATPHVAGAAALVKQRYPSWNATQIRNHLKNTATN
BG2-B08  (201) STYPGNRYVSMNGTSMATPHVAGAAALVKQRYPSWNATQIRNHLKNTATN
BG2-D10  (201) STYPGNRYVSMNGTSMATPHVAGAAALVKQRYPSWNATQIRNHLKNTATN
BG2-G08  (201) STYPGNRYVSMNGTSMATPHVAGAAALVKQRYPSWNATQIRNHLKNTATN
BG4-A09  (201) STYPGNRYVSMNGTSMATPHVAGAAALVKQRYPSWNATQIRNHLKNTATN
BG4-D10  (201) STYPGNRYASLSGTSMATPHVAGAAALVKQRYPSWNATQIRNHLKNTATN
BG5-E02  (201) STYPGNRYVSMNGTSMATPHVAGAAALVKQRYPSWNATQIRNHLKNTATN
BG5-E05  (201) STYPGNRYVSMNGTSMATPHVAGAAALVKQRYPSWNATQIRNHLKNTATN
BG5-F02  (201) STYPGNRYVSMNGTSMATPHVAGAAALVKQRYPSWNATQIRNHLKNTATN
BG5-G10  (201) STYPGNRYVSMNGTSMATPHVAGAAALVKQRYPSWNATQIRNHLKNTATN
BG6-A10  (201) STYPGNRYVSMNGTSMATPHVAGAAALVKQRYPSWNATQIRNHLKNTATN
BG6-D08  (201) STYPGNRYVSMNGTSMATPHVAGAAALVKQRYPSWNATQIRNHLKNTATN
BG8-B03  (201) STYPGNRYVSMNGTSMATPHVAGVAALVKQRYPSWNATQIRNHLKNTATN
Bgi02446 (201) STYPGNRYVSMNGTSMATPHVAGAAALVKQRYPSWNATQIRNHLKNTATN
DSM9728  (201) STYPGNRYASLNGTSMATPHVAGAAALVKQRYPSWNATQIRNHLKNTATN
DSM9731  (201) STYPGNRYVSMNGTSMATPHVAGAAALVKQRYPSWNATQIRNHLKNTATN
Consensus(201) STYPGNRYVSMNGTSMATPHVAGAAALVKQRYPSWNATQIRNHLKNTATN
              251       269
BG1-B08  (251) LGNTNLYGSGLVNAEAATR (SEQ ID NO:65)
BG1-C05  (251) LGNSSQFGSGLVNAEAATR (SEQ ID NO:61)
BG2-B08  (251) LGNSSQFGSGLVNAEAATR (SEQ ID NO:71)
BG2-D10  (251) LGNSSQFGSGLVNAEAATR (SEQ ID NO:63)
BG2-G08  (251) LGNSSQFGSGLVNAEAATR (SEQ ID NO:83)
BG4-A09  (251) LGNSSQFGSGLVNAEAATR (SEQ ID NO:67)
BG4-D10  (251) LGNSSQFGSGLVNAEAATR (SEQ ID NO:69)
BG5-E02  (251) LGNTNLYGSGLVNAEAATR (SEQ ID NO:81)
BG5-E05  (251) LGNSSQFGSGLVNAEAATR (SEQ ID NO:59)
BG5-F02  (251) LGNSSQFGSGLVNAEAATR (SEQ ID NO:57)
BG5-G10  (251) LGNTNLYGSGLVNAEAATR (SEQ ID NO:79)
BG6-A10  (251) LGNTNLYGSGLVNAEAATR (SEQ ID NO:75)
BG6-D08  (251) LGNTNLYGSGLVNAEAATR (SEQ ID NO:77)
BG8-B03  (251) LGNSSQFGSGLVNAEAATR (SEQ ID NO:73)
Bgi02446 (251) LGNSSQFGSGLVNAEAATR (SEQ ID NO:4)
DSM9728  (251) LGNSSQFGSGLVNAEAATR (SEQ ID NO:11)
DSM9731  (251) LGNSSQFGSGLVNAEAATR (SEQ ID NO:23)
Consensus(251) LGNSSQFGSGLVNAEAATR (SEQ ID NO:89)
```

FIG. 10C

SEQUENCE LISTING

```
<160> NUMBER OF SEQ ID NOS: 91

<210> SEQ ID NO 1
<211> LENGTH: 1149
<212> TYPE: DNA
<213> ORGANISM: B. gibsonii
<220> FEATURE:
<221> NAME/KEY: misc_feature
<222> LOCATION: (1)..(1149)
<223> OTHER INFORMATION: The nucleotide sequence of Bgi02446n

<400> SEQUENCE: 1
atgaaaagaa aagtaggaaa gcttatggtg gggcttgtat gtgtaacagc tctagtaacc      60
gtgacagatt ctgcatctgc ggcagaagaa aaagtaaaat acttaatagg tttcgaagaa     120
gaagcagaac ttgaagcctt cactgaggaa attgaccaag ttggtgtatt ttctgttgaa     180
gaacaaagtg tagctgagga tacgttagat attgatgtag acattattga tgaatatgat     240
```

```
tatattgatg tgttagctgt agaattagat cctgaggatg tagatgcgtt aagtgaagaa    300
gcaggtatct catttattga agaagacatt gaactgtcta ttcaacaaac agttccttgg    360
ggcattactc gtgtacaagc tccggctgtt cataaccgtg ggattacagg ttctggagta    420
agagtagcta tccttgattc agggatttca gcccatagtg atttgaatat ccgcggtgga    480
gctagctttg taccgggtga accaacgaca gctgatttaa atggacatgg tactcacgtg    540
gccggaacag tagcagctct aaataattca attggtgtca ttggtgttgc accgaatgct    600
gaattatatg ctgttaaagt acttggagca aatggaagcg gaagtgtaag tgggattgct    660
caaggtttag agtgggcggc aaccaataac atgcatattg cgaacatgag tctcggtagt    720
gattttccta gctctacact tgagcgtgca gtcaactatg caacaagccg tgatgtacta    780
gttattgcag cgactggtaa taacggttct ggttcagtag ctatcctgc tcgttatgca    840 aacgcaatgg ctgtaggagc gactgaccaa acaacagac gcgcaaactt ttctcagtat    900
ggtacgggaa ttgacatcgt agcacctggt gttaacgtac aaagtacgta tccaggtaac    960
cgttacgtga gtatgaatgg tacatctatg ctactccac acgtagctgg tgccgcagcg   1020
cttgtaaagc aacgctatcc gtcttggaat gcgactcaaa ttcgcaatca tctgaaaaat   1080
acagcaacaa atctaggaaa ctcttcacaa tttggtagtg gcctagttaa cgcagaagca   1140
gcaacacgt                                                            1149
```

<210> SEQ ID NO 2
<211> LENGTH: 383
<212> TYPE: PRT
<213> ORGANISM: B. gibsonii
<220> FEATURE:
<221> NAME/KEY: misc_feature
<222> LOCATION: (1)..(383)
<223> OTHER INFORMATION: The amino acid sequence of the preproenzyme
      encoded by Bgi02446n

<400> SEQUENCE: 2

Met Lys Arg Lys Val Gly Lys Leu Met Val Gly Leu Val Cys Val Thr
1               5                   10                  15

Ala Leu Val Thr Val Thr Asp Ser Ala Ser Ala Glu Glu Lys Val
            20                  25                  30

Lys Tyr Leu Ile Gly Phe Glu Glu Glu Ala Glu Leu Glu Ala Phe Thr
        35                  40                  45

Glu Glu Ile Asp Gln Val Gly Val Phe Ser Val Glu Glu Gln Ser Val
    50                  55                  60

Ala Glu Asp Thr Leu Asp Ile Asp Val Asp Ile Ile Asp Glu Tyr Asp
65                  70                  75                  80

Tyr Ile Asp Val Leu Ala Val Glu Leu Asp Pro Glu Asp Val Asp Ala
                85                  90                  95

Leu Ser Glu Glu Ala Gly Ile Ser Phe Ile Glu Glu Asp Ile Glu Leu
            100                 105                 110

Ser Ile Gln Gln Thr Val Pro Trp Gly Ile Thr Arg Val Gln Ala Pro
        115                 120                 125

Ala Val His Asn Arg Gly Ile Thr Gly Ser Gly Val Arg Val Ala Ile
    130                 135                 140

Leu Asp Ser Gly Ile Ser Ala His Ser Asp Leu Asn Ile Arg Gly Gly
145                 150                 155                 160

Ala Ser Phe Val Pro Gly Glu Pro Thr Thr Ala Asp Leu Asn Gly His
                165                 170                 175

```
Gly Thr His Val Ala Gly Thr Val Ala Ala Leu Asn Asn Ser Ile Gly
            180                 185                 190

Val Ile Gly Val Ala Pro Asn Ala Glu Leu Tyr Ala Val Lys Val Leu
        195                 200                 205

Gly Ala Asn Gly Ser Gly Ser Val Ser Gly Ile Ala Gln Gly Leu Glu
    210                 215                 220

Trp Ala Ala Thr Asn Asn Met His Ile Ala Asn Met Ser Leu Gly Ser
225                 230                 235                 240

Asp Phe Pro Ser Ser Thr Leu Glu Arg Ala Val Asn Tyr Ala Thr Ser
                245                 250                 255

Arg Asp Val Leu Val Ile Ala Ala Thr Gly Asn Asn Gly Ser Gly Ser
            260                 265                 270

Val Gly Tyr Pro Ala Arg Tyr Ala Asn Ala Met Ala Val Gly Ala Thr
        275                 280                 285

Asp Gln Asn Asn Arg Arg Ala Asn Phe Ser Gln Tyr Gly Thr Gly Ile
    290                 295                 300

Asp Ile Val Ala Pro Gly Val Asn Val Gln Ser Thr Tyr Pro Gly Asn
305                 310                 315                 320

Arg Tyr Val Ser Met Asn Gly Thr Ser Met Ala Thr Pro His Val Ala
                325                 330                 335

Gly Ala Ala Ala Leu Val Lys Gln Arg Tyr Pro Ser Trp Asn Ala Thr
            340                 345                 350

Gln Ile Arg Asn His Leu Lys Asn Thr Ala Thr Asn Leu Gly Asn Ser
        355                 360                 365

Ser Gln Phe Gly Ser Gly Leu Val Asn Ala Glu Ala Ala Thr Arg
    370                 375                 380

<210> SEQ ID NO 3
<211> LENGTH: 356
<212> TYPE: PRT
<213> ORGANISM: B. gibsonii
<220> FEATURE:
<221> NAME/KEY: misc_feature
<222> LOCATION: (1)..(356)
<223> OTHER INFORMATION: The amino acid sequence of the proenzyme
      encoded by Bgi02446n

<400> SEQUENCE: 3

Ala Glu Glu Lys Val Lys Tyr Leu Ile Gly Phe Glu Glu Ala Glu
1               5                   10                  15

Leu Glu Ala Phe Thr Glu Glu Ile Asp Gln Val Gly Val Phe Ser Val
                20                  25                  30

Glu Glu Gln Ser Val Ala Glu Asp Thr Leu Asp Ile Asp Val Asp Ile
            35                  40                  45

Ile Asp Glu Tyr Asp Tyr Ile Asp Val Leu Ala Val Glu Leu Asp Pro
        50                  55                  60

Glu Asp Val Asp Ala Leu Ser Glu Glu Ala Gly Ile Ser Phe Ile Glu
65                  70                  75                  80

Glu Asp Ile Glu Leu Ser Ile Gln Gln Thr Val Pro Trp Gly Ile Thr
                85                  90                  95

Arg Val Gln Ala Pro Ala Val His Asn Arg Gly Ile Thr Gly Ser Gly
            100                 105                 110

Val Arg Val Ala Ile Leu Asp Ser Gly Ile Ser Ala His Ser Asp Leu
        115                 120                 125

Asn Ile Arg Gly Gly Ala Ser Phe Val Pro Gly Glu Pro Thr Thr Ala
    130                 135                 140
```

```
Asp Leu Asn Gly His Gly Thr His Val Ala Gly Thr Val Ala Ala Leu
145                 150                 155                 160

Asn Asn Ser Ile Gly Val Ile Gly Val Ala Pro Asn Ala Glu Leu Tyr
            165                 170                 175

Ala Val Lys Val Leu Gly Ala Asn Gly Ser Gly Ser Val Ser Gly Ile
        180                 185                 190

Ala Gln Gly Leu Glu Trp Ala Ala Thr Asn Asn Met His Ile Ala Asn
    195                 200                 205

Met Ser Leu Gly Ser Asp Phe Pro Ser Ser Thr Leu Glu Arg Ala Val
210                 215                 220

Asn Tyr Ala Thr Ser Arg Asp Val Leu Val Ile Ala Ala Thr Gly Asn
225                 230                 235                 240

Asn Gly Ser Gly Ser Val Gly Tyr Pro Ala Arg Tyr Ala Asn Ala Met
            245                 250                 255

Ala Val Gly Ala Thr Asp Gln Asn Asn Arg Arg Ala Asn Phe Ser Gln
        260                 265                 270

Tyr Gly Thr Gly Ile Asp Ile Val Ala Pro Gly Val Asn Val Gln Ser
    275                 280                 285

Thr Tyr Pro Gly Asn Arg Tyr Val Ser Met Asn Gly Thr Ser Met Ala
290                 295                 300

Thr Pro His Val Ala Gly Ala Ala Ala Leu Val Lys Gln Arg Tyr Pro
305                 310                 315                 320

Ser Trp Asn Ala Thr Gln Ile Arg Asn His Leu Lys Asn Thr Ala Thr
            325                 330                 335

Asn Leu Gly Asn Ser Ser Gln Phe Gly Ser Gly Leu Val Asn Ala Glu
        340                 345                 350

Ala Ala Thr Arg
        355

<210> SEQ ID NO 4
<211> LENGTH: 269
<212> TYPE: PRT
<213> ORGANISM: B. gibsonii
<220> FEATURE:
<221> NAME/KEY: misc_feature
<222> LOCATION: (1)..(269)
<223> OTHER INFORMATION: The predicted amino acid sequence of the mature
      enzyme, Bgi02446 (269 amino acids)

<400> SEQUENCE: 4

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125
```

```
Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 5
<211> LENGTH: 93
<212> TYPE: DNA
<213> ORGANISM: Artificial Sequence
<220> FEATURE:
<223> OTHER INFORMATION: Synthetic: terminator sequence

<400> SEQUENCE: 5
ggttaccttg aatgtatata acattctca aagggatttc taataaaaaa cgctcggttg    60
ccgccgggcg ttttttatgc atcgatggaa ttc                                93

<210> SEQ ID NO 6
<211> LENGTH: 1071
<212> TYPE: DNA
<213> ORGANISM: Artificial Sequence
<220> FEATURE:
<223> OTHER INFORMATION: Synthetic: nucleotide sequence of the pro-
      mature gene encoding Bgi02446

<400> SEQUENCE: 6
gcagaagaaa aagtcaaata tctgatcggc tttgaagaag aagcagaact ggaagcattt    60
acggaagaaa ttgatcaagt tggcgttttt agcgtcgaag aacaatcagt tgcagaagat   120
acactggata tcgatgtcga tatcatcgac gaatatgact atattgatgt tctggcggtt   180
gaacttgatc cggaagatgt tgatgcactg tcagaagaag caggcattag ctttattgaa   240
gaagatatcg aactgagcat tcaacaaaca gttccgtggg gcattacaag agttcaagca   300
ccggcagttc ataatcgcgg aattacaggc tcaggcgtta gagttgcaat tctggattca   360
ggcatttcag cacatagcga tctgaatatt agaggcggag catcatttgt ccctggcgaa   420
ccgacaacag cagatctgaa tggccatggc acacatgttg caggcacagt tgcagcactg   480
aataattcaa ttggcgttat tggagttgca ccgaatgcag aactgtatgc agttaaagtt   540
cttggcgcaa atggctcagg ctcagtttca ggcattgcac aaggcctgga atgggcagca   600
acaaataaca tgcatattgc aaatatgtca ctgggctcag attttccgtc atcaacactg   660
gaacgcgcag ttaattatgc aacatcaaga gatgttctgg tcattgcagc aacaggcaat   720
aatggcagcg gctcagttgg ctatccggca agatatgcaa atgcaatggc agttggcgct   780
acagatcaaa ataatcgcag agcaaatttt agccaatatg gcacaggcat tgatattgtt   840
```

```
gcacctggcg ttaatgttca gtcaacatat ccgggaaatc gctatgtttc aatgaatggc    900
acatcaatgg caacaccgca tgtcgcaggc gcagcagcac tggttaaaca aagatatccg    960
tcatggaatg cgacacagat tcgcaatcat ctgaaaaata cagcaacaaa tctgggcaat   1020
tcaagccaat ttggctcagg cctggttaat gcagaagcag caacaagata a            1071
```

<210> SEQ ID NO 7
<211> LENGTH: 268
<212> TYPE: PRT
<213> ORGANISM: Artificial Sequence
<220> FEATURE:
<223> OTHER INFORMATION: Synthetic: amino acid sequence of the processed
      mature enzyme, Bgi02446 that was purified and used for further
      characterization (268 amino acids)

<400> SEQUENCE: 7

```
Gln Thr Val Pro Trp Gly Ile Thr Arg Val Gln Ala Pro Ala Val His
1               5                   10                  15

Asn Arg Gly Ile Thr Gly Ser Gly Val Arg Val Ala Ile Leu Asp Ser
            20                  25                  30

Gly Ile Ser Ala His Ser Asp Leu Asn Ile Arg Gly Gly Ala Ser Phe
        35                  40                  45

Val Pro Gly Glu Pro Thr Thr Ala Asp Leu Asn Gly His Gly Thr His
    50                  55                  60

Val Ala Gly Thr Val Ala Ala Leu Asn Asn Ser Ile Gly Val Ile Gly
65                  70                  75                  80

Val Ala Pro Asn Ala Glu Leu Tyr Ala Val Lys Val Leu Gly Ala Asn
                85                  90                  95

Gly Ser Gly Ser Val Ser Gly Ile Ala Gln Gly Leu Glu Trp Ala Ala
            100                 105                 110

Thr Asn Asn Met His Ile Ala Asn Met Ser Leu Gly Ser Asp Phe Pro
        115                 120                 125

Ser Ser Thr Leu Glu Arg Ala Val Asn Tyr Ala Thr Ser Arg Asp Val
    130                 135                 140

Leu Val Ile Ala Ala Thr Gly Asn Asn Gly Ser Gly Ser Val Gly Tyr
145                 150                 155                 160

Pro Ala Arg Tyr Ala Asn Ala Met Ala Val Gly Ala Thr Asp Gln Asn
                165                 170                 175

Asn Arg Arg Ala Asn Phe Ser Gln Tyr Gly Thr Gly Ile Asp Ile Val
            180                 185                 190

Ala Pro Gly Val Asn Val Gln Ser Thr Tyr Pro Gly Asn Arg Tyr Val
        195                 200                 205

Ser Met Asn Gly Thr Ser Met Ala Thr Pro His Val Ala Gly Ala Ala
    210                 215                 220

Ala Leu Val Lys Gln Arg Tyr Pro Ser Trp Asn Ala Thr Gln Ile Arg
225                 230                 235                 240

Asn His Leu Lys Asn Thr Ala Asn Leu Gly Asn Ser Ser Gln Phe
                245                 250                 255

Gly Ser Gly Leu Val Asn Ala Glu Ala Ala Thr Arg
            260                 265
```

<210> SEQ ID NO 8
<211> LENGTH: 1149
<212> TYPE: DNA
<213> ORGANISM: B. gibsonii
<220> FEATURE:
<221> NAME/KEY: misc_feature
<222> LOCATION: (1)..(1149)
<223> OTHER INFORMATION: The nucleotide sequence encoding the DSM 9728
      subtilisin

<400> SEQUENCE: 8

| | | | | | |
|---|---|---|---|---|---|
| atgaaaagaa | gagtaggaaa | gcttgtagtg | gggcttgttt | gtgtaacagc | tctagtaaca | 60 |
| gtaacagatt | ctgcatctgc | agcagaagaa | aaggtaaaat | acttaatagg | gtttgaagaa | 120 |
| gaagcagaac | ttgaagcctt | cactgaggaa | attgaccaag | ttggtgtgtt | ttctgttgaa | 180 |
| gaacaaagtg | tagctgagga | tacgttagat | attgatgtag | acattattga | tgaatatgat | 240 |
| tatattgatg | tattagccgt | agaattagat | cctgaggatg | tagatgcgtt | aagcgaagaa | 300 |
| gcaggtatct | catttattga | agaagacatt | gaactgtcta | tccaacaaac | ggttccttgg | 360 |
| ggcattactc | gtgtacaagc | tccagctgtg | cataaccgag | gagtaacagg | tctggtgta | 420 |
| agagtagcga | ttctagattc | aggaatctct | acacatagtg | atttaacgat | tcgcggtgga | 480 |
| gctagctttg | taccgggtga | accaacaacg | gctgatttaa | atggtcatgg | gactcacgtt | 540 |
| gcaggaacag | tggcagctct | taataattca | atcggtgtga | ttggtgtggc | accaagtgct | 600 |
| gatctatacg | ctgtaaaagt | acttggagca | aatggtagag | gaagcgttag | tggaattgct | 660 |
| caaggtctag | agtgggctgc | agcgaataac | atgcatattg | ctaacatgag | tctcggtagt | 720 |
| gatgcaccta | gtactacact | tgagcgtgca | gtcaactatg | cgacaagcca | aggtgtacta | 780 |
| gttattgcag | cgactggtaa | caacggttct | ggttcagttg | ctatcctgc | tcgttatgca | 840 |
| aacgcaatgg | ctgtaggagc | gactgaccaa | acaacagac | gtgcaaactt | ttctcagtat | 900 |
| ggtacaggaa | ttgacatcgt | agcaccaggg | gttaatgtac | aaagtacgta | tcctggaaac | 960 |
| cgctatgcaa | gtttaaatgg | tacatctatg | gctactccac | acgtagctgg | tgccgctgca | 1020 |
| cttgtaaagc | aacgctatcc | atcttggaat | gcaactcaaa | ttcgcaatca | tctgaaaaat | 1080 |
| acagcgacaa | atctaggaaa | ctcttcgcaa | tttggtagtg | gcctagtcaa | cgcagaagca | 1140 |
| gcaacacgt | | | | | | 1149 |

<210> SEQ ID NO 9
<211> LENGTH: 383
<212> TYPE: PRT
<213> ORGANISM: B. gibsonii
<220> FEATURE:
<221> NAME/KEY: misc_feature
<222> LOCATION: (1)..(383)
<223> OTHER INFORMATION: The amino acid sequence of the DSM 9728
      preproenzyme

<400> SEQUENCE: 9

Met Lys Arg Arg Val Gly Lys Leu Val Val Gly Leu Val Cys Val Thr
1               5                   10                  15

Ala Leu Val Thr Val Thr Asp Ser Ala Ser Ala Glu Glu Lys Val
            20                  25                  30

Lys Tyr Leu Ile Gly Phe Glu Glu Glu Ala Glu Leu Glu Ala Phe Thr
        35                  40                  45

Glu Glu Ile Asp Gln Val Gly Val Phe Ser Val Glu Glu Gln Ser Val
    50                  55                  60

Ala Glu Asp Thr Leu Asp Ile Asp Val Asp Ile Ile Asp Glu Tyr Asp
65                  70                  75                  80

Tyr Ile Asp Val Leu Ala Val Glu Leu Asp Pro Glu Asp Val Asp Ala
                85                  90                  95

Leu Ser Glu Glu Ala Gly Ile Ser Phe Ile Glu Glu Asp Ile Glu Leu
            100                 105                 110

Ser Ile Gln Gln Thr Val Pro Trp Gly Ile Thr Arg Val Gln Ala Pro
            115                 120                 125

Ala Val His Asn Arg Gly Val Thr Gly Ser Gly Val Arg Val Ala Ile
        130                 135                 140

Leu Asp Ser Gly Ile Ser Thr His Ser Asp Leu Thr Ile Arg Gly Gly
145                 150                 155                 160

Ala Ser Phe Val Pro Gly Glu Pro Thr Ala Asp Leu Asn Gly His
                165                 170                 175

Gly Thr His Val Ala Gly Thr Val Ala Ala Leu Asn Asn Ser Ile Gly
            180                 185                 190

Val Ile Gly Val Ala Pro Ser Ala Asp Leu Tyr Ala Val Lys Val Leu
        195                 200                 205

Gly Ala Asn Gly Arg Gly Ser Val Ser Gly Ile Ala Gln Gly Leu Glu
    210                 215                 220

Trp Ala Ala Ala Asn Asn Met His Ile Ala Asn Met Ser Leu Gly Ser
225                 230                 235                 240

Asp Ala Pro Ser Thr Thr Leu Glu Arg Ala Val Asn Tyr Ala Thr Ser
                245                 250                 255

Gln Gly Val Leu Val Ile Ala Ala Thr Gly Asn Asn Gly Ser Gly Ser
            260                 265                 270

Val Gly Tyr Pro Ala Arg Tyr Ala Asn Ala Met Ala Val Gly Ala Thr
        275                 280                 285

Asp Gln Asn Asn Arg Arg Ala Asn Phe Ser Gln Tyr Gly Thr Gly Ile
    290                 295                 300

Asp Ile Val Ala Pro Gly Val Asn Val Gln Ser Thr Tyr Pro Gly Asn
305                 310                 315                 320

Arg Tyr Ala Ser Leu Asn Gly Thr Ser Met Ala Thr Pro His Val Ala
                325                 330                 335

Gly Ala Ala Ala Leu Val Lys Gln Arg Tyr Pro Ser Trp Asn Ala Thr
            340                 345                 350

Gln Ile Arg Asn His Leu Lys Asn Thr Ala Thr Asn Leu Gly Asn Ser
        355                 360                 365

Ser Gln Phe Gly Ser Gly Leu Val Asn Ala Glu Ala Ala Thr Arg
    370                 375                 380

<210> SEQ ID NO 10
<211> LENGTH: 356
<212> TYPE: PRT
<213> ORGANISM: B. gibsonii
<220> FEATURE:
<221> NAME/KEY: misc_feature
<222> LOCATION: (1)..(356)
<223> OTHER INFORMATION: The amino acid sequence of the DMS 9728
      proenzyme

<400> SEQUENCE: 10

Ala Glu Glu Lys Val Lys Tyr Leu Ile Gly Phe Glu Glu Ala Glu
1               5                   10                  15

Leu Glu Ala Phe Thr Glu Glu Ile Asp Gln Val Gly Val Phe Ser Val
            20                  25                  30

Glu Glu Gln Ser Val Ala Glu Asp Thr Leu Asp Ile Asp Val Asp Ile
        35                  40                  45

Ile Asp Glu Tyr Asp Tyr Ile Asp Val Leu Ala Val Glu Leu Asp Pro
    50                  55                  60

Glu Asp Val Asp Ala Leu Ser Glu Glu Ala Gly Ile Ser Phe Ile Glu
65                  70                  75                  80

```
Glu Asp Ile Glu Leu Ser Ile Gln Gln Thr Val Pro Trp Gly Ile Thr
                85                  90                  95

Arg Val Gln Ala Pro Ala Val His Asn Arg Gly Val Thr Gly Ser Gly
            100                 105                 110

Val Arg Val Ala Ile Leu Asp Ser Gly Ile Ser Thr His Ser Asp Leu
        115                 120                 125

Thr Ile Arg Gly Gly Ala Ser Phe Val Pro Gly Glu Pro Thr Thr Ala
    130                 135                 140

Asp Leu Asn Gly His Gly Thr His Val Ala Gly Thr Val Ala Ala Leu
145                 150                 155                 160

Asn Asn Ser Ile Gly Val Ile Gly Val Ala Pro Ser Ala Asp Leu Tyr
                165                 170                 175

Ala Val Lys Val Leu Gly Ala Asn Gly Arg Gly Ser Val Ser Gly Ile
            180                 185                 190

Ala Gln Gly Leu Glu Trp Ala Ala Asn Asn Met His Ile Ala Asn
        195                 200                 205

Met Ser Leu Gly Ser Asp Ala Pro Ser Thr Thr Leu Glu Arg Ala Val
    210                 215                 220

Asn Tyr Ala Thr Ser Gln Gly Val Leu Val Ile Ala Thr Gly Asn
225                 230                 235                 240

Asn Gly Ser Gly Ser Val Gly Tyr Pro Ala Arg Tyr Ala Asn Ala Met
                245                 250                 255

Ala Val Gly Ala Thr Asp Gln Asn Asn Arg Arg Ala Asn Phe Ser Gln
            260                 265                 270

Tyr Gly Thr Gly Ile Asp Ile Val Ala Pro Gly Val Asn Val Gln Ser
        275                 280                 285

Thr Tyr Pro Gly Asn Arg Tyr Ala Ser Leu Asn Gly Thr Ser Met Ala
    290                 295                 300

Thr Pro His Val Ala Gly Ala Ala Leu Val Lys Gln Arg Tyr Pro
305                 310                 315                 320

Ser Trp Asn Ala Thr Gln Ile Arg Asn His Leu Lys Asn Thr Ala Thr
                325                 330                 335

Asn Leu Gly Asn Ser Ser Gln Phe Gly Ser Gly Leu Val Asn Ala Glu
            340                 345                 350

Ala Ala Thr Arg
        355

<210> SEQ ID NO 11
<211> LENGTH: 269
<212> TYPE: PRT
<213> ORGANISM: B. gibsonii
<220> FEATURE:
<221> NAME/KEY: misc_feature
<222> LOCATION: (1)..(269)
<223> OTHER INFORMATION: The predicted amino acid sequence of the mature
      form of the DSM 9728 subtilisin

<400> SEQUENCE: 11

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Thr His Ser Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60
```

His Val Ala Gly Thr Val Ala Ala Leu Asn Asn Ser Ile Gly Val Ile
 65                  70                  75                  80

Gly Val Ala Pro Ser Ala Asp Leu Tyr Ala Val Lys Val Leu Gly Ala
                 85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Ala Ser Leu Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 12
<211> LENGTH: 1149
<212> TYPE: DNA
<213> ORGANISM: B. gibsonii
<220> FEATURE:
<221> NAME/KEY: misc_feature
<222> LOCATION: (1)..(1149)
<223> OTHER INFORMATION: The nucleotide sequence encoding the DSM 9729
      subtilisin

<400> SEQUENCE: 12
atgaaaagaa gagtaggtaa gcttgtggtg gggcttgtat gtgtaacagc tctagtaacc      60
gtgacagatt ctgcatctgc ggcagaagaa aaagtaaaat acttaatagg ttttgaagaa     120
gaagcagaac ttgaagcctt cactgaggaa attgaccaag ttggtgtatt ttctgttgaa     180
gaacaaagtg tagctgagga tacgttagat attgatgtag acattattga tgaatatgat     240
tatattgatg tgttagctgt agaattagat cctgaggatg tagatgcgtt aagcgaagaa     300
gcaggtatct catttattga agaagacatt gaactgtcta ttcaacaaac agttccttgg     360
ggcattactc gtgtacaagc tccggctgtt cataaccgag ggattacagg ttctggagta     420
agagtagcta tccttgattc agggatttca gcccatagtg atttgaatat ccgcggtgga     480
gctagctttg taccgggtga accaacgacg gctgatttaa atggacatgg tactcacgtg     540
gccggaacag tagcagctct aaataattca attggtgtca ttggtgttgc accgaatgct     600
gacttatatg ctgttaaagt actcggagca aatggaagcg gaagtgtaag tgggattgct     660
caaggtttag agtgggcggc aaccaataac atgcatattg cgaacatgag tctcggtagt     720
gattttccta gctctacact tgagcgtgca gtcaactatg cgacaagccg tgatgtacta     780

```
gttattgcag cgactggtaa caacggttct ggttcagtag gctatcctgc tcgttatgca    840
aacgcaatgg ctgtaggagc gactgaccaa acaacagac gcgcaaactt ttctcagtac    900
ggtacaggaa ttgacatcgt agcacctgga gttaacgtac aaagtacgta tccaggaaac    960
cgttatgtga gtatgaatgg tacatctatg ccactccac atgtagctgg tgccgctgca    1020
cttgtaaagc aacgctatcc ttcttggaat gcgactcaaa ttcgcaatca tctgaaaaat    1080
acagcaacaa atctaggaaa ctcttcgcaa tttggtagtg gcctagttaa cgcagaagca    1140
gcaacacgt                                                           1149
```

<210> SEQ ID NO 13
<211> LENGTH: 383
<212> TYPE: PRT
<213> ORGANISM: B. gibsonii
<220> FEATURE:
<221> NAME/KEY: misc_feature
<222> LOCATION: (1)..(383)
<223> OTHER INFORMATION: The amino acid sequence of the DSM 9729 preproenzyme

<400> SEQUENCE: 13

Met Lys Arg Arg Val Gly Lys Leu Val Val Gly Leu Val Cys Val Thr
1               5                   10                  15

Ala Leu Val Thr Val Thr Asp Ser Ala Ser Ala Ala Glu Glu Lys Val
            20                  25                  30

Lys Tyr Leu Ile Gly Phe Glu Glu Ala Glu Leu Glu Ala Phe Thr
        35                  40                  45

Glu Glu Ile Asp Gln Val Gly Val Phe Ser Val Glu Glu Gln Ser Val
    50                  55                  60

Ala Glu Asp Thr Leu Asp Ile Asp Val Asp Ile Ile Asp Glu Tyr Asp
65                  70                  75                  80

Tyr Ile Asp Val Leu Ala Val Glu Leu Asp Pro Glu Asp Val Asp Ala
                85                  90                  95

Leu Ser Glu Glu Ala Gly Ile Ser Phe Ile Glu Glu Asp Ile Glu Leu
            100                 105                 110

Ser Ile Gln Gln Thr Val Pro Trp Gly Ile Thr Arg Val Gln Ala Pro
        115                 120                 125

Ala Val His Asn Arg Gly Ile Thr Gly Ser Gly Val Arg Val Ala Ile
    130                 135                 140

Leu Asp Ser Gly Ile Ser Ala His Ser Asp Leu Asn Ile Arg Gly Gly
145                 150                 155                 160

Ala Ser Phe Val Pro Gly Glu Pro Thr Thr Ala Asp Leu Asn Gly His
                165                 170                 175

Gly Thr His Val Ala Gly Thr Val Ala Ala Leu Asn Asn Ser Ile Gly
            180                 185                 190

Val Ile Gly Val Ala Pro Asn Ala Asp Leu Tyr Ala Val Lys Val Leu
        195                 200                 205

Gly Ala Asn Gly Ser Gly Ser Val Ser Gly Ile Ala Gln Gly Leu Glu
    210                 215                 220

Trp Ala Ala Thr Asn Asn Met His Ile Ala Asn Met Ser Leu Gly Ser
225                 230                 235                 240

Asp Phe Pro Ser Ser Thr Leu Glu Arg Ala Val Asn Tyr Ala Thr Ser
                245                 250                 255

Arg Asp Val Leu Val Ile Ala Ala Thr Gly Asn Asn Gly Ser Gly Ser
            260                 265                 270

Val Gly Tyr Pro Ala Arg Tyr Ala Asn Ala Met Ala Val Gly Ala Thr

```
                    275                 280                 285
Asp Gln Asn Asn Arg Arg Ala Asn Phe Ser Gln Tyr Gly Thr Gly Ile
    290                 295                 300

Asp Ile Val Ala Pro Gly Val Asn Val Gln Ser Thr Tyr Pro Gly Asn
305                 310                 315                 320

Arg Tyr Val Ser Met Asn Gly Thr Ser Met Ala Thr Pro His Val Ala
                325                 330                 335

Gly Ala Ala Leu Val Lys Gln Arg Tyr Pro Ser Trp Asn Ala Thr
            340                 345                 350

Gln Ile Arg Asn His Leu Lys Asn Thr Ala Thr Asn Leu Gly Asn Ser
        355                 360                 365

Ser Gln Phe Gly Ser Gly Leu Val Asn Ala Glu Ala Thr Arg
    370                 375                 380

<210> SEQ ID NO 14
<211> LENGTH: 356
<212> TYPE: PRT
<213> ORGANISM: B. gibsonii
<220> FEATURE:
<221> NAME/KEY: misc_feature
<222> LOCATION: (1)..(356)
<223> OTHER INFORMATION: The amino acid sequence of the DSM 9729
      proenzyme

<400> SEQUENCE: 14

Ala Glu Glu Lys Val Lys Tyr Leu Ile Gly Phe Glu Glu Glu Ala Glu
1               5                   10                  15

Leu Glu Ala Phe Thr Glu Glu Ile Asp Gln Val Gly Val Phe Ser Val
            20                  25                  30

Glu Glu Gln Ser Val Ala Glu Asp Thr Leu Asp Ile Asp Val Asp Ile
        35                  40                  45

Ile Asp Glu Tyr Asp Tyr Ile Asp Val Leu Ala Val Glu Leu Asp Pro
    50                  55                  60

Glu Asp Val Asp Ala Leu Ser Glu Glu Ala Gly Ile Ser Phe Ile Glu
65                  70                  75                  80

Glu Asp Ile Glu Leu Ser Ile Gln Gln Thr Val Pro Trp Gly Ile Thr
                85                  90                  95

Arg Val Gln Ala Pro Ala Val His Asn Arg Gly Ile Thr Gly Ser Gly
            100                 105                 110

Val Arg Val Ala Ile Leu Asp Ser Gly Ile Ser Ala His Ser Asp Leu
        115                 120                 125

Asn Ile Arg Gly Gly Ala Ser Phe Val Pro Gly Glu Pro Thr Thr Ala
    130                 135                 140

Asp Leu Asn Gly His Gly Thr His Val Ala Gly Thr Val Ala Ala Leu
145                 150                 155                 160

Asn Asn Ser Ile Gly Val Ile Gly Val Ala Pro Asn Ala Asp Leu Tyr
                165                 170                 175

Ala Val Lys Val Leu Gly Ala Asn Gly Ser Gly Ser Val Ser Gly Ile
            180                 185                 190

Ala Gln Gly Leu Glu Trp Ala Ala Thr Asn Asn Met His Ile Ala Asn
        195                 200                 205

Met Ser Leu Gly Ser Asp Phe Pro Ser Ser Thr Leu Glu Arg Ala Val
    210                 215                 220

Asn Tyr Ala Thr Ser Arg Asp Val Leu Val Ile Ala Ala Thr Gly Asn
225                 230                 235                 240

Asn Gly Ser Gly Ser Val Gly Tyr Pro Ala Arg Tyr Ala Asn Ala Met
```

-continued

```
                 245                 250                 255
Ala Val Gly Ala Thr Asp Gln Asn Asn Arg Arg Ala Asn Phe Ser Gln
            260                 265                 270

Tyr Gly Thr Gly Ile Asp Ile Val Ala Pro Gly Val Asn Val Gln Ser
        275                 280                 285

Thr Tyr Pro Gly Asn Arg Tyr Val Ser Met Asn Gly Thr Ser Met Ala
    290                 295                 300

Thr Pro His Val Ala Gly Ala Ala Leu Val Lys Gln Arg Tyr Pro
305                 310                 315                 320

Ser Trp Asn Ala Thr Gln Ile Arg Asn His Leu Lys Asn Thr Ala Thr
                325                 330                 335

Asn Leu Gly Asn Ser Ser Gln Phe Gly Ser Gly Leu Val Asn Ala Glu
            340                 345                 350

Ala Ala Thr Arg
        355

<210> SEQ ID NO 15
<211> LENGTH: 269
<212> TYPE: PRT
<213> ORGANISM: B. gibsonii
<220> FEATURE:
<221> NAME/KEY: misc_feature
<222> LOCATION: (1)..(269)
<223> OTHER INFORMATION: The predicted amino acid sequence of the mature
      form of the DSM 9729 subtilisin

<400> SEQUENCE: 15

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Asp Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
```

```
                225                 230                 235                 240
Arg Asn His Leu Lys Asn Thr Ala Thr Asn Leu Gly Asn Ser Ser Gln
                    245                 250                 255
Phe Gly Ser Gly Leu Val Asn Ala Glu Ala Ala Thr Arg
                260                 265

<210> SEQ ID NO 16
<211> LENGTH: 1149
<212> TYPE: DNA
<213> ORGANISM: B. gibsonii
<220> FEATURE:
<221> NAME/KEY: misc_feature
<222> LOCATION: (1)..(1149)
<223> OTHER INFORMATION: The nucleotide sequence encoding the DSM 9730
      subtilisin

<400> SEQUENCE: 16
atgaaaagaa gagtaggaaa gcttgtggtg gggcttgttt gtgtaacagc tctagtaact      60
gtaacagatt ctgcatctgc agcagaagaa aaggtaaaat acttaatagg gtttgaagaa     120
gaagcagaac ttgaagcctt cactgaggaa attgaccaag ttggtgtatt ttctgttgaa     180
gaacaaagtg tagctgagga tacgttagat attgatgtag acattattga tgaatatgat     240
tatattgatg tattagctgt agaattagat cctgaggatg tagatgcgtt aagcgaagaa     300
gcaggtatct catttattga agaagacatt gaactgtcta ttcaacaaac agttccttgg     360
ggcattactc gtgtacaagc tccggctgtt cataaccgag gagtaacagg gtctggtgta     420
agagtagcga ttctagattc aggaatctct acacatagtg atttaacgat ccgcggtgga     480
gctagctttg taccgggtga accaacaacg gctgatttaa atggtcatgg gactcacgtt     540
gcaggaacag tggcagctct taataattca atcggtgtga ttggtgtggc accaagtgct     600
gatctatacg ctgtaaaagt acttggagca atggtagag gaagcgttag tggaattgct     660
caaggtttag agtgggctgc agcgaataac atgcatattg ctaacatgag tctcggtagt     720
gatgcaccta gtactacact tgagcgtgca gtcaactatg cgacaagcca aggtgtacta     780
gttattgcag cgactggtaa caacggttct ggttcagtag ctatcctgc tcgttatgca     840
aacgcaatgg ctgtaggagc gactgaccaa acaacagacg cgcaaacctt ttctcagtac     900
ggtacaggaa ttgacatcgt agcacctgga gttaacgtac aaagtacgta tccaggaaac     960
cgttatgtga gtatgaatgg tacatctatg gccactccac atgtagctgg tgccgctgca    1020
cttgtaaagc aacgctatcc ttcttggaat gcgactcaaa ttcgcaatca tctgaaaaat    1080
acagcaacaa atctaggaaa ctcttcgcaa tttggtagtg gcctagtgaa cgcagaagca    1140
gcaacacgt                                                           1149

<210> SEQ ID NO 17
<211> LENGTH: 383
<212> TYPE: PRT
<213> ORGANISM: B. gibsonii
<220> FEATURE:
<221> NAME/KEY: misc_feature
<222> LOCATION: (1)..(383)
<223> OTHER INFORMATION: The amino acid sequence of the DSM 9730
      preproenzyme

<400> SEQUENCE: 17

Met Lys Arg Arg Val Gly Lys Leu Val Val Gly Leu Val Cys Val Thr
1               5                   10                  15
Ala Leu Val Thr Val Thr Asp Ser Ala Ser Ala Ala Glu Glu Lys Val
                20                  25                  30
```

Lys Tyr Leu Ile Gly Phe Glu Glu Ala Glu Leu Glu Ala Phe Thr
            35                  40                  45

Glu Glu Ile Asp Gln Val Gly Val Phe Ser Val Glu Glu Gln Ser Val
 50                  55                  60

Ala Glu Asp Thr Leu Asp Ile Asp Val Asp Ile Ile Asp Glu Tyr Asp
 65                  70                  75                  80

Tyr Ile Asp Val Leu Ala Val Glu Leu Asp Pro Glu Asp Val Asp Ala
                85                  90                  95

Leu Ser Glu Glu Ala Gly Ile Ser Phe Ile Glu Glu Asp Ile Glu Leu
            100                 105                 110

Ser Ile Gln Gln Thr Val Pro Trp Gly Ile Thr Arg Val Gln Ala Pro
        115                 120                 125

Ala Val His Asn Arg Gly Val Thr Gly Ser Gly Val Arg Val Ala Ile
    130                 135                 140

Leu Asp Ser Gly Ile Ser Thr His Ser Asp Leu Thr Ile Arg Gly Gly
145                 150                 155                 160

Ala Ser Phe Val Pro Gly Glu Pro Thr Thr Ala Asp Leu Asn Gly His
                165                 170                 175

Gly Thr His Val Ala Gly Thr Val Ala Ala Leu Asn Asn Ser Ile Gly
            180                 185                 190

Val Ile Gly Val Ala Pro Ser Ala Asp Leu Tyr Ala Val Lys Val Leu
        195                 200                 205

Gly Ala Asn Gly Arg Gly Ser Val Ser Gly Ile Ala Gln Gly Leu Glu
    210                 215                 220

Trp Ala Ala Ala Asn Asn Met His Ile Ala Asn Met Ser Leu Gly Ser
225                 230                 235                 240

Asp Ala Pro Ser Thr Thr Leu Glu Arg Ala Val Asn Tyr Ala Thr Ser
                245                 250                 255

Gln Gly Val Leu Val Ile Ala Ala Thr Gly Asn Asn Gly Ser Gly Ser
            260                 265                 270

Val Gly Tyr Pro Ala Arg Tyr Ala Asn Ala Met Ala Val Gly Ala Thr
        275                 280                 285

Asp Gln Asn Asn Arg Arg Ala Asn Phe Ser Gln Tyr Gly Thr Gly Ile
    290                 295                 300

Asp Ile Val Ala Pro Gly Val Asn Val Gln Ser Thr Tyr Pro Gly Asn
305                 310                 315                 320

Arg Tyr Val Ser Met Asn Gly Thr Ser Met Ala Thr Pro His Val Ala
                325                 330                 335

Gly Ala Ala Ala Leu Val Lys Gln Arg Tyr Pro Ser Trp Asn Ala Thr
            340                 345                 350

Gln Ile Arg Asn His Leu Lys Asn Thr Ala Thr Asn Leu Gly Asn Ser
        355                 360                 365

Ser Gln Phe Gly Ser Gly Leu Val Asn Ala Glu Ala Ala Thr Arg
    370                 375                 380

<210> SEQ ID NO 18
<211> LENGTH: 356
<212> TYPE: PRT
<213> ORGANISM: B. gibsonii
<220> FEATURE:
<221> NAME/KEY: misc_feature
<222> LOCATION: (1)..(356)
<223> OTHER INFORMATION: The amino acid sequence of the DSM 9730
      proenzyme

<400> SEQUENCE: 18

Ala Glu Glu Lys Val Lys Tyr Leu Ile Gly Phe Glu Glu Ala Glu
1               5                   10                  15

Leu Glu Ala Phe Thr Glu Gly Ile Asp Gln Val Gly Val Phe Ser Val
            20                  25                  30

Glu Glu Gln Ser Val Ala Glu Asp Thr Leu Asp Ile Asp Val Asp Ile
            35                  40                  45

Ile Asp Glu Tyr Asp Tyr Ile Asp Val Leu Ala Val Glu Leu Asp Pro
50                  55                  60

Glu Asp Val Asp Ala Leu Ser Glu Glu Ala Gly Ile Ser Phe Ile Glu
65                  70                  75                  80

Glu Asp Ile Glu Leu Ser Ile Gln Gln Thr Val Pro Trp Gly Ile Thr
                85                  90                  95

Arg Val Gln Ala Pro Ala Val His Asn Arg Gly Val Thr Gly Ser Gly
                100                 105                 110

Val Arg Val Ala Ile Leu Asp Ser Gly Ile Ser Thr His Ser Asp Leu
            115                 120                 125

Thr Ile Arg Gly Gly Ala Ser Phe Val Pro Gly Glu Pro Thr Thr Ala
130                 135                 140

Asp Leu Asn Gly His Gly Thr His Val Ala Gly Thr Val Ala Ala Leu
145                 150                 155                 160

Asn Asn Ser Ile Gly Val Ile Gly Val Ala Pro Ser Ala Asp Leu Tyr
                165                 170                 175

Ala Val Lys Val Leu Gly Ala Asn Gly Arg Gly Ser Val Ser Gly Ile
            180                 185                 190

Ala Gln Gly Leu Glu Trp Ala Ala Asn Asn Met His Ile Ala Asn
        195                 200                 205

Met Ser Leu Gly Ser Asp Ala Pro Ser Thr Thr Leu Glu Arg Ala Val
210                 215                 220

Asn Tyr Ala Thr Ser Gln Gly Val Leu Val Ile Ala Ala Thr Gly Asn
225                 230                 235                 240

Asn Gly Ser Gly Ser Val Gly Tyr Pro Ala Arg Tyr Ala Asn Ala Met
                245                 250                 255

Ala Val Gly Ala Thr Asp Gln Asn Asn Arg Arg Ala Asn Phe Ser Gln
            260                 265                 270

Tyr Gly Thr Gly Ile Asp Ile Val Ala Pro Gly Val Asn Val Gln Ser
            275                 280                 285

Thr Tyr Pro Gly Asn Arg Tyr Val Ser Met Asn Gly Thr Ser Met Ala
290                 295                 300

Thr Pro His Val Ala Gly Ala Ala Ala Leu Val Lys Gln Arg Tyr Pro
305                 310                 315                 320

Ser Trp Asn Ala Thr Gln Ile Arg Asn His Leu Lys Asn Thr Ala Thr
                325                 330                 335

Asn Leu Gly Asn Ser Ser Gln Phe Gly Ser Gly Leu Val Asn Ala Glu
            340                 345                 350

Ala Ala Thr Arg
        355

```
<210> SEQ ID NO 19
<211> LENGTH: 269
<212> TYPE: PRT
<213> ORGANISM: B. gibsonii
<220> FEATURE:
<221> NAME/KEY: misc_feature
<222> LOCATION: (1)..(269)
<223> OTHER INFORMATION: The predicted amino acid sequence of the mature
``` form of the DSM 9730 subtilisin

<400> SEQUENCE: 19

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Thr His Ser Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 20
<211> LENGTH: 1149
<212> TYPE: DNA
<213> ORGANISM: B. gibsonii
<220> FEATURE:
<221> NAME/KEY: misc_feature
<222> LOCATION: (1)..(1149)
<223> OTHER INFORMATION: The nucleotide sequence encoding the DSM 9731
      subtilisin

<400> SEQUENCE: 20
atgaaaagaa gagtaggaaa gcttgtagtg gggcttgttt gtgtaacagc tctagtaact      60
gtaacagatt ctgcatctgc agcagaagaa aaggtaaaat acttaatagg gtttgaagaa     120
gaagcagaac ttgaagcctt cactgaggaa attgaccaag ttggtgtgtt ttctgttgaa     180
gaacaaagtg tagctgagga tacgttagat attgatgtag acattattga tgaatatgat     240
tatattgatg tattagctgt agaattagat cctgaggatg tagatgcgtt aagtgaagaa     300
gcaggtatct catttattga agaagacatt gaactgtcta ttcaacaaac ggttccttgg     360

-continued

```
ggcattactc gtgtacaagc tccagctgtg cataaccgag gagtaacagg gtctggtgta     420
agagtagcga ttctagattc aggaatctct acacatagtg atttaacgat tcgcggtgga     480
gctagctttg taccgggtga accaacaacg gctgatttaa atggtcatgg gactcacgtt     540
gcaggaacag tggcagctct taataattca attggtgtga ttggtgtggc accaagtgct     600
gatctatacg ctgtaaaagt acttggagca atggtagag  gaagcgttag tggaattgct     660
caaggtctag agtgggctgc agcgaataac atgcatattg ctaacatgag tctcggtagt     720
gatgcaccta gtactacact tgagcgtgca gtcaactatg cgacaagcca aggtgtacta     780
gttattgcag cgactggtaa caacggttct ggttcagttg ctatcctgc  tcgttatgca     840 aacgcaatgg ctgtaggagc gactgaccaa acaacagac  gcgcaaactt ttctcaatat     900
ggttcaggaa ttgatatcgt agcaccagga gttaacgtac aaagtacgta tccaggaaac     960
cgttatgtga gtatgaatgg tacatctatg gccactccac acgtagctgg tgccgctgcg    1020
cttgtaaagc aacgctatcc atcttggaat gcgactcaaa ttcgcaatca tctgaaaaat    1080
acagcgacaa atctaggaaa ctcttcgcaa tttggtagtg gcctagtgaa cgcagaagca    1140
gcaacacgt                                                            1149
```

<210> SEQ ID NO 21
<211> LENGTH: 383
<212> TYPE: PRT
<213> ORGANISM: B. gibsonii
<220> FEATURE:
<221> NAME/KEY: misc_feature
<222> LOCATION: (1)..(383)
<223> OTHER INFORMATION: The amino acid sequence of the DSM 9731
      preproenzyme

<400> SEQUENCE: 21

```
Met Lys Arg Arg Val Gly Lys Leu Val Val Gly Leu Val Cys Val Thr
1               5                   10                  15

Ala Leu Val Thr Val Thr Asp Ser Ala Ser Ala Glu Glu Lys Val
            20                  25                  30

Lys Tyr Leu Ile Gly Phe Glu Glu Ala Glu Leu Glu Ala Phe Thr
        35                  40                  45

Glu Glu Ile Asp Gln Val Gly Val Phe Ser Val Glu Glu Gln Ser Val
    50                  55                  60

Ala Glu Asp Thr Leu Asp Ile Asp Val Asp Ile Asp Glu Tyr Asp
65                  70                  75                  80

Tyr Ile Asp Val Leu Ala Val Glu Leu Asp Pro Glu Asp Val Asp Ala
                85                  90                  95

Leu Ser Glu Glu Ala Gly Ile Ser Phe Ile Glu Glu Asp Ile Glu Leu
            100                 105                 110

Ser Ile Gln Gln Thr Val Pro Trp Gly Ile Thr Arg Val Gln Ala Pro
        115                 120                 125

Ala Val His Asn Arg Gly Val Thr Gly Ser Gly Val Arg Val Ala Ile
    130                 135                 140

Leu Asp Ser Gly Ile Ser Thr His Ser Asp Leu Thr Ile Arg Gly Gly
145                 150                 155                 160

Ala Ser Phe Val Pro Gly Glu Pro Thr Thr Ala Asp Leu Asn Gly His
                165                 170                 175

Gly Thr His Val Ala Gly Thr Val Ala Ala Leu Asn Asn Ser Ile Gly
            180                 185                 190

Val Ile Gly Val Ala Pro Ser Ala Asp Leu Tyr Ala Val Lys Val Leu
```

```
                195                 200                 205
Gly Ala Asn Gly Arg Gly Ser Val Ser Gly Ile Ala Gln Gly Leu Glu
            210                 215                 220
Trp Ala Ala Ala Asn Asn Met His Ile Ala Asn Met Ser Leu Gly Ser
225                 230                 235                 240
Asp Ala Pro Ser Thr Thr Leu Glu Arg Ala Val Asn Tyr Ala Thr Ser
                245                 250                 255
Gln Gly Val Leu Val Ile Ala Ala Thr Gly Asn Asn Gly Ser Gly Ser
            260                 265                 270
Val Gly Tyr Pro Ala Arg Tyr Ala Asn Ala Met Ala Val Gly Ala Thr
            275                 280                 285
Asp Gln Asn Asn Arg Arg Ala Asn Phe Ser Gln Tyr Gly Ser Gly Ile
            290                 295                 300
Asp Ile Val Ala Pro Gly Val Asn Val Gln Ser Thr Tyr Pro Gly Asn
305                 310                 315                 320
Arg Tyr Val Ser Met Asn Gly Thr Ser Met Ala Thr Pro His Val Ala
                325                 330                 335
Gly Ala Ala Ala Leu Val Lys Gln Arg Tyr Pro Ser Trp Asn Ala Thr
            340                 345                 350
Gln Ile Arg Asn His Leu Lys Asn Thr Ala Thr Asn Leu Gly Asn Ser
            355                 360                 365
Ser Gln Phe Gly Ser Gly Leu Val Asn Ala Glu Ala Ala Thr Arg
            370                 375                 380

<210> SEQ ID NO 22
<211> LENGTH: 356
<212> TYPE: PRT
<213> ORGANISM: B. gibsonii
<220> FEATURE:
<221> NAME/KEY: misc_feature
<222> LOCATION: (1)..(356)
<223> OTHER INFORMATION: The amino acid sequence of the DSM 9731
      proenzyme

<400> SEQUENCE: 22

Ala Glu Glu Lys Val Lys Tyr Leu Ile Gly Phe Glu Glu Ala Glu
1               5                   10                  15
Leu Glu Ala Phe Thr Glu Glu Ile Asp Gln Val Gly Val Phe Ser Val
            20                  25                  30
Glu Glu Gln Ser Val Ala Glu Asp Thr Leu Asp Ile Asp Val Asp Ile
        35                  40                  45
Ile Asp Glu Tyr Asp Tyr Ile Asp Val Leu Ala Val Glu Leu Asp Pro
    50                  55                  60
Glu Asp Val Asp Ala Leu Ser Glu Glu Ala Gly Ile Ser Phe Ile Glu
65                  70                  75                  80
Glu Asp Ile Glu Leu Ser Ile Gln Gln Thr Val Pro Trp Gly Ile Thr
                85                  90                  95
Arg Val Gln Ala Pro Ala Val His Asn Arg Gly Val Thr Gly Ser Gly
            100                 105                 110
Val Arg Val Ala Ile Leu Asp Ser Gly Ile Ser Thr His Ser Asp Leu
        115                 120                 125
Thr Ile Arg Gly Gly Ala Ser Phe Val Pro Gly Glu Pro Thr Thr Ala
    130                 135                 140
Asp Leu Asn Gly His Gly Thr His Val Ala Gly Thr Val Ala Ala Leu
145                 150                 155                 160
Asn Asn Ser Ile Gly Val Ile Gly Val Ala Pro Ser Ala Asp Leu Tyr
```

```
              165                 170                 175
Ala Val Lys Val Leu Gly Ala Asn Gly Arg Gly Ser Val Ser Gly Ile
            180                 185                 190

Ala Gln Gly Leu Glu Trp Ala Ala Asn Asn Met His Ile Ala Asn
        195                 200                 205

Met Ser Leu Gly Ser Asp Ala Pro Ser Thr Thr Leu Glu Arg Ala Val
    210                 215                 220

Asn Tyr Ala Thr Ser Gln Gly Val Leu Val Ile Ala Ala Thr Gly Asn
225                 230                 235                 240

Asn Gly Ser Gly Ser Val Gly Tyr Pro Ala Arg Tyr Ala Asn Ala Met
                245                 250                 255

Ala Val Gly Ala Thr Asp Gln Asn Asn Arg Arg Ala Asn Phe Ser Gln
            260                 265                 270

Tyr Gly Ser Gly Ile Asp Ile Val Ala Pro Gly Val Asn Val Gln Ser
        275                 280                 285

Thr Tyr Pro Gly Asn Arg Tyr Val Ser Met Asn Gly Thr Ser Met Ala
    290                 295                 300

Thr Pro His Val Ala Gly Ala Ala Leu Val Lys Gln Arg Tyr Pro
305                 310                 315                 320

Ser Trp Asn Ala Thr Gln Ile Arg Asn His Leu Lys Asn Thr Ala Thr
                325                 330                 335

Asn Leu Gly Asn Ser Ser Gln Phe Gly Ser Gly Leu Val Asn Ala Glu
            340                 345                 350

Ala Ala Thr Arg
        355

<210> SEQ ID NO 23
<211> LENGTH: 269
<212> TYPE: PRT
<213> ORGANISM: B. gibsonii
<220> FEATURE:
<221> NAME/KEY: misc_feature
<222> LOCATION: (1)..(269)
<223> OTHER INFORMATION: The predicted amino acid sequence of the mature
      form of the DSM 9731 subtilisin

<400> SEQUENCE: 23

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Thr His Ser Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
```

```
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Ser Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 24
<211> LENGTH: 269
<212> TYPE: PRT
<213> ORGANISM: B. gibsonii
<220> FEATURE:
<221> NAME/KEY: misc_feature
<222> LOCATION: (1)..(269)
<223> OTHER INFORMATION: WO2007131657-CAS91385

<400> SEQUENCE: 24

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Gln His Ser Asp Leu Thr Ile Arg Gly Gly Ala Ser
        35                  40                  45

Phe Ile Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ala Asp Ala
        115                 120                 125

Pro Ser Ser Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Ala Ser Leu Asn Gly Thr Ser Met Ala Thr Pro His Val Ala Gly Ala
    210                 215                 220

Ala Ala Leu Val Lys Gln Arg Asn Pro Ser Trp Asn Ala Thr Gln Ile
225                 230                 235                 240
```

```
Arg Asn His Leu Lys Asn Thr Ala Thr Asn Leu Gly Asn Ser Ser Gln
            245                 250                 255

Phe Gly Ser Gly Leu Val Asn Ala Glu Ala Ala Thr Arg
            260                 265

<210> SEQ ID NO 25
<211> LENGTH: 269
<212> TYPE: PRT
<213> ORGANISM: B. gibsonii
<220> FEATURE:
<221> NAME/KEY: misc_feature
<222> LOCATION: (1)..(269)
<223> OTHER INFORMATION: WO03054184-CAE48421

<400> SEQUENCE: 25

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Thr His Ser Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ile Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Ala Ser Leu Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
            245                 250                 255

Phe Gly Ser Gly Leu Val Asn Ala Glu Ala Ala Thr Arg
            260                 265

<210> SEQ ID NO 26
<211> LENGTH: 269
<212> TYPE: PRT
<213> ORGANISM: B. gibsonii
<220> FEATURE:
<221> NAME/KEY: misc_feature
<222> LOCATION: (1)..(269)
<223> OTHER INFORMATION: WO2008086916-CAV33594
```

<400> SEQUENCE: 26

Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Ile Leu Asp
            20                  25                  30

Ser Gly Ile Ser Gln His Ser Asp Leu Thr Ile Arg Gly Gly Ala Ser
        35                  40                  45

Phe Val Pro Gly Glu Pro Thr Thr Glu Asp Leu Asn Gly His Gly Thr
    50                  55                  60

His Val Ala Gly Thr Val Ala Ala Leu Asn Asn Ser Phe Gly Val Ile
65                  70                  75                  80

Gly Val Ala Pro Ser Ala Asp Leu Tyr Ala Val Lys Val Leu Gly Ala
                85                  90                  95

Gly Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ala Asp Ala
        115                 120                 125

Pro Ser Ser Thr Leu Glu Arg Ala Val Asn Tyr Ala Thr Ser Arg Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Ala Ser Leu Asn Gly Thr Ser Met Ala Thr Pro His Val Ala Gly Val
    210                 215                 220

Ala Ala Leu Val Lys Gln Arg Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Ile Arg
            260                 265

<210> SEQ ID NO 27
<211> LENGTH: 269
<212> TYPE: PRT
<213> ORGANISM: B. gibsonii
<220> FEATURE:
<221> NAME/KEY: misc_feature
<222> LOCATION: (1)..(269)
<223> OTHER INFORMATION: WO03054185-CAE48424

<400> SEQUENCE: 27

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30

Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile

```
                65                  70                  75                  80
Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265

<210> SEQ ID NO 28
<211> LENGTH: 269
<212> TYPE: PRT
<213> ORGANISM: Bacillus sp. strain EP655
<220> FEATURE:
<221> NAME/KEY: misc_feature
<222> LOCATION: (1)..(269)
<223> OTHER INFORMATION: US7642080-0004

<400> SEQUENCE: 28

Gln Gln Ser Val Pro Trp Gly Ile Thr Arg Val Gln Ala Pro Ala Ala
1               5                   10                  15

Ile Asn Arg Gly Thr Asn Gly Ser Gly Val Arg Ala Ala Val Leu Asp
            20                  25                  30

Thr Gly Ile Ser Thr His Ser Asp Leu Thr Ile Arg Gly Gly Ala Ser
        35                  40                  45

Phe Val Pro Gly Glu Pro Asn Thr Ser Asp Leu Asn Gly His Gly Thr
    50                  55                  60

His Val Ala Gly Thr Ile Ala Ala Leu Asn Asn Ser Ile Gly Val Val
65                  70                  75                  80

Gly Val Ala Pro Asn Ala Asp Leu Tyr Ala Val Lys Val Leu Gly Ala
                85                  90                  95

Asn Gly Arg Gly Ser Ile Gly Gly Ile Ala Gln Gly Leu Glu Trp Ala
            100                 105                 110

Ala Ala Asn Asn Met His Ile Ala Asn Leu Ser Leu Gly Ser Asp Ala
        115                 120                 125

Pro Ser Ser Thr Leu Glu Gln Ala Val Asn Tyr Ala Thr Ser Arg Gly
    130                 135                 140

Val Leu Val Ile Ala Ala Ser Gly Asn Asn Gly Ser Gly Asn Val Gly
145                 150                 155                 160
```

```
Tyr Pro Ala Arg Tyr Ala Asn Ala Met Ala Val Gly Ala Thr Asp Gln
            165                 170                 175

Asn Asn Asn Arg Ala Asn Phe Ser Gln Tyr Gly Ala Gly Leu Asp Ile
            180                 185                 190

Val Ala Pro Gly Val Gly Ile Gln Ser Thr Tyr Pro Gly Asn Arg Tyr
            195                 200                 205

Ala Ser Leu Asn Gly Thr Ser Met Ala Thr Pro His Val Ala Gly Ala
            210                 215                 220

Ala Ala Leu Val Lys Gln Arg Tyr Pro Ser Trp Ser Ala Ser Gln Ile
225                 230                 235                 240

Arg Asn His Leu Lys Asn Thr Ser Thr Asn Leu Gly Ser Ser Thr Leu
            245                 250                 255

Tyr Gly Ser Gly Leu Val Asn Ala Asp Ala Ala Ser Arg
            260                 265
```

<210> SEQ ID NO 29
<211> LENGTH: 269
<212> TYPE: PRT
<213> ORGANISM: Bacillus sp. strain p203
<220> FEATURE:
<221> NAME/KEY: misc_feature
<222> LOCATION: (1)..(269)
<223> OTHER INFORMATION: US7642080-0006

<400> SEQUENCE: 29

```
Gln Gln Ser Val Pro Trp Gly Ile Thr Arg Val Gln Ala Pro Ala Ala
1               5                   10                  15

Ile Asn Arg Gly Thr Asn Gly Ser Gly Val Arg Val Ala Val Leu Asp
            20                  25                  30

Thr Gly Ile Ser Thr His Ser Asp Leu Thr Ile Arg Gly Gly Ala Ser
            35                  40                  45

Phe Val Pro Gly Glu Pro Asn Thr Ser Asp Leu Asn Gly His Gly Thr
        50                  55                  60

His Val Ala Gly Thr Ile Ala Ala Leu Asn Asn Ser Ile Gly Val Val
65                  70                  75                  80

Gly Val Ala Pro Asn Ala Asp Leu Tyr Ala Val Lys Val Leu Gly Ala
                85                  90                  95

Asn Gly Arg Gly Ser Ile Gly Gly Ile Ala Gln Gly Leu Gly Trp Ala
            100                 105                 110

Ala Ala Asn Asn Met His Ile Ala Asn Leu Ser Leu Gly Ser Asp Ala
            115                 120                 125

Pro Ser Ser Thr Leu Glu Gln Ala Val Asn Tyr Ala Thr Ser Arg Gly
            130                 135                 140

Val Leu Val Ile Ala Ala Ser Gly Asn Gly Ser Gly Asn Val Gly
145                 150                 155                 160

Tyr Pro Ala Arg Tyr Ala Asn Ala Met Ala Val Gly Ala Thr Asp Gln
            165                 170                 175

Asn Asn Asn Arg Ala Asn Phe Ser Gln Tyr Gly Ala Gly Leu Asp Ile
            180                 185                 190

Val Ala Pro Gly Val Gly Ile Gln Ser Thr Tyr Pro Gly Asn Arg Tyr
            195                 200                 205

Ala Ser Leu Asn Gly Thr Ser Met Ala Thr Pro His Val Ala Gly Ala
            210                 215                 220

Ala Ala Leu Val Lys Gln Arg Tyr Pro Ser Trp Ser Ala Ser Gln Ile
225                 230                 235                 240
```

-continued

Arg Asn His Leu Lys Asn Thr Ser Thr Asn Leu Gly Ser Ser Thr Leu
                245                 250                 255

Tyr Gly Ser Gly Leu Val Asn Ala Asp Ala Ala Ser Arg
            260                 265

<210> SEQ ID NO 30
<211> LENGTH: 269
<212> TYPE: PRT
<213> ORGANISM: Bacillus sp. strain Zi344
<220> FEATURE:
<221> NAME/KEY: misc_feature
<222> LOCATION: (1)..(269)
<223> OTHER INFORMATION: US7642080-0002

<400> SEQUENCE: 30

Gln Gln Thr Val Pro Trp Gly Ile Gln Arg Val Gln Ala Pro Ala Val
1               5                  10                  15

Ile Asn Arg Gly Ile Asn Gly Ser Gly Val Arg Val Ala Val Leu Asp
                20                  25                  30

Ser Gly Ile Ser Ser His Ser Asp Leu Ser Ile Ser Gly Gly Val Ser
            35                  40                  45

Phe Val Pro Gly Glu Pro Thr Ile Ala Asp Gly Asn Gly His Gly Thr
        50                  55                  60

His Val Ala Gly Thr Ile Ala Ala Leu Asn Asn Ser Ile Gly Val Val
65                  70                  75                  80

Gly Val Ala Pro Asn Ala Gln Ile Tyr Gly Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met Asp Ile Ala Asn Leu Ser Leu Gly Ser Asp Ala
        115                 120                 125

Pro Ser Ser Thr Leu Glu Gln Ala Val Asn Phe Ala Thr Ser Arg Gly
130                 135                 140

Val Leu Val Val Ala Ala Ser Gly Asn Asn Gly Ser Gly Asn Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Ala Gly Leu Asp Ile
            180                 185                 190

Val Ala Pro Gly Val Gly Val Gln Ser Thr Tyr Pro Gly Asn Arg Tyr
        195                 200                 205

Val Ser Met Asn Gly Thr Ser Met Ala Ser Pro His Val Ala Gly Ala
210                 215                 220

Ala Ala Leu Val Lys Gln Arg Tyr Pro Ser Trp Ser Asn Thr Gln Ile
225                 230                 235                 240

Arg Asn His Leu Lys Asn Thr Ala Thr Asn Leu Gly Asn Thr Asn Gln
                245                 250                 255

Phe Gly Ser Gly Leu Val Asn Ala Asp Ala Ala Thr Arg
            260                 265

<210> SEQ ID NO 31
<211> LENGTH: 269
<212> TYPE: PRT
<213> ORGANISM: B. lentus
<220> FEATURE:
<221> NAME/KEY: misc_feature
<222> LOCATION: (1)..(269)
<223> OTHER INFORMATION: B_lentus_P29600

<400> SEQUENCE: 31

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 32
<211> LENGTH: 269
<212> TYPE: PRT
<213> ORGANISM: Bacillus sp. G-825-6
<220> FEATURE:
<221> NAME/KEY: misc_feature
<222> LOCATION: (1)..(269)
<223> OTHER INFORMATION: B_sp_Sendai_BAA06157

<400> SEQUENCE: 32

Asn Gln Val Thr Pro Trp Gly Ile Thr Arg Val Gln Ala Pro Thr Ala
1               5                   10                  15

Trp Thr Arg Gly Tyr Thr Gly Thr Gly Val Arg Val Ala Val Leu Asp
            20                  25                  30

Thr Gly Ile Ser Thr His Pro Asp Leu Asn Ile Arg Gly Gly Val Ser
        35                  40                  45

Phe Val Pro Gly Glu Pro Ser Tyr Gln Asp Gly Asn Gly His Gly Thr
50                  55                  60

His Val Ala Gly Thr Ile Ala Ala Leu Asn Asn Ser Ile Gly Val Val
65                  70                  75                  80

Gly Val Ala Pro Asn Ala Glu Leu Tyr Ala Val Lys Val Leu Gly Ala
                85                  90                  95

Asn Gly Ser Gly Ser Val Ser Ser Ile Ala Gln Gly Leu Gln Trp Thr
            100                 105                 110

Ala Gln Asn Asn Ile His Val Ala Asn Leu Ser Leu Gly Ser Pro Val
        115                 120                 125

Gly Ser Gln Thr Leu Glu Leu Ala Val Asn Gln Ala Thr Asn Ala Gly
    130                 135                 140

Val Leu Val Val Ala Ala Thr Gly Asn Asn Gly Ser Gly Thr Val Ser
145                 150                 155                 160

Tyr Pro Ala Arg Tyr Ala Asn Ala Leu Ala Val Gly Ala Thr Asp Gln
                165                 170                 175

Asn Asn Asn Arg Ala Ser Phe Ser Gln Tyr Gly Thr Gly Leu Asn Ile
            180                 185                 190

Val Ala Pro Gly Val Gly Ile Gln Ser Thr Tyr Pro Gly Asn Arg Tyr
        195                 200                 205

Ala Ser Leu Ser Gly Thr Ser Met Ala Thr Pro His Val Ala Gly Val
    210                 215                 220

Ala Ala Leu Val Lys Gln Lys Asn Pro Ser Trp Ser Asn Thr Gln Ile
225                 230                 235                 240

Arg Gln His Leu Thr Ser Thr Ala Thr Ser Leu Gly Asn Ser Asn Gln
                245                 250                 255

Phe Gly Ser Gly Leu Val Asn Ala Glu Ala Ala Thr Arg
            260                 265

<210> SEQ ID NO 33
<211> LENGTH: 269
<212> TYPE: PRT
<213> ORGANISM: Bacillus sp. G-825-6
<220> FEATURE:
<221> NAME/KEY: misc_feature
<222> LOCATION: (1)..(269)
<223> OTHER INFORMATION: Bacillus_sp_BAA05540

<400> SEQUENCE: 33

Ser Gln Thr Val Pro Trp Gly Ile Ser Phe Ile Asn Thr Gln Gln Ala
1               5                   10                  15

His Asn Arg Gly Ile Phe Gly Asn Gly Ala Arg Val Ala Val Leu Asp
            20                  25                  30

Thr Gly Ile Ala Ser His Pro Asp Leu Arg Ile Ala Gly Gly Ala Ser
        35                  40                  45

Phe Ile Ser Ser Glu Pro Ser Tyr His Asp Asn Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Asp Leu Tyr Ala Val Lys Val Leu Asp Arg
                85                  90                  95

Asn Gly Ser Gly Ser Leu Ala Ser Val Ala Gln Gly Ile Glu Trp Ala
            100                 105                 110

Ile Asn Asn Asn Met His Ile Ile Asn Met Ser Leu Gly Ser Thr Ser
        115                 120                 125

Gly Ser Ser Thr Leu Glu Leu Ala Val Asn Arg Ala Asn Asn Ala Gly
    130                 135                 140

Ile Leu Leu Val Gly Ala Ala Gly Asn Thr Gly Arg Gln Gly Val Asn
145                 150                 155                 160

Tyr Pro Ala Arg Tyr Ser Gly Val Met Ala Val Ala Val Asp Gln
                165                 170                 175

Asn Gly Gln Arg Ala Ser Phe Ser Thr Tyr Gly Pro Glu Ile Glu Ile
            180                 185                 190

Ser Ala Pro Gly Val Asn Val Asn Ser Thr Tyr Thr Gly Asn Arg Tyr
        195                 200                 205

Val Ser Leu Ser Gly Thr Ser Met Ala Thr Pro His Val Ala Gly Val
    210                 215                 220

Ala Ala Leu Val Lys Ser Arg Tyr Pro Ser Tyr Thr Asn Asn Gln Ile
225                 230                 235                 240

Arg Gln Arg Ile Asn Gln Thr Ala Thr Tyr Leu Gly Ser Pro Ser Leu
                245                 250                 255

Tyr Gly Asn Gly Leu Val His Ala Gly Arg Ala Thr Gln
            260                 265

<210> SEQ ID NO 34
<211> LENGTH: 275
<212> TYPE: PRT
<213> ORGANISM: B. amyloliquefaciens
<220> FEATURE:
<221> NAME/KEY: misc_feature
<222> LOCATION: (1)..(275)
<223> OTHER INFORMATION: B_amyloliquefaciens_CAA24990

<400> SEQUENCE: 34

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys

-continued

```
                    245                 250                 255
Leu Gly Asp Ser Phe Tyr Tyr Gly Lys Gly Leu Ile Asn Val Gln Ala
            260                 265                 270
Ala Ala Gln
        275

<210> SEQ ID NO 35
<211> LENGTH: 275
<212> TYPE: PRT
<213> ORGANISM: G. stearothermophilus
<220> FEATURE:
<221> NAME/KEY: misc_feature
<222> LOCATION: (1)..(275)
<223> OTHER INFORMATION: G_stearothermophilus_ABY25856

<400> SEQUENCE: 35

Ala Gln Ser Val Pro Tyr Gly Val Ser Gln Ile Lys Ala Pro Ala Leu
1               5                   10                  15

His Ser Gln Gly Phe Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Tyr Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Ile Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asn Ser Ser Asn Gln Arg Ala Ser Phe Ser Ser Val
            180                 185                 190

Gly Ser Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ala Phe Tyr Tyr Gly Lys Gly Leu Ile Asn Val Gln Ala
            260                 265                 270

Ala Ala Gln
        275

<210> SEQ ID NO 36
<211> LENGTH: 275
<212> TYPE: PRT
<213> ORGANISM: B. atrophaeus
```

```
<220> FEATURE:
<221> NAME/KEY: misc_feature
<222> LOCATION: (1)..(275)
<223> OTHER INFORMATION: B_atrophaeus_YP003972439

<400> SEQUENCE: 36

Ala Gln Ser Val Pro Tyr Gly Ile Ser Gln Ile Lys Ala Pro Ala Val
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ser Gly Gly Ala
        35                  40                  45

Ser Phe Val Pro Ser Glu Pro Asn Pro Phe Gln Asp Gly Asn Ser His
    50                  55                  60

Gly Thr His Val Ala Gly Thr Val Ala Ala Leu Asn Asn Ser Val Gly
65                  70                  75                  80

Val Leu Gly Val Ala Pro Ser Ala Ser Leu Tyr Ala Val Lys Val Leu
                85                  90                  95

Ser Ser Ser Gly Ser Gly Asp Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Gln Gly Ser Thr Ala Leu Lys Ala Val Val Asp Lys Ala Val Ser
    130                 135                 140

Gln Gly Ile Val Val Ala Ala Ala Gly Asn Ser Gly Ser Ser Gly
145                 150                 155                 160

Ser Thr Ser Thr Val Gly Tyr Pro Ala Lys Tyr Pro Ser Val Ile Ala
                165                 170                 175

Val Gly Ala Val Asp Ser Asn Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Ser Ser Tyr Gly Ser Tyr Asn Gly Thr Ser Met Ala Ser
    210                 215                 220

Pro His Val Ala Gly Ala Ala Ala Leu Val Leu Ser Lys His Pro Asn
225                 230                 235                 240

Trp Thr Asn Ser Gln Val Arg Asn Ser Leu Glu Ser Thr Ala Thr Asn
                245                 250                 255

Leu Gly Asn Ser Phe Tyr Tyr Gly Lys Gly Leu Ile Asn Val Gln Ala
            260                 265                 270

Ala Ala Gln
        275

<210> SEQ ID NO 37
<211> LENGTH: 275
<212> TYPE: PRT
<213> ORGANISM: B. subtilis
<220> FEATURE:
<221> NAME/KEY: misc_feature
<222> LOCATION: (1)..(275)
<223> OTHER INFORMATION: B_subtilis_BAN09118

<400> SEQUENCE: 37

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30
```

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
 50                  55                  60

Gly Thr His Val Ala Gly Thr Val Ala Ala Leu Asn Asn Thr Ile Gly
 65                  70                  75                  80

Val Leu Gly Val Ala Pro Ser Ala Ser Leu Tyr Ala Val Lys Val Leu
                 85                  90                  95

Asp Ser Thr Gly Ser Gly Gln Tyr Ser Trp Ile Ile Asn Gly Ile Glu
                100                 105                 110

Trp Ala Ile Ser Asn Asn Met Asp Val Ile Asn Met Ser Leu Gly Gly
            115                 120                 125

Pro Thr Gly Ser Thr Ala Leu Lys Thr Val Val Asp Lys Ala Val Ala
        130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
                180                 185                 190

Gly Ser Glu Leu Asp Val Met Ala Pro Gly Val Ser Ile Gln Ser Thr
            195                 200                 205

Leu Pro Gly Gly Thr Tyr Gly Ser Tyr Asn Gly Thr Ser Met Ala Thr
        210                 215                 220

Pro His Val Ala Gly Ala Ala Leu Ile Leu Ser Lys His Pro Thr
225                 230                 235                 240

Trp Ser Asn Ala Gln Val Arg Asp Arg Leu Glu Ser Thr Ala Thr Asn
                245                 250                 255

Leu Gly Ser Ser Phe Tyr Tyr Gly Lys Gly Leu Ile Asn Val Gln Ala
            260                 265                 270

Ala Ala Gln
        275

<210> SEQ ID NO 38
<211> LENGTH: 275
<212> TYPE: PRT
<213> ORGANISM: B. circulans
<220> FEATURE:
<221> NAME/KEY: misc_feature
<222> LOCATION: (1)..(275)
<223> OTHER INFORMATION: B_circulans_ADN04910

<400> SEQUENCE: 38

Ala Gln Thr Val Pro Tyr Gly Ile Pro Gln Ile Lys Ala Pro Ala Val
1               5                  10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
            35                  40                  45

Ser Phe Val Pro Ser Glu Pro Asn Ala Thr Gln Asp Phe Gln Ser His
 50                  55                  60

Gly Thr His Val Ala Gly Thr Ile Ala Ala Leu Asp Asn Thr Ile Gly
 65                  70                  75                  80

Val Leu Gly Val Ala Pro Ser Ala Ser Leu Tyr Ala Val Lys Val Leu
                 85                  90                  95

Asp Arg Asn Gly Asp Gly Gln Tyr Ser Trp Ile Ile Ser Gly Ile Glu

```
            100                 105                 110
Trp Ala Val Ala Asn Asn Met Asp Val Ile Asn Met Ser Leu Gly Gly
            115                 120                 125

Pro Asn Gly Ser Thr Ala Leu Lys Asn Ala Val Asp Thr Ala Asn Asn
        130                 135                 140

Arg Gly Val Val Val Ala Ala Ala Gly Asn Ser Gly Ser Thr Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Ser Asn Val Arg Asn Ser Ser Ser Ala
            180                 185                 190

Gly Pro Glu Leu Asp Val Ser Ala Pro Gly Thr Ser Ile Leu Ser Thr
        195                 200                 205

Val Pro Ser Arg Gly Tyr Thr Ser Tyr Thr Gly Thr Ser Met Ala Ser
210                 215                 220

Pro His Val Ala Gly Ala Ala Ala Leu Ile Leu Ser Lys Asn Pro Asn
225                 230                 235                 240

Leu Ser Asn Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Val Gln Ala
                260                 265                 270

Ala Ser Asn
        275
```

<210> SEQ ID NO 39
<211> LENGTH: 275
<212> TYPE: PRT
<213> ORGANISM: B. stratosphericus
<220> FEATURE:
<221> NAME/KEY: misc_feature
<222> LOCATION: (1)..(275)
<223> OTHER INFORMATION: B

```
Val Ala Asn Val Asn Ser Asn Val Arg Asn Ser Ser Ser Ala
            180                 185                 190

Gly Pro Glu Leu Asp Val Ser Ala Pro Gly Thr Ser Ile Leu Ser Thr
            195                 200                 205

Val Pro Ser Ser Gly Tyr Thr Ser Tyr Thr Gly Thr Ser Met Ala Ser
210                 215                 220

Pro His Val Ala Gly Ala Ala Ala Leu Ile Leu Ser Lys Tyr Pro Asn
225                 230                 235                 240

Leu Ser Thr Ser Gln Val Arg Gln Arg Leu Glu Asn Thr Ala Thr Pro
                245                 250                 255

Leu Gly Asn Ser Phe Tyr Tyr Gly Lys Gly Leu Ile Asn Val Gln Ala
                260                 265                 270

Ala Ser Asn
        275

<210> SEQ ID NO 40
<211> LENGTH: 274
<212> TYPE: PRT
<213> ORGANISM: B. licheniformis
<220> FEATURE:
<221> NAME/KEY: misc_feature
<222> LOCATION: (1)..(274)
<223> OTHER INFORMATION: B_licheniformis_CAJ70731.1

<400> SEQUENCE: 40

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
            35                  40                  45

Ser Phe Val Ala Gly Glu Ala Tyr Asn Thr Asp Gly Asn Gly His Gly
        50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
            115                 120                 125

Ser Gly Ser Thr Ala Met Lys Gln Ala Val Asp Asn Ala Tyr Ala Arg
        130                 135                 140

Gly Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
            195                 200                 205

Pro Thr Asn Thr Tyr Ala Thr Leu Asn Gly Thr Ser Met Ala Ser Pro
210                 215                 220

His Val Ala Gly Ala Ala Ala Leu Ile Leu Ser Lys His Pro Asn Leu
225                 230                 235                 240
```

-continued

Ser Ala Ser Gln Val Arg Asn Arg Leu Ser Ser Thr Ala Thr Tyr Leu
              245                 250                 255

Gly Ser Ser Phe Tyr Tyr Gly Lys Gly Leu Ile Asn Val Glu Ala Ala
            260                 265                 270

Ala Gln

<210> SEQ ID NO 41
<211> LENGTH: 275
<212> TYPE: PRT
<213> ORGANISM: B. pumilus
<220> FEATURE:
<221> NAME/KEY: misc_feature
<222> LOCATION: (1)..(275)
<223> OTHER INFORMATION: B_pumilus_ADK11996

<400> SEQUENCE: 41

Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Ala Ser Gly Ser Thr Ala Leu Lys Asn Ala Val Asp Thr Ala Asn Asn
    130                 135                 140

Arg Gly Val Val Val Ala Ala Gly Asn Ser Gly Ser Ser Gly
145                 150                 155                 160

Ser Arg Ser Thr Val Gly Tyr Pro Ala Lys Tyr Glu Ser Thr Ile Ala
                165                 170                 175

Val Ala Asn Val Asn Ser Asn Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Thr Ser Tyr Thr Gly Thr Ser Met Ala Ser
    210                 215                 220

Pro His Val Ala Gly Ala Ala Leu Ile Leu Ser Lys Asn Pro Asn
225                 230                 235                 240

Leu Thr Asn Ser Gln Val Arg Gln Arg Leu Glu Asn Thr Ala Thr Pro
                245                 250                 255

Leu Gly Asp Ser Phe Tyr Tyr Gly Lys Gly Leu Ile Asn Val Gln Ala
            260                 265                 270

Ala Ser Asn
        275

<210> SEQ ID NO 42
<211> LENGTH: 276
<212> TYPE: PRT
<213> ORGANISM: Bacillus sp.

<220> FEATURE:
<221> NAME/KEY: misc_feature
<222> LOCATION: (1)..(276)
<223> OTHER INFORMATION: B_sp_sprD_AAC43581

<400> SEQUENCE: 42

```
Ala Gln Thr Val Pro Tyr Gly Val Pro His Ile Lys Ala Asp Val Ala
1               5                   10                  15

His Ala Gln Asn Val Thr Gly Ser Gly Val Lys Val Ala Val Leu Asp
            20                  25                  30

Thr Gly Ile Asp Ala Ser His Glu Asp Leu Arg Val Gly Gly Ala
        35                  40                  45

Ser Phe Val Ser Glu Glu Pro Asp Ala Leu Thr Asp Gly Asn Gly His
50                  55                  60

Gly Thr His Val Ala Gly Thr Ile Ala Ala Leu Asn Asn Val Gly
65                  70                  75                  80

Val Leu Gly Val Ser Tyr Asp Val Asp Leu Tyr Ala Val Lys Val Leu
                85                  90                  95

Ser Ala Gly Gly Ser Gly Thr Leu Ala Gly Ile Ala Gln Gly Ile Glu
            100                 105                 110

Trp Ala Ile Asp Asn Asn Met Asp Val Ile Asn Met Ser Leu Gly Gly
        115                 120                 125

Ser Thr Gly Ser Thr Thr Leu Lys Gln Ala Ser Asp Asn Ala Tyr Asn
130                 135                 140

Ser Gly Ile Val Val Ile Ala Ala Gly Asn Ser Gly Ser Val Leu
145                 150                 155                 160

Gly Leu Val Asn Thr Ile Gly Tyr Pro Ala Arg Tyr Asp Ser Val Ile
                165                 170                 175

Ala Val Gly Ala Val Asp Ser Asn Asn Asn Arg Ala Ser Phe Ser Ser
            180                 185                 190

Val Gly Ser Gln Leu Glu Val Met Ala Pro Gly Val Ala Ile Asn Ser
        195                 200                 205

Thr Leu Pro Gly Asn Gln Tyr Gly Glu Leu Asn Gly Thr Ser Met Ala
210                 215                 220

Ser Pro His Val Ala Gly Ala Ala Ala Leu Leu Leu Ala Gln Asn Pro
225                 230                 235                 240

Asn Leu Thr Asn Val Gln Val Arg Glu Arg Leu Arg Asp Thr Ala Thr
                245                 250                 255

Asn Leu Gly Ser Ala Phe Asn Tyr Gly His Gly Val Ile Asn Leu Glu
            260                 265                 270

Arg Ala Leu Gln
        275
```

<210> SEQ ID NO 43
<211> LENGTH: 275
<212> TYPE: PRT
<213> ORGANISM: Bacillus sp.
<220> FEATURE:
<221> NAME/KEY: misc_feature
<222> LOCATION: (1)..(275)
<223> OTHER INFORMATION: Bacillus_sp_LG12sprC_AAC43580

<400> SEQUENCE: 43

```
Ala Gln Thr Val Pro Trp Gly Ile Pro His Ile Lys Ala Asp Lys Ala
1               5                   10                  15

His Ala Ala Gly Val Thr Gly Ser Gly Val Lys Val Ala Ile Leu Asp
            20                  25                  30
```

```
Thr Gly Ile Asp Ala Asn His Ala Asp Leu Asn Val Lys Gly Gly Ala
         35                  40                  45

Ser Phe Val Ser Gly Glu Pro Asn Ala Leu Gln Asp Gly Asn Gly His
 50                  55                  60

Gly Thr His Val Ala Gly Thr Val Ala Ala Leu Asn Asn Thr Val Gly
 65                  70                  75                  80

Val Leu Gly Val Ala Tyr Asn Ala Asp Leu Tyr Ala Val Lys Val Leu
                 85                  90                  95

Ser Ala Ser Gly Ser Gly Thr Leu Ser Gly Ile Ala Gln Gly Ile Glu
            100                 105                 110

Trp Ser Ile Ser Asn Gly Met Asn Val Ile Asn Met Ser Leu Gly Gly
            115                 120                 125

Ser Ser Gly Ser Thr Ala Leu Gln Gln Ala Cys Asn Asn Ala Tyr Asn
130                 135                 140

Arg Gly Ile Val Val Ile Ala Ala Ala Gly Asn Ser Gly Ser Ser Gly
145                 150                 155                 160

Asn Arg Asn Thr Met Gly Tyr Pro Ala Arg Tyr Ser Ser Val Ile Ala
                165                 170                 175

Val Gly Ala Val Ser Ser Asn Asn Thr Arg Ala Ser Phe Ser Ser Val
            180                 185                 190

Gly Ser Glu Leu Glu Val Met Ala Pro Gly Val Asn Ile Leu Ser Thr
        195                 200                 205

Thr Pro Gly Asn Asn Tyr Ala Ser Phe Asn Gly Thr Ser Met Ala Ala
210                 215                 220

Pro His Val Ala Gly Ala Ala Leu Ile Lys Ala Lys Tyr Pro Ser
225                 230                 235                 240

Met Thr Asn Val Gln Ile Arg Glu Arg Leu Lys Asn Thr Ala Thr Asn
                245                 250                 255

Leu Gly Asp Pro Phe Phe Tyr Gly Lys Gly Val Ile Asn Val Glu Ser
                260                 265                 270

Ala Leu Gln
        275

<210> SEQ ID NO 44
<211> LENGTH: 275
<212> TYPE: PRT
<213> ORGANISM: Bacillus sp.
<220> FEATURE:
<221> NAME/KEY: misc_feature
<222> LOCATION: (1)..(275)
<223> OTHER INFORMATION: Bacillus_sp_BAD11988

<400> SEQUENCE: 44

Ala Gln Thr Thr Pro Trp Gly Val Thr His Ile Asn Ala His Arg Ala
 1               5                  10                  15

His Ser Ser Gly Val Thr Gly Ser Gly Val Lys Val Ala Ile Leu Asp
                20                  25                  30

Thr Gly Ile His Ala Ser His Pro Asp Leu Asn Val Arg Gly Gly Ala
         35                  40                  45

Ser Phe Ile Ser Gly Glu Ser Asn Pro Tyr Ile Asp Ser Asn Gly His
 50                  55                  60

Gly Thr His Val Ala Gly Thr Val Ala Ala Leu Asn Asn Thr Val Gly
 65                  70                  75                  80

Val Leu Gly Val Ala Tyr Asn Ala Glu Leu Tyr Ala Val Lys Val Leu
                 85                  90                  95

Ser Ala Ser Gly Ser Gly Thr Leu Ser Gly Ile Ala Gln Gly Val Glu
```

```
                100                 105                 110
Trp Ser Ile Ala Asn Lys Met Asp Val Ile Asn Met Ser Leu Gly Gly
        115                 120                 125

Ser Ser Gly Ser Thr Ala Leu Gln Arg Ala Val Asp Asn Ala Tyr Arg
130                 135                 140

Asn Asn Ile Val Val Ala Ala Ala Gly Asn Ser Gly Ala Gln Gly
145                 150                 155                 160

Asn Arg Asn Thr Ile Gly Tyr Pro Ala Arg Tyr Ser Ser Val Ile Ala
                165                 170                 175

Val Gly Ala Val Asp Ser Asn Asn Arg Ala Ser Phe Ser Ser Val
        180                 185                 190

Gly Ser Glu Leu Glu Val Met Ala Pro Gly Val Ser Ile Leu Ser Thr
        195                 200                 205

Val Pro Gly Ser Ser Tyr Ala Ser Tyr Asn Gly Thr Ser Met Ala Ser
210                 215                 220

Pro His Val Ala Gly Ala Ala Ala Leu Leu Lys Ala Lys Tyr Pro Asn
225                 230                 235                 240

Trp Ser Ala Ala Gln Ile Arg Asn Lys Leu Asn Ser Thr Thr Thr Tyr
                245                 250                 255

Leu Gly Ser Ser Phe Tyr Tyr Gly Asn Gly Val Ile Asn Val Glu Arg
                260                 265                 270

Ala Leu Gln
        275

<210> SEQ ID NO 45
<211> LENGTH: 222
<212> TYPE: PRT
<213> ORGANISM: Artificial Sequence
<220> FEATURE:
<223> OTHER INFORMATION: Synthetic: Consensus sequence

<400> SEQUENCE: 45

Ala Gln Thr Val Pro Trp Gly Ile Ile Ala Pro Ala Val His Arg Gly
1               5                   10                  15

Thr Gly Ser Gly Val Lys Val Ala Val Leu Asp Thr Gly Ile His Pro
                20                  25                  30

Asp Leu Arg Gly Gly Ala Ser Phe Val Pro Gly Glu Pro Thr Asp Asn
            35                  40                  45

Gly His Gly Thr His Val Ala Gly Thr Val Ala Ala Leu Asn Asn Ser
        50                  55                  60

Ile Gly Val Leu Gly Val Ala Pro Ser Ala Leu Tyr Ala Val Lys Val
65                  70                  75                  80

Leu Gly Ala Asn Gly Ser Gly Ser Ser Gly Ile Ala Gln Gly Ile Glu
                85                  90                  95

Trp Ala Ala Asn Asn Met Asp Val Ile Asn Met Ser Leu Gly Gly Gly
                100                 105                 110

Ser Thr Leu Glu Ala Val Asn Ala Arg Gly Val Val Ala Ala Ala
        115                 120                 125

Gly Asn Gly Ser Gly Thr Val Gly Tyr Pro Ala Arg Tyr Ser Ile Ala
130                 135                 140

Val Gly Ala Val Asp Asn Asn Arg Ala Ser Phe Ser Ser Tyr Gly Glu
145                 150                 155                 160

Leu Asp Ala Pro Gly Val Ile Gln Ser Thr Tyr Pro Gly Asn Tyr Ala
                165                 170                 175

Ser Asn Gly Thr Ser Met Ala Thr Pro His Val Ala Gly Ala Ala Ala
```

```
                    180                 185                 190
Leu Val Lys Lys Pro Ser Trp Asn Gln Ile Arg Asn Leu Asn Thr Ala
            195                 200                 205

Thr Asn Leu Gly Ser Phe Tyr Gly Gly Leu Asn Ala Ala Ala
        210                 215                 220
```

<210> SEQ ID NO 46

<400> SEQUENCE: 46

000

<210> SEQ ID NO 47
<211> LENGTH: 34
<212> TYPE: PRT
<213> ORGANISM: Artificial Sequence
<220> FEATURE:
<223> OTHER INFORMATION: Synthetic: B. gibsonii-clade subtilisin motif
<220> FEATURE:
<221> NAME/KEY: misc_feature
<222> LOCATION: (2)..(2)
<223> OTHER INFORMATION: Xaa can Asn Arg Gly Val Thr Gly Ser Gly Val Arg Val Ala Ile Leu Asp Ser
            20                  25                  30

Gly Ile Ser Thr His Ser Asp Leu Thr Ile Arg Gly Gly Ala Ser Phe
        35                  40                  45

Val Pro Gly Glu Pro Thr Thr Ala Asp Leu Asn Gly His Gly Thr His
 50                  55                  60

Val Ala Gly Thr Val Ala Ala Leu Asn Asn Ser Ile Gly Val Ile Gly
 65                  70                  75                  80

Val Ala Pro Ser Ala Asp Leu Tyr Ala Val Lys Val Leu Gly Ala Asn
                85                  90                  95

Gly Arg Gly Ser Val Ser Gly Ile Ala Gln Gly Leu Glu Trp Ala Ala
            100                 105                 110

Ala Asn Asn Met His Ile Ala Asn Met Ser Leu Gly Ser Asp Ala Pro
        115                 120                 125

Ser Thr Thr Leu Glu Arg Ala Val Asn Tyr Ala Thr Ser Gln Gly Val
130                 135                 140

Leu Val Ile Ala Ala Thr Gly Asn Asn Gly Ser Gly Ser Val Gly Tyr
145                 150                 155                 160

Pro Ala Arg Tyr Ala Asn Ala Met Ala Val Gly Ala Thr Asp Gln Asn
                165                 170                 175

Asn Arg Arg Ala Asn Phe Ser Gln Tyr Gly Thr Gly Ile Asp Ile Val
            180                 185                 190

Ala Pro Gly Val Asn Val Gln Ser Thr Tyr Pro Gly Asn Arg Tyr Ala
        195                 200                 205

Ser Leu Asn Gly Thr Ser Met Ala Thr Pro His Val Ala Gly Ala Ala
210                 215                 220

Ala Leu Val Lys Gln Arg Tyr Pro Ser Trp Asn Ala Thr Gln Ile Arg
225                 230                 235                 240

Asn His Leu Lys Asn Thr Ala Thr Asn Leu Gly Asn Ser Ser Gln Phe
                245                 250                 255

Gly Ser Gly Leu Val Asn Ala Glu Ala Ala Thr Arg
            260                 265

<210> SEQ ID NO 50
<211> LENGTH: 268
<212> TYPE: PRT
<213> ORGANISM: Artificial Sequence
<220> FEATURE:
<223> OTHER INFORMATION: Synthetic: amino acid sequence of the processed
      mature form (268 amino acids), of the DSM 9729 subtilisin

<400> SEQUENCE: 50

Gln Thr Val Pro Trp Gly Ile Thr Arg Val Gln Ala Pro Ala Val His
1               5                   10                  15

Asn Arg Gly Ile Thr Gly Ser Gly Val Arg Val Ala Ile Leu Asp Ser
            20                  25                  30

Gly Ile Ser Ala His Ser Asp Leu Asn Ile Arg Gly Gly Ala Ser Phe
        35                  40                  45

Val Pro Gly Glu Pro Thr Thr Ala Asp Leu Asn Gly His Gly Thr His
 50                  55                  60

Val Ala Gly Thr Val Ala Ala Leu Asn Asn Ser Ile Gly Val Ile Gly
 65                  70                  75                  80

Val Ala Pro Asn Ala Asp Leu Tyr Ala Val Lys Val Leu Gly Ala Asn
                85                  90                  95

Gly Ser Gly Ser Val Ser Gly Ile Ala Gln Gly Leu Glu Trp Ala Ala
            100                 105                 110

```
Thr Asn Asn Met His Ile Ala Asn Met Ser Leu Gly Ser Asp Phe Pro
            115                 120                 125

Ser Ser Thr Leu Glu Arg Ala Val Asn Tyr Ala Thr Ser Arg Asp Val
        130                 135                 140

Leu Val Ile Ala Ala Thr Gly Asn Asn Gly Ser Gly Ser Val Gly Tyr
145                 150                 155                 160

Pro Ala Arg Tyr Ala Asn Ala Met Ala Val Gly Ala Thr Asp Gln Asn
                165                 170                 175

Asn Arg Arg Ala Asn Phe Ser Gln Tyr Gly Thr Gly Ile Asp Ile Val
            180                 185                 190

Ala Pro Gly Val Asn Val Gln Ser Thr Tyr Pro Gly Asn Arg Tyr Val
        195                 200                 205

Ser Met Asn Gly Thr Ser Met Ala Thr Pro His Val Ala Gly Ala Ala
        210                 215                 220

Ala Leu Val Lys Gln Arg Tyr Pro Ser Trp Asn Ala Thr Gln Ile Arg
225                 230                 235                 240

Asn His Leu Lys Asn Thr Ala Thr Asn Leu Gly Asn Ser Ser Gln Phe
                245                 250                 255

Gly Ser Gly Leu Val Asn Ala Glu Ala Ala Thr Arg
            260                 265

<210> SEQ ID NO 51
<211> LENGTH: 268
<212> TYPE: PRT
<213> ORGANISM: Artificial Sequence
<220> FEATURE:
<223> OTHER INFORMATION: Synthetic: amino acid sequence of the processed
      mature form (268 amino acids), of the DSM 9730 subtilisin

<400> SEQUENCE: 51

Gln Thr Val Pro Trp Gly Ile Thr Arg Val Gln Ala Pro Ala Val His
1               5                   10                  15

Asn Arg Gly Val Thr Gly Ser Gly Val Arg Val Ala Ile Leu Asp Ser
            20                  25                  30

Gly Ile Ser Thr His Ser Asp Leu Thr Ile Arg Gly Gly Ala Ser Phe
        35                  40                  45

Val Pro Gly Glu Pro Thr Thr Ala Asp Leu Asn Gly His Gly Thr His
    50                  55                  60

Val Ala Gly Thr Val Ala Ala Leu Asn Asn Ser Ile Gly Val Ile Gly
65                  70                  75                  80

Val Ala Pro Ser Ala Asp Leu Tyr Ala Val Lys Val Leu Gly Ala Asn
                85                  90                  95

Gly Arg Gly Ser Val Ser Gly Ile Ala Gln Gly Leu Glu Trp Ala Ala
            100                 105                 110

Ala Asn Asn Met His Ile Ala Asn Met Ser Leu Gly Ser Asp Ala Pro
        115                 120                 125

Ser Thr Thr Leu Glu Arg Ala Val Asn Tyr Ala Thr Ser Gln Gly Val
        130                 135                 140

Leu Val Ile Ala Ala Thr Gly Asn Asn Gly Ser Gly Ser Val Gly Tyr
145                 150                 155                 160

Pro Ala Arg Tyr Ala Asn Ala Met Ala Val Gly Ala Thr Asp Gln Asn
                165                 170                 175

Asn Arg Arg Ala Asn Phe Ser Gln Tyr Gly Thr Gly Ile Asp Ile Val
            180                 185                 190

Ala Pro Gly Val Asn Val Gln Ser Thr Tyr Pro Gly Asn Arg Tyr Val
```

```
                     195                 200                 205
Ser Met Asn Gly Thr Ser Met Ala Thr Pro His Val Ala Gly Ala Ala
        210                 215                 220

Ala Leu Val Lys Gln Arg Tyr Pro Ser Trp Asn Ala Thr Gln Ile Arg
225                 230                 235                 240

Asn His Leu Lys Asn Thr Ala Thr Asn Leu Gly Asn Ser Ser Gln Phe
                245                 250                 255

Gly Ser Gly Leu Val Asn Ala Glu Ala Ala Thr Arg
                260                 265
```

<210> SEQ ID NO 52
<211> LENGTH: 268
<212> TYPE: PRT
<213> ORGANISM: Artificial Sequence
<220> FEATURE:
<223> OTHER INFORMATION: Synthetic: amino acid sequence of the processed
      mature form (268 amino acids), of the DSM 9731 subtilisin

<400> SEQUENCE: 52

```
Gln Thr Val Pro Trp Gly Ile Thr Arg Val Gln Ala Pro Ala Val His
1               5                   10                  15

Asn Arg Gly Val Thr Gly Ser Gly Val Arg Val Ala Ile Leu Asp Ser
                20                  25                  30

Gly Ile Ser Thr His Ser Asp Leu Thr Ile Arg Gly Gly Ala Ser Phe
            35                  40                  45

Val Pro Gly Glu Pro Thr Thr Ala Asp Leu Asn Gly His Gly Thr His
        50                  55                  60

Val Ala Gly Thr Val Ala Ala Leu Asn Asn Ser Ile Gly Val Ile Gly
65                  70                  75                  80

Val Ala Pro Ser Ala Asp Leu Tyr Ala Val Lys Val Leu Gly Ala Asn
                85                  90                  95

Gly Arg Gly Ser Val Ser Gly Ile Ala Gln Gly Leu Glu Trp Ala Ala
            100                 105                 110

Ala Asn Asn Met His Ile Ala Asn Met Ser Leu Gly Ser Asp Ala Pro
        115                 120                 125

Ser Thr Thr Leu Glu Arg Ala Val Asn Tyr Ala Thr Ser Gln Gly Val
    130                 135                 140

Leu Val Ile Ala Ala Thr Gly Asn Asn Gly Ser Gly Ser Val Gly Tyr
145                 150                 155                 160

Pro Ala Arg Tyr Ala Asn Ala Met Ala Val Gly Ala Thr Asp Gln Asn
                165                 170                 175

Asn Arg Arg Ala Asn Phe Ser Gln Tyr Gly Ser Gly Ile Asp Ile Val
            180                 185                 190

Ala Pro Gly Val Asn Val Gln Ser Thr Tyr Pro Gly Asn Arg Tyr Val
        195                 200                 205

Ser Met Asn Gly Thr Ser Met Ala Thr Pro His Val Ala Gly Ala Ala
    210                 215                 220

Ala Leu Val Lys Gln Arg Tyr Pro Ser Trp Asn Ala Thr Gln Ile Arg
225                 230                 235                 240

Asn His Leu Lys Asn Thr Ala Thr Asn Leu Gly Asn Ser Ser Gln Phe
                245                 250                 255

Gly Ser Gly Leu Val Asn Ala Glu Ala Ala Thr Arg
            260                 265
```

<210> SEQ ID NO 53
<211> LENGTH: 810

<212> TYPE: DNA
<213> ORGANISM: Artificial Sequence
<220> FEATURE:
<223> OTHER INFORMATION: Synthetic: nucleotide sequence encoding the Bgi02446 subtilisin

<400> SEQUENCE: 53

```
caacaaacag tgccatgggg aattactcgt gtgcaagccc cagctgttca taaccgtgga      60
attacaggtt ctggtgtaag agttgctatc ctcgattcag gtatttccgc ccatagtgac     120
ttaaatattc gtggtggcgc tagctttgta ccaggggaac caacgactgc tgatttaaat     180
gggcatggca cgcatgtggc tgggacggta gctgctttaa acaattcgat tggcgttatt     240
ggcgtagcac cgaacgcgga actatacgct gttaaagtat tagggcgaa tggttcaggt     300
tcggtcagcg ggattgccca aggattgaa tgggcagcaa ccaataacat gcacattgct     360
aatatgagtt taggaagcga tttttccaagt tctacacttg agcgtgctgt taattatgcg     420
acttctagag atgttcttgt tattgcggca actgggaata acggttctgg ctcagtaggc     480
tatccggccc gttatgcgaa cgcaatggca gtcggagcta ctgaccaaaa caacagacgc     540
gccaactttt cacagtatgg cacggggatt gacattgtcg caccaggtgt aaacgtgcag     600
agcacatacc caggtaaccg ttatgtgagc atgaacggta tccgatggc tactcctcat     660
gttgcaggtg cagcagccct tgttaaacaa cgctatccat cttggaatgc gactcaaatc     720
cgcaatcatc taaagaatac ggcaacgaat ttaggaaact cttcacaatt tggaagcgga     780
cttgtcaatg cagaagcggc aacacgctaa                                      810
```

<210> SEQ ID NO 54
<211> LENGTH: 810
<212> TYPE: DNA
<213> ORGANISM: Artificial Sequence
<220> FEATURE:
<223> OTHER INFORMATION: Synthetic: nucleotide sequence encoding the DSM-9728 subtilisin

<400> SEQUENCE: 54

```
caacaaacag tgccatgggg aattactcgt gtgcaagccc cagctgttca taaccgtgga      60
gttacaggtt ctggtgtaag agttgctatc ctcgattcag gtatttccac acatagtgac     120
ttaacaattc gtggtggcgc tagctttgta ccaggggaac caacgactgc tgatttaaat     180
gggcatggca cgcatgtggc tgggacggta gctgctttaa acaattcgat tggcgttatt     240
ggcgtagcac cgtcagcgga tctatacgct gttaaagtat tagggcgaa tggtagaggt     300
tcggtcagcg ggattgccca aggattgaa tgggcagcag caaataacat gcacattgct     360
aatatgagtt taggaagcga tgcaccaagt acaacacttg agcgtgctgt taattatgcg     420
acttctcaag gcgttcttgt tattgcggca actgggaata acggttctgg ctcagtaggc     480
tatccggccc gttatgcgaa cgcaatggca gtcggagcta ctgaccaaaa caacagacgc     540
gccaactttt cacagtatgg cacggggatt gacattgtcg caccaggtgt aaacgtgcag     600
agcacatacc caggtaaccg ttatgcaagc ctgaacggta tccgatggc tactcctcat     660
gttgcaggtg cagcagccct tgttaaacaa cgctatccat cttggaatgc gactcaaatc     720
cgcaatcatc taaagaatac ggcaacgaat ttaggaaact cttcacaatt tggaagcgga     780
cttgtcaatg cagaagcggc aacacgctaa                                      810
```

<210> SEQ ID NO 55
<211> LENGTH: 810
<212> TYPE: DNA

<213> ORGANISM: Artificial Sequence
<220> FEATURE:
<223> OTHER INFORMATION: Synthetic: nucleotide sequence encoding the DSM-9731 subtilisin

<400> SEQUENCE: 55

```
caacaaacag tgccatgggg aattactcgt gtgcaagccc cagctgttca taaccgtgga      60
gttacaggtt ctggtgtaag agttgctatc ctcgattcag gtatttccac acatagtgac    120
ttaacaattc gtggtggcgc tagctttgta ccaggggaac caacgactgc tgatttaaat    180
gggcatggca cgcatgtggc tgggacggta gctgctttaa acaattcgat tggcgttatt    240
ggcgtagcac cgtcagcgga tctatacgct gttaaagtat tagggggcgaa tggtagaggt    300
tcggtcagcg ggattgccca aggattggaa tgggcagcag caaataacat gcacattgct    360
aatatgagtt taggaagcga tgcaccaagt acaacacttg agcgtgctgt taattatgcg    420
acttctcaag gcgttcttgt tattgcggca actgggaata acggttctgg ctcagtaggc    480
tatccggccc gttatgcgaa cgcaatggca gtcggagcta ctgaccaaaa caacagacgc    540
gccaactttt cacagtatgg ctcagggatt gacattgtcg caccaggtgt aaacgtgcag    600
agcacatacc caggtaaccg ttatgtgagc atgaacggta tcgatggc tactcctcat      660
gttgcaggtg cagcagccct tgttaaacaa cgctatccat cttggaatgc gactcaaatc    720
cgcaatcatc taaagaatac ggcaacgaat ttaggaaact cttcacaatt tggaagcgga    780
cttgtcaatg cagaagcggc aacacgctaa                                    810
```

<210> SEQ ID NO 56
<211> LENGTH: 807
<212> TYPE: DNA
<213> ORGANISM: Artificial Sequence
<220> FEATURE:
<223> OTHER INFORMATION: Synthetic: nucleotide sequence encoding the BG5-F02 subtilisin

<400> SEQUENCE: 56

```
caacaaacag tgccatgggg aattactcgt gtgcaagccc cagctgttca taaccgtgga      60
attacaggtt ctggtgtaag agttgctatc ctcgattcag gtatttccgc ccatagtgac    120
ttaaatattc gtggtggcgc tagctttgta ccaggggaac caacgactgc tgatttaaat    180
gggcatggca cgcatgtggc tgggacggta gctgctttaa acaattcgat tggcgttatt    240
ggcgtagcac cgaacgcgga actatacgct gttaaagtat tagggggcgaa tggttcaggt    300
tcggtcagcg ggattgccca aggattggaa tgggcagcaa ccataacat gcacattgct      360
aatatgagtt taggaagcga ttttccaagt tctacacttg agcgtgctgt taattatgcg    420
acttctcaag gcgttcttgt tattgcggca actgggaata acggttctgg ctcagtaggc    480
tatccggccc gttatgcgaa cgcaatggca gtcggagcta ctgaccaaaa caacagacgc    540
gccaactttt cacagtatgg cacgggaatt gacattgtcg caccaggtgt aaacgtgcag    600
agcacatacc caggtaaccg ttatgtgagc atgaacggta tcgatggc tactcctcat      660
gttgcaggtg cagcagccct tgttaaacaa cgctatccwt cttggaatgc gactcaaatc    720
cgcaatcatc tgaaaaatac ggcaacgaat ttaggaaact cttcacaatt tggaagcgga    780
cttgtcaatg cagaagcggc aacacgc                                        807
```

<210> SEQ ID NO 57
<211> LENGTH: 269
<212> TYPE: PRT
<213> ORGANISM: Artificial Sequence
<220> FEATURE:
<223> OTHER INFORMATION: Synthetic: predicted amino acid sequence of the mature form of the BG5-F02 subtilisin

<400> SEQUENCE: 57

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 58
<211> LENGTH: 807
<212> TYPE: DNA
<213> ORGANISM: Artificial Sequence
<220> FEATURE:
<223> OTHER INFORMATION: Synthetic: nucleotide sequence encoding the BG5-E05 subtilisin

<400> SEQUENCE: 58

```
caacaaacag tgccatgggg aattactcgt gtgcaagccc cagctgttca taaccgtgga      60
attacaggtt ctggtgtaag agttgctatc ctcgattcag gtatttccgc ccatagtgac     120
ttaaatattc gtggtggcgc tagctttgta ccaggggaac aacgactgc tgatttaaat      180 gggcatggca cgcatgtggc tgggacggta gctgctttaa acaattcgat tggcgttatt     240
ggcgtagcac cgaacgcgga actatacgct gttaaagtat taggggcgaa tggttcaggt     300
tcggtcagcg ggattgccca aggattggaa tggcagcaa ccaataacat gcacattgct      360
```

```
aatatgagtt taggaagcga ttttccaagt tctacacttg agcgtgctgt taattatgcg    420
acttctagag atgttcttgt tattgcggca actgggaata acggttctgg ctcagtaggc    480
tatccggccc gttatgcgaa cgcaatggca gtcggagcta ctgaccaaaa caacagacgc    540
gccaactttt cacagtatgg cgcagggctg acattgtcg caccaggtgt aaacgtgcag     600
agcacatacc caggtaaccg ttatgtgagc atgaacggta catcgatggc tactcctcat    660
gttgcaggtg cagcagccct tgttaaacaa cgctatccat cttggaatgc gactcaaatc    720
cgcaatcatc taaagaatac ggcaacgaat ttaggaaact cttcacaatt tggaagcgga    780
cttgtcaatg cagaagcggc aacacgc                                       807
```

<210> SEQ ID NO 59
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG5-E05 subtilisin

<400> SEQUENCE: 59

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
                20                  25                  30

Ser Gly Ile Ser Ala His Ser Asp Leu Asn Ile Arg Gly Gly Ala Ser
            35                  40                  45

Phe Val Pro Gly Glu Pro Thr Thr Ala Asp Leu Asn Gly His Gly Thr
        50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
                100                 105                 110

Ala Thr Asn Asn Met His Ile Ala Asn Met Ser Leu Gly Ser Asp Phe
            115                 120                 125

Pro Ser Ser Thr Leu Glu Arg Ala Val Asn Tyr Ala Thr Ser Arg Asp
        130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Ala Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 60
<211> LENGTH: 807
<212> TYPE: DNA
<213> ORGANISM: Artificial Sequence
<220> FEATURE:
<223> OTHER INFORMATION: Synthetic: nucleotide sequence encoding the
      BG1-C05 subtilisin

<400> SEQUENCE: 60

```
caacaaacag tgccatgggg aattactcgt gtgcaagccc cagctgttca taaccgtgga    60
attacaggtt ctggtgtaag agttgctatc ctcgattcag gtatttccgc ccatagtgac   120
ttaaatattc gtggtggcgc tagctttgta ccagggaaac aacgactgc tgatttaaat    180 gggcatggca cgcatgtggc tgggacggta gctgctttaa acaattcgat tggcgttatt   240
ggcgtagcac cgaacgcgga actatacgct gttaaagtat taggggcgaa tggtagaggt   300
tcggtcagcg ggattgccca aggattggaa tgggcagcaa ccaataacat gcacattgct   360
aatatgagtt taggaagcga tgcaccaagt actacacttg agcgtgctgt taattatgcg   420
acttctagag atgttcttgt tattgcggca actgggaata cggttctgg ctcagtaggc    480 tatccggccc gttatgcgaa cgcaatggca gtcggagcta ctgaccaaaa aacagacgc    540 gccaactttt cacagtatgg cacggggatt gacattgtcg caccaggtgt aaacgtgcag   600
agcacatacc caggtaaccg ttatgtgagc atgaacggta tcgatggc tactcctcat     660 gttgcaggtg cagcagccct tgttaaacaa cgctatccat cttggaatgc gactcaaatc   720
cgcaatcatc taaagaatac ggcaacgaat ttaggaaact cttcacaatt tggaagcgga   780
cttgtcaatg cagaagcggc aacacgc                                       807
```

<210> SEQ ID NO 61
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG1-C05 subtilisin

<400> SEQUENCE: 61

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160
```

Tyr Pro Ala Arg Tyr Ala Asn Ala Met Ala Val Gly Ala Thr Asp Gln
            165                 170                 175

Asn Asn Arg Arg Ala Asn Phe Ser Gln Tyr Gly Thr Gly Ile Asp Ile
        180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
        210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 62
<211> LENGTH: 807
<212> TYPE: DNA
<213> ORGANISM: Artificial Sequence
<220> FEATURE:
<223> OTHER INFORMATION: Synthetic: nucleotide sequence encoding the
      BG2-D10 subtilisin

<400> SEQUENCE: 62
caacaaacag tgccatgggg aattactcgt gtgcaagccc cagctgttca taaccgtgga      60
attacaggtt ctggtgtaag agttgctatc ctcgattcag gtatttccgc ccatagtgac     120
ttaaatattc gtggtggcgc tagctttgta ccaggggaac caacgactgc tgatttaaat     180
gggcatggca cgcatgtggc tgggacggta gctgctttaa caattcgat ggcgttatt      240 ggcgtagcac cgaacgcgga actatacgct gttaaagtat taggggcgaa tggttcaggt     300
tcggtcagcg ggattgccca aggattgaa tgggcagcaa ccaataacat gcacattgct      360
aatatgagtt taggaagcga tgcaccaagt acaacacttg agcgtgctgt taattatgcg     420
acttctcaag gcgttcttgt tattgcggca actgggaata acggttctgg ctcagtaggc     480
tatccggccc gttatgcgaa cgcaatggca gtcggagcta ctgaccaaaa caacagacgc     540
gccaactttt cacagtatgg cacggggatt gacattgtcg caccaggtgt aaacgtgcag     600
agcacatacc caggtaaccg ttatgtgagc atgaacggta tcgatggc tactcctcat       660 gttgcaggtg cagcagccct tgttaaacaa cgctatccat cttggaatgc gactcaaatc     720
cgcaatcatc taaagaatac ggcaacgaat ttaggaaact cttcacaatt tggaagcgga     780
cttgtcaatg cagaagcggc aacacgc                                         807

<210> SEQ ID NO 63
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG2-D10 subtilisin

<400> SEQUENCE: 63

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser

```
                    35                  40                  45
Phe Val Pro Gly Glu Pro Thr Thr Ala Asp Leu Asn Gly His Gly Thr
 50                  55                  60

His Val Ala Gly Thr Val Ala Ala Leu Asn Asn Ser Ile Gly Val Ile
 65                  70                  75                  80

Gly Val Ala Pro Asn Ala Glu Leu Tyr Ala Val Lys Val Leu Gly Ala
                     85                  90                  95

Asn Gly Ser Gly Ser Val Ser Gly Ile Ala Gln Gly Leu Glu Trp Ala
                100                 105                 110

Ala Thr Asn Asn Met His Ile Ala Asn Met Ser Leu Gly Ser Asp Ala
                115                 120                 125

Pro Ser Thr Thr Leu Glu Arg Ala Val Asn Tyr Ala Thr Ser Gln Gly
            130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
                180                 185                 190

Val Ala Pro Gly Val Asn Val Gln Ser Thr Tyr Pro Gly Asn Arg Tyr
                195                 200                 205

Val Ser Met Asn Gly Thr Ser Met Ala Thr Pro His Val Ala Gly Ala
210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
                260                 265

<210> SEQ ID NO 64
<211> LENGTH: 807
<212> TYPE: DNA
<213> ORGANISM: Artificial Sequence
<220> FEATURE:
<223> OTHER INFORMATION: Synthetic: nucleotide sequence encoding the
      BG1-B08 subtilisin

<400> SEQUENCE: 64
caacaaacag tgccatgggg aattactcgt gtgcaagccc cagctgttca taaccgtgga      60
attacaggtt ctggtgtaag agttgctatc ctcgattcag gtatttccgc ccatagtgac     120
ttaaatattc gtggtggcgc tagctttgta ccaggggaac caacgactgc tgatttaaat     180
gggcatggca cgcatgtggc tgggacggta gctgctttaa acaattcgat tggcgttatt     240
ggcgtagcac cgaacgcgga actatacgct gttaaagtat taggggcgaa tggttcaggt     300
tcggtcagcg ggattgccca aggattggaa tgggcagcaa ccataacat gcacattgct     360 aatatgagtt taggaagcga ttttccaagt tctacacttg agcgtgctgt taattatgcg     420
acttctcaag gcgttcttgt tattgcggca actgggaata acggttctgg ctcagtaggc     480
tatccggccc gttatgcgaa cgcaatggca gtcggagcta ctgaccaaaa caacagacgc     540
gccaactttt cacagtatgg cacggggatt gacattgtcg caccaggtgt aaacgtgcag     600
agcacatacc caggtaaccg ttatgtgagc atgaacggta catcgatggc tactcctcat     660
gttgcaggtg cagcagccct tgttaaacaa cgctatccat cttggaatgc gactcaaatc     720
```

```
cgcaatcatc taaagaatac ggcaacgaat ttaggaaaca caaatctgta tggaagcgga      780
cttgtcaatg cagaagcggc aacacgc                                          807
```

<210> SEQ ID NO 65
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG1-B08 subtilisin

<400> SEQUENCE: 65

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Thr Asn Leu
                245                 250                 255

Tyr Gly Ser Gly Leu Val Asn Ala Glu Ala Ala Thr Arg
            260                 265
```

<210> SEQ ID NO 66
<211> LENGTH: 807
<212> TYPE: DNA
<213> ORGANISM: Artificial Sequence
<220> FEATURE:
<223> OTHER INFORMATION: Synthetic: nucleotide sequence encoding the
      BG4-A09 subtilisin

<400> SEQUENCE: 66

```
caacaaacag tgccatgggg aattactcgt gtgcaagccc cagctgttca taaccgtgga      60
```

```
gttacaggtt ctggtgtaag agttgctgtt ctcgatacag gtatttccgc ccatagtgac    120
ttaaatattc gtggtggcgc tagctttgta ccagggaaac caacgactgc tgatttaaat    180
gggcatggca cgcatgtggc tgggacggta gctgctttaa acaattcgat tggcgttatt    240
ggcgtagcac cgaacgcgga actatacgct gttaaagtat taggggcgaa tggttcaggt    300
tcggtcagcg ggattgccca aggattggaa tgggcagcaa ccaataacat tcacattgct    360
aatatgagtt taggaacaga tgcaccaagt acaacacttg agcgtgctgt taattatgcg    420
acttctcaag gcgttcttgt tattgcggca actgggaata cggttctgg cacaatttca    480 tatccggccc gttatgcgaa cgcaatggca gtcggagcta ctgaccaaaa caacaatcgc    540
gcctcatttt cacagtatgg cgcagggctg gacattgtcg caccaggtgt aaacgtgcag    600
agcacatacc caggtaaccg ttatgtgagc atgaacggta tcgatggc tactcctcat    660 gttgcaggtg cagcagccct tgttaaacaa cgctatccat cttggaatgc gactcaaatc    720
cgcaatcatc taaagaatac ggcaacgaat ttaggaaact cttcacaatt tggaagcgga    780
cttgtcaatg cagaagcggc aacacgc                                         807
```

<210> SEQ ID NO 67
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG4-A09 subtilisin

<400> SEQUENCE: 67

```
Gln Gln Thr Val Pro Trp Gly Ile Thr Arg Val Gln Ala Pro Ala Val
1               5                   10                  15

His Asn Arg Gly Val Thr Gly Ser Gly Val Arg Val Ala Val Leu Asp
            20                  25                  30

Thr Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Ile His Ile Ala Asn Met Ser Leu Gly Thr Asp Ala
        115                 120                 125

Pro Ser Thr Thr Leu Glu Arg Ala Val Asn Tyr Ala Thr Ser Gln Gly
    130                 135                 140

Val Leu Val Ile Ala Ala Thr Gly Asn Gly Ser Gly Thr Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220
```

```
Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 68
<211> LENGTH: 807
<212> TYPE: DNA
<213> ORGANISM: Artificial Sequence
<220> FEATURE:
<223> OTHER INFORMATION: Synthetic: nucleotide sequence encoding the
      BG4-D10 subtilisin

<400> SEQUENCE: 68
caacaaacag tgccatgggg aattactcgt gtgcaagccc cagctgttca taaccgtgga     60
tttacaggtt ctggtgtaag agttgctatc ctcgattcag gtatttccac acatagtgac    120
ttaacaattc gtggtggcgc tagctttgta ccaggggaac caacgactgc tgatttaaat    180
gggcatggca cgcatgtggc tgggacggta gctgctttaa caattcgat ggcgttctg     240 ggcgtagcac cgaacgcgga actatacgct gttaaagtat taggggcgaa tggttcaggt    300
tcgattagcg ggattgccca aggattggaa tgggcagcag caaataacat gcacattgct    360
aatatgagtt taggaacaga tgcaccaagt tctacacttg agcgtgctgt taattatgcg    420
acttctcaag gcgttcttgt tattgcggca actgggaata acggttctgg cacaatttca    480
tatccggccc gttatgcgaa cgcaatggca gtcggagcta ctgaccaaaa aacagacgc    540 gccaactttt cacagtatgg ctcagggatt gacattgtcg caccaggtgt aaacgtgcag    600
agcacatacc caggtaaccg ttatgcaagc ctgtcaggta tcgatggc tactcctcat      660 gttgcaggtg cagcagccct tgttaaacaa cgctatccat cttggaatgc gactcaaatc    720
cgcaatcatc taaagaatac ggcaacgaat ttaggaaact cttcacaatt tggaagcgga    780
cttgtcaatg cagaagcggc aacacgc                                        807

<210> SEQ ID NO 69
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG4-D10 subtilisin

<400> SEQUENCE: 69

Gln Gln Thr Val Pro Trp Gly Ile Thr Arg Val Gln Ala Pro Ala Val
1               5                   10                  15

His Asn Arg Gly Phe Thr Gly Ser Gly Val Arg Val Ala Ile Leu Asp
                20                  25                  30

Ser Gly Ile Ser Thr His Ser Asp Leu Thr Ile Arg Gly Gly Ala Ser
            35                  40                  45

Phe Val Pro Gly Glu Pro Thr Thr Ala Asp Leu Asn Gly His Gly Thr
        50                  55                  60

His Val Ala Gly Thr Val Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Asn Gly Ser Gly Ser Ile Ser Gly Ile Ala Gln Gly Leu Glu Trp Ala
            100                 105                 110
```

Ala Ala Asn Asn Met His Ile Ala Asn Met Ser Leu Gly Thr Asp Ala
            115                 120                 125

Pro Ser Ser Thr Leu Glu Arg Ala Val Asn Tyr Ala Thr Ser Gln Gly
        130                 135                 140

Val Leu Val Ile Ala Ala Thr Gly Asn Asn Gly Ser Gly Thr Ile Ser
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Ser Gly Ile Asp Ile
            180                 185                 190

Val Ala Pro Gly Val Asn Val Gln Ser Thr Tyr Pro Gly Asn Arg Tyr
        195                 200                 205

Ala Ser Leu Ser Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 70
<211> LENGTH: 807
<212> TYPE: DNA
<213> ORGANISM: Artificial Sequence
<220> FEATURE:
<223> OTHER INFORMATION: Synthetic: nucleotide sequence encoding the
      BG2-B08 subtilisin

<400> SEQUENCE: 70
caacaaacag tgccatgggg aattactcgt gtgcaagccc cagctgttca taaccgtgga      60
attacaggtt ctggtgtaag agttgctatc ctcgattcag gtatttccgc ccatagtgac     120
ttaaatattc gtggtggcgc tagctttgta ccaggggaac caacgactgc tgatttaaat    180
gggcatggca cgcatgtggc tgggacggta gctgctttaa caattcgat ggcgttatt      240 ggcgtagcac cgaacgcgga actatacgct gttaaagtat taggggcgtc aggttcaggt    300
tcgattagcg ggattgccca aggattgcaa tgggcagcaa ccataacat gcacattgct    360 aatatgagtt taggaagcga tgcaccaagt acaacacttg agcgtgctgt taattatgcg    420
acttctagag atgttcttgt tattgcggca actgggaata acggttctgg ctcagtaggc    480
tatccggccc gttatgcgaa cgcaatggca gtcggagcta ctgaccaaaa caacagacgc    540
gccaactttt cacagtatgg cacgggatt gacattgtcg caccaggtgt aaacgtgcag    600
agcacatacc caggtaaccg ttatgtgagc atgaacggta tcgatggc tactcctcat     660 gttgcaggtg cagcagccct tgttaaacaa cgctatccat cttggaatgc gactcaaatc    720
cgcaatcatc taaagaatac ggcaacgaat ttaggaaact cttcacaatt tggaagcgga    780
cttgtcaatg cagaagcggc aacacgc                                        807

<210> SEQ ID NO 71
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG2-B08 subtilisin

<400> SEQUENCE: 71

| | | | | | | | | | | | | | | | |
|---|---|---|---|---|---|---|---|---|---|---|---|---|---|---|---|
|Gln|Gln|Thr|Val|Pro|Trp|Gly|Ile|Thr|Arg|Val|Gln|Ala|Pro|Ala|Val|
|1| | | |5| | | | |10| | | | |15| |
|His|Asn|Arg|Gly|Ile|Thr|Gly|Ser|Gly|Val|Arg|Val|Ala|Ile|Leu|Asp|
| | | |20| | | | |25| | | | |30| | |
|Ser|Gly|Ile|Ser|Ala|His|Ser|Asp|Leu|Asn|Ile|Arg|Gly|Gly|Ala|Ser|
| | |35| | | | |40| | | | |45| | | |
|Phe|Val|Pro|Gly|Glu|Pro|Thr|Thr|Ala|Asp|Leu|Asn|Gly|His|Gly|Thr|
| |50| | | | |55| | | | |60| | | | |
|His|Val|Ala|Gly|Thr|Val|Ala|Ala|Leu|Asn|Asn|Ser|Ile|Gly|Val|Ile|
|65| | | | |70| | | | |75| | | | |80|
|Gly|Val|Ala|Pro|Asn|Ala|Glu|Leu|Tyr|Ala|Val|Lys|Val|Leu|Gly|Ala|
| | | | |85| | | | |90| | | | |95| |
|Ser|Gly|Ser|Gly|Ser|Ile|Ser|Gly|Ile|Ala|Gln|Gly|Leu|Gln|Trp|Ala|
| | | | |100| | | | |105| | | | |110| |
|Ala|Thr|Asn|Asn|Met|His|Ile|Ala|Asn|Met|Ser|Leu|Gly|Ser|Asp|Ala|
| | | | |115| | | | |120| | | | |125| |
|Pro|Ser|Thr|Thr|Leu|Glu|Arg|Ala|Val|Asn|Tyr|Ala|Thr|Ser|Arg|Asp|
| |130| | | | |135| | | | |140| | | | |
|Val|Leu|Val|Ile|Ala|Ala|Thr|Gly|Asn|Asn|Gly|Ser|Gly|Ser|Val|Gly|
|145| | | | |150| | | | |155| | | | |160|
|Tyr|Pro|Ala|Arg|Tyr|Ala|Asn|Ala|Met|Ala|Val|Gly|Ala|Thr|Asp|Gln|
| | | | |165| | | | |170| | | | |175| |
|Asn|Asn|Arg|Arg|Ala|Asn|Phe|Ser|Gln|Tyr|Gly|Thr|Gly|Ile|Asp|Ile|
| | | |180| | | | |185| | | | |190| | |
|Val|Ala|Pro|Gly|Val|Asn|Val|Gln|Ser|Thr|Tyr|Pro|Gly|Asn|Arg|Tyr|
| | |195| | | | |200| | | | |205| | | |
|Val|Ser|Met|Asn|Gly|Thr|Ser|Met|Ala|Thr|Pro|His|Val|Ala|Gly|Ala|
| |210| | | | |215| | | | |220| | | | |
|Ala|Ala|Leu|Val|Lys|Gln|Arg|Tyr|Pro|Ser|Trp|Asn|Ala|Thr|Gln|Ile|
|225| | | | |230| | | | |235| | | | |240|
|Arg|Asn|His|Leu|Lys|Asn|Thr|Ala|Thr|Asn|Leu|Gly|Asn|Ser|Ser|Gln|
| | | | |245| | | | |250| | | | |255| |
|Phe|Gly|Ser|Gly|Leu|Val|Asn|Ala|Glu|Ala|Ala|Thr|Arg| | | |
| | | | |260| | | | |265| | | | | | |

<210> SEQ ID NO 72
<211> LENGTH: 807
<212> TYPE: DNA
<213> ORGANISM: Artificial Sequence
<220> FEATURE:
<223> OTHER INFORMATION: Synthetic: nucleotide sequence encoding the BG8-B03 subtilisin

<400> SEQUENCE: 72

| | | |
|---|---|---|
|gcacaaacag tgccatgggg aattactcgt gtgcaagccc cagctgttca taaccgtgga|  |60|
|attacaggtt ctggtgtaag aggttgctat cctcgattca ggtatttccg cccatagtga|  |120|
|cttaacaatt cgtggtggcg ctgctttgta ccaggggaac caacgactgc tgatttaaat|  |180|
|gggcatggca cgcatgtggc tggacggta gctgctttaa acaattcgat tggcgttatt|  |240|
|ggcgtagcac cgtcagcgga tctatacgct gttaaagtat taggggcgaa tggtagaggt|  |300|
|tcggtcagcg ggattgccca aggattggaa tgggcagcaa ccaataacat gcacattgct|  |360|
|aatatgagtt taggaagcga tgcaccaagt acaacacttg agcgtgctgt taattatgcg|  |420|
|acttctcaag gcgttcttgt tattgcggca actgggaata cggttctgg ctcagtaggc|  |480|

```
tatccggccc gttatgcgaa cgcaatggca gtcggagcta ctgaccaaaa caacaatcgc    540
gcctcatttt cacagtatgg cgcagggctg acattgtcg caccaggtgt aaacgtgcag    600
agcacatacc caggtaaccg ttatgtgagc atgaacggta catcgatggc tactcctcat    660
gttgcaggtg ttgcagccct tgttaaacaa cgctatccat cttggaatgc gactcaaatc    720
cgcaatcatc taaagaatac ggcaacgaat ttaggaaact cttcacaatt ggaagcgga    780 cttgtcaatg cagaagcggc aacacgc                                        807
```

<210> SEQ ID NO 73
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG8-B03 subtilisin

<400> SEQUENCE: 73

```
Ala Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Thr Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Val
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 74
<211> LENGTH: 807
<212> TYPE: DNA

<213> ORGANISM: Artificial Sequence
<220> FEATURE:
<223> OTHER INFORMATION: Synthetic: nucleotide sequence encoding the BG6-A10 subtilisin

<400> SEQUENCE: 74

```
caacaaacag tgccatgggg aattactcgt gtgcaagccc cagctgttca taaccgtgga      60
attacaggtt ctggtgtaag agttgctatc ctcgattcag gtatttccgc ccatagtgac     120
ttaaatattc gtggtggcgc tagctttgta ccaggggaac caacgactgc tgatttaaat     180
gggcatggca cgcatgtggc tgggacggta gctgctttaa acaattcgat tggcgttatt     240
ggcgtagcac cgaacgcgga actatacgct gttaaagtat tagggcgtc aggttcaggt      300
tcggtcagcg ggattgccca aggattggaa tgggcagcaa ccaataacat gcacattgct     360
aatatgagtt taggaagcga ttttccaagt tctacacttg agcgtgctgt taattatgcg     420
acttctagag atgttcttgt tattgcggca actgggaata cggttctgg ctcagtaggc      480
tatccggccc gttatgcgaa cgcaatggca gtcggagcta ctgaccaaaa aacagacgc     540
gccaactttt cacagtatgg cacggggatt gacattgtcg caccaggtgt aaacgtgcag     600
agcacatacc caggtaaccg ttatgtgagc atgaacggta catcgatggc tactcctcat     660
gttgcaggtg cagcagccct tgttaaacaa cgctatccat cttggaatgc gactcaaatc     720
cgcaatcatc taaagaatac ggcaacgaat ttaggaaaca caaatctgta tggaagcgga     780
cttgtcaatg cagaagcggc aacacgc                                         807
```

<210> SEQ ID NO 75
<211> LENGTH: 269
<212> TYPE: PRT
<213> ORGANISM: Artificial Sequence
<220> FEATURE:
<223> OTHER INFORMATION: Synthetic: predicted amino acid sequence of the mature form of the BG6-A10 subtilisin

<400> SEQUENCE: 75

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Ser Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175
```

```
Asn Asn Arg Arg Ala Asn Phe Ser Gln Tyr Gly Thr Gly Ile Asp Ile
                180                 185                 190

Val Ala Pro Gly Val Asn Val Gln Ser Thr Tyr Pro Gly Asn Arg Tyr
            195                 200                 205

Val Ser Met Asn Gly Thr Ser Met Ala Thr Pro His Val Ala Gly Ala
        210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Thr Asn Leu
                245                 250                 255

Tyr Gly Ser Gly Leu Val Asn Ala Glu Ala Ala Thr Arg
            260                 265

<210> SEQ ID NO 76
<211> LENGTH: 807
<212> TYPE: DNA
<213> ORGANISM: Artificial Sequence
<220> FEATURE:
<223> OTHER INFORMATION: Synthetic: nucleotide sequence encoding the
      BG6-D08 subtilisin

<400> SEQUENCE: 76
caacaatcag tgccatgggg aatttcacgt gtgcaagccc agctgttca taaccgtgga     60 attacaggtt caggtgtaag agttgctatc ctcgattcag gtattccgc ccatagtgac    120 ttaaatattc gtggtggcgc tagctttgta ccaggggaac caacgactgc tgatttaaat    180
gggcatggca cgcatgtggc tgggacggta gctgctttaa caattcgat ggcgttatt    240 ggcgtagcac cgtcagcgga tctatacgct gttaaagtat taggggcgaa tggttcaggt    300
tcggtcagcg ggattgccca aggattgaa tgggcagcag caataacat gcacattgct    360 aatatgagtt taggaagcga ttttccaagt tctacacttg agcgtgctgt taattatgcg    420
acttctagag atgttcttgt tattgcggca actgggaata acggttctgg ctcagtaggc    480
tatccggccc gttatgcgaa cgcaatggca gtcggagcta ctgaccaaaa caacagacgc    540
gccaactttt cacagtatgg cacggggatt gacattgtcg caccaggtgt aaacgtgcag    600
agcacatacc caggtaaccg ttatgtgagc atgaacggta tcgatggc tactcctcat    660 gttgcaggtg cagcagccct tgttaaacaa cgctatccat cttggaatgc gactcaaatc    720
cgcaatcatc taaagaatac ggcaacgaat ttaggaaaca caaatctgta tggaagcgga    780
cttgtcaatg cagaagcggc aacacgc                                        807

<210> SEQ ID NO 77
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG6-D08 subtilisin

<400> SEQUENCE: 77

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60
```

```
His Val Ala Gly Thr Val Ala Ala Leu Asn Asn Ser Ile Gly Val Ile
 65                  70                  75                  80
Gly Val Ala Pro Asn Ala Glu Leu Tyr Ala Val Lys Val Leu Gly Ala
                 85                  90                  95
Ser Gly Ser Gly Ser Val Ser Gly Ile Ala Gln Gly Leu Glu Trp Ala
            100                 105                 110
Ala Thr Asn Asn Met His Ile Ala Asn Met Ser Leu Gly Ser Asp Phe
        115                 120                 125
Pro Ser Ser Thr Leu Glu Arg Ala Val Asn Tyr Ala Thr Ser Arg Asp
130                 135                 140
Val Leu Val Ile Ala Ala Thr Gly Asn Asn Gly Ser Gly Ser Val Gly
145                 150                 155                 160
Tyr Pro Ala Arg Tyr Ala Asn Ala Met Ala Val Gly Ala Thr Asp Gln
                165                 170                 175
Asn Asn Arg Arg Ala Asn Phe Ser Gln Tyr Gly Thr Gly Ile Asp Ile
            180                 185                 190
Val Ala Pro Gly Val Asn Val Gln Ser Thr Tyr Pro Gly Asn Arg Tyr
        195                 200                 205
Val Ser Met Asn Gly Thr Ser Met Ala Thr Pro His Val Ala Gly Ala
210                 215                 220
Ala Ala Leu Val Lys Gln Arg Tyr Pro Ser Trp Asn Ala Thr Gln Ile
225                 230                 235                 240
Arg Asn His Leu Lys Asn Thr Ala Thr Asn Leu Gly Asn Thr Asn Leu
                245                 250                 255
Tyr Gly Ser Gly Leu Val Asn Ala Glu Ala Ala Thr Arg
            260                 265

<210> SEQ ID NO 78
<211> LENGTH: 807
<212> TYPE: DNA
<213> ORGANISM: Artificial Sequence
<220> FEATURE:
<223> OTHER INFORMATION: Synthetic: nucleotide sequence encoding the
      BG5-G10 subtilisin

<400> SEQUENCE: 78
caacaaacag tgccatgggg aattactcgt gtgcaagccc cagctgttca taaccgtgga      60
attacaggtt ctggtgtaag agttgctatc ctcgattcag gtatttccgc ccatagtgac     120
ttaaatattc gtggtggcgc tagctttgta ccaggggaac caacgactgc tgatttaaat     180
gggcatggca cgcatgtggc tgggacggta gctgctttaa acaattcgat tggcgttatt     240
ggcgtagcac cgtcagcgga tctatacgct gttaaagtat taggggcgaa tggttcaggt     300
tcggtcagcg ggattgccca aggattgaat gggcagcaa ccataacat gcacattgct      360 aatatgagtt taggaagcga ttttccaagt tctacacttg agcgtgctgt taattatgcg     420
acttctagag atgttcttgt tattgcggca actgggaata acggttctgg ctcagtaggc     480
tatccggccc gttatgcgaa cgcaatggca gtcggagcta ctgaccaaaa caacagacgc     540
gccaactttt cacagtatgg cacggggatt gacattgtcg caccaggtgt aaacgtgcag     600
agcacatacc caggtaaccg ttatgtgagc atgaacggta tcgatggc tactcctcat       660 gttgcaggtg cagcagccct tgttaaacaa cgctatccat cttggaatgc gactcaaatc     720
cgcaatcatc taaagaatac ggcaacgaat ttaggaaaca caaatctgta tggaagcgga     780
cttgtcaatg cagaagcggc aacacgc                                        807
```

```
<210> SEQ ID NO 79
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG5-G10 subtilisin

<400> SEQUENCE: 79

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Thr Asn Leu
                245                 250                 255

Tyr Gly Ser Gly Leu Val Asn Ala Glu Ala Ala Thr Arg
            260                 265

<210> SEQ ID NO 80
<211> LENGTH: 807
<212> TYPE: DNA
<213> ORGANISM: Artificial Sequence
<220> FEATURE:
<223> OTHER INFORMATION: Synthetic: nucleotide sequence encoding the
      BG5-E02 subtilisin

<400> SEQUENCE: 80
caacaaacag tgccatgggg aatttcacgt gtgcaagccc cagctgttca taaccgtgga     60
attacaggtt ctggtgtaag agttgctatc ctcgattcag gtatttccgc ccatagtgac    120
ttaaatattc gtggtggcgc tagctttgta ccaggggaac caacgactgc tgatttaaat    180
```

```
gggcatggca cgcatgtggc tgggacggta gctgctttaa caattcgat tggcgttatt    240 ggcgtagcac cgaacgcgga actatacgct gttaaagtat tagggcgtc aggttcaggt    300 tcgattagcg ggattgccca aggattggaa tgggcagcaa ccaataacat gcacattgct    360
aatatgagtt taggaagcga tgcaccaagt acaacacttg agcgtgctgt taattatgcg    420
acttctagag atgttcttgt tattgcggca actgggaata acggttctgg ctcagtaggc    480
tatccggccc gttatgcgaa cgcaatggca gtcggagcta ctgaccaaaa aacagacgc     540 gccaactttt cacagtatgg cacggggatt gacattgtcg caccaggtgt aaacgtgcag    600
agcacatacc caggtaaccg ttatgtgagc atgaacggta tcgcgatggc tactcctcat    660
gttgcaggtg cagcagccct tgttaaacaa cgctatccat cttggaatgc gactcaaatc    720
cgcaatcatc taaagaatac ggcaacgaat ttaggaaaca caaatctgta tggaagcgga    780
cttgtcaatg cagaagcggc aacacgc                                        807
```

<210> SEQ ID NO 81
<211> LENGTH: 269
<212> TYPE: PRT
<213> ORGANISM: Artificial Sequence
<220> FEATURE:
<223> OTHER INFORMATION: Synthetic: predicted amino acid sequence of the mature form of the BG5-E02 subtilisin

<400> SEQUENCE: 81

```
Gln Gln Thr Val Pro Trp Gly Ile Ser Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Ser Gly Ser Gly Ser Ile Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Thr Asn Leu
```

```
                    245                 250                 255
Tyr Gly Ser Gly Leu Val Asn Ala Glu Ala Ala Thr Arg
            260                 265

<210> SEQ ID NO 82
<211> LENGTH: 807
<212> TYPE: DNA
<213> ORGANISM: Artificial Sequence
<220> FEATURE:
<223> OTHER INFORMATION: Synthetic: nucleotide sequence encoding the
      BG2-G08 subtilisin

<400> SEQUENCE: 82
caacaaacag tgccatgggg aattactcgt gtgcaagccc cagctgttca taaccgtgga      60
attacaggtt ctggtgtaag agttgctatc ctcgattcag gtatttccgc ccatagtgac    120
ttaaatattc gtggtggcgc tagctttgta ccaggggaac aacgactgc tgatttaaat    180 gggcatggca cgcatgtggc tgggacggta gctgctttaa caattcgat ggcgttatt    240 ggcgtagcac cgaacgcgga actatacgct gttaaagtat taggggcgaa tggttcaggt    300
tcggtcagcg ggattgccca aggattggaa tgggcagcaa ccaataacat gcacattgct    360
aatatgagtt taggaagcga tgcaccaagt acaaacttg agcgtgctgt taattatgcg    420
acttctgcag gcgttcttgt tgttgcggca actgggaata acggttctgg ctcagtaggc    480
tatccggccc gttatgcgaa cgcaatggca gtcgagcta ctgaccaaaa caacagacgc    540 gccaacttt cacagtatgg cacggggatt gacattgtcg caccaggtgt aaacgtgcag    600
agcacatacc aggtaaccg ttatgtgagc atgaacggta tcgatggc tactcctcat    660 gttgcaggtg cagcagccct tgttaaacaa cgctatccat cttggaatgc gactcaaatc    720
cgcaatcatc taaagaatac ggcaacgaat ttaggaaact cttcacaatt tggaagcgga    780
cttgtcaatg cagaagcggc aacacgc                                        807

<210> SEQ ID NO 83
<211> LENGTH: 269
<212> TYPE: PRT
<213> ORGANISM: Artificial Sequence
<220> FEATURE:
<223> OTHER INFORMATION: Synthetic: predicted amino acid sequence of the
      mature form of the BG2-G08 subtilisin

<400> SEQUENCE: 83

Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125
```

```
Pro Ser Thr Thr Leu Glu Arg Ala Val Asn Tyr Ala Thr Ser Ala Gly
    130                 135                 140

Val Leu Val Val Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
            195                 200                 205

Val Ser Met Asn Gly Thr Ser Met Ala Thr Pro His Val Ala Gly Ala
210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265

<210> SEQ ID NO 84
<211> LENGTH: 274
<212> TYPE: PRT
<213> ORGANISM: B. licheniformis
<220> FEATURE:
<221> NAME/KEY: misc_feature
<222> LOCATION: (1)..(274)
<223> OTHER INFORMATION: The amino acid sequence of the mature form of
      B. licheniformis subtilisin BliD02339

<400> SEQUENCE: 84

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Pro
        115                 120                 125

Ser Gly Ser Thr Ala Met Lys Gln Ala Val Asp Asn Ala Tyr Ala Arg
    130                 135                 140

Gly Val Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Lys Leu Glu Val Met Ala Pro Gly Ala Gly Val Tyr Ser Thr Tyr
        195                 200                 205
```

Pro Thr Ser Thr Tyr Ala Thr Leu Asn Gly Thr Ser Met Ala Ser Pro
210                 215                 220

His Val Ala Gly Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
                260                 265                 270

Ala Gln

<210> SEQ ID NO 85
<211> LENGTH: 275
<212> TYPE: PRT
<213> ORGANISM: Bacillus sp. m3-13
<220> FEATURE:
<221> NAME/KEY: misc_feature
<222> LOCATION: (1)..(275)
<223> OTHER INFORMATION: The amino acid sequence of the mature form of
      Bacillus sp. m3-13 subtilisin E

<400> SEQUENCE: 85

Ala Gln Thr Val Pro Trp Gly Ile Pro His Ile Lys Ala Asp Lys Ala
1               5                   10                  15

His Ala Ser Gly Val Thr Gly Ser Gly Val Lys Val Ala Val Leu Asp
                20                  25                  30

Thr Gly Ile Asp Ala Asn His Ala Asp Leu Asn Val Lys Gly Gly Ala
            35                  40                  45

Ser Phe Val Ser Gly Glu Pro Asn Ala Leu Gln Asp Gly Asn Gly His
50                  55                  60

Gly Thr His Val Ala Gly Thr Val Ala Ala Leu Asn Asn Thr Thr Gly
65                  70                  75                  80

Val Leu Gly Val Ala Tyr Asn Ala Asp Leu Tyr Ala Val Lys Val Leu
                85                  90                  95

Ser Ala Ser Gly Ser Gly Thr Leu Ser Gly Ile Ala Gln Gly Ile Glu
            100                 105                 110

Trp Ser Ile Ala Asn Asp Met Asp Val Ile Asn Met Ser Leu Gly Gly
        115                 120                 125

Ser Thr Gly Ser Thr Ala Leu Gln Gln Ala Cys Asp Asn Ala Tyr Ala
130                 135                 140

Ser Gly Ile Val Val Val Ala Ala Ala Gly Asn Ser Gly Ser Lys Gly
145                 150                 155                 160

Lys Arg Asn Thr Met Gly Tyr Pro Ala Arg Tyr Ser Ser Val Ile Ala
                165                 170                 175

Val Gly Ala Val Asp Ser Ser Asn Asn Arg Ala Ser Phe Ser Ser Val
            180                 185                 190

Gly Ser Glu Leu Glu Val Met Ala Pro Gly Val Ser Ile Leu Ser Thr
        195                 200                 205

Thr Pro Gly Asn Asn Tyr Ser Phe Asn Gly Thr Ser Met Ala Ser
210                 215                 220

Pro His Val Ala Gly Ala Ala Leu Ile Lys Ala Lys Tyr Pro Ser
225                 230                 235                 240

Met Thr Asn Val Gln Ile Arg Glu Lys Leu Lys Asn Thr Ala Thr Asn
                245                 250                 255

Leu Gly Asp Ala Phe Tyr Tyr Gly His Gly Val Ile Asn Val Glu Ser
            260                 265                 270

Ala Leu Gln

<210> SEQ ID NO 86
<211> LENGTH: 275
<212> TYPE: PRT
<213> ORGANISM: Bacillus sp.
<220> FEATURE:
<221> NAME/KEY: misc_feature
<222> LOCATION: (1)..(275)
<223> OTHER INFORMATION: The amino acid sequence of the mature form of
      Bacillus sp. LG12 SprC AAC43580

<400> SEQUENCE: 86

Ala Gln Thr Val Pro Trp Gly Ile Pro His Ile Lys Ala Asp Lys Ala
1               5                   10                  15

His Ala Ala Gly Val Thr Gly Ser Gly Val Lys Val Ala Ile Leu Asp
                20                  25                  30

Thr Gly Ile Asp Ala Asn His Ala Asp Leu Asn Val Lys Gly Gly Ala
            35                  40                  45

Ser Phe Val Ser Gly Glu Pro Asn Ala Leu Gln Asp Gly Asn Gly His
        50                  55                  60

Gly Thr His Val Ala Gly Thr Val Ala Ala Leu Asn Asn Thr Thr Gly
65                  70                  75                  80

Val Leu Gly Val Ala Tyr Asn Ala Asp Leu Tyr Ala Val Lys Val Leu
                85                  90                  95

Ser Ala Ser Gly Ser Gly Thr Leu Ser Gly Ile Ala Gln Gly Ile Glu
            100                 105                 110

Trp Ser Ile Ser Asn Gly Met Asn Val Ile Asn Met Ser Leu Gly Gly
        115                 120                 125

Ser Ser Gly Ser Thr Ala Leu Gln Gln Ala Cys Asn Asn Ala Tyr Asn
130                 135                 140

Arg Gly Ile Val Val Ile Ala Ala Gly Asn Ser Gly Ser Ser Gly
145                 150                 155                 160

Asn Arg Asn Thr Met Gly Tyr Pro Ala Arg Tyr Ser Ser Val Ile Ala
                165                 170                 175

Val Gly Ala Val Ser Ser Asn Asn Thr Arg Ala Ser Phe Ser Ser Val
            180                 185                 190

Gly Ser Glu Leu Glu Val Met Ala Pro Gly Val Asn Ile Leu Ser Thr
        195                 200                 205

Thr Pro Gly Asn Asn Tyr Ala Ser Phe Asn Gly Thr Ser Met Ala Ala
    210                 215                 220

Pro His Val Ala Gly Ala Ala Leu Ile Lys Ala Lys Tyr Pro Ser
225                 230                 235                 240

Met Thr Asn Val Gln Ile Arg Glu Arg Leu Lys Asn Thr Ala Thr Asn
                245                 250                 255

Leu Gly Asp Pro Phe Phe Tyr Gly Lys Gly Val Ile Asn Val Glu Ser
            260                 265                 270

Ala Leu Gln
        275

<210> SEQ ID NO 87
<211> LENGTH: 268
<212> TYPE: PRT
<213> ORGANISM: B. lentus
<220> FEATURE:
<221> NAME/KEY: misc_feature
<222> LOCATION: (1)..(268)
<223> OTHER INFORMATION: The amino acid sequence of the mature form of
      B. lentus P29600

-continued

<400> SEQUENCE: 87

Gln Ser Val Pro Trp Gly Ile Ser Arg Val Gln Ala Pro Ala Ala His
1               5                   10                  15

Asn Arg Gly Leu Thr Gly Ser Gly Val Lys Val Ala Val Leu Asp Thr
            20                  25                  30

Gly Ile Ser Thr His Pro Asp Leu Asn Ile Arg Gly Gly Ala Ser Phe
        35                  40                  45

Val Pro Gly Glu Pro Ser Thr Gln Asp Gly Asn Gly His Gly Thr His
    50                  55                  60

Val Ala Gly Thr Ile Ala Ala Leu Asn Asn Ser Ile Gly Val Leu Gly
65                  70                  75                  80

Val Ala Pro Ser Ala Glu Leu Tyr Ala Val Lys Val Leu Gly Ala Ser
                85                  90                  95

Gly Ser Gly Ser Val Ser Ser Ile Ala Gln Gly Leu Glu Trp Ala Gly
            100                 105                 110

Asn Asn Gly Met His Val Ala Asn Leu Ser Leu Gly Ser Pro Ser Pro
        115                 120                 125

Ser Ala Thr Leu Glu Gln Ala Val Asn Ser Ala Thr Ser Arg Gly Val
    130                 135                 140

Leu Val Val Ala Ala Ser Gly Asn Ser Gly Ala Gly Ser Ile Ser Tyr
145                 150                 155                 160

Pro Ala Arg Tyr Ala Asn Ala Met Ala Val Gly Ala Thr Asp Gln Asn
                165                 170                 175

Asn Asn Arg Ala Ser Phe Ser Gln Tyr Gly Ala Gly Leu Asp Ile Val
            180                 185                 190

Ala Pro Gly Val Asn Val Gln Ser Thr Tyr Pro Gly Ser Thr Tyr Ala
        195                 200                 205

Ser Leu Asn Gly Thr Ser Met Ala Thr Pro His Val Ala Gly Ala Ala
    210                 215                 220

Ala Leu Val Lys Gln Lys Asn Pro Ser Trp Ser Asn Val Gln Ile Arg
225                 230                 235                 240

Asn His Leu Lys Asn Thr Ala Thr Ser Leu Gly Ser Thr Asn Leu Tyr
                245                 250                 255

Gly Ser Gly Leu Val Asn Ala Glu Ala Ala Thr Arg
            260                 265

<210> SEQ ID NO 88
<211> LENGTH: 275
<212> TYPE: PRT
<213> ORGANISM: B. amyloliquefaciens
<220> FEATURE:
<221> NAME/KEY: misc_feature
<222> LOCATION: (1)..(275)
<223> OTHER INFORMATION: The amino acid sequence of the mature form of
      B. amyloliquefaciens CAA24990

<400> SEQUENCE: 88

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

```
Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 89
<211> LENGTH: 268
<212> TYPE: PRT
<213> ORGANISM: Artificial Sequence
<220> FEATURE:
<223> OTHER INFORMATION: Synthetic: consensus sequence

<400> SEQUENCE: 89

Gln Gln Thr Val Pro Trp Gly Ile Thr Arg Val Gln Ala Pro Ala Val
  1               5                  10                  15

His Asn Arg Gly Ile Thr Gly Ser Gly Val Arg Val Ala Ile Leu Asp
                 20                  25                  30

Ser Gly Ile Ser Ala His Ser Asp Leu Asn Ile Arg Gly Gly Ala Ser
             35                  40                  45

Phe Val Pro Gly Glu Pro Thr Thr Ala Asp Leu Asn Gly His Gly Thr
         50                  55                  60

His Val Ala Gly Thr Val Ala Ala Leu Asn Asn Ser Ile Gly Val Ile
 65                  70                  75                  80

Gly Val Ala Pro Asn Ala Glu Leu Tyr Ala Val Lys Val Leu Gly Ala
                 85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Gly Val
    130                 135                 140
```

```
Leu Val Ile Ala Ala Thr Gly Asn Asn Gly Ser Gly Ser Val Gly Tyr
145                 150                 155                 160

Pro Ala Arg Tyr Ala Asn Ala Met Ala Val Gly Ala Thr Asp Gln Asn
                165                 170                 175

Asn Arg Arg Ala Asn Phe Ser Gln Tyr Gly Thr Gly Ile Asp Ile Val
            180                 185                 190

Ala Pro Gly Val Asn Val Gln Ser Thr Tyr Pro Gly Asn Arg Tyr Val
        195                 200                 205

Ser Met Asn Gly Thr Ser Met Ala Thr Pro His Val Ala Gly Ala Ala
    210                 215                 220

Ala Leu Val Lys Gln Arg Tyr Pro Ser Trp Asn Ala Thr Gln Ile Arg
225                 230                 235                 240

Asn His Leu Lys Asn Thr Ala Thr Asn Leu Gly Asn Ser Ser Gln Phe
                245                 250                 255

Gly Ser Gly Leu Val Asn Ala Glu Ala Ala Thr Arg
            260                 265
```
<210> SEQ ID NO 90
<211> LENGTH: 34
<212> TYPE: PRT
<213> ORGANISM: Artificial Sequence
<220> FEATURE:
<223> OTHER INFORMATION: Synthetic: B. gibsonii-clade subtilisin motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (18)..(23)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid

<400> SEQUENCE: 90

```
Asp Xaa Gly Ile Xaa Xaa His Ser Asp Leu Xaa Xaa Xaa Gly Gly Ala
1               5                   10                  15

Ser Xaa Xaa Xaa Xaa Xaa Xaa Thr Thr Ala Asp Leu Xaa Xaa His Gly
            20                  25                  30

Thr His
```

<210> SEQ ID NO 91
<211> LENGTH: 273
<212> TYPE: PRT
<213> ORGANISM: B. licheniformis

<400> SEQUENCE: 91

```
Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45
```

-continued

```
Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65              70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Ala Ala Ala Gly Asn Ser Gly Ser Ser Gly Ser
145             150                 155                 160

Thr Asn Thr Ile Gly Tyr Pro Ala Lys Tyr Asp Ser Val Ile Ala Val
                165                 170                 175

Gly Ala Val Asp Ser Asn Ser Arg Ala Ser Phe Ser Ser Val Gly Ala
                180                 185                 190

Glu Leu Glu Val Met Ala Pro Gly Ala Gly Val Tyr Ser Thr Tyr Pro
            195                 200                 205

Thr Asn Thr Tyr Ala Thr Leu Asn Gly Thr Ser Met Ala Ser Pro His
    210                 215                 220

Val Ala Gly Ala Ala Ala Leu Ile Leu Ser Lys His Pro Asn Leu Ser
225             230                 235                 240

Ala Ser Gln Val Arg Asn Arg Leu Ser Ser Thr Ala Thr Tyr Leu Gly
                245                 250                 255

Ser Ser Phe Tyr Tyr Gly Lys Gly Leu Ile Asn Val Glu Ala Ala Ala
            260                 265                 270

Gln
```

SERINE PROTEASES OF THE BACILLUS GIBSONII-CLADE

CROSS REFERENCE TO RELATED APPLICATIONS

This application is a 371 National Stage application of PCT/US2014/70107, filed on Dec. 12, 2014, which claims benefit of U.S. Provisional Patent Application Nos. 61/915,737, filed 13 Dec. 2013, and 62/069,200, filed 27 Oct. 2014, wherein the contents of both provisional applications are hereby incorporated herein by reference in their entirety.

SEQUENCE LISTING

The sequence listing submitted via EFS, in compliance with 37 C.F.R. § 1.52(e), is incorporated herein by reference. The sequence listing text file submitted via EFS contains the file "2015-01-08_40493-WO-PCT_ST25.txt" created on Feb. 5, 2015, which is 194 kilobytes in size.

FIELD

The present disclosure relates to serine proteases cloned from *Bacillus gibsonii*, and variants thereof. Compositions containing the serine proteases are suitable for use in cleaning fabrics and hard surfaces, as well as in a variety of industrial applications.

BACKGROUND

Serine proteases are enzymes (EC No. 3.4.21) possessing an active site serine that initiates hydrolysis of peptide bonds of proteins. There are two broad categories of serine proteases, based on their structure: chymotrypsin-like (trypsin-like) and *subtilisin*-like. The prototypical subtilisin (EC No. 3.4.21.62) was initially obtained from *B. subtilis*. Subtilisins and their homologues are members of the S8 peptidase family of the MEROPS classification scheme. Members of family S8 have a catalytic triad in the order Asp, His and Ser in their amino acid sequence.

Although serine proteases have long been known in the art of industrial enzymes, there remains a need for further serine proteases that are suitable for particular conditions and uses.

SUMMARY

The present compositions and methods relate to *B gibsonii*-clade subtilisins, including recombinant serine proteases cloned from *Bacillus gibsonii*, and variants thereof. The present compositions and methods further relate to recombinant serine proteases of the *B. gibsonii*-clade generated through conventional molecular biology techniques (see, e.g., Sambrook et al, Molecular Cloning: Cold Spring Harbor Laboratory Press). Compositions containing the serine proteases are suitable for use in cleaning fabrics and hard surfaces, as well as in a variety of industrial applications.

Some embodiments are directed to a recombinant polypeptide, or an active fragment thereof, of the *B. gibsonii*-clade, wherein the recombinant polypeptide or active fragment thereof has proteolytic activity. Other embodiments are directed to a recombinant polypeptide, or an active fragment thereof, of the *B. gibsonii*-clade, wherein the recombinant polypeptide or active fragment thereof has proteolytic activity, with the proviso that the *B. gibsonii*-clade does not comprise WO03054184-CAE48421, WO2007131657-CAS91385, WO2008086916-CAV33594, or NCBI Accession No. AGS78407.

Other embodiments are directed to a recombinant polypeptide, or active fragment thereof, of the *B. gibsonii*-clade that has proteolytic activity and comprises a DXGIXXHSDLXXXGGASXXXXXPTTADLNXHGTH (SEQ ID NO:47) or DXGIXXHSDLXXXGGASXXXXXXTTADLXXHGTH (SEQ ID NO:90) motif, wherein the initial D is the active site Aspartic acid residue and the penultimate H is the active site Histidine, and X is any amino acid. Another embodiment is directed to a recombinant polypeptide, or active fragment thereof, of the *B. gibsonii*-clade that has proteolytic activity and comprises an amino acid sequence of SEQ ID NO:47 or 90, wherein the initial D is the active site Aspartic acid residue and the penultimate H is the active site Histidine, and X is any amino acid, with the proviso that the *B. gibsonii*-clade does not comprise WO03054184-CAE48421, WO2007131657-CAS91385, WO2008086916-CAV33594, or NCBI Accession No. AGS78407.

Yet a further embodiment is directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:4, 7, 11, 15, 19, 23, 49, 50, 51, 52, 57, 59, 61, 63, 65, 67, 69, 71, 73, 75, 77, 79, 81, or 83.

Yet a further embodiment is directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:11, 15, 19, 23, 49, 50, 51, 52, 57, 59, 61, 63, 65, 67, 69, 71, 73, 75, 77, 79, 81, or 83.

Yet a further embodiment is directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO: 57, 59, 61, 63, 65, 67, 69, 71, 73, 75, 77, 79, 81, or 83.

Still further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:4, 7, 11, 15, 19, 23, 49, 50, 51, 52, 57, 59, 61, 63, 65, 67, 69, 71, 73, 75, 77, 79, 81, or 83, with the proviso that the *B. gibsonii*-clade does not comprise WO03054184-CAE48421, WO2007131657-CAS91385, WO2008086916-CAV33594, or NCBI Accession No. AGS78407.

Still further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the *B. gibsonii*-clade does not comprise WO03054184-CAE48421, WO2007131657-CA591385, WO2008086916-CAV33594, or NCBI Accession No. AGS78407.

Still further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:57, 59, 61, 63, 65, 67, 69, 71, 73, 75, 77, 79, 81, or 83, with the proviso that the *B. gibsonii*-clade does not comprise WO03054184-CAE48421, WO2007131657-CAS91385, WO2008086916-CAV33594, or NCBI Accession No. AGS78407.

Yet further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:4, 7, 11, 15, 19, 23, 49, 50, 51, 52, 57, 59, 61, 63, 65, 67, 69, 71, 73, 75, 77, 79, 81, or 83, with the proviso that the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83 does not comprise WO03054184-CAE48421 or WO2007131657-CAS91385.

Yet further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the amino acid sequence of SEQ ID NO:11, 15, 19, 23, 49, 50, 51, 52, 57, 59, 61, 63, 65, 67, 69, 71, 73, 75, 77, 79, 81, or 83 does not comprise WO03054184-CAE48421 or WO2007131657-CA591385.

Yet further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:57, 59, 61, 63, 65, 67, 69, 71, 73, 75, 77, 79, 81, or 83, with the proviso that the amino acid sequence of SEQ ID NO:57, 59, 61, 63, 65, 67, 69, 71, 73, 75, 77, 79, 81, or 83 does not comprise WO03054184-CAE48421 or WO2007131657-CAS91385.

Yet further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:4, 7, 11, 15, 19, 23, 49, 50, 51, 52, 57, 59, 61, 63, 65, 67, 69, 71, 73, 75, 77, 79, 81, or 83, with the proviso that the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83 does not comprise WO03054184-CAE48421, WO2007131657-CAS91385, or NCBI Accession No. AGS78407.

Yet further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the amino acid sequence of SEQ ID NO:11, 15, 19, 23, 49, 50, 51, 52, 57, 59, 61, 63, 65, 67, 69, 71, 73, 75, 77, 79, 81, or 83 does not comprise WO03054184-CAE48421, WO2007131657-CAS91385, or NCBI Accession No. AGS78407.

Yet further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:57, 59, 61, 63, 65, 67, 69, 71, 73, 75, 77, 79, 81, or 83, with the proviso that the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83 does not comprise WO03054184-CAE48421, WO2007131657-CAS91385, or NCBI Accession No. AGS78407.

A yet further embodiment is directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:4, 7, 11, 15, 19, 23, 49, 50, 51, 52, 57, 59, 61, 63, 65, 67, 69, 71, 73, 75, 77, 79, 81, or 83, with the proviso that the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83 does not comprise WO03054184-CAE48421 or WO2007131657-CAS91385, and with the further proviso that the *B. gibsonii*-clade does not comprise WO03054184-CAE48421, WO2007131657-CAS91385 or WO2008086916-CAV33594.

A yet further embodiment is directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the amino acid sequence of SEQ ID NO:11, 15, 19, 23, 49, 50, 51, 52, 57, 59, 61, 63, 65, 67, 69, 71, 73, 75, 77, 79, 81, or 83 does not comprise WO03054184-CAE48421 or WO2007131657-CAS91385, and with the further proviso that the *B. gibsonii*-clade does not comprise WO03054184-CAE48421, WO2007131657-CAS91385 or WO2008086916-CAV33594.

A yet further embodiment is directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:57, 59, 61, 63, 65, 67, 69, 71, 73, 75, 77, 79, 81, or 83, with the proviso that the amino acid sequence of SEQ ID NO:57, 59, 61, 63, 65, 67, 69, 71, 73, 75, 77, 79, 81, or 83 does not comprise WO03054184-CAE48421 or WO2007131657-CAS91385, and with the further proviso that the *B. gibsonii*-clade does not comprise WO03054184-CAE48421, WO2007131657-CAS91385 or WO2008086916-CAV33594.

A yet further embodiment is directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:4, 7, 11, 15, 19, 23, 49, 50, 51, 52, 57, 59, 61, 63, 65, 67, 69, 71, 73, 75, 77, 79, 81, or 83, with the proviso that the amino acid sequence of SEQ ID NO: 4, 7, 11, 15, 19, 23, 49, 50, 51, 52, 57, 59, 61, 63, 65, 67, 69, 69, 71, 75, 77, 79, 81, or 83 does not comprise WO03054184-CAE48421, WO2007131657-CAS91385, and NCBI Accession No. AGS78407, and with the further proviso that the *B. gibsonii*-clade does not comprise WO03054184-CAE48421, WO2007131657-CAS91385, WO2008086916-CAV33594, or NCBI Accession No. AGS78407.

A yet further embodiment is directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the amino acid sequence of SEQ ID NO:11, 15, 19, 23, 49, 50, 51, 52, 57, 59, 61, 63, 65, 67, 69, 71, 73, 75, 77, 79, 81, or 83 does not comprise WO03054184-CAE48421, WO2007131657-CAS91385, and NCBI Accession No. AGS78407, and with the further proviso that the *B. gibsonii*-clade does not comprise WO03054184-CAE48421, WO2007131657-CAS91385, WO2008086916-CAV33594, or NCBI Accession No. AGS78407.

A yet further embodiment is directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 or 90 further comprises an amino acid sequence having at least 70% identity to the amino acid sequence of SEQ ID NO:57, 59, 61, 63, 65, 67, 69, 71, 73, 75, 77, 79, 81, or 83, with the proviso that the amino acid sequence of SEQ ID NO:57, 59, 61, 63, 65, 67, 69, 71, 73, 75, 77, 79, 81, or 83 does not comprise WO03054184-CAE48421, WO2007131657-CAS91385, and NCBI Accession No. AGS78407, and with the further proviso that the *B. gibsonii*-clade does not comprise WO03054184-CAE48421, WO2007131657-CAS91385, WO2008086916-CAV33594, or NCBI Accession No. AGS78407.

Still further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 further comprises an amino acid sequence having at least 70% identity to the amino acid sequence of SEQ ID NO:4, 7, 11, 15, 19, 23, 49, 50, 51, or 52.

Yet further embodiments are directed to a recombinant polypeptide, or active fragment thereof, of the *B. gibsonii*-clade, wherein the recombinant polypeptide, or the active fragment thereof, having proteolytic activity and comprising an amino acid sequence of SEQ ID NO:47 further comprises an amino acid sequence having at least 70% identity to the amino acid sequence of SEQ ID NO:4, 7, 11, 15, 19, 23, 49, 50, 51, or 52, with the proviso that the amino acid sequence of SEQ ID NO:4, 7, 11, 15, 19, 23, 49, 50, 51, or 52 does not comprise WO03054184-CAE48421 or WO2007131657-CAS91385.

In some embodiments, the invention is a recombinant polypeptide, or an active fragment thereof, having proteolytic activity, comprising an amino acid sequence having at least 95% identity to the amino acid sequence of SEQ ID NO:4, 7, 11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421 or WO2007131657-CAS91385.

In some embodiments, the invention is a recombinant polypeptide, or an active fragment thereof, having proteolytic activity, comprising an amino acid sequence having at least 95% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421 or WO2007131657-CAS91385.

In some embodiments, the invention is a recombinant polypeptide, or an active fragment thereof, having proteolytic activity, comprising an amino acid sequence having at least 95% identity to the amino acid sequence of SEQ ID NO:57, 59, 61, 63, 65, 67, 69, 71, 73, 75, 77, 79, 81, or 83, with the proviso that the amino acid sequence does not comprise WO03054184-CAE48421 or WO2007131657-CAS91385.

In some embodiments, the invention is a recombinant polypeptide, or an active fragment thereof, having proteolytic activity, comprising an amino acid sequence having at least 95% identity to the amino acid sequence of SEQ ID NO:4, 7, 11, 15, 19, 23, 49, 50, 51, 52, 59, 61, 63, 65, 67, 69, 71, 73, 75, 77, 79, 81, or 83, with the proviso that the amino acid sequence does not comprise WO03054184-CAE48421, WO2007131657-CAS91385, or NCBI Accession No. AGS78407.

In some embodiments, the invention is a recombinant polypeptide, or an active fragment thereof, having proteolytic activity, comprising an amino acid sequence having at least 95% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421, WO2007131657-CAS91385, or NCBI Accession No. AGS78407.

In some embodiments, the invention is a recombinant polypeptide, or an active fragment thereof, having proteolytic activity, comprising an amino acid sequence having at least 95% identity to the amino acid sequence of SEQ ID NO:57, 59, 61, 63, 65, 67, 69, 71, 73, 75, 77, 79, 81, or 83, with the proviso that the amino acid sequence does not comprise WO03054184-CAE48421, WO2007131657-CAS91385, or NCBI Accession No. AGS78407.

In some embodiments, the invention is a recombinant polypeptide or an active fragment thereof having proteolytic activity, comprising an amino acid sequence having at least 95% identity to the amino acid sequence of SEQ ID NO:4, 7, 11, 15, 19, 23, 49, 50, 51, or 52, with the proviso that the amino acid sequence does not comprise WO03054184-CAE48421 or WO2007131657-CAS91385.

In some embodiments, the invention is a recombinant polypeptide or an active fragment thereof having proteolytic activity, comprising an amino acid sequence having at least 95% identity to the amino acid sequence of SEQ ID NO:4, 7, 11, 15, 19, or 23, with the proviso that the amino acid sequence does not comprise WO03054184-CAE48421 or WO2007131657-CAS91385.

In some embodiments, at least one of the foregoing recombinant polypeptides has protease activity, specifically casein hydrolysis. In some embodiments, at least one of the recombinant polypeptides retains at least 50% of its maximal protease activity at a pH range of 8 to 12. In some embodiments, at least one of the recombinant polypeptides retains at least 50% of its maximal protease activity at a temperature range of 50° C. to 75° C. In some embodiments, at least one of the recombinant polypeptides has cleaning activity in a detergent composition, including, for example, an automatic dish washing detergent and a laundry detergent.

In some embodiments, the invention is a composition comprising a surfactant and at least one of the recombinant polypeptides stated above. In some embodiments, the surfactant is selected from the group consisting of a non-ionic surfactant, an anionic surfactant, a cationic surfactant, a zwitterionic surfactant, an ampholytic surfactant, a semipolar non-ionic surfactant, and a combination thereof. In some embodiments, the composition is a detergent composition, such as a laundry detergent, a fabric softening detergent, a dishwashing detergent, and a hard-surface cleaning detergent. In some embodiments, the composition further comprises at least one calcium ion and/or zinc ion, at least one stabilizer, at least one bleaching agent, phosphate, or borate. In some embodiments the composition is phosphate-free and/or borate-free. In some embodiments, the composition is a granular, powder, solid, bar, liquid, tablet, gel, paste or unit dose composition. In some embodiments, the composition further comprising one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1,4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, perhydrolase, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, metalloproteases, additional serine proteases, and combinations thereof.

In some embodiments, the invention is a method of cleaning, comprising contacting a surface or an item with a composition listed above. In some embodiments, the invention is a method for producing a recombinant polypeptide comprising stably transforming a host cell with an expression vector comprising a polynucleotide encoding at least one of the recombinant polypeptides above.

Still other embodiments are directed to a polynucleotide comprising a nucleic acid sequence that: (i) encodes an amino acid sequence of SEQ ID NO:47 or 90; (ii) encodes an amino acid sequence of SEQ ID NO:47 or 90 and further encodes an amino acid sequence having 70% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83; iii) encodes an amino acid sequence having 70% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83; (iv) has at least 70% identity to SEQ ID NO:1, 8, 12, 16, 20, 53, 54, 55, 56, 58, 60, 62, 64, 66, 68, 70, 72, 74, 76, 78, 80, or 82; or (v) having complementarity to SEQ ID NO:1, 8, 12, 16, 20, 53, 54, 55, 56, 58, 60, 62, 64, 66, 68, 70, 72, 74, 76, 78, 80, or 82.

Still other embodiments are directed to a polynucleotide comprising a nucleic acid sequence that: (i) encodes an amino acid sequence of SEQ ID NO:47 or 90; (ii) encodes an amino acid sequence of SEQ ID NO:47 or 90 and further encodes an amino acid sequence having 70% identity to an amino acid sequence of SEQ ID NO:11, 15, 19, 23, 49, 50, 51, 52, 57, 59, 61, 63, 65, 67, 69, 71, 73, 75, 77, 79, 81, or 83; iii) encodes an amino acid sequence having 70% identity to an amino acid sequence of SEQ ID NO:11, 15, 19, 23, 49, 50, 51, 52, 57, 59, 61, 63, 65, 67, 69, 71, 73, 75, 77, 79, 81, or 83; (iv) has at least 70% identity to SEQ ID NO: 8, 12, 16, 20, 53, 54, 55, 56, 58, 60, 62, 64, 66, 68, 70, 72, 74, 76, 78, 80, or 82; or (v) having complementarity to SEQ ID NO:8, 12, 16, 20, 53, 54, 55, 56, 58, 60, 62, 64, 66, 68, 70, 72, 74, 76, 78, 80, or 82.

Still other embodiments are directed to a polynucleotide comprising a nucleic acid sequence that: (i) encodes an amino acid sequence of SEQ ID NO:47 or 90; (ii) encodes an amino acid sequence of SEQ ID NO:47 or 90 and further encodes an amino acid sequence having 70% identity to an amino acid sequence of SEQ ID NO:57, 59, 61, 63, 65, 67, 69, 71, 73, 75, 77, 79, 81, or 83; iii) encodes an amino acid sequence having 70% identity to an amino acid sequence of SEQ ID NO:57, 59, 61, 63, 65, 67, 69, 71, 73, 75, 77, 79, 81, or 83; (iv) has at least 70% identity to SEQ ID NO:53, 54, 55, 56, 58, 60, 62, 64, 66, 68, 70, 72, 74, 76, 78, 80, or 82; or (v) having complementarity to SEQ ID NO:53, 54, 55, 56, 58, 60, 62, 64, 66, 68, 70, 72, 74, 76, 78, 80, or 82.

Yet other embodiments are directed to a polynucleotide comprising a nucleic acid sequence that: (i) encodes an amino acid sequence of SEQ ID NO:47 or 90; (ii) encodes an amino acid sequence of SEQ ID NO:47 or 90 and further encodes an amino acid sequence having 70% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83; iii) encodes an amino acid sequence having 70% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83; (iv) has at least 70% identity to SEQ ID NO:1, 8, 12, 16, 20, 53, 54, 55, 56, 58, 60, 62, 64, 66, 68, 70, 72, 74, 76, 78, 80, or 82; or (v) having complementarity to SEQ ID NO:1, 8, 12, 16, 20, 53, 54, 55, 56, 58, 60, 62, 64, 66, 68, 70, 72, 74, 76, 78, 80, or 82; with the proviso that the nucleic acid sequence does not encode an amino acid sequence comprising WO03054184-CAE48421 or WO2007131657-CAS91385.

Yet other embodiments are directed to a polynucleotide comprising a nucleic acid sequence that: (i) encodes an amino acid sequence of SEQ ID NO:47 or 90; (ii) encodes an amino acid sequence of SEQ ID NO:47 or 90 and further encodes an amino acid sequence having 70% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83; iii) encodes an amino acid sequence having 70% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83; (iv) has at least 70% identity to SEQ ID NO:1, 8, 12, 16, 20, 53, 54, 55, 56, 58, 60, 62, 64, 66, 68, 70, 72, 74, 76, 78, 80, or 82; or (v) having complementarity to SEQ ID NO:1, 8, 12, 16, 20, 53, 54, 55, 56, 58, 60, 62, 64, 66, 68, 70, 72, 74, 76, 78, 80, or 82; with the proviso that the nucleic acid sequence does not encode an amino acid sequence comprising WO03054184-CAE48421, WO2007131657-CAS91385, or NCBI Accession No. AGS78407.

Yet other embodiments are directed to a polynucleotide comprising a nucleic acid sequence that: (i) encodes an amino acid sequence of SEQ ID NO:47 or 90; (ii) encodes an amino acid sequence of SEQ ID NO:47 or 90 and further encodes an amino acid sequence having 70% identity to an amino acid sequence of SEQ ID NO:11, 15, 19, 23, 49, 50, 51, 52, 57, 59, 61, 63, 65, 67, 69, 71, 73, 75, 77, 79, 81, or 83; iii) encodes an amino acid sequence having 70% identity to an amino acid sequence of SEQ ID NO:11, 15, 19, 23, 49, 50, 51, 52, 57, 59, 61, 63, 65, 67, 69, 71, 73, 75, 77, 79, 81, or 83; (iv) has at least 70% identity to SEQ ID NO:8, 12, 16, 20, 53, 54, 55, 56, 58, 60, 62, 64, 66, 68, 70, 72, 74, 76, 78, 80, or 82; or (v) having complementarity to SEQ ID NO:8, 12, 16, 20, 53, 54, 55, 56, 58, 60, 62, 64, 66, 68, 70, 72, 74, 76, 78, 80, or 82; with the proviso that the nucleic acid sequence does not encode an amino acid sequence comprising WO03054184-CAE48421 or WO2007131657-CAS91385.

Yet other embodiments are directed to a polynucleotide comprising a nucleic acid sequence that: (i) encodes an amino acid sequence of SEQ ID NO:47 or 90; (ii) encodes an amino acid sequence of SEQ ID NO:47 or 90 and further encodes an amino acid sequence having 70% identity to an amino acid sequence of SEQ ID NO:11, 15, 19, 23, 49, 50, 51, 52, 57, 59, 61, 63, 65, 67, 69, 71, 73, 75, 77, 79, 81, or 83; iii) encodes an amino acid sequence having 70% identity to an amino acid sequence of SEQ ID NO:11, 15, 19, 23, 49, 50, 51, 52, 57, 59, 61, 63, 65, 67, 69, 71, 73, 75, 77, 79, 81, or 83; (iv) has at least 70% identity to SEQ ID NO:8, 12, 16, 20, 53, 54, 55, 56, 58, 60, 62, 64, 66, 68, 70, 72, 74, 76, 78, 80, or 82; or (v) having complementarity to SEQ ID NO: 8, 12, 16, 20, 53, 54, 55, 56, 58, 60, 62, 64, 66, 68, 70, 72, 74, 76, 78, 80, or 82; with the proviso that the nucleic acid sequence does not encode an amino acid sequence comprising WO03054184-CAE48421, WO2007131657-CAS91385, or NCBI Accession No. AGS78407.

Yet other embodiments are directed to a polynucleotide comprising a nucleic acid sequence that: (i) encodes an amino acid sequence of SEQ ID NO:47 or 90; (ii) encodes an amino acid sequence of SEQ ID NO:47 or 90 and further encodes an amino acid sequence having 70% identity to an amino acid sequence of SEQ ID NO:57, 59, 61, 63, 65, 67, 69, 71, 73, 75, 77, 79, 81, or 83; iii) encodes an amino acid sequence having 70% identity to an amino acid sequence of SEQ ID NO:57, 59, 61, 63, 65, 67, 69, 71, 73, 75, 77, 79, 81, or 83; (iv) has at least 70% identity to SEQ ID NO:53, 54, 55, 56, 58, 60, 62, 64, 66, 68, 70, 72, 74, 76, 78, 80, or 82; or (v) having complementarity to SEQ ID NO: 53, 54, 55, 56, 58, 60, 62, 64, 66, 68, 70, 72, 74, 76, 78, 80, or 82; with the proviso that the nucleic acid sequence does not encode an amino acid sequence comprising WO03054184-CAE48421 or WO2007131657-CAS91385.

Yet other embodiments are directed to a polynucleotide comprising a nucleic acid sequence that: (i) encodes an amino acid sequence of SEQ ID NO:47 or 90; (ii) encodes an amino acid sequence of SEQ ID NO:47 or 90 and further encodes an amino acid sequence having 70% identity to an amino acid sequence of SEQ ID NO:57, 59, 61, 63, 65, 67, 69, 71, 73, 75, 77, 79, 81, or 83; iii) encodes an amino acid sequence having 70% identity to an amino acid sequence of SEQ ID NO:57, 59, 61, 63, 65, 67, 69, 71, 73, 75, 77, 79, 81, or 83; (iv) has at least 70% identity to SEQ ID NO:53, 54, 55, 56, 58, 60, 62, 64, 66, 68, 70, 72, 74, 76, 78, 80, or 82; or (v) having complementarity to SEQ ID NO:53, 54, 55, 56, 58, 60, 62, 64, 66, 68, 70, 72, 74, 76, 78, 80, or 82; with the proviso that the nucleic acid sequence does not encode an amino acid sequence comprising WO03054184-CAE48421, WO2007131657-CAS91385, or NCBI Accession No. AGS78407.

Some embodiments are directed to a polynucleotide comprising a nucleic acid sequence: (i) encoding an amino acid sequence having at least 70% identity to an amino acid sequence of SEQ ID NO:4, 7, 11, 15, 19, 23, 49, 50, 51, or 52; (ii) having at least 70% identity to SEQ ID NO:1, 6, 8, 12, 16, or 20; or (iii) having complementarity to SEQ ID NO:1, 6, 8, 12, 16, or 20.

BRIEF DESCRIPTION OF THE DRAWINGS

FIG. 4A-C provides an alignment of the amino acid sequence of the predicted mature form of Bgi02446 (SEQ ID NO:4) with the sequences of various bacterial serine proteases (SEQ ID NOs:24-44). A consensus sequence is shown below the alignment (SEQ ID NO:45).

FIG. 5 provides an alignment of the amino acid sequence of the predicted mature form of Bgi02446 (SEQ ID NO:4) with the amino acid sequences of serine proteases of other B. gibsonii-clade subtilisins (SEQ ID NOs:11, 15, 19 and 23).

FIG. 8A-B provides the structural alignment Bgi02446 (referred to in the figure as "BG46"), DSM9728, and DSM9731 with subtilisin BPN' from B. amyloliquefaciens (pdb 2ST1.a), subtilisin Carlsberg from B. licheniformis (pdb 3UNX.a), and the subtilisin from B. lentus (pdb 1JEA.a). Highlighted is a region of the structure-based alignment in which subtilisins DSM 9728, DSM 9731, and Bgi02446 sequences show a common motif extending between Asp (D)31 and His (H)64.

FIG. 10A-10C provides an alignment of the amino acid sequence of the B. gibsonii-clade proteases (SEQ ID NOs: 4, 11, 23, 57, 59, 61, 63, 65, 67, 69, 71, 73, 75, 77, 79, 81, and 83). A consensus sequence is shown below the alignment (SEQ ID NO:89).

DETAILED DESCRIPTION

Figure 1:
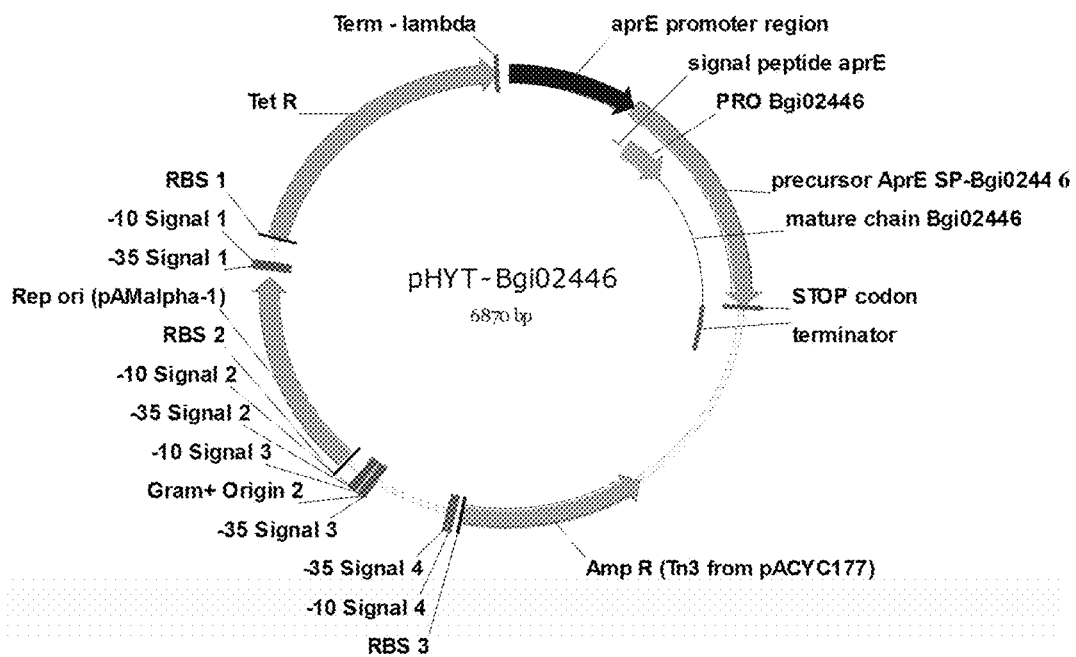
FIG. 1 provides a plasmid map of pHYT-Bgi02446 for expression of the Bgi02446 serine protease.

Described are compositions and methods relating to recombinant serine proteases from *B. gibsonii*-clade strains DSM 8722, DSM 9728, DSM 9729, DSM 9730, and DSM 9731. Further described are compositions and methods relating to recombinant serine proteases of the *B. gibsonii*-clade that are generated through conventional molecular biology techniques (see, e.g., Sambrook et al, Molecular Cloning: Cold Spring Harbor Laboratory Press). The compositions and methods are based, in part, on the observation that recombinant Bgi02446 has protease activity in the presence of a surfactant, in basic reaction conditions, and at elevated temperatures. The compositions and methods are further based, in part, on the observation that recombinant SEQ ID NO:4, 7, 11, 15, 19, 23, 49, 50, 51, 52, 57, 59, 61, 63, 65, 67, 69, 71, 73, 75, 77, 79, 81, or 83 have protease activity in the presence of a surfactant, in basic reaction conditions, and at elevated temperatures. These features of Bgi02446 subtilisin, make these *B. gibsonii*-clade subtilisins well suited for use in cleansing fabrics and hard surfaces, as well as in textile, leather and feather processing. Bgi02446, DSM 9728, DSM 9729, DSM 9730, DSM 9731, BG1-B08, BG1-C05, BG2-B08, BG2-D10, BG2-G08, BG4-A09, BG4-D10, BG5-E02, BG5-E05, BG5-F02, BG5-G10, BG6-A10, BG6-D08, and BG8-B03 subtilisins are also well suited for inclusion in compositions for protein degradation, including but not limited to laundry and dish washing detergents. Bgi02446, DSM 9728, DSM 9729, DSM 9730, DSM 9731, BG1-B08, BG1-C05, BG2-B08, BG2-D10, BG2-G08, BG4-A09, BG4-D10, BG5-E02, BG5-E05, BG5-F02, BG5-G10, BG6-A10, BG6-D08, and BG8-B03 subtilisins are also suited for inclusion in personal care compositions, as well as human food and animal feed applications.

I. Definitions

Prior to describing the present compositions and methods in detail, the following terms are defined for clarity. Terms and abbreviations not defined should be accorded their ordinary meaning as used in the art. Unless defined otherwise herein, all technical and scientific terms used herein have the same meaning as commonly understood by one of ordinary skill in the art. Unless otherwise indicated, the practice of the present disclosure involves conventional techniques commonly used in molecular biology, protein engineering, and microbiology. Although any methods and materials similar or equivalent to those described herein find use in the practice of the present disclosure, some suitable methods and materials are described herein. The terms defined immediately below are more fully described by reference to the Specification as a whole.

As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. It is to be understood that this disclosure is not limited to the particular methodology, protocols, and reagents described herein, absent an indication to the contrary.

It is intended that every maximum numerical limitation given throughout this Specification includes every lower numerical limitation, as if such lower numerical limitations were expressly written herein. Every minimum numerical limitation given throughout this Specification will include every higher numerical limitation, as if such higher numerical limitations were expressly written herein. Every numerical range given throughout this Specification will include every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

As used herein, the terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity. For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011 and U.S. Pat. No. 6,376,450). The pNA peptidyl assay (See e.g., Del Mar et al., Anal Biochem, 99:316-320, 1979) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 410 nm on a spectrophotometer and is proportional to the active enzyme concentration. In addition, absorbance measurements at 280 nanometers (nm) can be used to determine the total protein concentration in a sample of purified protein. The activity on substrate/protein concentration gives the enzyme specific activity.

The term "variant," with respect to a polypeptide, refers to a polypeptide that differs from a specified wild-type, parental, or reference polypeptide in that it includes one or more naturally-occurring or man-made substitutions, insertions, or deletions of an amino acid. Similarly, the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. gibsonii, B. pabuli, B. cereus, B. agaradhaerens, B akibai, B. clarkii*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores under stressful environmental conditions is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

As used herein, the term "mutation" refers to changes made to a reference amino acid or nucleic acid sequence. It is intended that the term encompass substitutions, insertions and deletions.

As used herein, the term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multicloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein, the term "expression cassette," "expression plasmid" or "expression vector" refers to a nucleic acid construct or vector generated recombinantly or synthetically for the expression of a nucleic acid of interest in a target cell. An expression vector or expression cassette typically comprises a promoter nucleotide sequence that drives expression of the foreign nucleic acid. The expression vector or cassette also typically includes any other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Many prokaryotic and eukaryotic expression vectors are commercially available.

As used herein, a "plasmid" refers to an extrachromosomal DNA molecule which is capable of replicating independently from the chromosomal DNA. A plasmid is double stranded (ds) and may be circular and is typically used as a cloning vector.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction. Transformation refers to the genetic alteration of a cell which results from the uptake, optional genomic incorporation, and expression of genetic material (e.g., DNA).

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

As used herein the term "gene" refers to a polynucleotide (e.g., a DNA segment), that encodes a polypeptide and includes regions preceding and following the coding regions. In some instances a gene includes intervening sequences (introns) between individual coding segments (exons).

As used herein, "recombinant" when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination" and "recombining" of polynucleotides or nucleic acids refer generally to the assembly or combining of two or more nucleic acid or polynucleotide strands or fragments to generate a new polynucleotide or nucleic acid.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms "host strain" and "host cell" refer to a suitable host for an expression vector comprising a DNA sequence of interest.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code. Mutations can be named by the one letter code for the parent amino acid, followed by a position number and then the one letter code for the variant amino acid. For example, mutating glycine (G) at position 87 to serine (S) is represented as "G087S" or "G87S. When describing modifications, a position followed by amino acids listed in parentheses indicates a list of substitutions at that position by any of the listed amino acids. For example, 6(L,I) means position 6 can be substituted with a leucine or isoleucine. At times, in a sequence, a slash (/) is used to define substitutions, e.g. F/V, indicates that the particular position may have a phenylalanine or valine at that position.

A "prosequence" or "propeptide sequence" refers to an amino acid sequence between the signal peptide sequence and mature protease sequence that is necessary for the proper folding and secretion of the protease; they are sometimes referred to as intramolecular chaperones. Cleavage of the prosequence or propeptide sequence results in a mature active protease. Bacterial serine proteases are often expressed as pro-enzymes.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wild-type" in reference to an amino acid sequence or nucleic acid sequence indicates that the amino acid sequence or nucleic acid sequence is a native or naturally-occurring sequence. As used herein, the term "naturally-occurring" refers to anything (e.g., proteins, amino acids, or nucleic acid sequences) that is found in nature. Conversely, the term "non-naturally occurring" refers to anything that is not found in nature (e.g., recombinant nucleic acids and protein sequences produced in the laboratory or modification of the wild-type sequence).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related proteins or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity that are naturally produced by *Bacillus*, as well as to serine proteases like those produced by *Bacillus* sources but which through the use of genetic engineering techniques are produced by other host cells transformed with a nucleic acid encoding the serine proteases.

The term "identical" in the context of two polynucleotide or polypeptide sequences refers to the nucleic acids or amino acids in the two sequences that are the same when aligned for maximum correspondence, as measured using sequence comparison or analysis algorithms.

As used herein, "% identity" or percent identity" or "PID" refers to protein sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous proteases" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul SF, Madde TL, Shaffer AA, Zhang J, Zhang Z, Miller W, Lipman DJ. Gapped BLAST and PSI BLAST a new generation of protein database search programs. Nucleic Acids Res 1997 Set 1; 25(17):3389-402). Using this information, proteins sequences can be grouped. A phylogenetic tree can be built using the amino acid sequences Amino acid sequences can be entered in a program such as the Vector NTI Advance suite and a Guide Tree can be created using the Neighbor Joining (NJ) method (Saitou and Nei, Mol Biol Evol, 4:406-425, 1987). The tree construction can be calculated using Kimura's correction for sequence distance and ignoring positions with gaps. A program such as AlignX can display the calculated distance values in parenthesis following the molecule name displayed on the phylogenetic tree.

Understanding the homology between molecules can reveal the evolutionary history of the molecules as well as information about their function; if a newly sequenced protein is homologous to an already characterized protein, there is a strong indication of the new protein's biochemical function. The most fundamental relationship between two entities is homology; two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system.

The CLUSTAL W algorithm is another example of a sequence alignment algorithm (See, Thompson et al., Nucleic Acids Res, 22:4673-4680, 1994). Default parameters for the CLUSTAL W algorithm include: Gap opening penalty=10.0; Gap extension penalty=0.05; Protein weight matrix=BLOSUM series; DNA weight matrix=IUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues×100) relative to the "reference" polypeptide. Such a variant would be encompassed by a variant having "at least 99% sequence identity" to the polypeptide.

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than a starting composition.

As used herein, the term "functional assay" refers to an assay that provides an indication of a protein's activity. In some embodiments, the term refers to assay systems in which a protein is analyzed for its ability to function in its usual capacity. For example, in the case of a protease, a functional assay involves determining the effectiveness of the protease to hydrolyze a proteinaceous substrate.

The term "cleaning activity" refers to a cleaning performance achieved by a serine protease polypeptide or reference protease under conditions prevailing during the proteolytic, hydrolyzing, cleaning, or other process of the disclosure. In some embodiments, cleaning performance of a serine protease polypeptide or reference protease may be determined by using various assays for cleaning one or more various enzyme sensitive stains on an item or surface (e.g., a stain resulting from food, grass, blood, ink, milk, oil, and/or egg protein). Cleaning performance of a variant or reference protease can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO 99/34011 and U.S. Pat. No. 6,605,458, both of which are herein incorporated by reference, as well as those cleaning assays and methods included in the Examples provided below.

The term "cleaning effective amount" of a serine protease polypeptide or reference protease refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "cleaning adjunct material" refers to any liquid, solid, or gaseous material included in cleaning composition other than a serine protease polypeptide of the disclosure. In some embodiments, the cleaning compositions of the present disclosure include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage form all-purpose washing agents, especially the so-called heavy-duty liquid (HDL) detergent or heavy-duty dry (HDD) detergent types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., non-fabric) surface cleaning compositions, including, but not limited to for example, hand or manual or automatic dishwashing detergent compositions, oral cleaning compositions, denture cleaning compositions, contact lens cleaning compositions, wound debridement compositions, and personal cleansing compositions.

As used herein, the term "detergent composition" or "detergent formulation" is used in reference to a composition intended for use in a wash medium for the cleaning of soiled or dirty objects, including particular fabric and/or non-fabric objects or items. Such compositions of the present disclosure are not limited to any particular detergent composition or formulation. Indeed, in some embodiments, the detergents of the disclosure comprise at least one serine protease polypeptide of the disclosure and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the disclosure, such as, but not limited to, cleaning compositions or detergent compositions, do not contain any phosphate (e.g., phosphate salt or phosphate builder).

As used herein, the term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc.

As used herein, "wash performance" of a protease (e.g., a serine protease polypeptide of the disclosure) refers to the contribution of a serine protease polypeptide to washing that provides additional cleaning performance to the detergent as compared to the detergent without the addition of the serine protease polypeptide to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The term "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

As used herein, the term "disinfecting" refers to the removal of contaminants from the surfaces, as well as the inhibition or killing of microbes on the surfaces of items. It is not intended that the present disclosure be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

II. Serine Protease Polypeptides

The present disclosure provides novel serine protease enzymes. The serine protease polypeptides of the present disclosure include isolated, recombinant, substantially pure, or non-naturally occurring polypeptides. In some embodiments, the polypeptides are useful in cleaning applications and can be incorporated into cleaning compositions that are useful in methods of cleaning an item or a surface in need thereof.

In some embodiments, the invention is a *B. gibsonii*-clade of subtilisins.

In other embodiments, the *B. gibsonii*-clade subtilisins are characterized by a DXGIXXHSDLXXXGGASXXXXXPTTADLNXHGTH (SEQ ID NO: 47) or DXGIXXHSDLXXXGGASXXXXXXTTADLXXHGTH (SEQ ID NO:90) motif, wherein the initial D is the active site Aspartic acid residue and the penultimate H is the active site Histidine, and X is any amino acid. In still other embodiments, the *B. gibsonii*-clade subtilisins are characterized by a DXGIXXHSDLXXXGGASXXXXXPTTADLNXHGTH (SEQ ID NO: 47) motif, wherein the initial D is the active site Aspartic acid residue and the penultimate H is the active site Histidine, and X is any amino acid. In further embodiments, the *B. gibsonii*-clade subtilisins are characterized by a DXGIXXHSDLXXXGGASXXXXXXTTADLXXHGTH (SEQ ID NO:90) motif, wherein the initial D is the active site Aspartic acid residue and the penultimate H is the active site Histidine, and X is any amino acid.

Some embodiments provide a *B. gibsonii*-clade of subtilisins comprising an amino acid sequence of SEQ ID NO:47 or 90 and further comprising an amino acid sequence having 70%, 75%, 80%, 85%, 90%, 95%, 96%, 97%, 98%, 99% or 100% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:47 or 90 and further comprising an amino acid sequence having 70%, 75%, 80%, 85%, 90%, 95%, 96%, 97%, 98%, 99% or 100% identity to an amino acid sequence of SEQ ID NO:11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:47 or 90 and further comprising an amino acid sequence having 70%, 75%, 80%, 85%, 90%, 95%, 96%, 97%, 98%, 99% or 100% identity to an amino acid sequence of SEQ ID NO:57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:47 or 90 and further comprising an amino acid sequence having 95%, 96%, 97%, 98%, 99% or 100% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:47 or 90 and further comprising an amino acid sequence having 95%, 96%, 97%, 98%, 99% or 100% identity to an amino acid sequence of SEQ ID NO:11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:47 or 90 and further comprising an amino acid sequence having 95%, 96%, 97%, 98%, 99% or 100% identity to an amino acid sequence of SEQ ID NO:57, 59, 61, 63, 65, 67, 69, 71, 73, 75, 77, 79, 81, or 83.

Some embodiments provide a *B. gibsonii*-clade of subtilisins comprising an amino acid sequence of SEQ ID NO:47 and further comprising an amino acid sequence having 70%, 75%, 80%, 85%, 90%, 95%, 96%, 97%, 98%, 99% or 100% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:47 and further comprising an amino acid sequence having 70%, 75%, 80%, 85%, 90%, 95%, 96%, 97%, 98%, 99% or 100% identity to an amino acid sequence of SEQ ID NO:11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:47 and further comprising an amino acid sequence having 70%, 75%, 80%, 85%, 90%, 95%, 96%, 97%, 98%, 99% or 100% identity to an amino acid sequence of SEQ ID NO:57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:47 and further comprising an amino acid sequence having 95%, 96%, 97%, 98%, 99% or 100% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:47 and further comprising an amino acid sequence having 95%, 96%, 97%, 98%, 99% or 100% identity to an amino acid sequence of SEQ ID NO:11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:47 and further comprising an amino acid sequence having 95%, 96%, 97%, 98%, 99% or 100% identity to an amino acid sequence of SEQ ID NO:57, 59, 61, 63, 65, 67, 69, 71, 73, 75, 77, 79, 81, or 83.

Some embodiments provide a *B. gibsonii*-clade of subtilisins comprising an amino acid sequence of SEQ ID NO:90 and further comprising an amino acid sequence having 70%, 75%, 80%, 85%, 90%, 95%, 96%, 97%, 98%, 99% or 100% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:90 and further comprising an amino acid sequence having 70%, 75%, 80%, 85%, 90%, 95%, 96%, 97%, 98%, 99% or 100% identity to an amino acid sequence of SEQ ID NO:11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:90 and further comprising an amino acid sequence having 70%, 75%, 80%, 85%, 90%, 95%, 96%, 97%, 98%, 99% or 100% identity to an amino acid sequence of SEQ ID NO:57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:90 and further comprising an amino acid sequence having 95%, 96%, 97%, 98%, 99% or 100% identity to an amino acid sequence of SEQ ID NO:4, 7, 11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:90 and further comprising an amino acid sequence having 95%, 96%, 97%, 98%, 99% or 100% identity to an amino acid sequence of SEQ ID NO:11, 15, 19, 23, 49, 50, 51, 52, 57, 59, 61, 63, 65, 67, 69, 71, 73, 75, 77, 79, 81, or 83. Some embodiments provide a *B. gibsonii*-clade of subtilisins comprising an amino acid sequence of SEQ ID NO:90 and further comprising an amino acid sequence having 95%, 96%, 97%, 98%, 99% or 100% identity to an amino acid sequence of SEQ ID NO:57, 59, 61, 63, 65, 67, 69, 71, 73, 75, 77, 79, 81, or 83.

In some embodiments, the *B. gibsonii*-clade does not comprise WO03054184-CAE48421, WO2007131657-CAS91385, WO2008086916-CAV33594, or NCBI Accession No. AGS78407. References CAE48421, CAS91385, and CAV33594 are Accession Nos. listed in the Genome Quest Database (See also Table 7-2). Refer AGS78407 is an Accession No. listed in the NCBI database (See also Table 7-1).

In some embodiments, the polypeptide of the present invention is a polypeptide of 70%, 75%, 80%, 85%, 90%, 95%, 96%, 97%, 98%, 99% or 100% sequence identity to SEQ ID NO: 4, 7, 11, 15, 19, 23, 49, 50, 51, 52, 57, 59, 61, 63, 65, 67, 69, 71, 73, 75, 77, 79, 81, or 83. In some embodiments, the polypeptide of the present invention is a polypeptide having 95%, 96%, 97%, 98%, 99% or 100% sequence identity to SEQ ID NO: 4, 7, 11, 15, 19, 23, 49, 50, 51, 52, 57, 59, 61, 63, 65, 67, 69, 71, 73, 75, 77, 79, 81, or 83. In some embodiments, the polypeptide of the present invention is a polypeptide having 96%, 97%, 98%, 99% or 100% sequence identity to SEQ ID NO: 4, 7, 11, 15, 19, 23, 49, 50, 51, 52, 57, 59, 61, 63, 65, 67, 69, 71, 73, 75, 77, 79, 81, or 83. In some embodiments, the polypeptide of the present invention, is a polypeptide having a specified degree of amino acid sequence homology to the exemplified polypeptides, e.g., 70%, 75%, 80%, 85%, 90%, 95%, 96%, 97%, 98%, 99% or 100% sequence identity to SEQ ID NO:4, 7, 11, 15, 19, 23, 49, 50, 51, or 52. In some embodiments, the polypeptide of the present invention is a polypeptide having 95%, 96%, 97%, 98%, 99% or 100% sequence identity to SEQ ID NO:4, 7, 11, 15, 19, 23, 49, 50, 51, or 52. In some embodiments, the polypeptide of the present invention is a polypeptide having 70%, 75%, 80%, 85%, 90%, 95%, 96%, 97%, 98%, 99% or 100% sequence identity to SEQ ID NO:57, 59, 61, 63, 65, 67, 69, 71, 73, 75, 77, 79, 81, or 832. In some embodiments, the polypeptide of the present invention is a polypeptide having 95%, 96%, 97%, 98%, 99% or 100% sequence identity to SEQ ID NO:57, 59, 61, 63, 65, 67, 69, 71, 73, 75, 77, 79, 81, or 83.

In some embodiments, the amino acid sequence of SEQ ID NO:4, 7, 11, 15, 19, 23, 49, 50, 51, 52, 57, 59, 61, 63, 65, 67, 69, 71, 73, 75, 77, 79, 81, or 83 does not comprise WO03054184-CAE48421 or WO2007131657-CAS91385. In some embodiments, the amino acid sequence of SEQ ID NO:4, 7, 11, 15, 19, 23, 49, 50, 51, 52, 57, 59, 61, 63, 65, 67, 69, 71, 73, 75, 77, 79, 81, or 83 does not comprise WO03054184-CAE48421, WO2007131657-CAS91385, or NCBI Accession No. AGS78407. In some embodiments, the amino acid sequence of SEQ ID NO:11, 15, 19, 23, 49, 50, 51, 52, 57, 59, 61, 63, 65, 67, 69, 71, 73, 75, 77, 79, 81, or 83 does not comprise WO03054184-CAE48421 or WO2007131657-CAS91385. In some embodiments, the amino acid sequence of SEQ ID NO:11, 15, 19, 23, 49, 50, 51, 52, 57, 59, 61, 63, 65, 67, 69, 71, 73, 75, 77, 79, 81, or 83 does not comprise WO03054184-CAE48421, WO2007131657-CAS91385, or NCBI Accession No. AGS78407. In some embodiments, the amino acid sequence of SEQ ID NO:57, 59, 61, 63, 65, 67, 69, 71, 73, 75, 77, 79, 81, or 83 does not comprise WO03054184-CAE48421 or WO2007131657-CAS91385. In some embodiments, the amino acid sequence of SEQ ID NO:57, 59, 61, 63, 65, 67, 69, 71, 73, 75, 77, 79, 81, or 83 does not comprise WO03054184-CAE48421, WO2007131657-CAS91385, or NCBI Accession No. AGS78407. In some embodiments, the polypeptide or active fragment thereof of the present invention does not comprise WO03054184-CAE48421 or WO2007131657-CAS91385. In some embodiments, the polypeptide or active fragment thereof of the present invention does not comprise WO03054184-CAE48421, WO2007131657-CAS91385, or NCBI Accession No. AGS78407.

In some embodiments, the polypeptide of the present invention is a polypeptide, wherein the polypeptide comprises an amino acid sequence selected from the group consisting of SEQ ID NO: 4, 7, 11, 15, 19, 23, 49, 50, 51, 52, 57, 59, 61, 63, 65, 67, 69, 71, 73, 75, 77, 79, 81, or 83, or a variant having an N-terminal deletion. In some embodiments, the polypeptide of the present invention is a polypeptide, wherein the polypeptide comprises an amino acid sequence selected from the group consisting of SEQ ID NO:4, 7, 11, 15, 19, 23, 49, 50, 51, or 52, or a variant having an N-terminal deletion. In some embodiments, the polypeptide of the present invention is a polypeptide, wherein the polypeptide comprises an amino acid sequence selected from the group consisting of SEQ ID NO:57, 59, 61, 63, 65, 67, 69, 71, 73, 75, 77, 79, 81, or 83, or a variant having an N-terminal deletion. In some embodiments, the polypeptide described above is a recombinant polypeptide. Homology can be determined by amino acid sequence alignment, e.g., using a program such as BLAST, ALIGN, or CLUSTAL, as described herein. In some embodiments, the polypeptide is an isolated, recombinant, substantially pure, or non-naturally occurring enzyme having protease activity.

Also provided is a polypeptide enzyme having protease activity, said enzyme comprising an amino acid sequence which differs from the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83 by no more than 50, no more than 40, no more than 30, no more than 25, no more than 20, no more than 15, no more than 10, no more than 9, no more than 8, no more than 7, no more than 6, no more than 5, no more than 4, no more than 3, no more than 2, or no more than 1 amino acid residue(s), when aligned using any of the previously described alignment methods. Further provided is a polypeptide enzyme having protease activity, said enzyme comprising an amino acid sequence which differs from the amino acid sequence of SEQ ID NO: SEQ ID NO:4, 7, 11, 15, 19, 23, 49, 50, 51, or 52 by no more than 50, no more than 40, no more than 30, no more than 25, no more than 20, no more than 15, no more than 10, no more than 9, no more than 8, no more than 7, no more than 6, no more than 5, no more than 4, no more than 3, no more than 2, or no more than 1 amino acid residue(s), when aligned using any of the previously described alignment methods. Even further provided is a polypeptide enzyme having protease activity, said enzyme comprising an amino acid sequence which differs from the amino acid sequence of SEQ ID NO:57, 59, 61, 63, 65, 67, 69, 71, 73, 75, 77, 79, 81, or 83 by no more than 50, no more than 40, no more than 30, no more than 25, no more than 20, no more than 15, no more than 10, no more than 9, no more than 8, no more than 7, no more than 6, no more than 5, no more than 4, no more than 3, no more than 2, or no more than 1 amino acid residue(s), when aligned using any of the previously described alignment methods.

As noted above, the variant enzyme polypeptides of the invention have enzymatic activities (e.g., protease activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant serine protease enzyme polypeptides of the invention are described infra. The enzymatic activity (e.g., protease enzyme activity) of an enzyme polypeptide of the invention can be determined readily using procedures well known to those of ordinary skill in the art. The Examples presented infra describe methods for evaluating the enzymatic activity and cleaning performance. The performance of polypeptide enzymes of the invention in removing stains (e.g., a protein stain such as blood/milk/ink or egg yolk), cleaning hard surfaces, or cleaning laundry, dishware or tableware item(s) can be readily determined using procedures well known in the art and/or by using procedures set forth in the Examples. In some embodiments, the invention is a recombinant polypeptide or active fragment thereof of the invention, wherein the polypeptide has protease activity in the presence of a surfactant. In some embodiments, the protease activity comprises casein hydrolysis activity. In some embodiments, the protease activity comprises dimethylcasein hydrolysis activity.

The serine protease polypeptides of the present invention can have protease activity over a broad range of pH conditions. In some embodiments, the serine protease polypeptides have protease activity on azo-casein as a substrate, as demonstrated in Example 4. In some embodiments, the serine protease polypeptides have protease activity at a pH of from about 4.0 to about 12.0. In some embodiments, the serine protease polypeptides have protease activity at a pH of from about 8.0 to about 12.0. In some embodiments, the serine protease polypeptides have at least 50%, 60%, 70%, 80% or 90% of maximal protease activity at a pH of from about 8.0 to about 12.0. In some embodiments, the serine protease polypeptides have protease activity at a pH above 8.0, 8.5, 9.0, 9.5, 10.0, 10.5, 11.0 or 11.5. In some embodiments, the serine protease polypeptides have protease activity at a pH below 12.0, 11.5, 11.0, 10.5, 10.0, 9.5, 9.0 or 8.5.

In some embodiments, the serine protease polypeptides of the present invention have protease activity at a temperature range from about 10° C. to about 90° C. In some embodiments, the serine protease polypeptides of the present invention have protease activity at a temperature range of from about 50° C. to about 75° C. In some embodiments, the serine protease polypeptides have at least 50%, 60%, 70%, 80% or 90% of maximal protease activity at a temperature of from about 50° C. to about 75° C. In some embodiments, the serine proteases have activity at a temperature above 50° C., 55° C., 60° C., 65° C., or 70° C. In some embodiments, the serine proteases have activity at a temperature below 75° C., 70° C., 65° C., 60° C., or 55° C.

In some embodiments, the serine protease polypeptides of the present invention demonstrate cleaning performance in a cleaning composition. Cleaning compositions often include ingredients harmful to the stability and performance of enzymes, making cleaning compositions a harsh environment for enzymes, e.g. serine proteases, to retain function. Thus, it is not trivial for an enzyme to be put in a cleaning composition and expect enzymatic function (e.g. serine protease activity, such as demonstrated by cleaning performance). In some embodiments, the serine protease polypeptides of the present invention demonstrate cleaning performance in automatic dishwashing (ADW) detergent compositions. In some embodiments, the cleaning performance in automatic dishwashing (ADW) detergent compositions includes cleaning of egg yolk stains. In some embodiments, the serine protease polypeptides of the present invention demonstrate cleaning performance in laundry detergent compositions. In some embodiments, the cleaning performance in laundry detergent compositions includes cleaning of blood/milk/ink stains. In each of the cleaning compositions, the serine protease polypeptides of the present invention demonstrate cleaning performance with or without a bleach component.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleotides in one or more codons such that a particular codon encodes the same or a different amino acid, resulting in either a silent variation (e.g., when the encoded amino acid is not altered by the nucleotide mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded polypeptide enzyme compared to the polypeptide enzyme encoded by the original nucleic acid sequence. A nucleic acid sequence of the invention can also be modified to include one or more codons that provide for optimum expression in an expression system (e.g., bacterial expression system), while, if desired, said one or more codons still encode the same amino acid(s).

In some embodiments, the present invention provides a *B. gibsonii*-clade of subtilisins having a desired enzymatic activity (e.g., protease enzyme activity or cleaning performance activity). In some embodiments, the invention provides a *B. gibsonii*-clade of subtilisins having protease enzyme activity. In other embodiments, the invention provides a *B. gibsonii*-clade of subtilisins having cleaning performance activity. In some embodiments, the *B. gibsonii*-clade of subtilisins having the desired enzymatic activity comprises a recombinant polypeptide, or an active fragment thereof, comprising an amino acid sequence having at least 70%, 75%, 80%, 85%, 90%, 95%, 96%, 97%, 98%, 99% or 100% identity to the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421 or WO2007131657-CAS91385. In some embodiments, the *B. gibsonii*-clade of subtilisins having the desired enzymatic activity comprises a recombinant polypeptide, or an active fragment thereof, comprising an amino acid sequence having at least 95%, 96%, 97%, 98%, 99% or 100% identity to the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421 or WO2007131657-CAS91385. In some embodiments, the *B. gibsonii*-clade of subtilisins having the desired enzymatic activity comprises a recombinant polypeptide, or an active fragment thereof, comprising an amino acid sequence having at least 70%, 75%, 80%, 85%, 90%, 95%, 96%, 97%, 98%, 99% or 100% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421 or WO2007131657-CAS91385. In some embodiments, the *B. gibsonii*-clade of subtilisins having the desired enzymatic activity comprises a recombinant polypeptide, or an active fragment thereof, comprising an amino acid sequence having at least 95%, 96%, 97%, 98%, 99% or 100% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421 or WO2007131657-CAS91385. In some embodiments, the *B. gibsonii*-clade of subtilisins having the desired enzymatic activity comprises a recombinant polypeptide, or an active fragment thereof, comprising an amino acid sequence having at least 70%, 75%, 80%, 85%, 90%, 95%, 96%, 97%, 98%, 99% or 100% identity to the amino acid sequence of SEQ ID NO:57, 59, 61, 63, 65, 67, 69, 71, 73, 75, 77, 79, 81, or 83, with the proviso that the amino acid sequence does not comprise WO03054184-CAE48421 or WO2007131657-CAS91385. In some embodiments, the *B. gibsonii*-clade of subtilisins having the desired enzymatic activity comprises a recombinant polypeptide, or an active fragment thereof, comprising an amino acid sequence having at least 95%, 96%, 97%, 98%, 99% or 100% identity to the amino acid sequence of SEQ ID NO:57, 59, 61, 63, 65, 67, 69, 71, 73, 75, 77, 79, 81, or 83, with the proviso that the amino acid sequence does not comprise WO03054184-CAE48421 or WO2007131657-CAS91385. In some embodiments, the *B. gibsonii*-clade of subtilisins having the desired enzymatic activity comprises a recombinant polypeptide, or an active fragment thereof, comprising an amino acid sequence having at least 95%, 96%, 97%, 98%, 99% or 100% identity to the amino acid sequence of SEQ ID NO:4, 7, 11, 15, 19, 23, 49, 50, 51, or 52, with the proviso that the amino acid sequence does not comprise WO03054184-CAE48421 or WO2007131657-CAS91385. In some embodiments, the *B. gibsonii*-clade of subtilisins having the desired enzymatic activity comprises a recombinant polypeptide, or an active fragment thereof, comprising an amino acid sequence having at least 95% identity to the amino acid sequence of SEQ ID NO:4, 7, 11, 15, 19, 23, 49, 50, 51, or 52, with the proviso that the amino acid sequence does not comprise WO03054184-CAE48421 or WO2007131657-CAS91385. In some embodiments, the *B. gibsonii*-clade of subtilisins having the desired enzymatic activity comprises a recombinant polypeptide, or an active fragment thereof, comprising an amino acid sequence having at least 95% identity to the amino acid sequence of SEQ ID NO:11, 15, 19, 23, 49, 50, 51, or 52, with the proviso that the amino acid sequence does not comprise WO03054184-CAE48421, WO2007131657-CAS91385, or AGS78407. In some embodiments, the *B. gibsonii*-clade of subtilisins having the desired enzymatic activity comprises a recombinant polypeptide, or an active fragment thereof, comprising an amino acid sequence having at least 95% identity to the amino acid sequence of SEQ ID NO:4, 7, 11, 15, 19, 23, 49, 50, 51, 52, 57, 59, 61, 63, 65, 67, 69, 71, 73, 75, 77, 79, 81, or 83 with the proviso that the amino acid sequence does not comprise WO03054184-CAE48421, WO2007131657-CAS91385 or NCBI Accession No. AGS78407. In some embodiments, the *B. gibsonii*-clade of subtilisins having the desired enzymatic activity comprises a recombinant polypeptide, or an active fragment thereof, comprising an amino acid sequence having at least 70%, 75%, 80%, 85%, 90%, 95%, 96%, 97%, 98%, 99% or 100% identity to the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421, WO2007131657-CAS91385 or NCBI Accession No. AGS78407. In some embodiments, the *B. gibsonii*-clade of subtilisins having the desired enzymatic activity comprises a recombinant polypeptide, or an active fragment thereof, comprising an amino acid sequence having at least 95%, 96%, 97%, 98%, 99% or 100% identity to the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421, WO2007131657-CAS91385 or NCBI Accession No. AGS78407. In some embodiments, the *B. gibsonii*-clade of subtilisins having the desired enzymatic activity comprises a recombinant polypeptide, or an active fragment thereof, comprising an amino acid sequence having at least 70%, 75%, 80%, 85%, 90%, 95%, 96%, 97%, 98%, 99% or 100% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421, WO2007131657-CAS91385 or NCBI Accession No. AGS78407. In some embodiments, the *B. gibsonii*-clade of subtilisins having the desired enzymatic activity comprises a recombinant polypeptide, or an active fragment thereof, comprising an amino acid sequence having at least 95%, 96%, 97%, 98%, 99% or 100% identity to the amino acid sequence of SEQ ID NO:11, 15, 19, 23, 49, 50, 51, 52, 57, 59, 61, 63, 65, 67, 69, 71, 73, 75, 77, 79, 81, or 83, with the proviso that the amino acid sequence does not comprise WO03054184-CAE48421, WO2007131657-CAS91385 or NCBI Accession No. AGS78407. In some embodiments, the *B. gibsonii*-clade of subtilisins having the desired enzymatic activity comprises a recombinant polypeptide, or an active fragment thereof, comprising an amino acid sequence having at least 70%, 75%, 80%, 85%, 90%, 95%, 96%, 97%, 98%, 99% or 100% identity to the amino acid sequence of SEQ ID NO:57, 59, 61, 63, 65, 67, 69, 71, 73, 75, 77, 79, 81, or 83, with the proviso that the amino acid sequence does not comprise WO03054184-CAE48421, WO2007131657-CAS91385 or NCBI Accession No. AGS78407. In some embodiments, the *B. gibsonii*-clade of subtilisins having the desired enzymatic activity comprises a recombinant polypeptide, or an active fragment thereof, comprising an amino acid sequence having at least 95%, 96%, 97%, 98%, 99% or 100% identity to the amino acid sequence of SEQ ID NO:57, 59, 61, 63, 65, 67, 69, 71, 73, 75, 77, 79, 81, or 83, with the proviso that the amino acid sequence does not comprise WO03054184-CAE48421, WO2007131657-CAS91385 or NCBI Accession No. AGS78407. In some embodiments, the *B. gibsonii*-clade of subtilisins having the desired enzymatic activity comprises a recombinant polypeptide, or an active fragment thereof, comprising an amino acid sequence having at least 95%, 96%, 97%, 98%, 99% or 100% identity to the amino acid sequence of SEQ ID NO:4, 7, 11, 15, 19, 23, 49, 50, 51, or 52, with the proviso that the amino acid sequence does not comprise WO03054184-CAE48421, WO2007131657-CAS91385 or NCBI Accession No. AGS78407. In some embodiments, the *B. gibsonii*-clade of subtilisins having the desired enzymatic activity comprises a recombinant polypeptide, or an active fragment thereof, comprising an amino acid sequence having at least 95% identity to the amino acid sequence of SEQ ID NO:4, 7, 11, 15, 19, 23, 49, 50, 51, or 52, with the proviso that the amino acid sequence does not comprise WO03054184-CAE48421, WO2007131657-CAS91385 or NCBI Accession No. AGS78407. In some embodiments, the *B. gibsonii*-clade of subtilisins having the desired enzymatic activity comprises a recombinant polypeptide, or an active fragment thereof, comprising an amino acid sequence having at least 95% identity to the amino acid sequence of SEQ ID NO:11, 15, 19, 23, 49, 50, 51, or 52, with the proviso that the amino acid sequence does not comprise WO03054184-CAE48421 or WO2007131657-CAS91385. In some embodiments, the *B. gibsonii*-clade of subtilisins having the desired enzymatic activity comprises a recombinant polypeptide, or an active fragment thereof, comprising an amino acid sequence having at least 95% identity to the amino acid sequence of SEQ ID NO:4, 7, 11, 15, 19, 23, 49, 50, 51, 52, 57, 59, 61, 63, 65, 67, 69, 71, 73, 75, 77, 79, 81, or 83 with the proviso that the amino acid sequence does not comprise WO03054184-CAE48421, WO2007131657-CAS91385 or NCBI Accession No. AGS78407.

In some embodiments, the present invention provides a genus of enzyme polypeptides having the desired enzymatic activity (e.g., protease enzyme activity or cleaning performance activity) which comprise sequences having the amino acid substitutions described herein and also which comprise one or more additional amino acid substitutions, such as conservative and non-conservative substitutions, wherein the polypeptide exhibits, maintains, or approximately maintains the desired enzymatic activity (e.g., proteolytic activity, as reflected in the cleaning activity or performance of the polypeptide enzyme of SEQ ID NO:4, 7, 11, 15, 19, 23, 49, 50, 51, 52, 57, 59, 61, 63, 65, 67, 69, 71, 73, 75, 77, 79, 81, or 83). In some embodiments, the proteolytic activity is reflected in the cleaning activity or performance of the polypeptide enzyme of SEQ ID NO: SEQ ID NO:4, 7, 11, 15, 19, 23, 49, 50, 51, 52, 57, 59, 61, 63, 65, 67, 69, 71, 73, 75, 77, 79, 81, or 83. In some embodiments, the proteolytic activity is reflected in the cleaning activity or performance of the polypeptide enzyme of SEQ ID NO:11, 15, 19, 23, 49, 50, 51, 52, 57, 59, 61, 63, 65, 67, 69, 71, 73, 75, 77, 79, 81, or 83. In some embodiments, the proteolytic activity is reflected in the cleaning activity or performance of the polypeptide enzyme of SEQ ID NO:57, 59, 61, 63, 65, 67, 69, 71, 73, 75, 77, 79, 81, or 83. Amino acid substitutions in accordance with the invention may include, but are not limited to, one or more non-conservative substitutions and/or one or more conservative amino acid substitutions. A conservative amino acid residue substitution typically involves exchanging a member within one functional class of amino acid residues for a residue that belongs to the same functional class (conservative amino acid residues are considered functionally homologous or conserved in calculating percent functional homology). A conservative amino acid substitution typically involves the substitution of an amino acid in an amino acid sequence with a functionally similar amino acid. For example, alanine, glycine, serine, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine.

Conservatively substituted variations of a polypeptide sequence of the invention (e.g., variant serine proteases of the invention) include substitutions of a small percentage, sometimes less than 5%, 4%, 3%, 2%, or 1%, or less than 10, 9, 8, 7, 6, 5, 4, 3, 2, or 1 amino acid substitutions of the amino acids of the polypeptide sequence, with a conservatively selected amino acid of the same conservative substitution group.

III. Nucleic Acids Encoding Serine Proteases

The invention provides isolated, non-naturally occurring, or recombinant nucleic acids which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include serine protease polypeptides having enzymatic activity (e.g., proteolytic activity) which are useful in cleaning applications and cleaning compositions for cleaning an item or a surface (e.g., surface of an item) in need of cleaning.

In some embodiments, a polynucleotide of the present invention, is a polynucleotide having a specified degree of nucleic acid homology to the exemplified polynucleotide. In some embodiments, a polynucleotide of the present invention has a nucleic acid sequence having at least 50, 60, 65, 70, 75, 80, 85, 90, 91, 92, 93, 94, 95, 96, 97, 98, 99 or 100% identity to SEQ ID NO:1, 8, 12, 16, 20, 53, 54, 55, 56, 58, 60, 62, 64, 66, 68, 70, 72, 74, 76, 78, 80, or 82. In some embodiments, a polynucleotide of the present invention has a nucleic acid sequence having at least 50, 60, 65, 70, 75, 80, 85, 90, 91, 92, 93, 94, 95, 96, 97, 98, 99 or 100% identity to SEQ ID NO: 1, 12, 16, 20, 53, 54, 55, 56, 58, 60, 62, 64, 66, 68, 70, 72, 74, 76, 78, 80, or 82. In some embodiments, a polynucleotide of the present invention has a nucleic acid sequence having at least 50, 60, 65, 70, 75, 80, 85, 90, 91, 92, 93, 94, 95, 96, 97, 98, 99 or 100% identity to SEQ ID NO:53, 54, 55, 56, 58, 60, 62, 64, 66, 68, 70, 72, 74, 76, 78, 80, or 82. In other embodiments, the polynucleotide of the present invention may also have a complementary nucleic acid sequence to SEQ ID NO: 1, 12, 16, 20, 53, 54, 55, 56, 58, 60, 62, 64, 66, 68, 70, 72, 74, 76, 78, 80, or 82. In other embodiments, the polynucleotide of the present invention may also have a complementary nucleic acid sequence to SEQ ID NO:12, 16, 20, 53, 54, 55, 56, 58, 60, 62, 64, 66, 68, 70, 72, 74, 76, 78, 80, or 82. In other embodiments, the polynucleotide of the present invention may also have a complementary nucleic acid sequence to SEQ ID NO:53, 54, 55, 56, 58, 60, 62, 64, 66, 68, 70, 72, 74, 76, 78, 80, or 82. In some embodiments, a polynucleotide of the present invention has a nucleic acid sequence that encodes an amino acid sequence having at least 70%, 75%, 80%, 85%, 90%, 95%, 96%, 97%, 98%, 99% or 100% sequence identity to the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83. In some embodiments, a polynucleotide of the present invention has a nucleic acid sequence that encodes an amino acid sequence having at least 70%, 75%, 80%, 85%, 90%, 95%, 96%, 97%, 98%, 99% or 100% sequence identity to the amino acid sequence of SEQ ID NO:4, 7, 11, 15, 19, 23, 49, 50, 51, or 52. In some embodiments, a polynucleotide of the present invention has a nucleic acid sequence that encodes an amino acid sequence having at least 70%, 75%, 80%, 85%, 90%, 95%, 96%, 97%, 98%, 99% or 100% sequence identity to the amino acid sequence of SEQ ID NO: 57, 59, 61, 63, 65, 67, 69, 71, 73, 75, 77, 79, 81, or 83. In some embodiments, a polynucleotide of the present invention has a nucleic acid sequence that encodes an amino acid sequence having at least 95%, 96%, 97%, 98%, 99% or 100% sequence identity to the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83. In some embodiments, a polynucleotide of the present invention has a nucleic acid sequence that encodes an amino acid sequence having at least 95%, 96%, 97%, 98%, 99% or 100% sequence identity to the amino acid sequence of SEQ ID NO:4, 7, 11, 15, 19, 23, 49, 50, 51, or 52. In some embodiments, a polynucleotide of the present invention has a nucleic acid sequence that encodes an amino acid sequence having at least 95%, 96%, 97%, 98%, 99% or 100% sequence identity to the amino acid sequence of SEQ ID NO: 57, 59, 61, 63, 65, 67, 69, 71, 73, 75, 77, 79, 81, or 83. Homology can be determined by amino acid sequence alignment, e.g., using a program such as BLAST, ALIGN, or CLUSTAL, as described herein.

In a further embodiment, the polynucleotide of the present invention encodes an amino acid sequence of SEQ ID NO:47 and further encodes an amino acid sequence having at least 70%, 75%, 80%, 85%, 90%, 95%, 96%, 97%, 98%, 99% or 100% sequence identity to the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83. In a further embodiment, the polynucleotide of the present invention encodes an amino acid sequence of SEQ ID NO:47 and further encodes an amino acid sequence having at least 95%, 96%, 97%, 98%, 99% or 100% sequence identity to the amino acid sequence of SEQ ID NO: 4, 7, 11, 15, 19, 23, 49, 50, 51, 52, 57, 59, 61, 63, 65, 67, 69, 71, 73, 75, 77, 79, 81, or 83 In a further embodiment, the polynucleotide of the present invention encodes an amino acid sequence of SEQ ID NO:47 and further encodes an amino acid sequence having at least 70%, 75%, 80%, 85%, 90%, 95%, 96%, 97%, 98%, 99% or 100% sequence identity to the amino acid sequence of SEQ ID NO: 11, 15, 19, 23, 49, 50, 51, 52, 57, 59, 61, 63, 65, 67, 69, 71, 73, 75, 77, 79, 81, or 83. In a further embodiment, the polynucleotide of the present invention encodes an amino acid sequence of SEQ ID NO:47 and further encodes an amino acid sequence having at least 95%, 96%, 97%, 98%, 99% or 100% sequence identity to the amino acid sequence of SEQ ID NO: 11, 15, 19, 23, 49, 50, 51, 52, 57, 59, 61, 63, 65, 67, 69, 71, 73, 75, 77, 79, 81, or 83. In a further embodiment, the polynucleotide of the present invention encodes an amino acid sequence of SEQ ID NO:47 and further encodes an amino acid sequence having at least 70%, 75%, 80%, 85%, 90%, 95%, 96%, 97%, 98%, 99% or 100% sequence identity to the amino acid sequence of SEQ ID NO: 57, 59, 61, 63, 65, 67, 69, 71, 73, 75, 77, 79, 81, or 83. In a further embodiment, the polynucleotide of the present invention encodes an amino acid sequence of SEQ ID NO:47 and further encodes an amino acid sequence having at least 95%, 96%, 97%, 98%, 99% or 100% sequence identity to the amino acid sequence of SEQ ID NO: 57, 59, 61, 63, 65, 67, 69, 71, 73, 75, 77, 79, 81, or 83.

In some embodiments, the invention provides an isolated, recombinant, substantially pure, or non-naturally occurring nucleic acid comprising a nucleotide sequence encoding any polypeptide (including any fusion protein, etc.) of the invention described above in the section entitled "Polypeptides of the Invention" and elsewhere herein. In some embodiments, the invention provides a synthetically derived nucleic acid comprising a nucleotide sequence encoding any polypeptide (including any fusion protein, etc.) of the invention described herein. The invention also provides an isolated, recombinant, substantially pure, or non-naturally-occurring nucleic acid comprising a nucleotide sequence encoding a combination of two or more of any polypeptides of the invention described above and elsewhere herein. The invention also provides a synthetically derived nucleic acid comprising a nucleotide sequence encoding a combination of two or more of any polypeptides of the invention described herein. The present invention provides nucleic acids encoding a serine protease polypeptide of the present invention, wherein the serine protease polypeptide is a mature form having proteolytic activity. In some embodiments, the serine protease is expressed recombinantly with a homologous pro-peptide sequence (e.g., Bgi02446 pro-peptide).

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the nucleic acids of the invention can be also facilitated by any suitable method known in the art, including but not limited to chemical synthesis using the classical phosphoramidite method (See e.g., Beaucage et al. Tetrahedron Letters 22:1859-69 [1981]); or the method described by Matthes et al. (See, Matthes et al., EMBO J. 3:801-805 [1984]), as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann Rev. Biochem. 53:323 [1984]; and Itakura et al., Science 198:1056 [1984]).

As indicated above, recombinant DNA techniques useful in modification of nucleic acids are well known in the art. For example, techniques such as restriction endonuclease digestion, ligation, reverse transcription and cDNA production, and polymerase chain reaction (e.g., PCR) are known and readily employed by those of skill in the art. Nucleotides of the invention may also be obtained by screening cDNA libraries using one or more oligonucleotide probes that can hybridize to or PCR-amplify polynucleotides which encode a serine protease polypeptide polypeptide(s) of the invention. Procedures for screening and isolating cDNA clones and PCR amplification procedures are well known to those of skill in the art and described in standard references known to those skilled in the art. Some nucleic acids of the invention can be obtained by altering a naturally occurring polynucleotide backbone (e.g., that encodes an enzyme or parent protease) by, for example, a known mutagenesis procedure (e.g., site-directed mutagenesis, site saturation mutagenesis, and in vitro recombination). A variety of methods are known in the art that are suitable for generating modified polynucleotides of the invention that encode serine protease polypeptides of the invention, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches.

IV. Vectors, Host Cells, and Methods for Producing Serine Proteases

The present invention provides vectors comprising at least one serine protease polynucleotide of the invention described herein (e.g., a polynucleotide encoding a serine protease polypeptide of the invention described herein), expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector, although other methods are available and known in the art. Such cells are typically referred to as host cells. Some such cells comprise bacterial cells, including, but are not limited to Bacillus sp. cells, such as B. subtilis cells. The invention also provides recombinant cells (e.g., recombinant host cells) comprising at least one serine protease polypeptide of the invention.

In some embodiments, the invention provides a vector comprising a nucleic acid or polynucleotide of the invention. In some embodiments, the vector is an expression vector or expression cassette in which a polynucleotide sequence of the invention which encodes a serine protease polypeptide of the invention is operably linked to one or additional nucleic acid segments required for efficient gene expression (e.g., a promoter operably linked to the polynucleotide of the invention which encodes a serine protease polypeptide of the invention). A vector may include a transcription terminator and/or a selection gene, such as an antibiotic resistance gene, that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pC194, pJH101, pE194, pHP13 (See, Harwood and Cutting [eds.], Chapter 3, Molecular Biological Methods for Bacillus, John Wiley & Sons [1990]; suitable replicating plasmids for B. subtilis include those listed on p. 92) See also, Perego, Integrational Vectors for Genetic Manipulations in B. subtilis, in Sonenshein et al., [eds.] B. subtilis and Other Gram-Positive Bacteria: Biochemistry, Physiology and Molecular Genetics, American Society for Microbiology, Washington, D.C. [1993], pp. 615-624), and p2JM103BBI.

For expression and production of a protein of interest (e.g., serine protease polypeptide) in a cell, at least one expression vector comprising at least one copy of a polynucleotide encoding the serine protease polypeptide, and in some instances comprising multiple copies, is transformed into the cell under conditions suitable for expression of the serine protease. In some embodiments of the present invention, a polynucleotide sequence encoding the serine protease polypeptide (as well as other sequences included in the vector) is integrated into the genome of the host cell, while in other embodiments, a plasmid vector comprising a polynucleotide sequence encoding the serine protease polypeptide remains as autonomous extrachromosomal element within the cell. The invention provides both extrachromosomal nucleic acid elements as well as incoming nucleotide sequences that are integrated into the host cell genome. The vectors described herein are useful for production of the serine protease polypeptides of the invention. In some embodiments, a polynucleotide construct encoding the serine protease polypeptide is present on an integrating vector that enables the integration and optionally the amplification of the polynucleotide encoding the serine protease polypeptide into the host chromosome. Examples of sites for integration are well known to those skilled in the art. In some embodiments, transcription of a polynucleotide encoding a serine protease polypeptide of the invention is effectuated by a promoter that is the wild-type promoter for the selected precursor protease. In some other embodiments, the promoter is heterologous to the precursor protease, but is functional in the host cell. Specifically, examples of suitable promoters for use in bacterial host cells include, but are not limited to, for example, the amyE, amyQ, amyL, pstS, sacB, pSPAC, pAprE, pVeg, pHpaII promoters, the promoter of the B. stearothermophilus maltogenic amylase gene, the B. amyloliquefaciens (BAN) amylase gene, the B. subtilis alkaline protease gene, the B. clausii alkaline protease gene the B. pumilis xylosidase gene, the B. thuringiensis cryIIIA, and the B. licheniformis alpha-amylase gene. Additional promoters include, but are not limited to the A4 promoter, as well as phage Lambda PR or PL promoters, and the E. coli lac, trp or tac promoters.

Serine protease polypeptides of the present invention can be produced in host cells of any suitable microorganism, including bacteria and fungi. In some embodiments, serine protease polypeptides of the present invention can be produced in Gram-positive bacteria. In some embodiments, the host cells are Bacillus spp., Streptomyces spp., Escherichia spp., Aspergillus spp., Trichoderma spp., Pseudomonas spp., Corynebacterium spp., Saccharomyces spp., or Pichia spp. In some embodiments, the serine protease polypeptides are produced by Bacillus sp. host cells. Examples of Bacillus sp. host cells that find use in the production of the serine protease polypeptides of the invention include, but are not limited to B. licheniformis, B. lentus, B. subtilis, B. amyloliquefaciens, B. lentus, B. brevis, B. stearothermophilus, B. alkalophilus, B. coagulans, B. circulans, B. pumilis, B. thuringiensis, B. clausii, B. megaterium, Myceliopthera spp, and Yarrowia spp, as well as other organisms within the genus Bacillus. In some embodiments, B. subtilis host cells are used for production of serine protease polypeptides. U.S. Pat. Nos. 5,264,366 and 4,760,025 (RE 34,606) describe various Bacillus host strains that can be used for producing serine protease polypeptide of the invention, although other suitable strains can be used.

Several bacterial strains that can be used to produce serine protease polypeptides of the invention include non-recombinant (i.e., wild-type) Bacillus sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a B. subtilis host strain and particularly a recombinant B. subtilis host strain. Numerous B. subtilis strains are known, including, but not limited to for example, 1A6 (ATCC 39085), 168 (1A01), SB 19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics 73:215-228 [1973]; See also, U.S. Pat. Nos. 4,450,235 and 4,302,544, and EP 0134048, each of which is incorporated by reference in its entirety). The use of B. subtilis as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the Bacillus host cell is a Bacillus sp. that includes a mutation or deletion in at least one of the following genes, degU, degS, degR and degQ. In some embodiments, the mutation is in a degU gene, and in some embodiments the mutation is degU(Hy)32 (See e.g., Msadek et al., J. Bacteriol. 172:824-834 [1990]; and Olmos et al., Mol. Gen. Genet. 253:562-567 [1997]). In some embodiments, the Bacillus host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered *Bacillus* strain of the invention. In some embodiments, these mutations occur alone, while in other embodiments, combinations of mutations are present. In some embodiments, an altered *Bacillus* host cell strain that can be used to produce a serine protease polypeptide of the invention is a *Bacillus* host strain that already includes a mutation in one or more of the above-mentioned genes. In addition, *Bacillus* sp. host cells that comprise mutation(s) and/or deletions of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments, the *Bacillus* sp. host cell comprises a deletion of 9 protease genes (See e.g., U.S. Pat. Appl. Pub. No. 2005/0202535, incorporated herein by reference).

Host cells are transformed with at least one nucleic acid encoding at least one serine protease polypeptide of the invention using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Those of skill in the art are well aware of suitable methods for introducing nucleic acid sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and transfection, transduction, and protoplast fusion are well known and suited for use in the present invention. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154:1077-1087 [1983]; and Weinrauch et al., J. Bacteriol. 169:1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a serine protease polypeptide of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one serine protease polypeptide or at least one nucleic acid of the invention.

In some embodiments, host cells transformed with at least one polynucleotide sequence encoding at least one serine protease polypeptide of the invention are cultured in a suitable nutrient medium under conditions permitting the expression of the present protease, after which the resulting protease is recovered from the culture. In some embodiments, the protease produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.).

In some embodiments, a serine protease polypeptide produced by a recombinant host cell is secreted into the culture medium. A nucleic acid sequence that encodes a purification facilitating domain may be used to facilitate purification of proteins. A vector or DNA construct comprising a polynucleotide sequence encoding a serine protease polypeptide may further comprise a nucleic acid sequence encoding a purification facilitating domain to facilitate purification of the serine protease polypeptide (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, Calif.) between the purification domain and the heterologous protein also find use to facilitate purification.

Assays for detecting and measuring the enzymatic activity of an enzyme, such as a serine protease polypeptide of the invention, are well known. Various assays for detecting and measuring activity of proteases (e.g., serine protease polypeptides of the invention), are also known to those of ordinary skill in the art. In particular, assays are available for measuring protease activity that are based on the release of acid-soluble peptides from casein or hemoglobin, measured as absorbance at 280 nm or colorimetrically using the Folin method. Other exemplary assays involve the solubilization of chromogenic substrates (See e.g., Ward, "Proteinases," in Fogarty (ed.)., Microbial Enzymes and Biotechnology, Applied Science, London, [1983], pp. 251-317). Other exemplary assays include, but are not limited to succinyl-Ala-Ala-Pro-Phe-para nitroanilide assay (suc-AAPF-pNA) and the 2,4,6-trinitrobenzene sulfonate sodium salt assay (TNBS assay). Numerous additional references known to those in the art provide suitable methods (See e.g., Wells et al., Nucleic Acids Res. 11:7911-7925 [1983]; Christianson et al., Anal. Biochem. 223:119-129 [1994]; and Hsia et al., Anal Biochem. 242:221-227 [1999]).

A variety of methods can be used to determine the level of production of a mature protease (e.g., mature serine protease polypeptides of the present invention) in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature serine protease polypeptide of the invention. A mature serine protease polypeptide does not include a signal peptide or a propeptide sequence. Some methods comprise making or producing a serine protease polypeptide of the invention in a recombinant bacterial host cell, such as for example, a *Bacillus* sp. cell (e.g., a *B. subtilis* cell). In some embodiments, the invention provides a method of producing a serine protease polypeptide of the invention, the method comprising cultivating a recombinant host cell comprising a recombinant expression vector comprising a nucleic acid encoding a serine protease polypeptide of the invention under conditions conducive to the production of the serine protease polypeptide. Some such methods further comprise recovering the serine protease polypeptide from the culture.

In some embodiments the invention provides methods of producing a serine protease polypeptide of the invention, the methods comprising: (a) introducing a recombinant expression vector comprising a nucleic acid encoding a serine protease polypeptide of the invention into a population of cells (e.g., bacterial cells, such as *B. subtilis* cells); and (b) culturing the cells in a culture medium under conditions conducive to produce the serine protease polypeptide encoded by the expression vector. Some such methods further comprise: (c) isolating the serine protease polypeptide from the cells or from the culture medium.

V. Compositions Comprising Serine Proteases

A. Fabric and Home Care Products

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. Compositions of the invention include cleaning compositions, such as detergent compositions. In the exemplified detergent compositions, the enzymes levels are expressed by pure enzyme by weight of the total composition and unless otherwise specified, the detergent ingredients are expressed by weight of the total compositions.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the serine protease polypeptides of the present invention. The precise nature of these additional components, and levels of incorporation thereof, will depend on the physical form of the composition and the nature of the cleaning operation for which it is to be used. Suitable adjunct materials include, but are not limited to, bleach catalysts, other enzymes, enzyme stabilizing systems, chelants, optical brighteners, soil release polymers, dye transfer agents, dispersants, suds suppressors, dyes, perfumes, colorants, filler salts, fluorescers, fabric conditioners, hydrolyzable surfactants, preservatives, antioxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, 6,326,348, 6,610,642, 6,605,458, 5,705,464, 5,710,115, 5,698,504, 5,695,679, 5,686,014 and 5,646,101 all of which are incorporated herein by reference. In embodiments in which the cleaning adjunct materials are not compatible with the serine protease polypeptides of the present invention in the cleaning compositions, then suitable methods of keeping the cleaning adjunct materials and the protease(s) separated (i.e., not in contact with each other) until combination of the two components is appropriate are used. Such separation methods include any suitable method known in the art (e.g., gelcaps, encapsulation, tablets, physical separation, etc.). The aforementioned adjunct ingredients may constitute the balance of the cleaning compositions of the present invention.

The cleaning compositions of the present invention are advantageously employed for example, in laundry applications, hard surface cleaning applications, dishwashing applications, including automatic dishwashing and hand dishwashing, as well as cosmetic applications such as dentures, teeth, hair and skin cleaning. The enzymes of the present invention are also suited for use in contact lens cleaning and wound debridement applications. In addition, due to the unique advantages of increased effectiveness in lower temperature solutions, the enzymes of the present invention are ideally suited for laundry applications. Furthermore, the enzymes of the present invention find use in granular and liquid compositions.

The serine protease polypeptides of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more proteases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the serine protease polypeptides provided herein, alone or in combination with other proteases and/or additional enzymes. The required level of enzyme is achieved by the addition of one or more serine protease polypeptides of the present invention. Typically the present cleaning compositions comprise at least about 0.0001 weight percent, from about 0.0001 to about 10, from about 0.001 to about 1, or from about 0.01 to about 0.1 weight percent of at least one of the serine protease polypeptides of the present invention.

The cleaning compositions herein are typically formulated such that, during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 9 to about 11. In some embodiments, the cleaning compositions of the present invention can be formulated to have an alkaline pH under wash conditions, such as a pH of from about 8.0 to about 12.0, or from about 8.5 to about 11.0, or from about 9.0 to about 11.0. In some embodiments, the cleaning compositions of the present invention can be formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionized water at 20° C., measured using a conventional pH meter. Techniques for controlling pH at recommended usage levels include the use of buffers, alkalis, acids, etc., and are well known to those skilled in the art.

In some embodiments, when the serine protease polypeptide (s) is/are employed in a granular composition or liquid, it is desirable for the serine protease polypeptide to be in the form of an encapsulated particle to protect the serine protease polypeptide from other components of the granular composition during storage. In addition, encapsulation is also a means of controlling the availability of the serine protease polypeptide during the cleaning process. In some embodiments, encapsulation enhances the performance of the serine protease polypeptide (s) and/or additional enzymes. In this regard, the serine protease polypeptides of the present invention are encapsulated with any suitable encapsulating material known in the art. In some embodiments, the encapsulating material typically encapsulates at least part of the serine protease polypeptide (s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP 0 922 499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPAN-CEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

There are a variety of wash conditions including varying detergent formulations, wash water volumes, wash water temperatures, and lengths of wash time, to which proteases involved in washing are exposed. A low detergent concentration system includes detergents where less than about 800 ppm of the detergent components are present in the wash water. A medium detergent concentration includes detergents where between about 800 ppm and about 2000 ppm of the detergent components are present in the wash water. A high detergent concentration system includes detergents where greater than about 2000 ppm of the detergent components are present in the wash water. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

Different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million.

TABLE I

Water Hardness

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |

TABLE I-continued

Water Hardness

| Water | Grains per gallon | Parts per million |
|---|---|---|
| Hard | 7.0 to 10.5 | 120 to 180 |
| Very hard | greater than 10.5 | greater than 180 |

Accordingly, in some embodiments, the present invention provides serine protease polypeptides that show surprising wash performance in at least one set of wash conditions (e.g., water temperature, water hardness, and/or detergent concentration). In some embodiments, the serine protease polypeptides of the present invention are comparable in wash performance to other serine protease polypeptide proteases. In some embodiments of the present invention, the serine protease polypeptides provided herein exhibit enhanced oxidative stability, enhanced thermal stability, enhanced cleaning capabilities under various conditions, and/or enhanced chelator stability. In addition, the serine protease polypeptides of the present invention find use in cleaning compositions that do not include detergents, again either alone or in combination with builders and stabilizers.

In some embodiments of the present invention, the cleaning compositions comprise at least one serine protease polypeptide of the present invention at a level from about 0.00001% to about 10% by weight of the composition and the balance (e.g., about 99.999% to about 90.0%) comprising cleaning adjunct materials by weight of composition. In some other embodiments of the present invention, the cleaning compositions of the present invention comprises at least one serine protease polypeptide at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, additional serine proteases, acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, metalloproteases, non-serine proteases, oxidases, pectate lyases, pectin acetyl esterases, pectinases, pentosanases, perhydrolase, peroxidases, phenoloxidases, phosphatases, phospholipases, phytases, polygalacturonases, pullulanases, reductases, rhamnogalacturonases, beta-glucanases, tannases, transglutaminases, xylan acetyl-esterases, xylanases, xyloglucanases, and xylosidases, or any combinations or mixtures thereof. In some embodiments, a combination of enzymes is used (i.e., a "cocktail") comprising conventional applicable enzymes like amylase, lipase, cutinase and/or cellulase in conjunction with a protease is used.

In addition to the serine protease polypeptides provided herein, any other suitable protease finds use in the compositions of the present invention. Suitable proteases include those of animal, vegetable or microbial origin. In some embodiments, microbial proteases are used. In some embodiments, chemically or genetically modified mutants are included. In some embodiments, the protease is a serine protease, preferably an alkaline microbial protease or a trypsin-like protease. Examples of alkaline proteases include subtilisins, especially those derived from *Bacillus* (e.g., *subtilisin, lentus, amyloliquefaciens, subtilisin* Carlsberg, *subtilisin* 309, *subtilisin* 147 and *subtilisin* 168). Additional examples include those mutant proteases described in U.S. Pat. Nos. RE 34,606; 5,955,340; 5,700,676; 6,312,936; and 6,482,628, all of which are incorporated herein by reference. Additional protease examples include, but are not limited to trypsin (e.g., of porcine or bovine origin), and the *Fusarium* protease described in WO 89/06270. In some embodiments, commercially available protease enzymes that find use in the present invention include, but are not limited to MAXATASE®, MAXACAL™ MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (Genencor); ALCALASE®, SAVINASE®, PRIMASE®, DURAZYM™, POLARZYME®, OVOZYME®, KANNASE®, LIQUANASE®, NEUTRASE®, RELASE® and ESPERASE® (Novozymes); BLAP™ and BLAP™ variants (Henkel Kommanditgesellschaft auf Aktien, Duesseldorf, Germany), and KAP (*B. alkalophilus* subtilisin; Kao Corp., Tokyo, Japan). Various proteases are described in WO95/23221, WO 92/21760, WO 09/149200, WO 09/149144, WO 09/149145, WO 11/072099, WO 10/056640, WO 10/056653, WO 11/140364, WO 12/151534, U.S. Pat. Publ. No. 2008/0090747, and U.S. Pat. Nos. 5,801,039, 5,340,735, 5,500,364, 5,855,625, US RE 34,606, 5,955,340, 5,700,676, 6,312,936, 6,482,628, 8,530, 219, and various other patents. In some further embodiments, metalloproteases find use in the present invention, including but not limited to the metalloproteases described in WO1999014341, WO1999033960, WO1999014342, WO1999034003, WO2007044993, WO2009058303, WO2009058661, and WO2014194032, WO2014194034, and WO2014194054. Exemplary metalloproteases include nprE, the recombinant form of neutral metalloprotease expressed in *B. subtilis* (See e.g., WO 07/044993), and PMN, the purified neutral metalloprotease from *B. amyloliquefaciens*.

In addition, any suitable lipase finds use in the present invention. Suitable lipases include, but are not limited to those of bacterial or fungal origin. Chemically or genetically modified mutants are encompassed by the present invention. Examples of useful lipases include *Humicola lanuginosa* lipase (See e.g., EP 258 068, and EP 305 216), *Rhizomucor miehei* lipase (See e.g., EP 238 023), *Candida* lipase, such as *C. antarctica* lipase (e.g., the *C. antarctica* lipase A or B; See e.g., EP 214 761), *Pseudomonas* lipases such as *P. alcaligenes* lipase and *P. pseudoalcaligenes* lipase (See e.g., EP 218 272), *P. cepacia* lipase (See e.g., EP 331 376), *P. stutzeri* lipase (See e.g., GB 1,372,034), *P. fluorescens* lipase, *Bacillus* lipase (e.g., *B. subtilis* lipase [Dartois et al., Biochem. Biophys. Acta 1131:253-260 [1993]); *B. stearothermophilus* lipase [See e.g., JP 64/744992]; and *B. pumilus* lipase [See e.g., WO 91/16422]).

Furthermore, a number of cloned lipases find use in some embodiments of the present invention, including but not limited to *Penicillium camembertii* lipase (See, Yamaguchi et al., Gene 103:61-67 [1991]), *Geotricum candidum* lipase (See, Schimada et al., J. Biochem., 106:383-388 [1989]), and various *Rhizopus* lipases such as *R. delemar* lipase (See, Hass et al., Gene 109:117-113 [1991]), a *R. niveus* lipase (Kugimiya et al., Biosci. Biotech. Biochem. 56:716-719 [1992]) and *R. oryzae* lipase.

Other types of lipase polypeptide enzymes such as cutinases also find use in some embodiments of the present invention, including but not limited to the cutinase derived from *Pseudomonas mendocina* (See, WO 88/09367), and the cutinase derived from *Fusarium solani pisi* (See, WO 90/09446).

Additional suitable lipases include lipases such as M1 LIPASE™, LUMA FAST™, and LIPOMAX™ (Genencor); LIPEX®, LIPOLASE® and LIPOLASE® ULTRA (Novozymes); and LIPASE P™ "Amano" (Amano Pharmaceutical Co. Ltd., Japan).

In some embodiments of the present invention, the cleaning compositions of the present invention further comprise lipases at a level from about 0.00001% to about 10% of additional lipase by weight of the composition and the balance of cleaning adjunct materials by weight of composition. In some other embodiments of the present invention, the cleaning compositions of the present invention also comprise lipases at a level of about 0.0001% to about 10%, about 0.001% to about 5%, about 0.001% to about 2%, about 0.005% to about 0.5% lipase by weight of the composition.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296, 839). Additional suitable amylases include those found in WO9510603, WO9526397, WO9623874, WO9623873, WO9741213, WO9919467, WO0060060, WO0029560, WO9923211, WO9946399, WO0060058, WO0060059, WO9942567, WO0114532, WO02092797, WO0166712, WO0188107, WO0196537, WO0210355, WO9402597, WO0231124, WO9943793, WO9943794, WO2004113551, WO2005001064, WO2005003311, WO0164852, WO2006063594, WO2006066594, WO2006066596, WO2006012899, WO2008092919, WO2008000825, WO2005018336, WO2005066338, WO2009140504, WO2005019443, WO2010091221, WO2010088447, WO0134784, WO2006012902, WO2006031554, WO2006136161, WO2008101894, WO2010059413, WO2011098531, WO2011080352, WO2011080353, WO2011080354, WO2011082425, WO2011082429, WO2011076123, WO2011087836, WO2011076897, WO94183314, WO9535382, WO9909183, WO9826078, WO9902702, WO9743424, WO9929876, WO9100353, WO9605295, WO9630481, WO9710342, WO2008088493, WO2009149419, WO2009061381, WO2009100102, WO2010104675, WO2010117511, and WO2010115021. Commercially available amylases that find use in the present invention include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In some other embodiments of the present invention, the cleaning compositions of the present invention also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME®, CAREZYME® (Novozymes), REVITALENZ™ 100 (Danisco US Inc), and KAC-500 (B)™ (Kao Corporation). In some embodiments, cellulases are incorporated as portions or fragments of mature wild-type or variant cellulases, wherein a portion of the N-terminus is deleted (See e.g., U.S. Pat. No. 5,874,276). Additional suitable cellulases include those found in WO2005054475, WO2005056787, U.S. Pat. Nos. 7,449, 318, and 7,833,773. In some embodiments, the cleaning compositions of the present invention further comprise cellulases at a level from about 0.00001% to about 10% of additional cellulase by weight of the composition and the balance of cleaning adjunct materials by weight of composition. In some other embodiments of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114, 6,602,842, and 6,440,991, all of which are incorporated herein by reference). Commercially available mannanases that find use in the present invention include, but are not limited to MANNASTAR®, PURABRITE™, and MANNAWAY®. In some embodiments, the cleaning compositions of the present invention further comprise mannanases at a level from about 0.00001% to about 10% of additional mannanase by weight of the composition and the balance of cleaning adjunct materials by weight of composition. In some embodiments of the present invention, the cleaning compositions of the present invention also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In some other embodiments of the present invention, the cleaning compositions of the present invention also comprise peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO2005/056782, WO2007106293, WO2008063400, WO2008106214, and WO2008106215). In addition, in some embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present invention. It is also contemplated that the varying levels of the serine protease polypeptide (s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

In some embodiments, an effective amount of one or more serine protease polypeptide (s) provided herein is included in compositions useful for cleaning a variety of surfaces in need of proteinaceous stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. Notably, the present invention also provides cleaning compositions suitable for personal care, including oral care (including dentrifices, toothpastes, mouthwashes, etc., as well as denture cleaning compositions), skin, and hair cleaning compositions. It is intended that the present invention encompass detergent compositions in any form (i.e., liquid, granular, bar, semi-solid, gels, emulsions, tablets, capsules, etc.).

By way of example, several cleaning compositions wherein the serine protease polypeptides of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use in detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the serine protease polypeptides of the present invention. Thus, in some embodiments, the compositions comprising at least one serine protease polypeptide of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one serine protease polypeptide of the present invention are fabric cleaning compositions such as those described in U.S. Pat. Nos. 6,610,642 and 6,376,450. In addition, the serine protease polypeptides of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one serine protease polypeptide provided herein. Thus, in some embodiments, the compositions comprising at least one serine protease polypeptide of the present invention is a hard surface cleaning composition such as those described in U.S. Pat. Nos. 6,610,642, 6,376,450, and 6,376,450.

In yet further embodiments, the present invention provides dishwashing compositions comprising at least one serine protease polypeptide provided herein. Thus, in some embodiments, the compositions comprising at least one serine protease polypeptide of the present invention is a hard surface cleaning composition such as those in U.S. Pat. Nos. 6,610,642 and 6,376,450. In some still further embodiments, the present invention provides dishwashing compositions comprising at least one serine protease polypeptide provided herein. In some further embodiments, the compositions comprising at least one serine protease polypeptide of the present invention comprise oral care compositions such as those in U.S. Pat. Nos. 6,376,450, and 6,376,450. The formulations and descriptions of the compounds and cleaning adjunct materials contained in the aforementioned U.S. Pat. Nos. 6,376,450, 6,605,458, 6,605,458, and 6,610,642, find use with the serine protease polypeptides provided herein.

The cleaning compositions of the present invention are formulated into any suitable form and prepared by any process chosen by the formulator (See e.g., U.S. Pat. Nos. 5,879,584; 5,691,297; 5,574,005; 5,569,645; 5,565,422; 5,516,448; 5,489,392; and 5,486,303, all of which are incorporated herein by reference. When a low pH cleaning composition is desired, the pH of such composition is adjusted via the addition of a material such as monoethanolamine or an acidic material such as HCl.

In some embodiments, the cleaning compositions according to the present invention comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR—N(CH$_2$COOM)$_2$ where R is C$_{1-12}$ alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl)glutamic acid (SMGL), N-(2-sulfoethyl) glutamic acid (SEGL), IDS (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,Ndiacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400μ to about 1200μ and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulphuric acid. In some instances, the acidifying particle of the invention is a highly active particle comprising a high level of amino carboxylic builder. Sulphuric acid has been found to further contribute to the stability of the final particle.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP 2 100 949).

In some embodiments, builders for use herein include phosphate builders and non-phosphate builders. In some embodiments, the builder is a phosphate builder. In some embodiments, the builder is a non-phosphate builder. If present, builders are used in a level of from 0.1% to 80%, or from 5 to 60%, or from 10 to 50% by weight of the composition. In some embodiments the product comprises a mixture of phosphate and non-phosphate builders. Suitable phosphate builders include mono-phosphates, di-phosphates, tri-polyphosphates or oligomeric-poylphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition of the invention. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present invention. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP 2 100 949). In some embodiments, the non-ionic surfactant can be ethoxylated nonionic surfactants, epoxy-capped poly(oxyalkylated) alcohols and amine oxides surfactants.

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1% to about 20%. In some embodiments, silicates are present at a level of from about 5% to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts, such as calcium formate. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO 07/145964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleaches, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP 2 100 949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP 2 100 949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612, 5,227,084, 4,810,410, WO 99/06521, and EP 2 100 949).

In some embodiments, the cleaning compositions of the present invention contain one or more catalytic metal complexes. In some embodiments, a metal-containing bleach catalyst finds use. In some embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2]

hexadecane). Suitable transition metal MRLs are readily prepared by known procedures (See e.g., WO 2000/32601, and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present invention comprise from about 0.1% to about 5% by weight of one or more metal care agent.

In some embodiments, the cleaning composition is a high density liquid (HDL) composition having a variant serine protease polypeptide protease. The HDL liquid laundry detergent can comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof); and optionally non-ionic surfactant (selected from a group of linear or branched or random chain, substituted or unsubstituted alkyl alkoxylated alcohol, for example a $C_8$-$C_{18}$ alkyl ethoxylated alcohol and/or $C_6$-$C_{12}$ alkyl phenol alkoxylates), optionally wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from a group of alkanolamine sulpho-betaines); ampholytic surfactants; semi-polar non-ionic surfactants and mixtures thereof.

The composition can comprise optionally, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated $C_1$-$C_6$ carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$ alkyl group, polypropylene, polybutylene, vinyl ester of a saturated $C_1$-$C_6$ mono-carboxylic acid, $C_1$-$C_6$ alkyl ester of acrylic or methacrylic acid, and mixtures thereof.

The composition can comprise additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example Repel-o-tex SF, SF-2 and SRP6, Texcare SRA100, SRA300, SRN100, SRN170, SRN240, SRN300 and SRN325, Marloquest SL), anti-redeposition polymers (0.1 wt % to 10 wt %, include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); cellulosic polymer (including those selected from alkyl cellulose, alkyl alkoxyalkyl cellulose, carboxyalkyl cellulose, alkyl carboxyalkyl cellulose examples of which include carboxymethyl cellulose, methyl cellulose, methyl hydroxyethyl cellulose, methyl carboxymethyl cellulose, and mixtures thereof) and polymeric carboxylate (such as maleate/acrylate random copolymer or polyacrylate homopolymer).

The composition can further comprise saturated or unsaturated fatty acid, preferably saturated or unsaturated $C_{12}$-$C_{24}$ fatty acid (0 wt % to 10 wt %); deposition aids (examples for which include polysaccharides, preferably cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic cellulose such as cationic hydoxyethyl cellulose, cationic starch, cationic polyacylamides, and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof.

The composition may optionally include enzymes (generally about 0.01 wt % active enzyme to 0.5 wt % active enzyme) selected from proteases, amylases, lipases, cellulases, choline oxidases, peroxidases/oxidases, pectate lyases, mannanases, cutinases, laccases, phospholipases, lysophospholipases, acyltransferases, perhydrolases, arylesterases, and any mixture thereof. The composition may comprise an enzyme stabilizer (examples of which include polyols such as propylene glycol or glycerol, sugar or sugar alcohol, lactic acid, reversible protease inhibitor, boric acid, or a boric acid derivative, e.g., an aromatic borate ester, or a phenyl boronic acid derivative such as 4-formylphenyl boronic acid).

The composition can further comprise silicone or fatty-acid based suds suppressors; hueing dyes, calcium and magnesium cations, visual signaling ingredients, anti-foam (0.001 wt % to about 4.0 wt %), and/or structurant/thickener (0.01 wt % to 5 wt %, selected from the group consisting of diglycerides and triglycerides, ethylene glycol distearate, microcrystalline cellulose, cellulose based materials, microfiber cellulose, biopolymers, xanthan gum, gellan gum, and mixtures thereof).

The composition can be any liquid form, for example a liquid or gel form, or any combination thereof.

In some embodiments, the cleaning compositions of the present invention are provided in unit dose form, including tablets, capsules, sachets, pouches, and multi-compartment pouches. In some embodiments, the unit dose format is designed to provide controlled release of the ingredients within a multi-compartment pouch (or other unit dose format). Suitable unit dose and controlled release formats are known in the art (See e.g., EP 2 100 949, WO 02/102955, U.S. Pat. Nos. 4,765,916 and 4,972,017, and WO 04/111178 for materials suitable for use in unit dose and controlled release formats). In some embodiments, the unit dose form is provided by tablets wrapped with a water-soluble film or water-soluble pouches. Various unit dose formats are provided in EP 2 100 947 and WO2013/165725 (which is hereby incorporated by reference), and are known in the art.

In some embodiments, the cleaning composition is a high density powder (HDD) composition having a variant serine protease polypeptide protease. The HDD powder laundry detergent can comprise a detersive surfactant including anionic detersive surfactants (e.g. linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (e.g., linear or branched or random chain, substituted or unsubstituted $C_8$-$C_{18}$ alkyl ethoxylates, and/or $C_6$-$C_{12}$ alkyl phenol alkoxylates), cationic detersive surfactants (e.g., alkyl pyridinium compounds, alkyl quaternary ammonium compounds, alkyl quaternary phosphonium compounds, alkyl ternary sulphonium compounds, and mixtures thereof), zwitterionic and/or amphoteric detersive surfactants (e.g., alkanolamine sulpho-betaines); ampholytic surfactants; semi-polar non-ionic surfactants and mixtures thereof; builders (phosphate free builders (e.g., zeolite builders examples of which include zeolite A, zeolite X, zeolite P and zeolite MAP in the range of 0 wt % to less than 10 wt %1; phosphate builders [examples of which include sodium tri-polyphosphate in the range of 0 wt % to less than 10 wt %]; citric acid, citrate salts and nitrilotriacetic acid or salt thereof in the range of less than 15 wt %); silicate salt (e.g. sodium or potassium silicate or sodium meta-silicate in the range of 0 wt % to less than 10 wt %, or layered silicate (SKS-6)); carbonate salt (e.g. sodium carbonate and/or sodium bicarbonate in the range of 0 wt % to less than 10 wt %); and bleaching agents (including photobleaches, (e.g., sulfonated zinc phthalocyanines, sulfonated aluminum phthalocyanines, xanthenes dyes, and mixtures thereof); hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, and nonanoyloxybenzene sulfonate-NOBS, nitrile quats, and mixtures thereof); sources of hydrogen peroxide (e.g., inorganic perhydrate salts examples of which include mono or tetra hydrate sodium salt of perborate, percarbonate, persulfate, perphosphate, or persilicate); preformed hydrophilic and/or hydrophobic peracids (e.g., percarboxylic acids and salts, percarbonic acids and salts, perimidic acids and salts, peroxymonosulfuric acids and salts), and mixtures thereof and/or bleach catalysts (e.g., imine bleach boosters (e.g., iminium cations and polyions); iminium zwitterions; modified amines; modified amine oxides; N-sulphonyl imines; N-phosphonyl imines; N-acyl imines; thiadiazole dioxides; perfluoroimines; cyclic sugar ketones and mixtures thereof; and metal-containing bleach catalyst (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid) and water-soluble salts thereof).

The composition can further include enzymes, e.g., proteases, amylases, lipases, cellulases, choline oxidases, peroxidases/oxidases, pectate lyases, mannanases, cutinases, laccases, phospholipases, lysophospholipases, acyltransferase, perhydrolase, arylesterase, and any mixture thereof.

The composition can further comprise additional detergent ingredients including perfume microcapsules, starch encapsulated perfume accord, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an automatic dishwashing (ADW) detergent composition having a serine protease of the present invention. The ADW detergent composition can comprise two or more non-ionic surfactants selected from a group of ethoxylated non-ionic surfactants, alcohol alkoxylated surfactants, epoxy-capped poly(oxyalkylated) alcohols, or amine oxide surfactants present in amounts from 0 to 10% by weight; builders in the range of 5-60% comprising either phosphate (mono-phosphates, di-phosphates, tri-polyphosphates or oligomeric-poylphosphates, preferred sodium tripolyphosphate-STPP or phosphate-free builders [amino acid based compounds, examples of which include MGDA (methyl-glycine-diacetic acid), and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), B-alaninediacetic acid (B-ADA) and their salts], homopolymers and copolymers of polycarboxylic acids and their partially or completely neutralized salts, monomeric polycarboxylic acids and hydroxycarboxylic acids and their salts in the range of 0.5% to 50% by weight; sulfonated/carboxylated polymers (provide dimensional stability to the product) in the range of about 0.1% to about 50% by weight; drying aids in the range of about 0.1% to about 10% by weight (selected from polyesters, especially anionic polyesters optionally together with further monomers with 3 to 6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1% to about 20% by weight (sodium or potassium silicates for example sodium disilicate, sodium meta-silicate and crystalline phyllosilicates); bleach-inorganic (for example perhydrate salts such as perborate, percarbonate, perphosphate, persulfate and persilicate salts) and organic (for example organic peroxyacids including diacyl and tetraacylperoxides, especially diperoxydodecanedioc acid, diperoxytetradecanedioc acid, and diperoxyhexadecanedioc acid); bleach activators—organic peracid precursors in the range from about 0.1% to about 10% by weight; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1% to 5% by weight (selected from benzatriazoles, metal salts and complexes, and/or silicates); enzymes in the range from about 0.01 to 5.0 mg of active enzyme per gram of automatic dishwashing detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, pectate lyases, pectin acetyl esterases, pectinases, pentosanases, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, and xylosidases, and any mixture thereof); and enzyme stabilizer components (selected from oligosaccharides, polysaccharides and inorganic divalent metal salts).

In some embodiments, the cleaning composition is borate-free. In some embodiments, the cleaning composition is phosphate-free. In some embodiments, the cleaning composition can have less than 10 ppm, or less than 5 ppm or less than 1 ppm of borates and/or, phosphates in the composition.

Representative detergent formulations that beneficially include a serine protease polypeptide of the present invention include the detergent formulations found in WO2013063460, pages 78-152, and in particular the tables of pages 94 to 152 are hereby incorporated by reference. The serine proteases are normally incorporated into the detergent composition at a level of from 0.00001% to 10% of enzyme protein by weight of the composition. In some embodiments, the detergent composition comprises more than 0.0001%, 0.001%, 0.01%, or 0.1% of the serine protease by weight of the composition. In some embodiments, the detergent composition comprises less than 1%, 0.1%, 0.01%, or 0.001% of the serine protease by weight of the composition.

B. Textile Processing

Also provided are compositions and methods of treating fabrics (e.g., to desize a textile) using a serine protease polypeptide of the present invention. Fabric-treating methods are well known in the art (see, e.g., U.S. Pat. No. 6,077,316). For example, the feel and appearance of a fabric can be improved by a method comprising contacting the fabric with a serine protease in a solution. The fabric can be treated with the solution under pressure.

A serine protease of the present invention can be applied during or after the weaving of a textile, or during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. A serine protease of the present invention can be applied during or after the weaving to remove these sizing starch or starch derivatives. After weaving, the serine protease can be used to remove the size coating before further processing the fabric to ensure a homogeneous and wash-proof result.

A serine protease of the present invention can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. The serine protease can be used in methods of finishing denim garments (e.g., a "bio-stoning process"), enzymatic desizing and providing softness to fabrics, and/or finishing process.

C. Leather and Feather Processing

The serine protease polypeptides described herein find further use in the enzyme aided removal of proteins from animals and their subsequent degradation or disposal, such as feathers, skin, hair, hide, and the like. In some instances, immersion of the animal carcass in a solution comprising a serine protease polypeptide of the present invention can act to protect the skin from damage in comparison to the traditional immersion in scalding water or the defeathering process. In one embodiment, feathers can be sprayed with an isolated serine protase polypeptide of the present invention under conditions suitable for digesting or initiating degradation of the plumage. In some embodiments, a serine protease of the present invention can be used, as above, in combination with an oxidizing agent.

In some embodiments, removal of the oil or fat associated with raw feathers is assisted by using a serine protease polypeptide of the present invention. In some embodiments, the serine protease polypeptides are used in compositions for cleaning the feathers as well as to sanitize and partially dehydrate the fibers. In yet other embodiments, the disclosed serine protease polypeptides find use in recovering protein from plumage. In some other embodiments, the serine protease polypeptides are applied in a wash solution in combination with 95% ethanol or other polar organic solvent with or without a surfactant at about 0.5% (v/v).

D. Animal Feed Applications

In a further aspect of the invention, the serine protease polypeptides of the present invention can be used as a component of an animal feed composition, animal feed additive and/or pet food comprising a serine protease and variants thereof. The present invention further relates to a method for preparing such an animal feed composition, animal feed additive composition and/or pet food comprising mixing the serine protease polypeptide with one or more animal feed ingredients and/or animal feed additive ingredients and/or pet food ingredients. Furthermore, the present invention relates to the use of the serine protease polypeptide in the preparation of an animal feed composition and/or animal feed additive composition and/or pet food.

The term "animal" includes all non-ruminant and ruminant animals. In a particular embodiment, the animal is a non-ruminant animal, such as a horse and a mono-gastric animal. Examples of mono-gastric animals include, but are not limited to, pigs and swine, such as piglets, growing pigs, sows; poultry such as turkeys, ducks, chicken, broiler chicks, layers; fish such as salmon, trout, tilapia, catfish and carps; and crustaceans such as shrimps and prawns. In a further embodiment the animal is a ruminant animal including, but not limited to, cattle, young calves, goats, sheep, giraffes, bison, moose, elk, yaks, water buffalo, deer, camels, alpacas, llamas, antelope, pronghorn and nilgai.

In the present context, it is intended that the term "pet food" is understood to mean a food for a household animal such as, but not limited to, dogs, cats, gerbils, hamsters, chinchillas, fancy rats, guinea pigs; avian pets, such as *canaries*, parakeets, and parrots; reptile pets, such as turtles, lizards and snakes; and aquatic pets, such as tropical fish and frogs.

The terms "animal feed composition," "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

E. Paper Pulp Bleaching

The protease polypeptides described herein find further use in the enzyme aided bleaching of paper pulps such as chemical pulps, semi-chemical pulps, kraft pulps, mechanical pulps or pulps prepared by the sulfite method. In general terms, paper pulps are incubated with a protease polypeptide of the present invention under conditions suitable for bleaching the paper pulp.

In some embodiments, the pulps are chlorine free pulps bleached with oxygen, ozone, peroxide or peroxyacids. In some embodiments, the protease polypeptides are used in enzyme aided bleaching of pulps produced by modified or continuous pulping methods that exhibit low lignin contents. In some other embodiments, the protease polypeptides are applied alone or preferably in combination with xylanase and/or endoglucanase and/or alpha-galactosidase and/or cellobiohydrolase enzymes.

F. Protein Degradation

The protease polypeptides described herein find further use in the enzyme aided removal of proteins from animals and their subsequent degradation or disposal, such as feathers, skin, hair, hide, and the like. In some instances, immersion of the animal carcass in a solution comprising a protease polypeptide of the present invention can act to protect the skin from damage in comparison to the traditional immersion in scalding water or the defeathering process. In one embodiment, feathers can be sprayed with an isolated protease polypeptide of the present invention under conditions suitable for digesting or initiating degradation of the plumage. In some embodiments, a protease of the present invention can be used, as above, in combination with an oxidizing agent.

In some embodiments, removal of the oil or fat associated with raw feathers is assisted by using a protease polypeptide of the present invention. In some embodiments, the protease polypeptides are used in compositions for cleaning the feathers as well as to sanitize and partially dehydrate the fibers. In some other embodiments, the protease polypeptides are applied in a wash solution in combination with 95% ethanol or other polar organic solvent with or without a surfactant at about 0.5% (v/v). In yet other embodiments, the disclosed protease polypeptides find use in recovering protein from plumage. The disclosed protease polypeptides may be used alone or in combination in suitable feather processing and proteolytic methods, such as those disclosed in PCT/EP2013/065362, PCT/EP2013/065363, and PCT/EP2013/065364, which are hereby incorporated by reference. In some embodiments, the recovered protein can be subsequently used in animal or fish feed.

G. Tissue Debridement

The protease polypeptides described herein find further use in the enzyme aided debridement of tissue. This involves the removal of dead or damaged tissue, for example, removal from wounds to aid in healing.

H. Tissue Culture

The protease polypeptides described herein find further use in tissue culture. In particular, proteases of the present invention can be used to suspend or resuspend cells adherent to a cell culture wall, such as during the process of harvesting cells. Proteases of the present invention can be used to cleave protein bonds between cultured cells and the dish, allowing cells to become suspended in solution.

I. Food Applications

The protease polypeptides described herein find further use as a food additive, a digestive aide or a food processing aid.

EXAMPLES

The following examples are provided to demonstrate and illustrate certain preferred embodiments and aspects of the present disclosure and should not be construed as limiting.

In the experimental disclosure which follows, the following abbreviations apply: ADW (automatic dish washing); BMI (blood/milk/ink); BSA (bovine serum albumin); CAPS (N-cyclohexyl-3-aminopropanesulfonic acid); CHES (N-cyclohexyl-2-aminoethanesulfonic acid); DMC (dimethyl casein); HDD (heavy duty dry/powder); HDL (heavy duty liquid); HEPES (4-(2-hydroxyethyl)-1-piperazineethanesulfonic acid); MTP (microtiter plate); ND (not done); OD (optical density); PCR (polymerase chain reaction); ppm (parts per million); QS (quantity sufficient); rpm (revolutions per minute); AAPF (succinyl-Ala-Ala-Pro-Phe-p-nitroanilide); TNBSA (2,4,6-trinitrobenzene sulfonic acid); v/v (volume to volume); w/v (weight to volume).

Example 1

Cloning of *Bacillus gibsonii* Serine Protease Bgi02446

The *B. gibsonii* DSM 8722 strain (obtained from Leibniz-Institut DSMZ—Deutsche Sammlung von Mikroorganismen and Zellkulturen GmbH) was selected as a potential source for enzymes useful in various industrial applications. The entire genome of the *B. gibsonii* DSM 8722 strain was sequenced using ILLUMINA® sequencing by synthesis technology. Genome sequencing and assembly of the sequence data was performed by BaseClear (Leiden, The Netherlands). Contigs were annotated by BioXpr (Namur, Belgium). One of the genes identified this way in *B. gibsonii* DSM 8722 encodes a serine protease that showed homology to serine proteases of other bacteria.

The nucleotide sequence of Bgi02446n is set forth as SEQ ID NO:1:

ATGAAAAGAAAAGTAGGAAAGCTTATGGTGGGGCTTGTATGTGTAACAGC

TCTAGTAACCGTGACAGATTCTGCATCTGCGGCAGAAGAAAAAGTAAAAT

ACTTAATAGGTTTCGAAGAAGAAGCAGAACTTGAAGCCTTCACTGAGGAA

ATTGACCAAGTTGGTGTATTTTCTGTTGAAGAACAAAGTGTAGCTGAGGA

TACGTTAGATATTGATGTAGACATTATTGATGAATATGATTATATTGATG

TGTTAGCTGTAGAATTAGATCCTGAGGATGTAGATGCGTTAAGTGAAGAA

-continued
```
GCAGGTATCTCATTTATTGAAGAAGACATTGAACTGTCTATTCAACAAAC

AGTTCCTTGGGGCATTACTCGTGTACAAGCTCCGGCTGTTCATAACCGTG

GGATTACAGGTTCTGGAGTAAGAGTAGCTATCCTTGATTCAGGGATTTCA

GCCCATAGTGATTTGAATATCCGCGGTGGAGCTAGCTTTGTACCGGGTGA

ACCAACGACAGCTGATTTAAATGGACATGGTACTCACGTGGCCGGAACAG

TAGCAGCTCTAAATAATTCAATTGGTGTCATTGGTGTTGCACCGAATGCT

GAATTATATGCTGTTAAAGTACTTGGAGCAAATGGAAGCGGAAGTGTAAG

TGGGATTGCTCAAGGTTTAGAGTGGGCGGCAACCAATAACATGCATATTG

CGAACATGAGTCTCGGTAGTGATTTTCCTAGCTCTACACTTGAGCGTGCA

GTCAACTATGCAACAAGCCGTGATGTACTAGTTATTGCAGCGACTGGTAA

TAACGGTTCTGGTTCAGTAGGCTATCCTGCTCGTTATGCAAACGCAATGG

CTGTAGGAGCGACTGACCAAAACAACAGACGCGCAAACTTTTCTCAGTAT

GGTACGGGAATTGACATCGTAGCACCTGGTGTTAACGTACAAAGTACGTA

TCCAGGTAACCGTTACGTGAGTATGAATGGTACATCTATGGCTACTCCAC

ACGTAGCTGGTGCCGCAGCGCTTGTAAAGCAACGCTATCCGTCTTGGAAT

GCGACTCAAATTCGCAATCATCTGAAAAATACAGCAACAAATCTAGGAAA

CTCTTCACAATTTGGTAGTGGCCTAGTTAACGCAGAAGCAGCAACACGT.
```

The amino acid sequence of the preproenzyme encoded by Bgi02446n is set forth as SEQ ID NO:2:

*MKRKVGKLMVGLVCVTALVTVTDSASA*AEEKVKYLIGFEEEAELEAFTE

EIDQVGVFSVEEQSVAEDTLDIDVDII

DEYDYIDVLAVELDPEDVDALSEEAGISFIEEDIELSIQQTVPWGITRVQ

APAVHNRGITGSGVRVAILDSGISAHSDLNIRGGASFVPGEPTTADLNGH

GTHVAGTVAALNNSIGVIGVAPNAELYAVKVLGANGSGSVSGIAQGLEWA

ATNNMHIANMSLGSDFPSSTLERAVNYATSRDVLVIAATGNNGSGSVGYP

ARYANAMAVGATDQNNRRANFSQYGTGIDIVAPGVNVQSTYPGNRYVSMN

GTSMATPHVAGAAALVKQRYPSWNATQIRNHLKNTATNLGNSSQFGSGLV

NAEAATR.

The amino acid sequence of the proenzyme encoded by Bgi02446n is set forth as SEQ ID NO:3:

AEEKVKYLIGFEEEAELEAFTEEIDQVGVFSVEEQSVAEDTLDIDVDIID

EYDYIDVLAVELDPEDVDALSEEAGISFIEEDIELSIQQTVPWGITRVQA

PAVHNRGITGSGVRVAILDSGISAHSDLNIRGGASFVPGEPTTADLNGHG

THVAGTVAALNNSIGVIGVAPNAELYAVKVLGANGSGSVSGIAQGLEWAA

TNNMHIANMSLGSDFPSSTLERAVNYATSRDVLVIAATGNNGSGSVGYPA

RYANAMAVGATDQNNRRANFSQYGTGIDIVAPGVNVQSTYPGNRYVSMNG

TSMATPHVAGAAALVKQRYPSWNATQIRNHLKNTATNLGNSSQFGSGLVN

AEAATR.

At the N-terminus, the preproenzyme has a signal peptide with a predicted length of 27 amino acids (in bold italics in SEQ ID NO:2) as determined using SignalP-NN (Emanuelsson et al., Nature Protocols, 2:953-971, 2007). The presence of a signal sequence indicates that this serine protease is a secreted enzyme. Like other serine proteases, the enzyme has a pro-sequence with a predicted length of 87 amino acids (in italics in SEQ ID NOs:2 and 3). The pro-sequence prediction was based on knowledge of the pro-mature junction in homologous serine proteases such as BPN' (Wells et al., Nucleic Acids Res, 11: 7911-25, 1983) and PB92 protease (van der Laan et al., Appl Environ Microbiol, 57:901-909, 1991).

The predicted amino acid sequence of the mature enzyme, Bgi02446 (269 amino acids), is set forth as SEQ ID NO:4:

QQTVPWGITRVQAPAVHNRGITGSGVRVAILDSGISAHSDLNIRGGASFV

PGEPTTADLNGHGTHVAGTVAALNNSIGVIGVAPNAELYAVKVLGANGSG

SVSGIAQGLEWAATNNMHIANMSLGSDFPSSTLERAVNYATSRDVLVIAA

TGNNGSGSVGYPARYANAMAVGATDQNNRRANFSQYGTGIDIVAPGVNVQ

STYPGNRYVSMNGTSMATPHVAGAAALVKQRYPSWNATQIRNHLKNTATN

LGNSSQFGSGLVNAEAATR.

Example 2

Heterologous Expression of Bgi02446

The Bgi02446 protease was produced in *B. subtilis* using an expression cassette consisting of the *B. subtilis* aprE promoter, the *B. subtilis* aprE signal peptide sequence, the native Bgi02446 protease pro-peptide, the mature Bgi02446 protease and a BPN' terminator. The Bgi02446 expression cassette was cloned into the pHYT replicating shuttle vector and transformed. The pHYT vector was derived from pHY300PLK (Takara) by adding a terminator after the tetracycline resistance gene using the BstEII and EcoRI sites (terminator sequence: GGTTACCTTG AATGTATATA AACATTCTCA AAGGGATTTC TAATAAAAAA CGCTCGGTTG CCGCCGGGCG TTTTTTATGC ATCGATGGAA TTC set forth as SEQ ID NO:5). The HindIII site in pHY300PLK was also removed using a linker cloned into the BamHI and HindIII sites (linker sequence: GGATCCTGAC TGCCTGAGCT T set forth as SEQ ID NO: 48). A map of the pHYT vector for expression of the Bgi02446 serine protease (pHYT-Bgi02446) is shown in FIG. 1.

A synthetic gene encoding the pro-mature region of Bgi02446 that it is modified by introducing several silent codon changes was cloned into the pHYT vector. The nucleotide sequence for this alternative Bgi02446 gene is shown in SEQ ID NO: 6.

The synthetic nucleotide sequence of the pro-mature gene encoding Bgi02446 is set forth as SEQ ID NO:6:

```
GCAGAAGAAAAAGTCAAATATCTGATCGGCTTTGAAGAAGAAGCAGAACT

GGAAGCATTTACGGAAGAAATTGATCAAGTTGGCGTTTTTAGCGTCGAAG

AACAATCAGTTGCAGAAGATACACTGGATATCGATGTCGATATCATCGAC

GAATATGACTATATTGATGTTCTGGCGGTTGAACTTGATCCGGAAGATGT

TGATGCACTGTCAGAAGAAGCAGGCATTAGCTTTATTGAAGAAGATATCG

AACTGAGCATTCAACAAACAGTTCCGTGGGGCATTACAAGAGTTCAAGCA

CCGGCAGTTCATAATCGCGGAATTACAGGCTCAGGCGTTAGAGTTGCAAT
```

-continued
```
TCTGGATTCAGGCATTTCAGCACATAGCGATCTGAATATTAGAGGCGGAG

CATCATTTGTCCCTGGCGAACCGACAACAGCAGATCTGAATGGCCATGGC

ACACATGTTGCAGGCACAGTTGCAGCACTGAATAATTCAATTGGCGTTAT

TGGAGTTGCACCGAATGCAGAACTGTATGCAGTTAAAGTTCTTGGCGCAA

ATGGCTCAGGCTCAGTTTCAGGCATTGCACAAGGCCTGGAATGGGCAGCA

ACAAATAACATGCATATTGCAAATATGTCACTGGGCTCAGATTTTCCGTC

ATCAACACTGGAACGCGCAGTTAATTATGCAACATCAAGAGATGTTCTGG

TCATTGCAGCAACAGGCAATAATGGCAGCGGCTCAGTTGGCTATCCGGCA

AGATATGCAAATGCAATGGCAGTTGGCGCTACAGATCAAATAATCGCAG

AGCAAATTTTAGCCAATATGGCACAGGCATTGATATTGTTGCACCTGGCG

TTAATGTTCAGTCAACATATCCGGGAAATCGCTATGTTTCAATGAATGGC

ACATCAATGGCAACACCGCATGTCGCAGGCGCAGCAGCACTGGTTAAACA

AAGATATCCGTCATGGAATGCGACACAGATTCGCAATCATCTGAAAAATA

CAGCAACAAATCTGGGCAATTCAAGCCAATTTGGCTCAGGCCTGGTTAAT

GCAGAAGCAGCAACAAGATAA
```

To produce Bgi02446, a *B. subtilis* transformant containing pHYT-Bgi02446 was cultivated in an enriched semi-defined media based on MOPs buffer, with urea as major nitrogen source, glucose as the main carbon source, and supplemented with 1% soytone for robust cell growth. The media was supplemented with 25 ppm tetracycline. After incubation (2 days at 32° C.), Bgi02446 protease was detected in the growth medium. After centrifugation and filtration, culture supernatants with Bgi02446 protease were used for assays and purification.

Protein was quantified by the stain-free Imager Criterion method. This method is based on utilization of stain-free precast PAGE gels, where the intensity of each protein band depends on the number of tryptophan residues present in the protein of interest. The CRITERION™ TGX (Tris-Glycine extended) STAIN-FREE™ precast gels for PAGE include unique trihalo compounds. This allows rapid fluorescent detection of proteins with the GEL DOC™ EZ imaging system. The trihalo compounds react with tryptophan residues in a UV-induced reaction to produce fluorescence, which can be easily detected by the Gel Doc EZ imager within the gels. Reagents used in the assay include: Concentrated (10×) Laemmli Sample Buffer (Kem-En-Tec, Catalogue No. 42556); either 18- or 26-well Criterion TGX Strain-Free Precast gels (Bio-Rad, Catalogue Nos. 567-8124 and 567-8125 respectively); and protein markers "Precision Plus Protein Standards" (Bio-Rad, Catalogue No. 161-0363). The assay was carried out as follows: 25 µl protein sample and 25 µl 0.5 M HCl were added to a 96-well PCR plate on ice to inactivate the protease and prevent self-hydrolysis. 50 µl of the acid protein mix was added to 50 µL sample buffer containing 0.385 mg DTT in the 96-well PCR plate. Afterwards the chamber was filled with running buffer, and the gel cassette was set. Then 10 µL of each sample together with markers were loaded in each pocket. Electrophoresis was started at 200 V for 35 min Following electrophoresis, the gel was transferred to an Imager, and Image Lab software was used for calculation of the intensity of each band. By knowing the protein amount and the tryptophan content of the standard sample, a calibration curve was made. The amount of experimental sample was determined by extrapolation of the band intensity and tryptophan numbers to protein concentration. This protein quantification method was employed to prepare samples of Bgi02446 for use in the assays described in subsequent examples.

A sample of isolated Bgi02446 protease was analyzed by LC-MS/MS as described subsequently. In preparation for sequence confirmation, including N- and C-terminal determination, a sample of Bgi02446 protease was subjected to a series of chemical treatments in a 10 kDa spinfilter. The sample was denatured and reduced/alkylated by urea and DTT/Iodoacetamide treatment. A guanidination step was performed to convert lysines to homoarginines to protect lysine side chains from acetylation. The acetylation reaction using Sulfo-NHS-Acetate (Sulfosuccinimidyl Acetate) only modifies the protein N-terminal residue. The sample is then mixed with a buffer containing 40 v/v % $^{18}$O water:60 v/v % $^{16}$O water and the proteolytic enzymes used for protein digestion. The resulting peptides will contain mixtures of $^{18}$O and $^{16}$O, except for the Carboxyl terminus which will retain the native $^{16}$O, as will be apparent from the isotopic pattern of the peptides. The peptide, originating from the protein N-terminus, will appear as the only acetylated peptide. The resulting peptides were separated and analyzed using a nano-LC system followed by LTQ Orbitrap (Thermo Fisher) high resolution mass spectrometer. The amino acid sequences were deduced from the MS/MS fragment spectra of the peptides. Based on this analysis, the N-terminus of the isolated protein was confirmed to begin with Q at position 2 from the predicted mature sequence.

The amino acid sequence of the processed mature enzyme, Bgi02446 that was purified and used for further characterization (268 amino acids), is set forth as SEQ ID NO:7:

```
QTVPWGITRVQAPAVHNRGITGSGVRVAILDSGISAHSDLNIRGGASFVP

GEPTTADLNGHGTHVAGTVAALNNSIGVIGVAPNAELYAVKVLGANGSGS

VSGIAQGLEWAATNNMHIANMSLGSDFPSSTLERAVNYATSRDVLVIAAT

GNNGSGSVGYPARYANAMAVGATDQNNRRANFSQYGTGIDIVAPGVNVQS

TYPGNRYVSMNGTSMATPHVAGAAALVKQRYPSWNATQIRNHLKNTATNL

GNSSQFGSGLVNAEAATR.
```

Example 3

Protease Activity of Bgi02446

Figure 2:
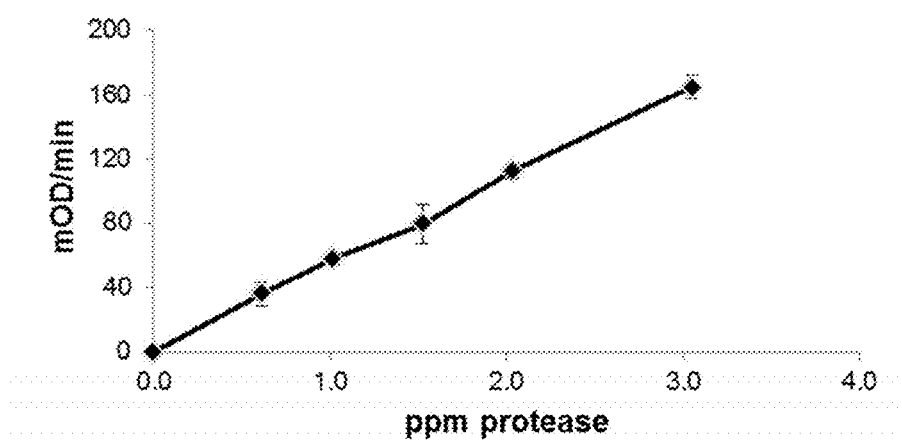
FIG. 2 provides a plot of the protease activity of Bgi02446 on a DMC substrate.

The protease activity of the Bgi02446 was tested by measuring the hydrolysis of a dimethyl casein (DMC) substrate. The reagent solutions used for the DMC assay were: 2.5% w/v DMC (Sigma C-9801) in 100 mM sodium carbonate buffer pH 9.5, 0.075% TNBSA (Thermo Scientific) in Reagent A. Reagent A: 45.4 g $Na_2B_4O_7.10H_2O$ (Merck) in 15 mL 4 N NaOH to reach a final volume of 1000 mL in deionized water. Protease supernatants were diluted in dilution solution: 10 mM NaCl, 0.1 mM $CaCl_2$, 0.005% Tween-80 to the desired concentration to achieve a linear response during hydrolysis over 5 min. A 96-well microtiter plate (MTP) was filled with 95 µl DMC substrate followed by the addition of 5 µl diluted protease supernatant. 100 µL of TNBSA in Reagent A was then added with slow mixing. Activity was measured at 405 nm over 5 min using a SpectraMax plate reader in kinetic mode at RT. The absorbance of a blank containing no protease was subtracted from each sample reading. The protease activity was expressed as mOD/min. The protease activity curve for Bgi02446 is shown in FIG. 2. The specific activity of Bgi02446 protease in the DMC assay was found to be 55 mOD/min/ppm (where ppm is the final concentration of protease in the assay). The specific activities of *B. lentus* P29600 and *B. amyloliquefaciens* CAA24990 proteases were found to be 54 and 23 mOD/min/ppm respectively, under the same assay conditions.

Example 4 pH Profile of Bgi02446

The pH dependence of proteolytic activity of Bgi02446 was examined using an azo-casein substrate in a 50 mM acetate/bis-Tris/HEPES/CHES buffer including 50 mM $CaCl_2$. The effect of pH at a range of 4 to 12 was measured in 1 pH unit increments. One Protaxyme AK tablet (Megazyme, Ireland) was added to a glass test tube together with 1.9 mL buffer and a magnetic stirrer, followed by gentle hydration at 40° C. for 5 min in a temperature controlled water bath fitted with magnetic stirrer. A 100 µl sample of freshly prepared protease (diluted in deionised water to an appropriate concentration for the assay) was added to the prehydrated substrate and the reaction was carried out at 40° C. for 10 min. To stop the reaction, 10 mL of a 2% w/v Tris buffer pH 12 was added and the solution was stirred and immediately filtered through a Whatman No. 1 filter. The supernatant was collected and the absorbance at 590 nm was measured for the supernatant to quantify the product of the reaction. The absorbance from a buffer-only control was subtracted from each sample reading, and the resulting values were converted to percentages of relative activity, by defining the activity at the optimal pH as 100%. Bgi02446 was determined to maintain≥50% activity over the pH range of 8 to 12, under the conditions of this assay.

Example 5

Temperature Profile of Bgi02446

The temperature dependence of proteolytic activity of Bgi02446 was measured using an azo-casein substrate in a 50 mM acetate/bis-Tris/HEPES/CHES buffer including 50 mM $CaCl_2$ at pH 9. The activity was measured at temperatures between 30° C. and 80° C. in 10° C. increments. One Protaxyme AK tablet (Megazyme, Ireland) was added to a glass test tube together with 1.9 mL of buffer and a magnetic stirrer, followed by gentle hydration at set temperatures for 5 min in a temperature-controlled water bath fitted with magnetic stirrer. A 100 µl sample of freshly prepared protease (diluted in deionized water to an appropriate concentration for the assay) was added to the prehydrated substrate and the reaction was carried out at temperatures between 30° C. and 80° C. for 10 min To terminate the reaction, 10 mL of a 2% w/v Tris buffer pH 12 was added and solution was stirred and filtered immediately through a Whatman No. 1 filter. The supernatant was collected and the absorbance at 590 nm was measured for the supernatant to quantify the product of the reaction. The absorbance from a buffer-only control was subtracted from each sample reading, and the resulting values were converted to percentages of relative activity, by defining the activity at the optimal temperature at 100%. Bgi02446 was determined to retain≥50% activity over a range of 50-75° C., under the conditions of this assay.

Example 6

Cleaning Performance of Bgi02446

The cleaning performance of Bgi02446 was tested on BMI (blood/milk/ink on cotton) microswatches (EMPA-116, Center for Testmaterials, The Netherlands) for laundry based applications, and on egg yolk (egg yolk on polyacryl fabric, aged and colored with carbon black dye) microswatches (PAS-38, Center for Testmaterials, The Netherlands) for dish based applications. MTPs (Corning 9017) containing pre-rinsed, pre-punched (to fit on MTP) swatches, and filled with detergent prior to enzyme addition. Commercial detergents were heat-inactivated to remove existing enzyme activity and dosed as described on Table 6-1.

Heavy duty liquid (HDL) laundry detergents were inactivated by heating at 95° C. for 4 hours in a water bath. Heavy duty dry (HDD) laundry detergents were inactivated by preparing a 10% w/v solution and heating at 95° C. for 4 hours. After heating both HDD and HDL detergents for 4 hours, existing protease activity was determined to be non-existent.

Washing solutions with the Final Detergent Wash concentrations (g/L) described in Table 6-1 were made up and used in the cleaning performance assay.

TABLE 6-1

Detergent Conditions for Cleaning Performance Assays

| Detergent* | Type | Detergent Wash Conc. (g/L) | Hardness Conc. (ppm) | Buffer | pH |
|---|---|---|---|---|---|
| OMO color | HDD | 5.3 | 250 | 2 mM $NaCO_3$ | 10.6 |
| Kirkland Ultra | HDD | 1.09 | 150 | 2 mM $NaCO_3$ | 10.6 |
| OMO K & K | HDL | 2.8 | 250 | 5 mM Na HEPES | 8.2 |
| Kirkland Ultra | HDL | 0.71 | 150 | 5 mM Na HEPES | 8.2 |
| GSM-B 10.5 | ADW | 3 | 374 | unbuffered | ~10.5 |
| GSM-B 9 | ADW | 3 | 374 | unbuffered, +1M citrate to adjust pH | 9 |

*Detergent sources: Kirkland Ultra HDD and HDL (Sun Products) were purchased from local supermarket in the United States in 2012. OMO color HDD and OMO Klein & Krachtig (Unilever) were purchased from local supermarkets in The Netherlands in 2013. GSM-B was purchased from WFK Testgewebe GmbH, Germany.

TABLE 6-2

GSM-B pH 10.5 Phosphate-Free ADW Detergent Ingredients

| Component | Weight % |
|---|---|
| Sodium citrate dehydrate | 30.0 |
| Maleic acid/acrylic acid copolymer sodium salt (SOKALAN ® CP5; BASF) | 12.0 |
| Sodium perborate monohydrate | 5.0 |
| TAED | 2.0 |
| Sodium disilicate: Protil A (Cognis) | 25.0 |
| Linear fatty alcohol ethoxylate | 2.0 |
| Sodium carbonate anhydrous | add to 100 |

Aliquots of enzyme were added to a detergent-filled microswatch plate to reach a final volume of 200 µL with a 0.04 to 10 ppm final enzyme concentration for cleaning performance assay. Laundry cleaning assays with HDL or HDD detergents was carried out at 25° C. for 15 min, while automatic dish (ADW) assays were carried out at 40° C. for 30 min.

Figure 3A:
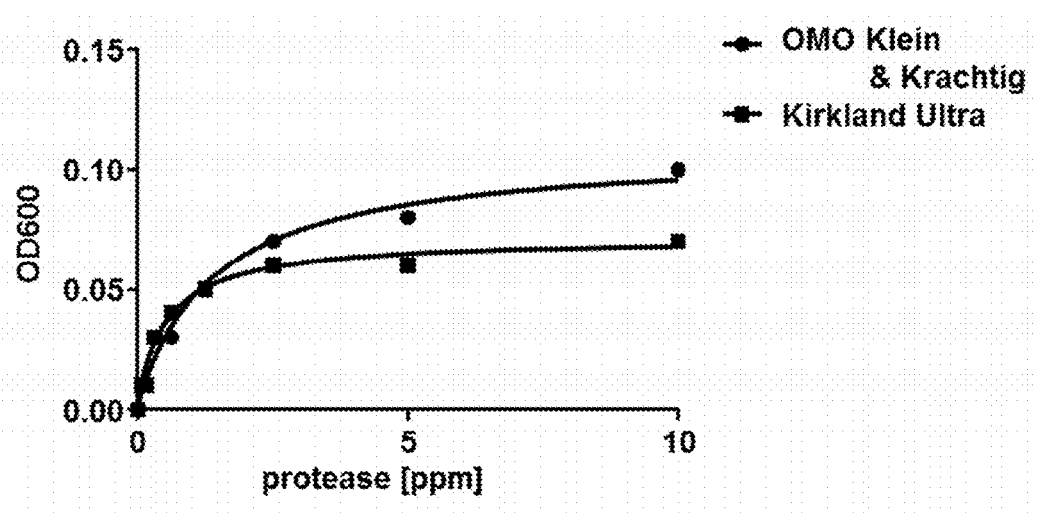
FIG. 3A provides cleaning efficiency curves of Bgi02446 in heavy duty liquid (HDL) laundry detergents.
Figure 3B:
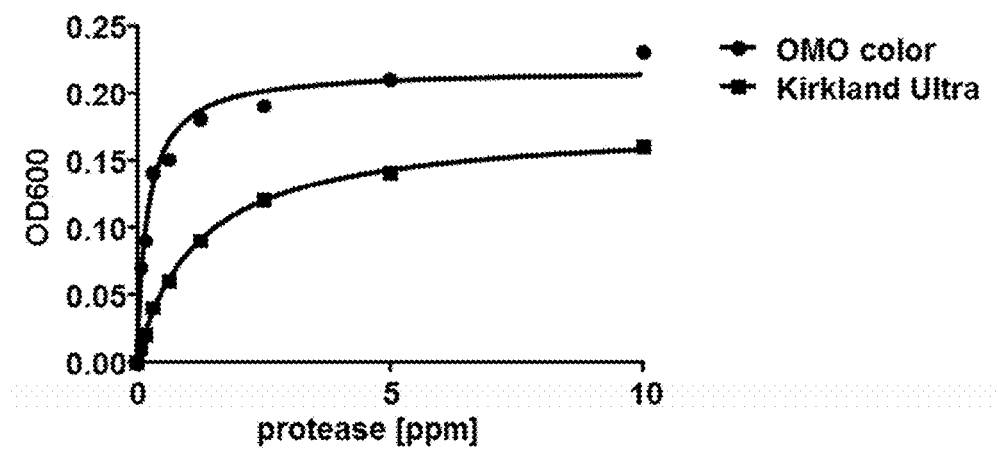
FIG. 3B provides cleaning efficiency curves of Bgi02446 in heavy duty dry (HDD) laundry detergents.
Figure 3C:
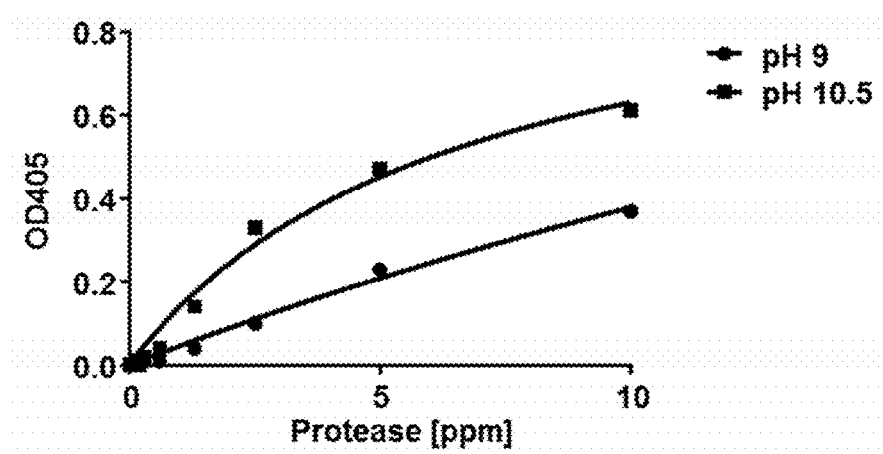
FIG. 3C provides cleaning efficiency curves of Bgi02446 in automatic dish washing (ADW) detergents.

Following incubation, 100 µL of supernatant was transferred to a fresh MTP (Costar 9017) and absorbance was read at 600 nm for EMPA-116 swatches, or at 405 nm for PAS-38 swatches, using the SpectraMax plate reader. The absorbance from a buffer only control was subtracted and the resulting OD values at 600 nm (for HDL and HDD detergents) and 405 nm (for ADW detergents) were plotted as a function of protease concentration. The data was fitted using the Langmuir equation. The cleaning performance of Bgi02446 in various detergents is shown in FIGS. 3A-3C.

Example 7

Identification of Homologous Proteases

The amino acid sequence (269 residues) of the predicted mature form of Bgi02446 (SEQ ID NO:4) was subjected to a BLAST search (Altschul et al., Nucleic Acids Res, 25:3389-402, 1997) against the NCBI non-redundant protein database. A similar search was run against the Genome Quest Patent database with search parameters set to default values using SEQ ID NO:4 as the query sequence. Subsets of the search results are shown in Tables 7-1 and 7-2. Percent identity (PID) for both search sets was defined as the number of identical residues divided by the number of aligned residues in the pairwise alignment. The column labeled "Sequence Length" refers to the length (in amino acids) of the protein sequences associated with the listed Accession Nos., while the column labeled "Aligned Length" refers to the length (in amino acids) of the aligned protein sequences, which was used for the PID calculation.

TABLE 7-1

Percent Identity (PID) Shared by Bgi02446 with Entries in the NCBI non-Redundant Protein Database

| Accession No. | PID | Organism | Sequence Length | Alignment Length |
|---|---|---|---|---|
| AGS78407 | 100.0 | *Bacillus gibsonii* | 375 | 269 |
| AAA22212 | 80.3 | *Bacillus alcalophilus* | 380 | 269 |
| BAD63300 | 79.9 | *Bacillus clausii* KSM-K16 | 380 | 269 |
| P29600 | 79.9 | *Bacillus lentus* | 269 | 269 |
| BAA06157 | 78.1 | *Bacillus* sp. Sendai | 382 | 269 |
| BAA25184 | 77.7 | *Bacillus* sp. AprN | 379 | 269 |
| ADK62564 | 65.8 | *Bacillus* sp. B001 | 375 | 269 |
| BAA05540 | 63.9 | *Bacillus* sp. AprM | 361 | 269 |
| ADD64465 | 63.2 | *Bacillus* sp. JB99 | 361 | 269 |
| BAA06158 | 62.1 | *Bacillus* sp. ALP I | 374 | 272 |
| ADC49870 | 62.1 | *Bacillus pseudofirmus* OF4 | 374 | 272 |
| AAC43580 | 61.3 | *Bacillus* sp. SprC | 378 | 272 |
| BAD11988.2 | 58.8 | *Bacillus* sp. KSM-LD1 SA | 376 | 272 |
| YP_003972439 | 58.4 | *Bacillus atrophaeus* 1942 | 382 | 274 |
| CAA24990 | 56.6 | *Bacillus amyloliquefaciens* | 376 | 274 |
| BAN09118 | 56.2 | *Bacillus subtilis* | 381 | 274 |
| BAD21128 | 56.0 | *Bacillus* sp. KSM-LD1 SB | 377 | 273 |
| CAA74536 | 55.8 | *Bacillus subtilis* str. 168 | 381 | 274 |
| AGC81872 | 55.5 | *Bacillus methylotrophicus* | 382 | 274 |
| WP_010329279 | 55.5 | *Bacillus vallismortis* | 381 | 274 |
| WP_010333625 | 55.5 | *Bacillus mojavensis* | 381 | 274 |
| AGS78407 | 100.0 | *Bacillus gibsonii* | 375 | 269 |
| CAJ70731 | 55.3 | *Bacillus licheniformis* | 379 | 273 |
| ABY25856 | 54.7 | *Geobacillus stearothermophilus* | 382 | 274 |
| WP_007497196 | 54.6 | *Bacillus stratosphericus* | 383 | 273 |
| AAC43581 | 54.2 | *Bacillus* sp. SprD | 379 | 273 |
| WP_006636716 | 54.2 | *Bacillus sonorensis* | 378 | 273 |
| AFP23380 | 54.2 | *Bacillus lehensis* | 276 | 273 |
| ADN04910 | 53.8 | *Bacillus circulans* | 275 | 273 |
| ADK11996 | 53.8 | *Bacillus pumilus* | 383 | 273 |

TABLE 7-2

Percent Identity (PID) Shared by Bgi02446 with Entries in the Genome Quest Database

| Patent - SEQ ID NO/Accession No. listed in Genome Quest | PID | Organism | Sequence Length | Alignment Length |
|---|---|---|---|---|
| WO03054184-CAE48421 | 95.2 | *B. gibsonii* | 383 | 269 |
| WO2007131657-CAS91385 | 94.4 | *B. gibsonii* | 383 | 269 |
| WO2008086916-CAV33594 | 93.3 | *B. gibsonii* | 383 | 269 |
| WO03054185-CAE48424 | 89.9 | *B. gibsonii* | 383 | 269 |
| WO2011110625-0002 | 89.6 | *Bacillus* sp. | 269 | 269 |
| WO2012119955-0005 | 88.9 | *Bacillus* sp. | 269 | 269 |
| WO2012119955-0004 | 88.5 | *Bacillus* sp. | 269 | 269 |
| WO2012119955-0006 | 88.5 | *Bacillus* sp. | 269 | 269 |
| U.S. Pat. No. 7,642,080-0002 | 87.4 | *Bacillus* sp. strain Zi344 | 381 | 269 |
| U.S. Pat. No. 7,507,569-0002 | 87.3 | Artificial Sequence | 269 | 268 |
| U.S. Pat. No. 7,507,569-0004 | 85.5 | Artificial Sequence | 269 | 268 |
| U.S. Pat. No. 7,507,569-0006 | 85.1 | Artificial Sequence | 269 | 268 |
| U.S. Pat. No. 7,642,080-0006 | 84.8 | *Bacillus* sp. strain p203 | 383 | 269 |
| U.S. Pat. No. 7,642,080-0004 | 84.8 | *Bacillus* sp. strain EP655 | 383 | 269 |
| U.S. Pat. No. 7,262,042-0004 | 80.6 | *B. alkalophilus* | 268 | 268 |
| WO2011130222-0004 | 80.6 | *B. clausii* | 269 | 268 |

The amino acid sequence of the predicted mature form of Bgi02446 (SEQ ID NO:4) was aligned with the amino acid sequences of multiple proteases listed in Tables 7-1 and 7-2 using CLUSTALW software (Thompson et al., Nucleic Acids Research, 22:4673-4680, 1994) with the default parameters. FIG. 4A-C shows the CLUSTAL W (1.83) multiple sequence alignment. The nucleotide sequence encoding Bgi02446 (SEQ ID NO:1) was aligned with the nucleotide sequence encoding the *B. gibsonii* protease of WO03054184-CAE48421. Over an alignment length of 1149 nucleotides, the two sequences were determined to be 91.6% identical using BLAST or GAP style parameters, and 91.3% identical using Needle style parameters.

Example 8

Identification of Additional *Bacillus gibsonii*-clade Proteases

Additional subtilisins were identified by sequencing the genomes of *B. gibsonii* strains: DSM 9728, DSM 9729, DSM 9730 and DSM 9731 (DSMZ (Leibniz-Institut DSMZ —Deutsche Sammlung von Mikroorganismen and Zellkulturen GmbH)). Genome sequencing, assembly and annotation were essentially as described in Example 1. The genomes encoded a subtilisin similar but not identical to Bgi02446.

The nucleotide sequence encoding the DSM 9728 subtilisin is set forth as SEQ ID NO:8:

ATGAAAAGAAGAGTAGGAAAGCTTGTAGTGGGGCTTGTTTGTGTAACAGC

TCTAGTAACAGTAACAGATTCTGCATCTGCAGCAGAAGAAAAGGTAAAAT

ACTTAATAGGGTTTGAAGAAGAAGCAGAACTTGAAGCCTTCACTGAGGAA

ATTGACCAAGTTGGTGTGTTTTCTGTTGAAGAACAAAGTGTAGCTGAGGA

TACGTTAGATATTGATGTAGACATTATTGATGAATATGATTATATTGATG

TATTAGCCGTAGAATTAGATCCTGAGGATGTAGATGCGTTAAGCGAAGAA

GCAGGTATCTCATTTATTGAAGAAGACATTGAACTGTCTATCCAACAAAC

GGTTCCTTGGGGCATTACTCGTGTACAAGCTCCAGCTGTGCATAACCGAG

GAGTAACAGGGTCTGGTGTAAGAGTAGCGATTCTAGATTCAGGAATCTCT

ACACATAGTGATTTAACGATTCGCGGTGGAGCTAGCTTTGTACCGGGTGA

ACCAACAACGGCTGATTTAAATGGTCATGGGACTCACGTTGCAGGAACAG

TGGCAGCTCTTAATAATTCAATCGGTGTGATTGGTGTGGCACCAAGTGCT

GATCTATACGCTGTAAAAGTACTTGGAGCAAATGGTAGAGGAAGCGTTAG

TGGAATTGCTCAAGGTCTAGAGTGGGCTGCAGCGAATAACATGCATATTG

CTAACATGAGTCTCGGTAGTGATGCACCTAGTACTACACTTGAGCGTGCA

GTCAACTATGCGACAAGCCAAGGTGTACTAGTTATTGCAGCGACTGGTAA

CAACGGTTCTGGTTCAGTTGGCTATCCTGCTCGTTATGCAAACGCAATGG

CTGTAGGAGCGACTGACCAAAACAACAGACGTGCAAACTTTTCTCAGTAT

GGTACAGGAATTGACATCGTAGCACCAGGGGTTAATGTACAAAGTACGTA

TCCTGGAAACCGCTATGCAAGTTTAAATGGTACATCTATGGCTACTCCAC

ACGTAGCTGGTGCCGCTGCACTTGTAAAGCAACGCTATCCATCTTGGAAT

GCAACTCAAATTCGCAATCATCTGAAAAATACAGCGACAAATCTAGGAAA

CTCTTCGCAATTTGGTAGTGGCCTAGTCAACGCAGAAGCAGCAACACGT.

The amino acid sequence of the DSM 9728 preproenzyme is set forth as SEQ ID NO:9:

MKRRVGKLVVGLVCVTALVTVTDSASAAEEKVKYLIGFEEEAELEAFTEE

IDQVGVFSVEEQSVAEDTLDIDVDIIDEYDYIDVLAVELDPEDVDALSEE

AGISFIEEDIELSIQQTVPWGITRVQAPAVHNRGVTGSGVRVAILDSGIS

THSDLTIRGGASFVPGEPTTADLNGHGTHVAGTVAALNNSIGVIGVAPSA

DLYAVKVLGANGRGSVSGIAQGLEWAAANNMHIANMSLGSDAPSTTLERA

VNYATSQGVLVIAATGNNGSGSVGYPARYANAMAVGATDQNNRRANFSQY

GTGIDIVAPGVNVQSTYPGNRYASLNGTSMATPHVAGAAALVKQRYPSWN

ATQIRNHLKNTATNLGNSSQFGSGLVNAEAATR.

The amino acid sequence of the DMS 9728 proenzyme is set forth as SEQ ID NO:10:

AEEKVKYLIGFEEEAELEAFTEEIDQVGVFSVEEQSVAEDTLDIDVDIID

EYDYIDVLAVELDPEDVDALSEEAGISFIEEDIELSIQQTVPWGITRVQA

PAVHNRGVTGSGVRVAILDSGISTHSDLTIRGGASFVPGEPTTADLNGHG

THVAGTVAALNNSIGVIGVAPSADLYAVKVLGANGRGSVSGIAQGLEWAA

ANNMHIANMSLGSDAPSTTLERAVNYATSQGVLVIAATGNNGSGSVGYPA

RYANAMAVGATDQNNRRANFSQYGTGIDIVAPGVNVQSTYPGNRYASLNG

TSMATPHVAGAAALVKQRYPSWNATQIRNHLKNTATNLGNSSQFGSGLVN

AEAATR.

The predicted amino acid sequence of the mature form of the DSM 9728 *subtilisin* is set forth as SEQ ID NO:11:

QQTVPWGITRVQAPAVHNRGVTGSGVRVAILDSGISTHSDLTIRGGASFV

PGEPTTADLNGHGTHVAGTVAALNNSIGVIGVAPSADLYAVKVLGANGRG

SVSGIAQGLEWAAANNMHIANMSLGSDAPSTTLERAVNYATSQGVLVIAA

TGNNGSGSVGYPARYANAMAVGATDQNNRRANFSQYGTGIDIVAPGVNVQ

STYPGNRYASLNGTSMATPHVAGAAALVKQRYPSWNATQIRNHLKNTATN

LGNSSQFGSGLVNAEAATR.

The amino acid sequence of the processed mature form (268 amino acids), of the DSM 9728 subtilisin is set forth as SEQ ID NO:49:

QTVPWGITRVQAPAVHNRGVTGSGVRVAILDSGISTHSDLTIRGGASFVP

GEPTTADLNGHGTHVAGTVAALNNSIGVIGVAPSADLYAVKVLGANGRGS

VSGIAQGLEWAAANNMHIANMSLGSDAPSTTLERAVNYATSQGVLVIAAT

GNNGSGSVGYPARYANAMAVGATDQNNRRANFSQYGTGIDIVAPGVNVQS

TYPGNRYASLNGTSMATPHVAGAAALVKQRYPSWNATQIRNHLKNTATNL

GNSSQFGSGLVNAEAATR.

The nucleotide sequence encoding the DSM 9729 subtilisin is set forth as SEQ ID NO:12:

ATGAAAAGAAGAGTAGGTAAGCTTGTGGTGGGGCTTGTATGTGTAACAGC

TCTAGTAACCGTGACAGATTCTGCATCTGCGGCAGAAGAAAAAGTAAAAT

```
-continued
ACTTAATAGGTTTTGAAGAAGAAGCAGAACTTGAAGCCTTCACTGAGGAA

ATTGACCAAGTTGGTGTATTTTCTGTTGAAGAACAAAGTGTAGCTGAGGA

TACGTTAGATATTGATGTAGACATTATTGATGAATATGATTATATTGATG

TGTTAGCTGTAGAATTAGATCCTGAGGATGTAGATGCGTTAAGCGAAGAA

GCAGGTATCTCATTTATTGAAGAAGACATTGAACTGTCTATTCAACAAAC

AGTTCCTTGGGGCATTACTCGTGTACAAGCTCCGGCTGTTCATAACCGAG

GGATTACAGGTTCTGGAGTAAGAGTAGCTATCCTTGATTCAGGGATTTCA

GCCCATAGTGATTTGAATATCCGCGGTGGAGCTAGCTTTGTACCGGGTGA

ACCAACGACGGCTGATTTAAATGGACATGGTACTCACGTGGCCGGAACAG

TAGCAGCTCTAAATAATTCAATTGGTGTCATTGGTGTTGCACCGAATGCT

GACTTATATGCTGTTAAAGTACTCGGAGCAAATGGAAGCGGAAGTGTAAG

TGGGATTGCTCAAGGTTTAGAGTGGGCGGCAACCAATAACATGCATATTG

CGAACATGAGTCTCGGTAGTGATTTTCCTAGCTCTACACTTGAGCGTGCA

GTCAACTATGCGACAAGCCGTGATGTACTAGTTATTGCAGCGACTGGTAA

CAACGGTTCTGGTTCAGTAGGCTATCCTGCTCGTTATGCAAACGCAATGG

CTGTAGGAGCGACTGACCAAAACAACAGACGCGCAAACTTTTCTCAGTAC

GGTACAGGAATTGACATCGTAGCACCTGGAGTTAACGTACAAAGTACGTA

TCCAGGAAACCGTTATGTGAGTATGAATGGTACATCTATGGCCACTCCAC

ATGTAGCTGGTGCCGCTGCACTTGTAAAGCAACGCTATCCTTCTTGGAAT

GCGACTCAAATTCGCAATCATCTGAAAAATACAGCAACAAATCTAGGAAA

CTCTTCGCAATTTGGTAGTGGCCTAGTTAACGCAGAAGCAGCAACACGT.
```

The amino acid sequence of the DSM 9729 preproenzyme is set forth as SEQ ID NO:13:

MKRRVGKLVVGLVCVTALVTVTDSASAAEEKVKYLIGFEEEAELEAFTEE
IDQVGVFSVEEQSVAEDTLDIDVDIIDEYDYIDVLAVELDPEDVDALSEE
AGISFTEEDIELSIQQTVPWGITRVQAPAVHNRGITGSGVRVAILDSGIS
AHSDLNIRGGASFVPGEPTTADLNGHGTHVAGTVAALNNSIGVIGVAPNA
DLYAVKVLGANGSGSVSGIAQGLEWAATNNMHIANMSLGSDFPSSTLERA
VNYATSRDVLVIAATGNNGSGSVGYPARYANAMAVGATDQNNRRANFSQY
GTGIDIVAPGVNVQSTYPGNRYVSMNGTSMATPHVAGAAALVKQRYPSWN
ATQIRNHLKNTATNLGNSSQFGSGLVNAEAATR.

The amino acid sequence of the DSM 9729 proenzyme is set forth as SEQ ID NO:14:

AEEKVKYLIGFEEEAELEAFTEEIDQVGVFSVEEQSVAEDTLDIDVDIID
EYDYIDVLAVELDPEDVDALSEEAGISFIEEDIELSIQQTVPWGITRVQA
PAVHNRGITGSGVRVAILDSGISAHSDLNIRGGASFVPGEPTTADLNGHG
THVAGTVAALNNSIGVIGVAPNADLYAVKVLGANGSGSVSGIAQGLEWAA
TNNMHIANMSLGSDFPSSTLERAVNYATSRDVLVIAATGNNGSGSVGYPA
RYANAMAVGATDQNNRRANFSQYGTGIDIVAPGVNVQSTYPGNRYVSMNG
TSMATPHVAGAAALVKQRYPSWNATQIRNHLKNTATNLGNSSQFGSGLVN
AEAATR.

The predicted amino acid sequence of the mature form of the DSM 9729 *subtilisin* is set forth as SEQ ID NO:15:

QQTVPWGITRVQAPAVHNRGITGSGVRVAILDSGISAHSDLNIRGGASFV
PGEPTTADLNGHGTHVAGTVAALNNSIGVIGVAPNADLYAVKVLGANGSG
SVSGIAQGLEWAATNNMHIANMSLGSDFPSSTLERAVNYATSRDVLVIAA
TGNNGSGSVGYPARYANAMAVGATDQNNRRANFSQYGTGIDIVAPGVNVQ
STYPGNRYVSMNGTSMATPHVAGAAALVKQRYPSWNATQIRNHLKNTATN
LGNSSQFGSGLVNAEAATR.

The amino acid sequence of the processed mature form (268 amino acids), of the DSM 9729 subtilisin is set forth as SEQ ID NO: 50:

QTVPWGITRVQAPAVHNRGITGSGVRVAILDSGISAHSDLNIRGGASFVP
GEPTTADLNGHGTHVAGTVAALNNSIGVIGVAPNADLYAVKVLGANGSGS
VSGIAQGLEWAATNNMHIANMSLGSDFPSSTLERAVNYATSRDVLVIAAT
GNNGSGSVGYPARYANAMAVGATDQNNRRANFSQYGTGIDIVAPGVNVQS
TYPGNRYVSMNGTSMATPHVAGAAALVKQRYPSWNATQIRNHLKNTATNL
GNSSQFGSGLVNAEAATR

The nucleotide sequence encoding the DSM 9730 subtilisin is set forth as SEQ ID NO:16:

```
ATGAAAAGAAGAGTAGGAAAGCTTGTGGTGGGGCTTGTTTGTGTAACAGC

TCTAGTAACTGTAACAGATTCTGCATCTGCAGCAGAAGAAAAGGTAAAAT

ACTTAATAGGGTTTGAAGAAGAAGCAGAACTTGAAGCCTTCACTGAGGAA

ATTGACCAAGTTGGTGTATTTTCTGTTGAAGAACAAAGTGTAGCTGAGGA

TACGTTAGATATTGATGTAGACATTATTGATGAATATGATTATATTGATG

TATTAGCTGTAGAATTAGATCCTGAGGATGTAGATGCGTTAAGCGAAGAA

GCAGGTATCTCATTTATTGAAGAAGACATTGAACTGTCTATTCAACAAAC

AGTTCCTTGGGGCATTACTCGTGTACAAGCTCCGGCTGTTCATAACCGAG

GAGTAACAGGGTCTGGTGTAAGAGTAGCGATTCTAGATTCAGGAATCTCT

ACACATAGTGATTTAACGATCCGCGGTGGAGCTAGCTTTGTACCGGGTGA

ACCAACAACGGCTGATTTAAATGGTCATGGGACTCACGTTGCAGGAACAG

TGGCAGCTCTTAATAATTCAATCGGTGTGATTGGTGTGGCACCAAGTGCT

GATCTATACGCTGTAAAAGTACTTGGAGCAAATGGTAGAGGAAGCGTTAG

TGGAATTGCTCAAGGTTTAGAGTGGGCTGCAGCGAATAACATGCATATTG

CTAACATGAGTCTCGGTAGTGATGCACCTAGTACTACACTTGAGCGTGCA

GTCAACTATGCGACAAGCCAAGGTGTACTAGTTATTGCAGCGACTGGTAA

CAACGGTTCTGGTTCAGTAGGCTATCCTGCTCGTTATGCAAACGCAATGG

CTGTAGGAGCGACTGACCAAAACAACAGACGCGCAAACTTTTCTCAGTAC

GGTACAGGAATTGACATCGTAGCACCTGGAGTTAACGTACAAAGTACGTA

TCCAGGAAACCGTTATGTGAGTATGAATGGTACATCTATGGCCACTCCAC

ATGTAGCTGGTGCCGCTGCACTTGTAAAGCAACGCTATCCTTCTTGGAAT

GCGACTCAAATTCGCAATCATCTGAAAAATACAGCAACAAATCTAGGAAA

CTCTTCGCAATTTGGTAGTGGCCTAGTGAACGCAGAAGCAGCAACACGT.
```

The amino acid sequence of the DSM 9730 preproenzyme is set forth as SEQ ID NO:17:

MKRRVGKLVVGLVCVTALVTVTDSASAAEEKVKYLIGFEEEAELEAFTEE
IDQVGVFSVEEQSVAEDTLDIDVDIIDEYDYIDVLAVELDPEDVDALSEE
AGISFIEEDIELSIQQTVPWGITRVQAPAVHNRGVTGSGVRVAILDSGIS
THSDLTIRGGASFVPGEPTTADLNGHGTHVAGTVAALNNSIGVIGVAPSA
DLYAVKVLGANGRGSVSGIAQGLEWAAANNMHIANMSLGSDAPSTTLERA
VNYATSQGVLVIAATGNNGSGSVGYPARYANAMAVGATDQNNRRANFSQY
GTGIDIVAPGVNVQSTYPGNRYVSMNGTSMATPHVAGAAALVKQRYPSWN
ATQIRNHLKNTATNLGNSSQFGSGLVNAEAATR.

The amino acid sequence of the DSM 9730 proenzyme is set forth as SEQ ID NO:18:

AEEKVKYLIGFEEEAELEAFTEEIDQVGVFSVEEQSVAEDTLDIDVDIID
EYDYIDVLAVELDPEDVDALSEEAGISFIEEDIELSIQQTVPWGITRVQA
PAVHNRGVTGSGVRVAILDSGISTHSDLTIRGGASFVPGEPTTADLNGHG
THVAGTVAALNNSIGVIGVAPSADLYAVKVLGANGRGSVSGIAQGLEWAA
ANNMHIANMSLGSDAPSTTLERAVNYATSQGVLVIAATGNNGSGSVGYPA
RYANAMAVGATDQNNRRANFSQYGTGIDIVAPGVNVQSTYPGNRYVSMNG
TSMATPHVAGAAALVKQRYPSWNATQIRNHLKNTATNLGNSSQFGSGLVN
AEAATR.

The predicted amino acid sequence of the mature form of the DSM 9730 *subtilisin* is set forth as SEQ ID NO:19:

QQTVPWGITRVQAPAVHNRGVTGSGVRVAILDSGISTHSDLTIRGGASFV
PGEPTTADLNGHGTHVAGTVAALNNSIGVIGVAPSADLYAVKVLGANGRG
SVSGIAQGLEWAAANNMHIANMSLGSDAPSTTLERAVNYATSQGVLVIAA
TGNNGSGSVGYPARYANAMAVGATDQNNRRANFSQYGTGIDIVAPGVNVQ
STYPGNRYVSMNGTSMATPHVAGAAALVKQRYPSWNATQIRNHLKNTATN
LGNSSQFGSGLVNAEAATR.

The amino acid sequence of the processed mature form (268 amino acids), of the DSM 9730 subtilisin is set forth as SEQ ID NO: 51:

QTVPWGITRVQAPAVHNRGVTGSGVRVAILDSGISTHSDLTIRGGASFVP
GEPTTADLNGHGTHVAGTVAALNNSIGVIGVAPSADLYAVKVLGANGRGS
VSGIAQGLEWAAANNMHIANMSLGSDAPSTTLERAVNYATSQGVLVIAAT
GNNGSGSVGYPARYANAMAVGATDQNNRRANFSQYGTGIDIVAPGVNVQS
TYPGNRYVSMNGTSMATPHVAGAAALVKQRYPSWNATQIRNHLKNTATNL
GNSSQFGSGLVNAEAATR.

The nucleotide sequence encoding the DSM 9731 subtilisin is set forth as SEQ ID NO:20:

ATGAAAAGAAGAGTAGGAAAGCTTGTAGTGGGCTTGTTTGTGTAACAGC
TCTAGTAACTGTAACAGATTCTGCATCTGCAGCAGAAGAAAAGGTAAAAT
ACTTAATAGGGTTTGAAGAAGAAGCAGAACTTGAAGCCTTCACTGAGGAA
ATTGACCAAGTTGGTGTGTTTTCTGTTGAAGAACAAAGTGTAGCTGAGGA
TACGTTAGATATTGATGTAGACATTATTGATGAATATGATTATATTGATG
TATTAGCTGTAGAATTAGATCCTGAGGATGTAGATGCGTTAAGTGAAGAA
GCAGGTATCTCATTTATTGAAGAAGACATTGAACTGTCTATTCAACAAAC
GGTTCCTTGGGGCATTACTCGTGTACAAGCTCCAGCTGTGCATAACCGAG
GAGTAACAGGGTCTGGTGTAAGAGTAGCGATTCTAGATTCAGGAATCTCT
ACACATAGTGATTTAACGATTCGCGGTGGAGCTAGCTTTGTACCGGGTGA
ACCAACAACGGCTGATTTAAATGGTCATGGGACTCACGTTGCAGGAACAG
TGGCAGCTCTTAATAATTCAATTGGTGTGATTGGTGTGGCACCAAGTGCT
GATCTATACGCTGTAAAAGTACTTGGAGCAAATGGTAGAGGAAGCGTTAG
TGGAATTGCTCAAGGTCTAGAGTGGGCTGCAGCGAATAACATGCATATTG
CTAACATGAGTCTCGGTAGTGATGCACCTAGTACTACACTTGAGCGTGCA
GTCAACTATGCGACAAGCCAAGGTGTACTAGTTATTGCAGCGACTGGTAA
CAACGGTTCTGGTTCAGTTGGCTATCCTGCTCGTTATGCAAACGCAATGG
CTGTAGGAGCGACTGACCAAAACAACAGACGCGCAAACTTTTCTCAATAT
GGTTCAGGAATTGATATCGTAGCACCAGGAGTTAACGTACAAAGTACGTA
TCCAGGAAACCGTTATGTGAGTATGAATGGTACATCTATGGCCACTCCAC
ACGTAGCTGGTGCCGCTGCGCTTGTAAAGCAACGCTATCCATCTTGGAAT
GCGACTCAAATTCGCAATCATCTGAAAAATACAGCGACAAATCTAGGAAA
CTCTTCGCAATTTGGTAGTGGCCTAGTGAACGCAGAAGCAGCAACACGT.

The amino acid sequence of the DSM 9731 preproenzyme is set forth as SEQ ID NO:21:

MKRRVGKLVVGLVCVTALVTVTDSASAAEEKVKYLIGFEEEAELEAFTEE
IDQVGVFSVEEQSVAEDTLDIDVDIIDEYDYIDVLAVELDPEDVDALSEE
AGISFIEEDIELSIQQTVPWGITRVQAPAVHNRGVTGSGVRVAILDSGIS
THSDLTIRGGASFVPGEPTTADLNGHGTHVAGTVAALNNSIGVIGVAPSA
DLYAVKVLGANGRGSVSGIAQGLEWAAANNMHIANMSLGSDAPSTTLERA
VNYATSQGVLVIAATGNNGSGSVGYPARYANAMAVGATDQNNRRANFSQY
GSGIDIVAPGVNVQSTYPGNRYVSMNGTSMATPHVAGAAALVKQRYPSWN
ATQIRNHLKNTATNLGNSSQFGSGLVNAEAATR.

The amino acid sequence of the DSM 9731 proenzyme is set forth as SEQ ID NO:22:

AEEKVKYLIGFEEEAELEAFTEEIDQVGVFSVEEQSVAEDTLDIDVDIID
EYDYIDVLAVELDPEDVDALSEEAGISFIEEDIELSIQQTVPWGITRVQA
PAVHNRGVTGSGVRVAILDSGISTHSDLTIRGGASFVPGEPTTADLNGHG
THVAGTVAALNNSIGVIGVAPSADLYAVKVLGANGRGSVSGIAQGLEWAA
ANNMHIANMSLGSDAPSTTLERAVNYATSQGVLVIAATGNNGSGSVGYPA
RYANAMAVGATDQNNRRANFSQYGSGIDIVAPGVNVQSTYPGNRYVSMNG
TSMATPHVAGAAALVKQRYPSWNATQIRNHLKNTATNLGNSSQFGSGLVN
AEAATR.

The predicted amino acid sequence of the mature form of the DSM 9731 subtilisin is set forth as SEQ ID NO:23:

QQTVPWGITRVQAPAVHNRGVTGSGVRVAILDSGISTHSDLTIRGGASFV

PGEPTTADLNGHGTHVAGTVAALNNSIGVIGVAPSADLYAVKVLGANGRG

SVSGIAQGLEWAAANNMHIANMSLGSDAPSTTLERAVNYATSQGVLVIAA

TGNNGSGSVGYPARYANAMAVGATDQNNRRANFSQYGSGIDIVAPGVNVQ

STYPGNRYVSMNGTSMATPHVAGAAALVKQRYPSWNATQIRNHLKNTATN

LGNSSQFGSGLVNAEAATR.

The amino acid sequence of the processed mature form (268 amino acids), of the DSM 9731 subtilisin is set forth as SEQ ID NO:52:

QTVPWGITRVQAPAVHNRGVTGSGVRVAILDSGISTHSDLTIRGGASFVP

GEPTTADLNGHGTHVAGTVAALNNSIGVIGVAPSADLYAVKVLGANGRGS

VSGIAQGLEWAAANNMHIANMSLGSDAPSTTLERAVNYATSQGVLVIAAT

GNNGSGSVGYPARYANAMAVGATDQNNRRANFSQYGSGIDIVAPGVNVQS

TYPGNRYVSMNGTSMATPHVAGAAALVKQRYPSWNATQIRNHLKNTATNL

GNSSQFGSGLVNAEAATR.

An alignment of the amino acid sequences of the predicted mature forms of the DSM 9728, DSM 9729, DSM 9730, DSM 9731 and Bgi02446 subtilisins is shown in FIG. 5. The sequences were aligned using CLUSTALW software (Thompson et al., Nucleic Acids Research, 22:4673-4680, 1994) with default parameters.

TABLE 8-1

Percent Identity (PID) Shared by Bgi02446 with Other B. gibsonii Subtilases

| PID | Bgi02446 | DSM9728 | DSM9729 | DSM9730 | DSM9731 |
|---|---|---|---|---|---|
| Bgi02446 | 100 | 95.2 | 99.6 | 95.9 | 95.5 |
| DSM9728 | 95.2 | 100 | 95.5 | 99.3 | 98.9 |
| DSM9729 | 99.6 | 95.5 | 100 | 96.3 | 95.9 |
| DSM9730 | 95.9 | 99.3 | 96.3 | 100 | 99.6 |
| DSM9731 | 95.5 | 98.9 | 95.9 | 99.6 | 100 |

Figure 6:
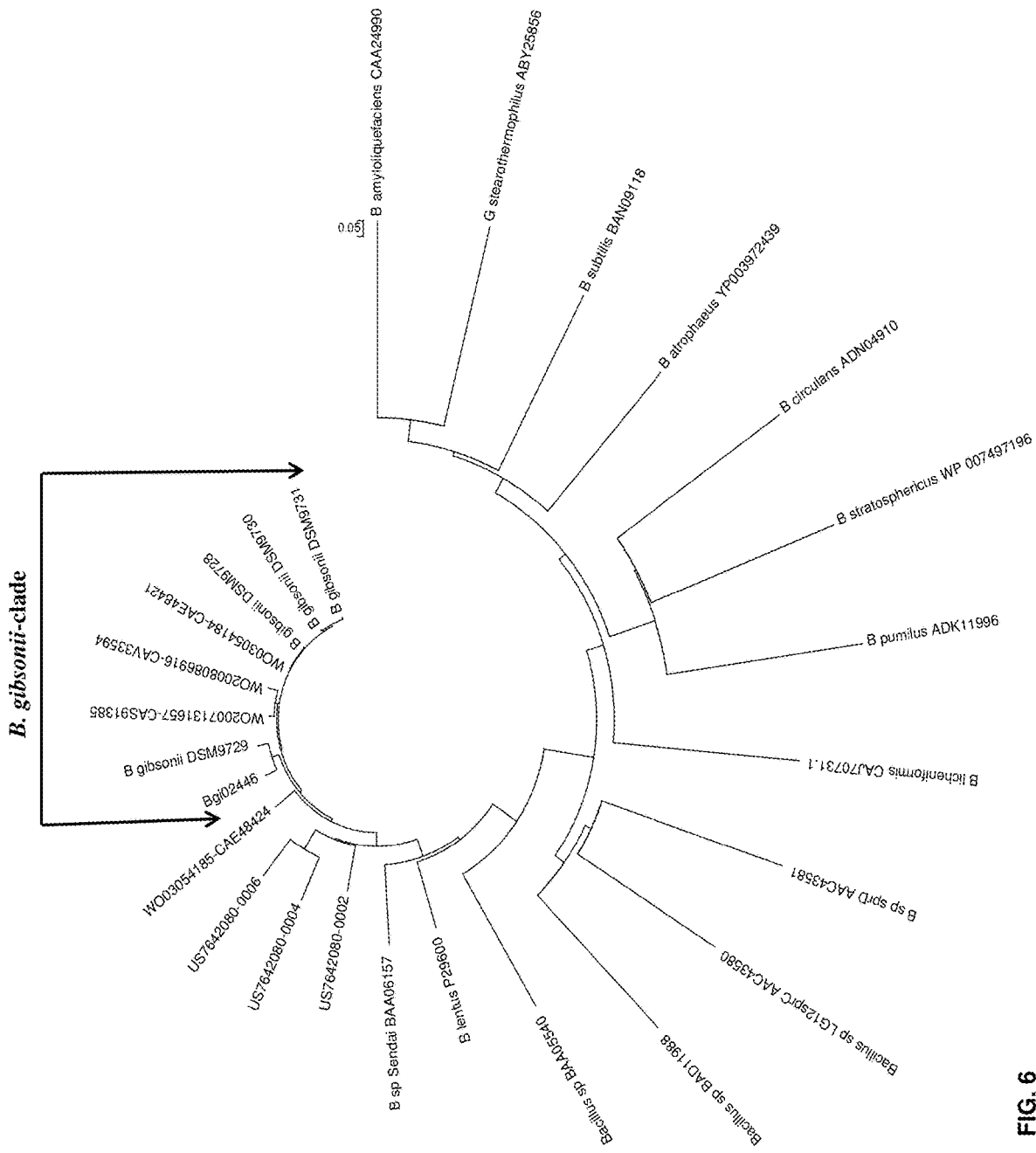
FIG. 6 provides a phylogenetic tree of the B. gibsonii-clade subtilisins and various other bacterial serine proteases.
Figure 7A:
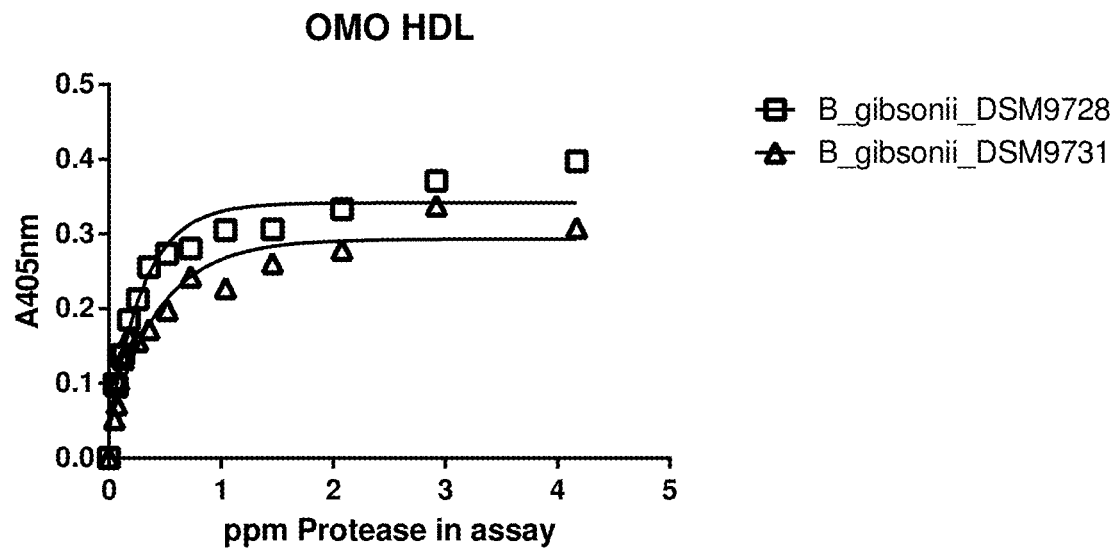
FIG. 7A provides cleaning efficiency curves of DSM9728, and DSM9731 in heavy duty liquid (HDL) laundry detergents.
Figure 7B:
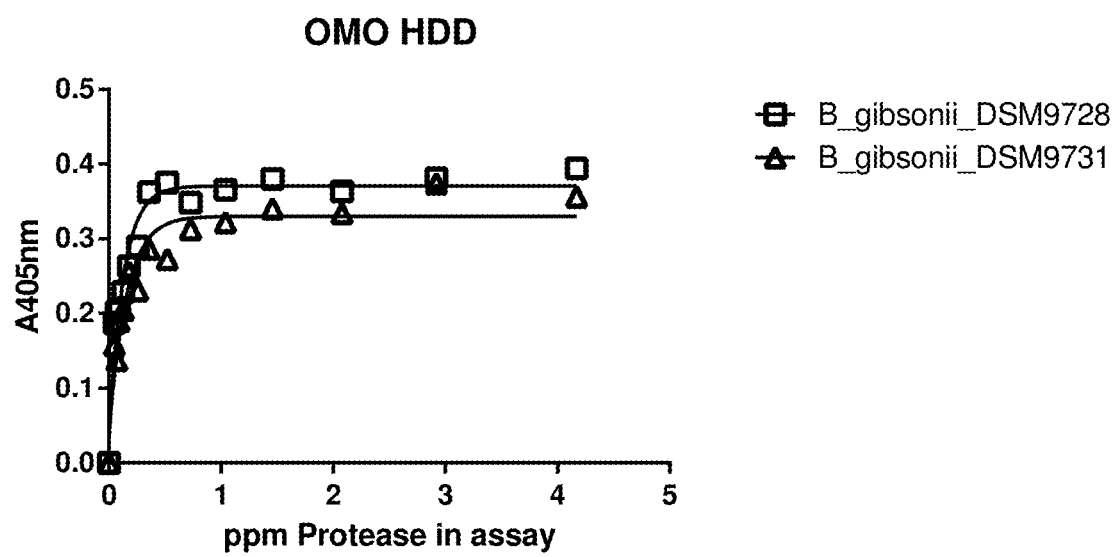
FIG. 7B provides cleaning efficiency curves of DSM9728, and DSM9731 in heavy duty dry (HDD) laundry detergents.
Figure 7C:
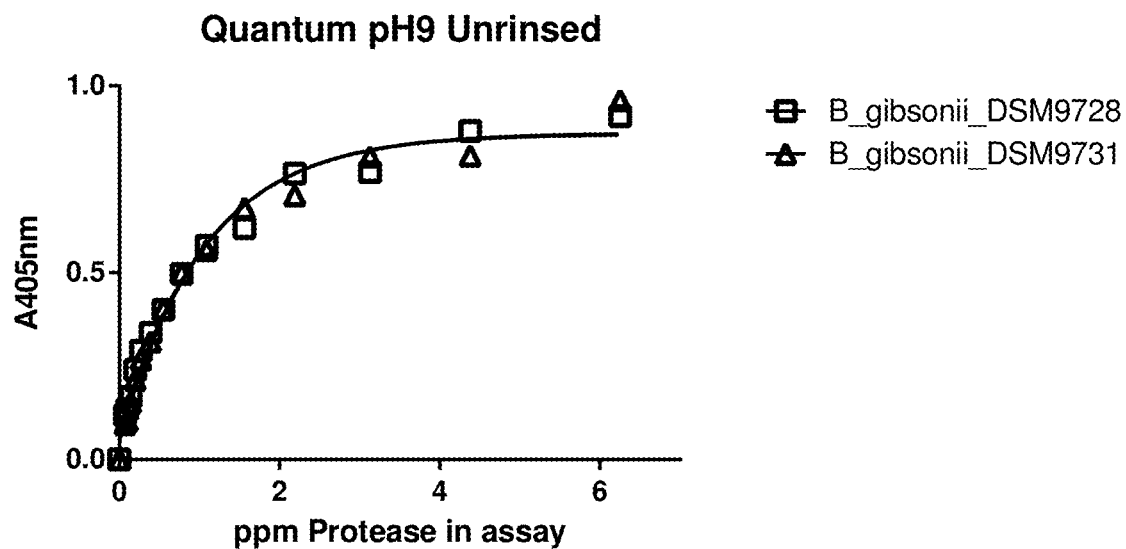
FIGS. 7C-7F provides cleaning efficiency curves of DSM9728, and DSM9731 in automatic dish washing (ADW) detergents.
Figure 7D:
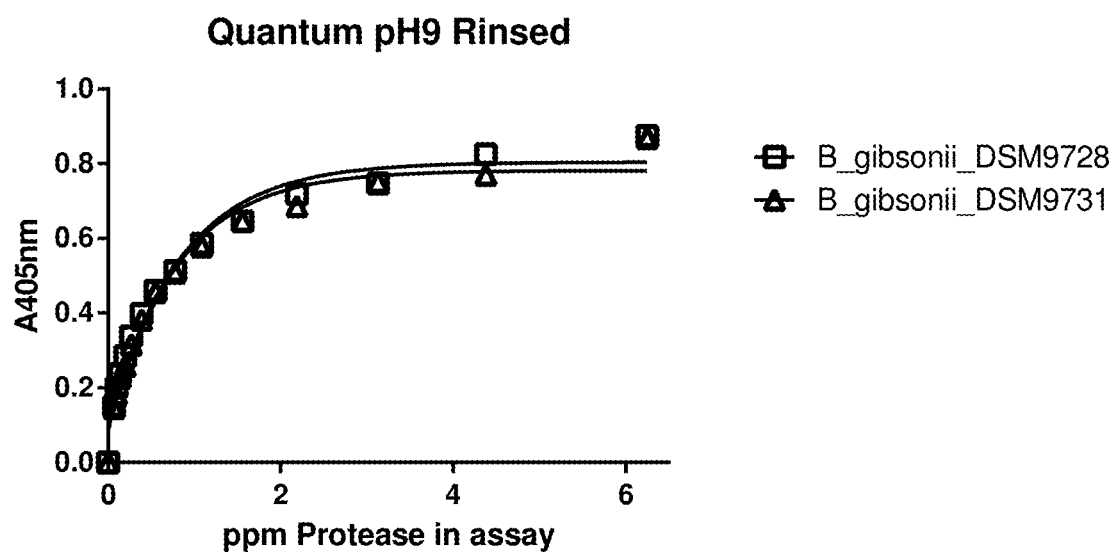
Figure 7E:
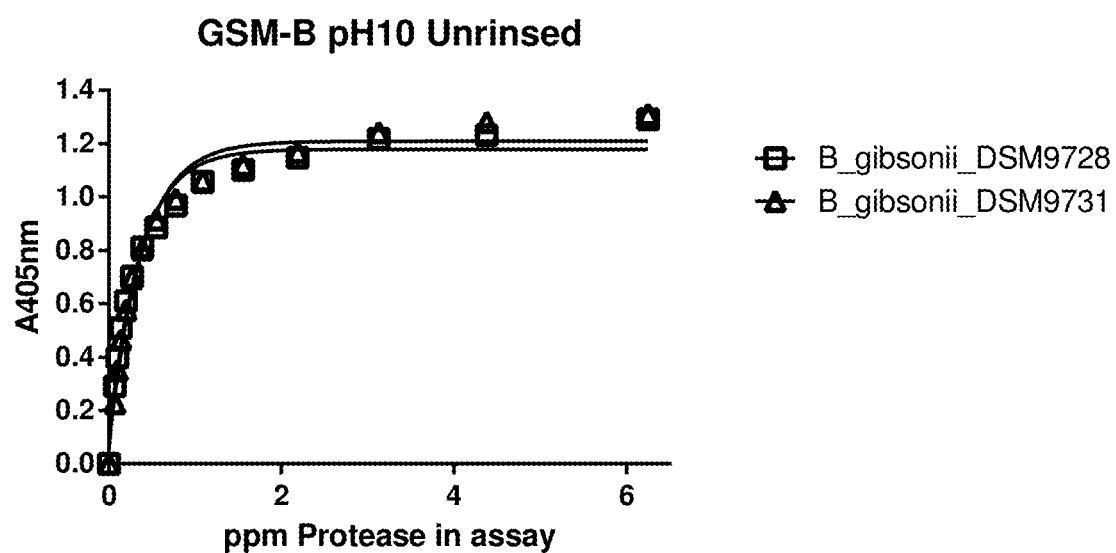
Figure 7F:
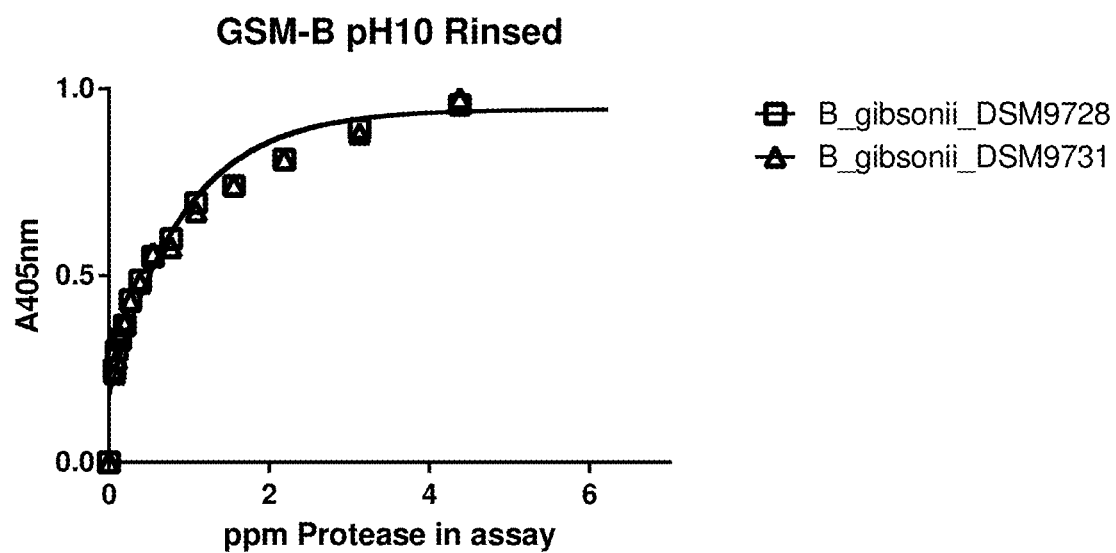

A phylogenetic tree for amino acid sequences of the predicted mature forms of the *B. gibsonii*-clade members: Bgi02446 (SEQ ID NO:4), DSM9728 (SEQ ID NO:11), DSM9729 (SEQ ID NO:15), DSM9730 (SEQ ID NO:19), and DSM9731 (SEQ ID NO:23) was built using the amino acid sequences of multiple proteases listed in Tables 7-1 and 7-2, in addition to the amino acid sequences of the mature forms of the Bgi02446, DSM 9728, DSM 9729, DSM 9730, and DSM 9731 subtilisins. The sequences were entered in the Vector NTI Advance suite and a Guide Tree was created using the Neighbor Joining (NJ) method (Saitou and Nei, Mol Biol Evol, 4:406-425, 1987). The NJ method works on a matrix of distances between all pairs of sequences to be analyzed. These distances are related to the degree of divergence between the sequences. The Guide Tree is calculated after the sequences are aligned. The tree construction was calculated using the following parameters. Kimura's correction for sequence distance and ignoring positions with gaps. AlignX displays the calculated distance values in parenthesis following the molecule name displayed on the tree shown in FIG. 6. The Bgi02446, DSM 9728, DSM 9729, DSM 9730, and DSM 9731 subtilisins all cluster in the same region (as shown in FIG. 6) to form the *B. gibsonii*-clade.

Example 9

Cleaning Performance of *Bacillus gibsonii* Proteases

The cleaning performance of *B. gibsonii* proteases, Bgi02446, DSM 9728, and DSM 9731 was tested on BMI (blood/milk/ink on cotton) microswatches (EMPA-116, Center for Testmaterials, The Netherlands) for laundry based applications, and on egg yolk (egg yolk on polyacryl fabric, aged and colored with carbon black dye) microswatches (PAS-38, Center for Testmaterials, The Netherlands) for dish based applications as described in Example 6. MTPs (Corning 9017) containing pre-punched (to fit on MTP) swatches, were either rinsed or unrinsed for the ADW assays, and filled with detergent prior to enzyme addition. One microswatch was used in HDD and 2 microswatches were used in HDL assays. The cleaning performance of the proteases in various detergents is shown in FIGS. 7A-7F.

Example 10

Unique Features of *Bacillus gibsonii* Proteases

A structure based alignment (FIG. 8A-B) of the amino acid sequences of the mature forms of the DSM 9728 (SEQ ID NO:11), DSM 9731 (SEQ ID NO:23) and Bgi02446 (SEQ ID NO: 4) subtilisins with BPN' subtilisin from *B. amyloliquefaciens* (pdb entry 2STI), Carlsberg from *B. licheniformis* (pdb entry 1CSE), *B. lentus* subtilisin (pdb entry 1JEA), was performed using the "align" option in the Molecular Operating Environment (MOE) software (Chemical Computing Group, Montreal, Quebec, Canada) to look for structural similarities. The alignment applies conserved structural motifs as an additional guide to conventional sequence alignment. This alignment was performed using standard program defaults present in the 2012.10 distribution of MOE.

In FIG. 8A-B a region of the structure-based alignment in which subtilisins DSM 9728, DSM 9731 and Bgi02446 sequences show a common motif extending between Asp (D)31 and His (H)64 is highlighted. In all these enzymes, the catalytic triad is formed by Asp (D)31, His (H)61 and Ser (S)214. The motif DXGIXXHSDLXXXGGASXXXXXPT-TADLNXHGTH (SEQ ID NO:47) or DXGIXXHS-DLXXXGGASXXXXXXTTADLXXHGTH (SEQ ID NO:90) contains the sequence TTADL that is unique to DSM 9728, DSM 9731 and Bgi02446 sequences, and also shared by other *B gibsonii* subtilisins previously identified (CAS91385, CAE48421, CAE48424). Refer to phylogenetic tree of subtilisins in FIG. 6 to see that all the *B. gibsonii* subtilisins cluster in the same region to form the *B. gibsonii*-clade. All of the *B. gibsonii*-clade subtilisins share the motif DXGIXXHSDLXXXGGASXXXXXPTTADLNXHGTH (SEQ ID NO:47) or DXGIXXHSDLXXXG-GASXXXXXXTTADLXXHGTH (SEQ ID NO:90).

Figure 9:
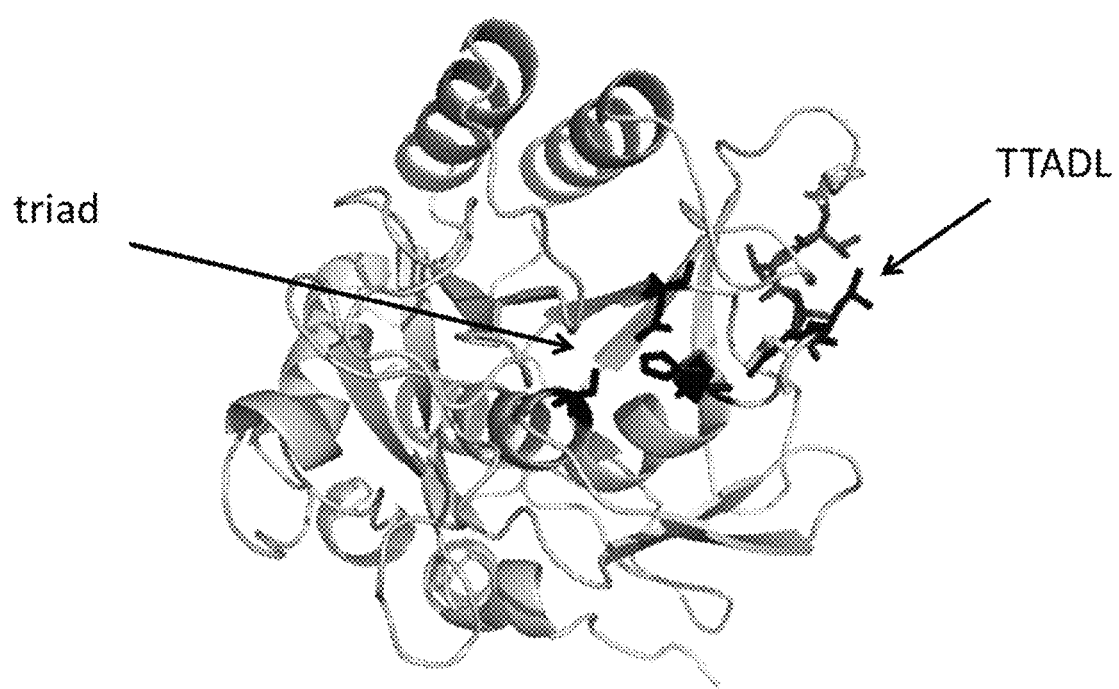
FIG. 9 shows the location of the TTADL conserved residues, a component of the motif, in the B. gibsonii subtilisins (DSM 9728, DSM 9731, and Bgi02446) modeled on the structure of B. lentus subtilisin (pdb entry 1JEA) with respect to the catalytic triad. Residue side chains of the catalytic triad common to all serine proteinases are shown as sticks.

FIG. 9 shows the location of the TTADL conserved residues in the *B. gibsonii*-clade subtilisins (DSM 9728, DSM 9731 and Bgi02446) modeled on the structure of *B. lentus* subtilisin (pdb entry 1JEA) with respect to the catalytic triad. The conserved residues form a loop leading into the catalytic residue His (H)61 of the *B. gibsonii* subtilisins (SEQ ID NO 4). The close proximity of the conserved residues to the catalytic His (H)61 residue and this loop are believed to be key factors affecting proteolytic stability and activity of the enzyme. Also noted is that the Serine at position 39 that occurs in a preceding loop, follows the catalytic aspartic acid (Asp 32) and differs from the proline residue found at the homologous position in commercial subtilisins found in products today. Without being limited to any particular theory, this loop is smaller than what is found in subtilisin BPN' and Carlsberg and the additional flexibility expected from the presence of a serine instead of proline might also benefit performance.

Example 11

Generation of Additional *B. gibsonii*-clade Subtilisins

DNA manipulations to generate additional *B. gibsonii*-clade subtilisins were carried out using conventional molecular biology techniques (see, e.g., Sambrook et al, Molecular Cloning: Cold Spring Harbor Laboratory Press). The variants were expressed, recovered in a manner similar to that described in the previous examples, and the supernatants used for assay.

A nucleotide sequence encoding the Bgi02446 subtilisin is set forth as SEQ ID NO:53:

```
CAACAAACAGTGCCATGGGGAATTACTCGTGTGCAAGCCCCAGCTGTTCA
TAACCGTGGAATTACAGGTTCTGGTGTAAGAGTTGCTATCCTCGATTCAG
GTATTTCCGCCCATAGTGACTTAAATATTCGTGGTGGCGCTAGCTTTGTA
CCAGGGGAACCAACGACTGCTGATTTAAATGGGCATGGCACGCATGTGGC
TGGGACGGTAGCTGCTTTAAACAATTCGATTGGCGTTATTGGCGTAGCAC
CGAACGCGGAACTATACGCTGTTAAAGTATTAGGGGCGAATGGTTCAGGT
TCGGTCAGCGGGATTGCCCAAGGATTGGAATGGGCAGCAACCAATAACAT
GCACATTGCTAATATGAGTTTAGGAAGCGATTTTCCAAGTTCTACACTTG
AGCGTGCTGTTAATTATGCGACTTCTAGAGATGTTCTTGTTATTGCGGCA
ACTGGGAATAACGGTTCTGGCTCAGTAGGCTATCCGGCCCGTTATGCGAA
CGCAATGGCAGTCGGAGCTACTGACCAAAACAACAGACGCGCCAACTTTT
CACAGTATGGCACGGGGATTGACATTGTCGCACCAGGTGTAAACGTGCAG
AGCACATACCCAGGTAACCGTTATGTGAGCATGAACGGTACATCGATGGC
TACTCCTCATGTTGCAGGTGCAGCAGCCCTTGTTAAACAACGCTATCCAT
CTTGGAATGCGACTCAAATCCGCAATCATCTAAAGAATACGGCAACGAAT
TTAGGAAACTCTTCACAATTTGGAAGCGGACTTGTCAATGCAGAAGCGGC
AACACGCTAA.
```

A nucleotide sequence encoding the DSM-9728 subtilisin is set forth as SEQ ID NO:54:

```
CAACAAACAGTGCCATGGGGAATTACTCGTGTGCAAGCCCCAGCTGTTCA
TAACCGTGGAGTTACAGGTTCTGGTGTAAGAGTTGCTATCCTCGATTCAG
GTATTTCCACACATAGTGACTTAACAATTCGTGGTGGCGCTAGCTTTGTA
CCAGGGGAACCAACGACTGCTGATTTAAATGGGCATGGCACGCATGTGGC
```

-continued

```
TGGGACGGTAGCTGCTTTAAACAATTCGATTGGCGTTATTGGCGTAGCAC
CGTCAGCGGATCTATACGCTGTTAAAGTATTAGGGGCGAATGGTAGAGGT
TCGGTCAGCGGGATTGCCCAAGGATTGGAATGGGCAGCAGCAAATAACAT
GCACATTGCTAATATGAGTTTAGGAAGCGATGCACCAAGTACAACACTTG
AGCGTGCTGTTAATTATGCGACTTCTCAAGGCGTTCTTGTTATTGCGGCA
ACTGGGAATAACGGTTCTGGCTCAGTAGGCTATCCGGCCCGTTATGCGAA
CGCAATGGCAGTCGGAGCTACTGACCAAAACAACAGACGCGCCAACTTTT
CACAGTATGGCACGGGGATTGACATTGTCGCACCAGGTGTAAACGTGCAG
AGCACATACCCAGGTAACCGTTATGCAAGCCTGAACGGTACATCGATGGC
TACTCCTCATGTTGCAGGTGCAGCAGCCCTTGTTAAACAACGCTATCCAT
CTTGGAATGCGACTCAAATCCGCAATCATCTAAAGAATACGGCAACGAAT
TTAGGAAACTCTTCACAATTTGGAAGCGGACTTGTCAATGCAGAAGCGGC
AACACGCTAA.
```

The nucleotide sequence encoding the DSM-9731 subtilisin is set forth as SEQ ID NO:55:

```
CAACAAACAGTGCCATGGGGAATTACTCGTGTGCAAGCCCCAGCTGTTCA
TAACCGTGGAGTTACAGGTTCTGGTGTAAGAGTTGCTATCCTCGATTCAG
GTATTTCCACACATAGTGACTTAACAATTCGTGGTGGCGCTAGCTTTGTA
CCAGGGGAACCAACGACTGCTGATTTAAATGGGCATGGCACGCATGTGGC
TGGGACGGTAGCTGCTTTAAACAATTCGATTGGCGTTATTGGCGTAGCAC
CGTCAGCGGATCTATACGCTGTTAAAGTATTAGGGGCGAATGGTAGAGGT
TCGGTCAGCGGGATTGCCCAAGGATTGGAATGGGCAGCAGCAAATAACAT
GCACATTGCTAATATGAGTTTAGGAAGCGATGCACCAAGTACAACACTTG
AGCGTGCTGTTAATTATGCGACTTCTCAAGGCGTTCTTGTTATTGCGGCA
ACTGGGAATAACGGTTCTGGCTCAGTAGGCTATCCGGCCCGTTATGCGAA
CGCAATGGCAGTCGGAGCTACTGACCAAAACAACAGACGCGCCAACTTTT
CACAGTATGGCTCAGGGATTGACATTGTCGCACCAGGTGTAAACGTGCAG
AGCACATACCCAGGTAACCGTTATGTGAGCATGAACGGTACATCGATGGC
TACTCCTCATGTTGCAGGTGCAGCAGCCCTTGTTAAACAACGCTATCCAT
CTTGGAATGCGACTCAAATCCGCAATCATCTAAAGAATACGGCAACGAAT
TTAGGAAACTCTTCACAATTTGGAAGCGGACTTGTCAATGCAGAAGCGGC
AACACGCTAA.
```

The nucleotide sequence encoding the BG5-F02 subtilisin is set forth as SEQ ID NO:56:

```
CAACAAACAGTGCCATGGGGAATTACTCGTGTGCAAGCCCCAGCTGTTCA
TAACCGTGGAATTACAGGTTCTGGTGTAAGAGTTGCTATCCTCGATTCAG
GTATTTCCGCCCATAGTGACTTAAATATTCGTGGTGGCGCTAGCTTTGTA
CCAGGGGAACCAACGACTGCTGATTTAAATGGGCATGGCACGCATGTGGC
TGGGACGGTAGCTGCTTTAAACAATTCGATTGGCGTTATTGGCGTAGCAC
CGAACGCGGAACTATACGCTGTTAAAGTATTAGGGGCGAATGGTTCAGGT
```

```
TCGGTCAGCGGGATTGCCCAAGGATTGGAATGGGCAGCAACCAATAACAT

GCACATTGCTAATATGAGTTTAGGAAGCGATTTTCCAAGTTCTACACTTG

AGCGTGCTGTTAATTATGCGACTTCTCAAGGCGTTCTTGTTATTGCGGCA

ACTGGGAATAACGGTTCTGGCTCAGTAGGCTATCCGGCCCGTTATGCGAA

CGCAATGGCAGTCGGAGCTACTGACCAAAACAACAGACGCGCCAACTTTT

CACAGTATGGCACGGGAATTGACATTGTCGCACCAGGTGTAAACGTGCAG

AGCACATACCCAGGTAACCGTTATGTGAGCATGAACGGTACATCGATGGC

TACTCCTCATGTTGCAGGTGCAGCAGCCCTTGTTAAACAACGCTATCCWT

CTTGGAATGCGACTCAAATCCGCAATCATCTGAAAAATACGGCAACGAAT

TTAGGAAACTCTTCACAATTTGGAAGCGGACTTGTCAATGCAGAAGCGGC

AACACGC.
```

The predicted amino acid sequence of the mature form of the BG5-F02 subtilisin is set forth as SEQ ID NO:57:

```
QQTVPWGITRVQAPAVHNRGITGSGVRVAILDSGISAHSDLNIRGGASFV

PGEPTTADLNGHGTHVAGTVAALNNSIGVIGVAPNAELYAVKVLGANGSG

SVSGIAQGLEWAATNNMHIANMSLGSDFPSSTLERAVNYATSQGVLVIAA

TGNNGSGSVGYPARYANAMAVGATDQNNRRANFSQYGTGIDIVAPGVNVQ

STYPGNRYVSMNGTSMATPHVAGAAALVKQRYPSWNATQIRNHLKNTATN

LGNSSQFGSGLVNAEAATR.
```

The nucleotide sequence encoding the BG5-E05 subtilisin is set forth as SEQ ID NO:58:

```
CAACAAACAGTGCCATGGGGAATTACTCGTGTGCAAGCCCCAGCTGTTCA

TAACCGTGGAATTACAGGTTCTGGTGTAAGAGTTGCTATCCTCGATTCAG

GTATTTCCGCCCATAGTGACTTAAATATTCGTGGTGGCGCTAGCTTTGTA

CCAGGGGAACCAACGACTGCTGATTTAAATGGGCATGGCACGCATGTGGC

TGGGACGGTAGCTGCTTTAAACAATTCGATTGGCGTTATTGGCGTAGCAC

CGAACGCGGAACTATACGCTGTTAAAGTATTAGGGGCGAATGGTTCAGGT

TCGGTCAGCGGGATTGCCCAAGGATTGGAATGGGCAGCAACCAATAACAT

GCACATTGCTAATATGAGTTTAGGAAGCGATTTTCCAAGTTCTACACTTG

AGCGTGCTGTTAATTATGCGACTTCTAGAGATGTTCTTGTTATTGCGGCA

ACTGGGAATAACGGTTCTGGCTCAGTAGGCTATCCGGCCCGTTATGCGAA

CGCAATGGCAGTCGGAGCTACTGACCAAAACAACAGACGCGCCAACTTTT

CACAGTATGGCGCAGGGCTGGACATTGTCGCACCAGGTGTAAACGTGCAG

AGCACATACCCAGGTAACCGTTATGTGAGCATGAACGGTACATCGATGGC

TACTCCTCATGTTGCAGGTGCAGCAGCCCTTGTTAAACAACGCTATCCAT

CTTGGAATGCGACTCAAATCCGCAATCATCTAAAGAATACGGCAACGAAT

TTAGGAAACTCTTCACAATTTGGAAGCGGACTTGTCAATGCAGAAGCGGC

AACACGC.
```

The predicted amino acid sequence of the mature form of the BG5-E05 subtilisin is set forth as SEQ ID NO:59:

```
QQTVPWGITRVQAPAVHNRGITGSGVRVAILDSGISAHSDLNIRGGASFV

PGEPTTADLNGHGTHVAGTVAALNNSIGVIGVAPNAELYAVKVLGANGSG

SVSGIAQGLEWAATNNMHIANMSLGSDFPSSTLERAVNYATSRDVLVIAA

TGNNGSGSVGYPARYANAMAVGATDQNNRRANFSQYGAGLDIVAPGVNVQ

STYPGNRYVSMNGTSMATPHVAGAAALVKQRYPSWNATQIRNHLKNTATN

LGNSSQFGSGLVNAEAATR.
```

The nucleotide sequence encoding the BG1-C05 subtilisin is set forth as SEQ ID NO:60:

```
CAACAAACAGTGCCATGGGGAATTACTCGTGTGCAAGCCCCAGCTGTTCA

TAACCGTGGAATTACAGGTTCTGGTGTAAGAGTTGCTATCCTCGATTCAG

GTATTTCCGCCCATAGTGACTTAAATATTCGTGGTGGCGCTAGCTTTGTA

CCAGGGGAACCAACGACTGCTGATTTAAATGGGCATGGCACGCATGTGGC

TGGGACGGTAGCTGCTTTAAACAATTCGATTGGCGTTATTGGCGTAGCAC

CGAACGCGGAACTATACGCTGTTAAAGTATTAGGGGCGAATGGTAGAGGT

TCGGTCAGCGGGATTGCCCAAGGATTGGAATGGGCAGCAACCAATAACAT

GCACATTGCTAATATGAGTTTAGGAAGCGATGCACCAAGTACTACACTTG

AGCGTGCTGTTAATTATGCGACTTCTAGAGATGTTCTTGTTATTGCGGCA

ACTGGGAATAACGGTTCTGGCTCAGTAGGCTATCCGGCCCGTTATGCGAA

CGCAATGGCAGTCGGAGCTACTGACCAAAACAACAGACGCGCCAACTTTT

CACAGTATGGCACGGGATTGACATTGTCGCACCAGGTGTAAACGTGCAG

AGCACATACCCAGGTAACCGTTATGTGAGCATGAACGGTACATCGATGGC

TACTCCTCATGTTGCAGGTGCAGCAGCCCTTGTTAAACAACGCTATCCAT

CTTGGAATGCGACTCAAATCCGCAATCATCTAAAGAATACGGCAACGAAT

TTAGGAAACTCTTCACAATTTGGAAGCGGACTTGTCAATGCAGAAGCGGC

AACACGC.
```

The predicted amino acid sequence of the mature form of the BG1-C05 subtilisin is set forth as SEQ ID NO:61:

```
QQTVPWGITRVQAPAVHNRGITGSGVRVAILDSGISAHSDLNIRGGASFV

PGEPTTADLNGHGTHVAGTVAALNNSIGVIGVAPNAELYAVKVLGANGRG

SVSGIAQGLEWAATNNMHIANMSLGSDAPSTTLERAVNYATSRDVLVIAA

TGNNGSGSVGYPARYANAMAVGATDQNNRRANFSQYGTGIDIVAPGVNVQ

STYPGNRYVSMNGTSMATPHVAGAAALVKQRYPSWNATQIRNHLKNTATN

LGNSSQFGSGLVNAEAATR.
```

The nucleotide sequence encoding the BG2-D10 subtilisin is set forth as SEQ ID NO:62:

```
CAACAAACAGTGCCATGGGGAATTACTCGTGTGCAAGCCCCAGCTGTTCA

TAACCGTGGAATTACAGGTTCTGGTGTAAGAGTTGCTATCCTCGATTCAG

GTATTTCCGCCCATAGTGACTTAAATATTCGTGGTGGCGCTAGCTTTGTA

CCAGGGGAACCAACGACTGCTGATTTAAATGGGCATGGCACGCATGTGGC

TGGGACGGTAGCTGCTTTAAACAATTCGATTGGCGTTATTGGCGTAGCAC
```

-continued

```
CGAACGCGGAACTATACGCTGTTAAAGTATTAGGGGCGAATGGTTCAGGT
TCGGTCAGCGGGATTGCCCAAGGATTGGAATGGGCAGCAACCAATAACAT
GCACATTGCTAATATGAGTTTAGGAAGCGATGCACCAAGTACAACACTTG
AGCGTGCTGTTAATTATGCGACTTCTCAAGGCGTTCTTGTTATTGCGGCA
ACTGGGAATAACGGTTCTGGCTCAGTAGGCTATCCGGCCCGTTATGCGAA
CGCAATGGCAGTCGGAGCTACTGACCAAAACAACAGACGCGCCAACTTTT
CACAGTATGGCACGGGGATTGACATTGTCGCACCAGGTGTAAACGTGCAG
AGCACATACCCAGGTAACCGTTATGTGAGCATGAACGGTACATCGATGGC
TACTCCTCATGTTGCAGGTGCAGCAGCCCTTGTTAAACAACGCTATCCAT
CTTGGAATGCGACTCAAATCCGCAATCATCTAAAGAATACGGCAACGAAT
TTAGGAAACTCTTCACAATTTGGAAGCGGACTTGTCAATGCAGAAGCGGC
AACACGC.
```

The predicted amino acid sequence of the mature form of the BG2-D10 subtilisin is set forth as SEQ ID NO:63:

```
QQTVPWGITRVQAPAVHNRGITGSGVRVAILDSGISAHSDLNIRGGASFV
PGEPTTADLNGHGTHVAGTVAALNNSIGVIGVAPNAELYAVKVLGANGSG
SVSGIAQGLEWAATNNMHIANMSLGSDAPSTTLERAVNYATSQGVLVIAA
TGNNGSGSVGYPARYANAMAVGATDQNNRRANFSQYGTGIDIVAPGVNVQ
STYPGNRYVSMNGTSMATPHVAGAAALVKQRYPSWNATQIRNHLKNTATN
LGNSSQFGSGLVNAEAATR.
```

The nucleotide sequence encoding the BG1-B08 subtilisin is set forth as SEQ ID NO:64:

```
CAACAAACAGTGCCATGGGGAATTACTCGTGTGCAAGCCCCAGCTGTTCA
TAACCGTGGAATTACAGGTTCTGGTGTAAGAGTTGCTATCCTCGATTCAG
GTATTTCCGCCCATAGTGACTTAAATATTCGTGGTGGCGCTAGCTTTGTA
CCAGGGGAACCAACGACTGCTGATTTAAATGGGCATGGCACGCATGTGGC
TGGGACGGTAGCTGCTTTAAACAATTCGATTGGCGTTATTGGCGTAGCAC
CGAACGCGGAACTATACGCTGTTAAAGTATTAGGGGCGAATGGTTCAGGT
TCGGTCAGCGGGATTGCCCAAGGATTGGAATGGGCAGCAACCAATAACAT
GCACATTGCTAATATGAGTTTAGGAAGCGATTTTCCAAGTTCTACACTTG
AGCGTGCTGTTAATTATGCGACTTCTCAAGGCGTTCTTGTTATTGCGGCA
ACTGGGAATAACGGTTCTGGCTCAGTAGGCTATCCGGCCCGTTATGCGAA
CGCAATGGCAGTCGGAGCTACTGACCAAAACAACAGACGCGCCAACTTTT
CACAGTATGGCACGGGATTGACATTGTCGCACCAGGTGTAAACGTGCAG
AGCACATACCCAGGTAACCGTTATGTGAGCATGAACGGTACATCGATGGC
TACTCCTCATGTTGCAGGTGCAGCAGCCCTTGTTAAACAACGCTATCCAT
CTTGGAATGCGACTCAAATCCGCAATCATCTAAAGAATACGGCAACGAAT
TTAGGAAACACAAATCTGTATGGAAGCGGACTTGTCAATGCAGAAGCGGC
AACACGC.
```

The predicted amino acid sequence of the mature form of the BG1-B08 subtilisin is set forth as SEQ ID NO:65:

```
QQTVPWGITRVQAPAVHNRGITGSGVRVAILDSGISAHSDLNIRGGASFV
PGEPTTADLNGHGTHVAGTVAALNNSIGVIGVAPNAELYAVKVLGANGSG
SVSGIAQGLEWAATNNMHIANMSLGSDFPSSTLERAVNYATSQGVLVIAA
TGNNGSGSVGYPARYANAMAVGATDQNNRRANFSQYGTGIDIVAPGVNVQ
STYPGNRYVSMNGTSMATPHVAGAAALVKQRYPSWNATQIRNHLKNTATN
LGNTNLYGSGLVNAEAATR.
```

The nucleotide sequence encoding the BG4-A09 subtilisin is set forth as SEQ ID NO:66:

```
CAACAAACAGTGCCATGGGGAATTACTCGTGTGCAAGCCCCAGCTGTTCA
TAACCGTGGAGTTACAGGTTCTGGTGTAAGAGTTGCTGTTCTCGATACAG
GTATTTCCGCCCATAGTGACTTAAATATTCGTGGTGGCGCTAGCTTTGTA
CCAGGGGAACCAACGACTGCTGATTTAAATGGGCATGGCACGCATGTGGC
TGGGACGGTAGCTGCTTTAAACAATTCGATTGGCGTTATTGGCGTAGCAC
CGAACGCGGAACTATACGCTGTTAAAGTATTAGGGGCGAATGGTTCAGGT
TCGGTCAGCGGGATTGCCCAAGGATTGGAATGGGCAGCAACCAATAACAT
TCACATTGCTAATATGAGTTTAGGAACAGATGCACCAAGTACAACACTTG
AGCGTGCTGTTAATTATGCGACTTCTCAAGGCGTTCTTGTTATTGCGGCA
ACTGGGAATAACGGTTCTGGCACAATTTCATATCCGGCCCGTTATGCGAA
CGCAATGGCAGTCGGAGCTACTGACCAAAACAACAATCGCGCCTCATTTT
CACAGTATGGCGCAGGGCTGGACATTGTCGCACCAGGTGTAAACGTGCAG
AGCACATACCCAGGTAACCGTTATGTGAGCATGAACGGTACATCGATGGC
TACTCCTCATGTTGCAGGTGCAGCAGCCCTTGTTAAACAACGCTATCCAT
CTTGGAATGCGACTCAAATCCGCAATCATCTAAAGAATACGGCAACGAAT
TTAGGAAACTCTTCACAATTTGGAAGCGGACTTGTCAATGCAGAAGCGGC
AACACGC.
```

The predicted amino acid sequence of the mature form of the BG4-A09 subtilisin is set forth as SEQ ID NO:67:

```
QQTVPWGITRVQAPAVHNRGVTGSGVRVAVLDTGISAHSDLNIRGGASFV
PGEPTTADLNGHGTHVAGTVAALNNSIGVIGVAPNAELYAVKVLGANGSG
SVSGIAQGLEWAATNNIHIANMSLGTDAPSTTLERAVNYATSQGVLVIAA
TGNNGSGTISYPARYANAMAVGATDQNNNRASFSQYGAGLDIVAPGVNVQ
STYPGNRYVSMNGTSMATPHVAGAAALVKQRYPSWNATQIRNHLKNTATN
LGNSSQFGSGLVNAEAATR.
```

The nucleotide sequence encoding the BG4-D10 subtilisin is set forth as SEQ ID NO:68:

```
CAACAAACAGTGCCATGGGGAATTACTCGTGTGCAAGCCCCAGCTGTTCA
TAACCGTGGGATTTACAGGTTCTGGTGTAAGAGTTGCTATCCTCGATTCAG
GTATTTCCACACATAGTGACTTAACAATTCGTGGTGGCGCTAGCTTTGTA
CCAGGGGAACCAACGACTGCTGATTTAAATGGGCATGGCACGCATGTGGC
TGGGACGGTAGCTGCTTTAAACAATTCGATTGGCGTTCTGGGCGTAGCAC
```

-continued
```
CGAACGCGGAACTATACGCTGTTAAAGTATTAGGGGCGAATGGTTCAGGT

TCGATTAGCGGGATTGCCCAAGGATTGGAATGGGCAGCAGCAAATAACAT

GCACATTGCTAATATGAGTTTAGGAACAGATGCACCAAGTTCTACACTTG

AGCGTGCTGTTAATTATGCGACTTCTCAAGGCGTTCTTGTTATTGCGGCA

ACTGGGAATAACGGTTCTGGCACAATTTCATATCCGGCCCGTTATGCGAA

CGCAATGGCAGTCGGAGCTACTGACCAAAACAACAGACGCGCCAACTTTT

CACAGTATGGCTCAGGGATTGACATTGTCGCACCAGGTGTAAACGTGCAG

AGCACATACCCAGGTAACCGTTATGCAAGCCTGTCAGGTACATCGATGGC

TACTCCTCATGTTGCAGGTGCAGCAGCCCTTGTTAAACAACGCTATCCAT

CTTGGAATGCGACTCAAATCCGCAATCATCTAAAGAATACGGCAACGAAT

TTAGGAAACTCTTCACAATTTGGAAGCGGACTTGTCAATGCAGAAGCGGC

AACACGC.
```

The predicted amino acid sequence of the mature form of the BG4-D10 subtilisin is set forth as SEQ ID NO:69:

```
QQTVPWGITRVQAPAVHNRGFTGSGVRVAILDSGISTHSDLTIRGGASFV

PGEPTTADLNGHGTHVAGTVAALNNSIGVLGVAPNAELYAVKVLGANGSG

SISGIAQGLEWAAANNMHIANMSLGTDAPSSTLERAVNYATSQGVLVIAA

TGNNGSGTISYPARYANAMAVGATDQNNRRANFSQYGSGIDIVAPGVNVQ

STYPGNRYASLSGTSMATPHVAGAAALVKQRYPSWNATQIRNHLKNTATN

LGNSSQFGSGLVNAEAATR.
```

The nucleotide sequence encoding the BG2-B08 subtilisin is set forth as SEQ ID NO:70:

```
CAACAAACAGTGCCATGGGGAATTACTCGTGTGCAAGCCCCAGCTGTTCA

TAACCGTGGAATTACAGGTTCTGGTGTAAGAGTTGCTATCCTCGATTCAG

GTATTTCCGCCCATAGTGACTTAAATATTCGTGGTGGCGCTAGCTTTGTA

CCAGGGGAACCAACGACTGCTGATTTAAATGGGCATGGCACGCATGTGGC

TGGGACGGTAGCTGCTTTAAACAATTCGATTGGCGTTATTGGCGTAGCAC

CGAACGCGGAACTATACGCTGTTAAAGTATTAGGGGCGTCAGGTTCAGGT

TCGATTAGCGGGATTGCCCAAGGATTGCAATGGGCAGCAACCAATAACAT

GCACATTGCTAATATGAGTTTAGGAAGCGATGCACCAAGTACAACACTTG

AGCGTGCTGTTAATTATGCGACTTCTAGAGATGTTCTTGTTATTGCGGCA

ACTGGGAATAACGGTTCTGGCTCAGTAGGCTATCCGGCCCGTTATGCGAA

CGCAATGGCAGTCGGAGCTACTGACCAAAACAACAGACGCGCCAACTTTT

CACAGTATGGCACGGGATTGACATTGTCGCACCAGGTGTAAACGTGCAG

AGCACATACCCAGGTAACCGTTATGTGAGCATGAACGGTACATCGATGGC

TACTCCTCATGTTGCAGGTGCAGCAGCCCTTGTTAAACAACGCTATCCAT

CTTGGAATGCGACTCAAATCCGCAATCATCTAAAGAATACGGCAACGAAT

TTAGGAAACTCTTCACAATTTGGAAGCGGACTTGTCAATGCAGAAGCGGC

AACACGC.
```

The predicted amino acid sequence of the mature form of the BG2-B08 subtilisin is set forth as SEQ ID NO:71:

```
QQTVPWGITRVQAPAVHNRGITGSGVRVAILDSGISAHSDLNIRGGASFV

PGEPTTADLNGHGTHVAGTVAALNNSIGVIGVAPNAELYAVKVLGASGSG

SISGIAQGLQWAATNNMHIANMSLGSDAPSTTLERAVNYATSRDVLVIAA

TGNNGSGSVGYPARYANAMAVGATDQNNRRANFSQYGTGIDIVAPGVNVQ

STYPGNRYVSMNGTSMATPHVAGAAALVKQRYPSWNATQIRNHLKNTATN

LGNSSQFGSGLVNAEAATR.
```

The nucleotide sequence encoding the BG8-B03 subtilisin is set forth as SEQ ID NO:72:

```
GCACAAACAGTGCCATGGGGAATTACTCGTGTGCAAGCCCCAGCTGTTCA

TAACCGTGGAATTACAGGTTCTGGTGTAAGAGGTTGCTATCCTCGATTCA

GGTATTTCCGCCCATAGTGACTTAACAATTCGTGGTGGCGCTGCTTTGTA

CCAGGGGAACCAACGACTGCTGATTTAAATGGGCATGGCACGCATGTGGC

TGGGACGGTAGCTGCTTTAAACAATTCGATTGGCGTTATTGGCGTAGCAC

CGTCAGCGGATCTATACGCTGTTAAAGTATTAGGGGCGAATGGTAGAGGT

TCGGTCAGCGGGATTGCCCAAGGATTGGAATGGGCAGCAACCAATAACAT

GCACATTGCTAATATGAGTTTAGGAAGCGATGCACCAAGTACAACACTTG

AGCGTGCTGTTAATTATGCGACTTCTCAAGGCGTTCTTGTTATTGCGGCA

ACTGGGAATAACGGTTCTGGCTCAGTAGGCTATCCGGCCCGTTATGCGAA

CGCAATGGCAGTCGGAGCTACTGACCAAAACAACAATCGCGCCTCATTTT

CACAGTATGGCGCAGGGCTGGACATTGTCGCACCAGGTGTAAACGTGCAG

AGCACATACCCAGGTAACCGTTATGTGAGCATGAACGGTACATCGATGGC

TACTCCTCATGTTGCAGGTGTTGCAGCCCTTGTTAAACAACGCTATCCAT

CTTGGAATGCGACTCAAATCCGCAATCATCTAAAGAATACGGCAACGAAT

TTAGGAAACTCTTCACAATTTGGAAGCGGACTTGTCAATGCAGAAGCGGC

AACACGC.
```

The predicted amino acid sequence of the mature form of the BG8-B03 subtilisin is set forth as SEQ ID NO:73:

```
AQTVPWGITRVQAPAVHNRGITGSGVRVAILDSGISAHSDLTIRGGASFV

PGEPTTADLNGHGTHVAGTVAALNNSIGVIGVAPSADLYAVKVLGANGRG

SVSGIAQGLEWAATNNMHIANMSLGSDAPSTTLERAVNYATSQGVLVIAA

TGNNGSGSVGYPARYANAMAVGATDQNNRASFSQYGAGLDIVAPGVNVQ

STYPGNRYVSMNGTSMATPHVAGVAALVKQRYPSWNATQIRNHLKNTATN

LGNSSQFGSGLVNAEAATR.
```

The nucleotide sequence encoding the BG6-A10 subtilisin is set forth as SEQ ID NO:74:

```
CAACAAACAGTGCCATGGGGAATTACTCGTGTGCAAGCCCCAGCTGTTCA

TAACCGTGGAATTACAGGTTCTGGTGTAAGAGTTGCTATCCTCGATTCAG

GTATTTCCGCCCATAGTGACTTAAATATTCGTGGTGGCGCTAGCTTTGTA

CCAGGGGAACCAACGACTGCTGATTTAAATGGGCATGGCACGCATGTGGC

TGGGACGGTAGCTGCTTTAAACAATTCGATTGGCGTTATTGGCGTAGCAC
```

```
CGAACGCGGAACTATACGCTGTTAAAGTATTAGGGGCGTCAGGTTCAGGT

TCGGTCAGCGGGATTGCCCAAGGATTGGAATGGGCAGCAACCAATAACAT

GCACATTGCTAATATGAGTTTAGGAAGCGATTTTCCAAGTTCTACACTTG

AGCGTGCTGTTAATTATGCGACTTCTAGAGATGTTCTTGTTATTGCGGCA

ACTGGGAATAACGGTTCTGGCTCAGTAGGCTATCCGGCCCGTTATGCGAA

CGCAATGGCAGTCGGAGCTACTGACCAAAACAACAGACGCGCCAACTTTT

CACAGTATGGCACGGGGATTGACATTGTCGCACCAGGTGTAAACGTGCAG

AGCACATACCCAGGTAACCGTTATGTGAGCATGAACGGTACATCGATGGC

TACTCCTCATGTTGCAGGTGCAGCAGCCCTTGTTAAACAACGCTATCCAT

CTTGGAATGCGACTCAAATCCGCAATCATCTAAAGAATACGGCAACGAAT

TTAGGAAACACAAATCTGTATGGAAGCGGACTTGTCAATGCAGAAGCGGC

AACACGC.
```

The predicted amino acid sequence of the mature form of the BG6-A10 subtilisin is set forth as SEQ ID NO:75:

```
QQTVPWGITRVQAPAVHNRGITGSGVRVAILDSGISAHSDLNIRGGASFV

PGEPTTADLNGHGTHVAGTVAALNNSIGVIGVAPNAELYAVKVLGASGSG

SVSGIAQGLEWAATNNMHIANMSLGSDFPSSTLERAVNYATSRDVLVIAA

TGNNGSGSVGYPARYANAMAVGATDQNNRRANFSQYGTGIDIVAPGVNVQ

STYPGNRYVSMNGTSMATPHVAGAAALVKQRYPSWNATQIRNHLKNTATN

LGNTNLYGSGLVNAEAATR.
```

The nucleotide sequence encoding the BG6-D08 subtilisin is set forth as SEQ ID NO:76:

```
CAACAATCAGTGCCATGGGAATTTCACGTGTGCAAGCCCCAGCTGTTCA

TAACCGTGGAATTACAGGTTCAGGTGTAAGAGTTGCTATCCTCGATTCAG

GTATTTCCGCCCATAGTGACTTAAATATTCGTGGTGGCGCTAGCTTTGTA

CCAGGGGAACCAACGACTGCTGATTTAAATGGGCATGGCACGCATGTGGC

TGGGACGGTAGCTGCTTTAAACAATTCGATTGGCGTTATTGGCGTAGCAC

CGTCAGCGGATCTATACGCTGTTAAAGTATTAGGGGCGAATGGTTCAGGT

TCGGTCAGCGGGATTGCCCAAGGATTGGAATGGGCAGCAAATAACAT

GCACATTGCTAATATGAGTTTAGGAAGCGATTTTCCAAGTTCTACACTTG

AGCGTGCTGTTAATTATGCGACTTCTAGAGATGTTCTTGTTATTGCGGCA

ACTGGGAATAACGGTTCTGGCTCAGTAGGCTATCCGGCCCGTTATGCGAA

CGCAATGGCAGTCGGAGCTACTGACCAAAACAACAGACGCGCCAACTTTT

CACAGTATGGCACGGGGATTGACATTGTCGCACCAGGTGTAAACGTGCAG

AGCACATACCCAGGTAACCGTTATGTGAGCATGAACGGTACATCGATGGC

TACTCCTCATGTTGCAGGTGCAGCAGCCCTTGTTAAACAACGCTATCCAT

CTTGGAATGCGACTCAAATCCGCAATCATCTAAAGAATACGGCAACGAAT

TTAGGAAACACAAATCTGTATGGAAGCGGACTTGTCAATGCAGAAGCGGC

AACACGC.
```

The predicted amino acid sequence of the mature form of the BG6-D08 subtilisin is set forth as SEQ ID NO:77:

```
QQTVPWGITRVQAPAVHNRGITGSGVRVAILDSGISAHSDLNIRGGASFV

PGEPTTADLNGHGTHVAGTVAALNNSIGVIGVAPNAELYAVKVLGASGSG

SVSGIAQGLEWAATNNMHIANMSLGSDFPSSTLERAVNYATSRDVLVIAA

TGNNGSGSVGYPARYANAMAVGATDQNNRRANFSQYGTGIDIVAPGVNVQ

STYPGNRYVSMNGTSMATPHVAGAAALVKQRYPSWNATQIRNHLKNTATN

LGNTNLYGSGLVNAEAATR.
```

The nucleotide sequence encoding the BG5-G10 subtilisin is set forth as SEQ ID NO:78:

```
CAACAAACAGTGCCATGGGGAATTACTCGTGTGCAAGCCCCAGCTGTTCA

TAACCGTGGAATTACAGGTTCTGGTGTAAGAGTTGCTATCCTCGATTCAG

GTATTTCCGCCCATAGTGACTTAAATATTCGTGGTGGCGCTAGCTTTGTA

CCAGGGGAACCAACGACTGCTGATTTAAATGGGCATGGCACGCATGTGGC

TGGGACGGTAGCTGCTTTAAACAATTCGATTGGCGTTATTGGCGTAGCAC

CGTCAGCGGATCTATACGCTGTTAAAGTATTAGGGGCGAATGGTTCAGGT

TCGGTCAGCGGGATTGCCCAAGGATTGGAATGGGCAGCAACCAATAACAT

GCACATTGCTAATATGAGTTTAGGAAGCGATTTTCCAAGTTCTACACTTG

AGCGTGCTGTTAATTATGCGACTTCTAGAGATGTTCTTGTTATTGCGGCA

ACTGGGAATAACGGTTCTGGCTCAGTAGGCTATCCGGCCCGTTATGCGAA

CGCAATGGCAGTCGGAGCTACTGACCAAAACAACAGACGCGCCAACTTTT

CACAGTATGGCACGGGGATTGACATTGTCGCACCAGGTGTAAACGTGCAG

AGCACATACCCAGGTAACCGTTATGTGAGCATGAACGGTACATCGATGGC

TACTCCTCATGTTGCAGGTGCAGCAGCCCTTGTTAAACAACGCTATCCAT

CTTGGAATGCGACTCAAATCCGCAATCATCTAAAGAATACGGCAACGAAT

TTAGGAAACACAAATCTGTATGGAAGCGGACTTGTCAATGCAGAAGCGGC

AACACGC.
```

The predicted amino acid sequence of the mature form of the BG5-G10 subtilisin is set forth as SEQ ID NO:79:

```
QQTVPWGITRVQAPAVHNRGITGSGVRVAILDSGISAHSDLNIRGGASFV

PGEPTTADLNGHGTHVAGTVAALNNSIGVIGVAPSADLYAVKVLGANGSG

SVSGIAQGLEWAATNNMHIANMSLGSDFPSSTLERAVNYATSRDVLVIAA

TGNNGSGSVGYPARYANAMAVGATDQNNRRANFSQYGTGIDIVAPGVNVQ

STYPGNRYVSMNGTSMATPHVAGAAALVKQRYPSWNATQIRNHLKNTATN

LGNTNLYGSGLVNAEAATR.
```

The nucleotide sequence encoding the BG5-E02 subtilisin is set forth as SEQ ID NO:80:

```
CAACAAACAGTGCCATGGGAATTTCACGTGTGCAAGCCCCAGCTGTTCA

TAACCGTGGAATTACAGGTTCTGGTGTAAGAGTTGCTATCCTCGATTCAG

GTATTTCCGCCCATAGTGACTTAAATATTCGTGGTGGCGCTAGCTTTGTA

CCAGGGGAACCAACGACTGCTGATTTAAATGGGCATGGCACGCATGTGGC

TGGGACGGTAGCTGCTTTAAACAATTCGATTGGCGTTATTGGCGTAGCAC
```

```
CGAACGCGGAACTATACGCTGTTAAAGTATTAGGGGCGTCAGGTTCAGGT

TCGATTAGCGGGATTGCCCAAGGATTGGAATGGGCAGCAACCAATAACAT

GCACATTGCTAATATGAGTTTAGGAAGCGATGCACCAAGTACAACACTTG

AGCGTGCTGTTAATTATGCGACTTCTAGAGATGTTCTTGTTATTGCGGCA

ACTGGGAATAACGGTTCTGGCTCAGTAGGCTATCCGGCCCGTTATGCGAA

CGCAATGGCAGTCGGAGCTACTGACCAAAACAACAGACGCGCCAACTTTT

CACAGTATGGCACGGGGATTGACATTGTCGCACCAGGTGTAAACGTGCAG

AGCACATACCCAGGTAACCGTTATGTGAGCATGAACGGTACATCGATGGC

TACTCCTCATGTTGCAGGTGCAGCAGCCCTTGTTAAACAACGCTATCCAT

CTTGGAATGCGACTCAAATCCGCAATCATCTAAAGAATACGGCAACGAAT

TTAGGAAACACAAATCTGTATGGAAGCGGACTTGTCAATGCAGAAGCGGC

AACACGC.
```

The predicted amino acid sequence of the mature form of the BG5-E02 subtilisin is set forth as SEQ ID NO:81:

```
QQTVPWGISRVQAPAVHNRGITGSGVRVAILDSGISAHSDLNIRGGASFV

PGEPTTADLNGHGTHVAGTVAALNNSIGVIGVAPNAELYAVKVLGASGSG

SISGIAQGLEWAATNNMHIANMSLGSDAPSTTLERAVNYATSRDVLVIAA

TGNNGSGSVGYPARYANAMAVGATDQNNRRANFSQYGTGIDIVAPGVNVQ

STYPGNRYVSMNGTSMATPHVAGAAALVKQRYPSWNATQIRNHLKNTATN

LGNTNLYGSGLVNAEAATR.
```

The nucleotide sequence encoding the BG2-G08 subtilisin is set forth as SEQ ID NO:82:

```
CAACAAACAGTGCCATGGGGAATTACTCGTGTGCAAGCCCCAGCTGTTCA

TAACCGTGGAATTACAGGTTCTGGTGTAAGAGTTGCTATCCTCGATTCAG

GTATTTCCGCCCATAGTGACTTAAATATTCGTGGTGGCGCTAGCTTTGTA

CCAGGGGAACCAACGACTGCTGATTTAAATGGGCATGGCACGCATGTGGC

TGGGACGGTAGCTGCTTTAAACAATTCGATTGGCGTTATTGGCGTAGCAC

CGAACGCGGAACTATACGCTGTTAAAGTATTAGGGGCGAATGGTTCAGGT

TCGGTCAGCGGGATTGCCCAAGGATTGGAATGGGCAGCAACCAATAACAT

GCACATTGCTAATATGAGTTTAGGAAGCGATGCACCAAGTACAACACTTG

AGCGTGCTGTTAATTATGCGACTTCTGCAGGCGTTCTTGTTGTTGCGGCA

ACTGGGAATAACGGTTCTGGCTCAGTAGGCTATCCGGCCCGTTATGCGAA

CGCAATGGCAGTCGGAGCTACTGACCAAAACAACAGACGCGCCAACTTTT

CACAGTATGGCACGGGGATTGACATTGTCGCACCAGGTGTAAACGTGCAG

AGCACATACCCAGGTAACCGTTATGTGAGCATGAACGGTACATCGATGGC

TACTCCTCATGTTGCAGGTGCAGCAGCCCTTGTTAAACAACGCTATCCAT

CTTGGAATGCGACTCAAATCCGCAATCATCTAAAGAATACGGCAACGAAT

TTAGGAAACTCTTCACAATTTGGAAGCGGACTTGTCAATGCAGAAGCGGC

AACACGC.
```

The predicted amino acid sequence of the mature form of the BG2-G08 subtilisin is set forth as SEQ ID NO:83:

```
QQTVPWGITRVQAPAVHNRGITGSGVRVAILDSGISAHSDLNIRGGASFV

PGEPTTADLNGHGTHVAGTVAALNNSIGVIGVAPNAELYAVKVLGANGSG

SVSGIAQGLEWAATNNMHIANMSLGSDAPSTTLERAVNYATSAGVLVVAA

TGNNGSGSVGYPARYANAMAVGATDQNNRRANFSQYGTGIDIVAPGVNVQ

STYPGNRYVSMNGTSMATPHVAGAAALVKQRYPSWNATQIRNHLKNTATN

LGNSSQFGSGLVNAEAATR.
```

Example 12

Cleaning Performance Comparison of Several *B. gibsonii*-clade Subtilisins and other Known Subtilisins The relative cleaning performance of *Bacillus gibsonii* proteases: Bgi02446, DSM 9728, and DSM 9731, as well as subtilisins from other *Bacillus* species: *B. licheniformis* (Blid02330 (SEQ ID NO:84)), *Bacillus* sp. m3-13 ((subtilisin E (SEQ ID NO:85)), *Bacillus* sp. LG12 (LG12 SprC (SEQ ID NO:86)), *B. lentus* (P29600 (SEQ ID NO:87)), and *B. amyloliquefaciens* (CAA24990 (SEQ ID NO:88)), was measured on BMI (blood/milk/ink on cotton) microswatches for laundry based applications, and on egg yolk (for dish based applications) as described in Example 6. The detergents used: Kirkland Ultra HDD (Sun Products), OMO Klein & Krachtig HDL (Unilever), and GSM-B pH10.5 for ADW are described in Table 6.1. The relative cleaning performance of the proteases in various detergents is shown in Table 12.1, where the LG12 SprC subtilisin was the baseline against which improvements or reductions in cleaning performance were ranked.

The amino acid sequence of the mature form of *B. licheniformis* subtilisin BliD02339 is set forth as SEQ ID NO:84:

```
AQTVPYGIPLIKADKVQAQGFKGANVKVAVLDTGIQASHPDLNVVGGASF

VAGEAYNTDGNGHGTHVAGTVAALDNTTGVLGVAPNVSLYAVKVLNSSGS

GSYSGIVSGIEWATTNGMDVINMSLGGPSGSTAMKQAVDNAYARGVVVVA

AAGNSGSSGNTNTIGYPAKYDSVIAVGAVDSNSNRASFSSVGAKLEVMAP

GAGVYSTYPTSTYATLNGTSMASPHVAGAAALILSKHPNLSASQVRNRLS

STATYLGSSFYYGKGLINVEAAAQ.
```

The amino acid sequence of the mature form of *Bacillus* sp. m3-13 subtilisin E is set forth as SEQ ID NO:85:

```
AQTVPWGIPHIKADKAHASGVTGSGVKVAVLDTGIDANHADLNVKGGASF

VSGEPNALQDGNGHGTHVAGTVAALNNTTGVLGVAYNADLYAVKVLSASG

SGTLSGIAQGIEWSIANDMDVINMSLGGSTGSTALQQACDNAYASGIVVV

AAAGNSGSKGKRNTMGYPARYSSVIAVGAVDSSNNRASFSSVGSELEVMA

PGVSILSTTPGNNYSSFNGTSMASPHVAGAAALIKAKYPSMTNVQIREKL

KNTATNLGDAFYYGHGVINVESALQ.
```

The amino acid sequence of the mature form of *Bacillus* sp. LG12 SprC AAC43580 is set forth as SEQ ID NO:86:

AQTVPWGIPHIKADKAHAAGVTGSGVKVAILDTGIDANHADLNVKGGASF

VSGEPNALQDGNGHGTHVAGTVAALNNTTGVLGVAYNADLYAVKVLSASG

SGTLSGIAQGIEWSISNGMNVINMSLGGSSGSTALQQACNNAYNRGIVVI

AAAGNSGSSGNRNTMGYPARYSSVIAVGAVSSNNTRASFSSVGSELEVMA

PGVNILSTTPGNNYASFNGTSMAAPHVAGAAALIKAKYPSMTNVQIRERL

KNTATNLGDPFFYGKGVINVESALQ.

The amino acid sequence of the mature form of *B. lentus* P29600 is set forth as SEQ ID NO: 87:

QSVPWGISRVQAPAAHNRGLTGSGVKVAVLDTGISTHPDLNIRGGASFVP

GEPSTQDGNGHGTHVAGTIAALNNSIGVLGVAPSAELYAVKVLGASGSGS

VSSIAQGLEWAGNNGMHVANLSLGSPSPSATLEQAVNSATSRGVLVVAAS

GNSGAGSISYPARYANAMAVGATDQNNNRASFSQYGAGLDIVAPGVNVQS

TYPGSTYASLNGTSMATPHVAGAAALVKQKNPSWSNVQIRNHLKNTATSL

GSTNLYGSGLVNAEAATR.

The amino acid sequence of the mature form of *B. amyloliquefaciens* CAA24990 is set forth as SEQ ID NO:88:

AQSVPYGVSQIKAPALHSQGYTGSNVKVAVIDSGIDSSHPDLKVAGGASM

VPSETNPFQDNNSHGTHVAGTVAALNNSIGVLGVAPSASLYAVKVLGADG

SGQYSWIINGIEWAIANNMDVINMSLGGPSGSAALKAAVDKAVASGVVVV

AAAGNEGTSGSSSTVGYPGKYPSVIAVGAVDSSNQRASFSSVGPELDVMA

PGVSIQSTLPGNKYGAYNGTSMASPHVAGAAALILSKHPNWTNTQVRSSL

ENTTTKLGDSFYYGKGLINVQAAAQ.

TABLE 12.1

Relative cleaning performance of various *B gibsonii*-clade subtilisins versus other subtilisins

| | | Relative Cleaning Performance +/− is neutral; + is okay; ++ is good; +++ is better; ++++ is even better; and +++++ is the best | | |
|---|---|---|---|---|
| *Bacillus* Organism | Subtilisin | ADW | HDL | HDD |
| *B. gibsonii* | Bgi02446 | +++ | ++ | ++++ |
| *B. gibsonii* | DSM9728 | +++ | + | ND* |
| *B. gibsonii* | DSM9731 | +++ | +/− | ND* |
| *B. lichemformis* | Blid02339 | +/− | +/− | +/− |
| *Bacillus* sp. m3-13 | subtilisin E | + | +/− | +/− |
| *Bacillus* sp. LG12 | LG12 SprC | + | + | + |
| *B. lentus* | P29600 | ++ | ++ | +++++ |
| *B. amyloliquefaciens* | CAA24990 | + | ++ | + |

*Not determined

Example 13

Cleaning Performance and Stability of *Bacillus gibsonii*-clade Proteases

*B. gibsonii*-clade protease determination from culture supernatant was performed with an Agilent (U)HPLC system. A calibration curve (0 ppm-500 ppm) using purified Bgi02466 protein was prepared. *B. gibsonii*-clade proteases were diluted 10 fold in the dilution buffer (Tris 25 mM, pH 7.4, 5 mM CaCl2) and then mixed on a 1:1 ratio with an Acetonitrile buffer (Tris 22.5 mM, pH 7.4, 4.5 mM CaCl2, 9% acetonitrile). Afterwards the samples were filtered using a 45 µm filterplate and loaded via an auto-sampler onto a reverse phase column (Zorbax 300 SB-C3 column, 2.1×100 mm & 2.1×50 mm, both with 1.8 µm beadsize). The samples were eluted from the column with a gradient of Buffer A (0.1% Trifluoroacatic acid) and Buffer B (0.07% Acetonitrile). The flow rate was 1 mL/min with a 4 min run and a 1 min post run equilibration. Absorbance was measured at 220 nm, and peaks were integrated using ChemStation software (Agilent Technologies). The protein concentration of the samples was calculated based on a standard curve of the purified parent enzyme.

The cleaning performance of each *B. gibsonii*-clade protease described in Example 11 and Bgi02446, DSM 9728, and DSM 9731 was measured in (i) liquid laundry detergent OMO Klein & Krachtig (OMO HDL) using BMI microswatches (EMPA-116), and (ii) dish based applications (ADW) using GSM-B pH 10.5 formula and egg yolk microswatches (PAS-38) as described in Example 6. For the ADW assays, the pre-punched PAS-38 swatches were either rinsed or unrinsed. To prepare rinsed PAS38 swatches, 180 µl 10 mM CAPS buffer of pH11 was added to micro plates containing PAS38 µswatches. The plates were sealed and incubated in an iEMS incubator for 30 min at 60° C. and 1100 rpm shaking. After incubation the buffer was removed using a Biotek plate washer, and the swatches were rinsed with demi water to remove any residual CAPS buffer. The plates were air dried prior to usage in the performance assay.

Following incubation, absorbance was read at 405 nm for EMPA-116 and PAS-38 swatches, using the SpectraMax plate reader. Absorbance results were obtained by subtracting the value for a blank control (no enzyme) from each sample value. The cleaning PI for each assay condition was obtained by dividing the absorbance values for a given protein by that of Bgi02446 at the same concentration. The Bgi02446 value was determined by fitting the standard curve of the parent to a Langmuir fit or Hill Sigmodial fit. The cleaning performance of the new proteases in various detergents is shown in Table 13.1 as PI compared to the wildtype Bgi02446 subtilisin.

Variants were tested for stability under two stress conditions to measure protein stability by measuring the residual activity following incubation at elevated temperature. One testing condition was: 50 mM Tris pH9; 1 mM EDTA; 0.005% Tween (Tris/EDTA), with incubation at 52° C. The other testing condition was: 50 mM Tris pH9; 2 mM CaCl2; 0.005% Tween, (Tris/CA) with incubation at 72° C. Diluted enzyme sample was mixed in stressor and unstressed protease activity was measured. The diluted sample in stressor was incubated at elevated temperature and after incubation the stressed protease activity was measured. For the unstressed condition, enzyme was assayed immediately for activity on DMC. For the stressed condition, the PCR plate was sealed and incubated at elevated temperature for 5 minutes using an Eppendorf 384 Thermocycler, then assayed for activity. Stressed and unstressed activity was measured by hydrolysis of the synthetic substrate DMC: The reagent solutions used for the DMC assay were: 2.5% Dimethylcasein (DMC, Sigma) in 100 mM Sodium Carbonate pH 9.5, 0.075% TNBSA (2,4,6-trinitrobenzene sulfonic acid, Thermo Scientific) in Reagent A. Reagent A: 45.4 g Na2B4O7.10H20 (Merck) in 15 mL 4N NaOH to reach a final volume of 1000 mL in MQ water, Dilution Solution: 10 mM NaCl, 0.1 mM CaCl2, 0.005% Tween-80, 0.02% Na-azide. MTPs (Greiner PS-microwell 384) were filled with 47.5 uL DMC substrate following the addition of 2.5 uL of 20 ppm protease supernatant. 50 uL of TNBSA in reagent A was then added with slow mixing. Activity was measured at 405 nm over 5 minutes using a SpectraMax plate reader in kinetic mode at RT. Activity was expressed as mOD*min-1% Residual activities were calculated by taking a ratio of the stressed to unstressed activity and multiplying by 100. Stability PIs were obtained by dividing the residual activity of protein in question by that of Bgi02446 and results are shown on Table 13.1.

TABLE 13.1

Cleaning Performance and Stability of *B. Gibsonii*-clade subtilisins

| Protein | ADW pH 10.5 rinsed | ADW pH 10.5 unrinsed | OMO HDL | Tris/EDTA stability | Tris/Ca stability |
|---|---|---|---|---|---|
| BG1-B08 | 1.1 | 1.0 | 1.2 | 1.4 | 1.4 |
| BG1-C05 | 1.8 | 3.2 | 1.4 | 1.0 | 1.1 |
| BG2-B08 | 1.3 | 1.5 | 1.0 | 1.2 | 1.2 |
| BG2-D10 | 1.3 | 1.3 | 1.3 | 1.0 | 1.1 |
| BG2-G08 | 1.1 | 1.1 | 1.1 | 1.1 | 1.4 |
| BG4-A09 | 1.3 | 1.3 | 1.1 | 2.0 | 2.0 |
| BG4-D10 | 1.1 | 1.1 | 1.0 | 1.6 | 1.8 |
| BG5-E02 | 1.2 | 1.7 | 1.3 | 1.7 | 1.7 |
| BG5-E05 | 1.0 | 1.0 | 0.9 | 1.6 | 1.4 |
| BG5-F02 | 1.0 | 1.1 | 1.1 | 1.1 | 1.0 |
| BG5-G10 | 1.1 | 1.2 | 1.1 | 1.6 | 1.4 |
| BG6-A10 | 1.1 | 1.2 | 0.9 | 1.4 | 1.3 |
| BG6-D08 | 1.0 | 1.0 | 1.1 | 1.5 | 1.1 |
| BG8-B03 | 1.3 | 1.4 | 1.0 | 1.5 | 1.1 |
| Bgi02446 | 1 | 0.96 | 1.1 | 1 | 1 |
| DSM9728 | 1.2 | 1.8 | 0.95 | 0.25 | 0.28 |
| DSM9731 | 1.2 | 1.6 | 0.9 | 0.4 | 0.65 |

Example 14

Sequence Analysis of *B. gibsonii*-clade Subtilisins

The amino acid sequences of the predicted mature forms of BG1-B08 (SEQ ID NO:65), BG1-C05 (SEQ ID NO:61), BG2-B08 (SEQ ID NO:71), BG2-D10 (SEQ ID NO:63), BG2-G08 (SEQ ID NO:83), BG4-A09 (SEQ ID NO:67), BG4-D10 (SEQ ID NO:69), BG5-E02 (SEQ ID NO:81), BG5-E05 (SEQ ID NO:59), BG5-F02 (SEQ ID NO:57), BG5-G10 (SEQ ID NO:79), BG6-A10 (SEQ ID NO:75), BG6-D08 (SEQ ID NO:77), BG8-B03 (SEQ ID NO:73), Bgi02446 (SEQ ID NO:4), DSM9728 (SEQ ID NO:11), DSM9729 (SEQ ID NO:15), DSM9730 (SEQ ID NO:19), and DSM9731 (SEQ ID NO:23) were aligned using CLUSTALW software (Thompson et al., Nucleic Acids Research, 22:4673-4680, 1994) with the default parameters. FIG. 10A-C shows the CLUSTAL W (1.83) multiple sequence alignment. Analysis of the sequences aligned in FIG. 10A-C showed that they all contain the sequence motif set forth in SEQ ID NO: 47 or 90.

A phylogenetic tree for amino acid sequence of the predicted mature form of the *B. gibsonii*-clade members: BG1-B08 (SEQ ID NO:65), BG1-C05 (SEQ ID NO:61), BG2-B08 (SEQ ID NO:71), BG2-D10 (SEQ ID NO:63), BG2-G08 (SEQ ID NO:83), BG4-A09 (SEQ ID NO:67), BG4-D10 (SEQ ID NO:69), BG5-E02 (SEQ ID NO:81), BG5-E05 (SEQ ID NO:59), BG5-F02 (SEQ ID NO:57), BG5-G10 (SEQ ID NO:79), BG6-A10 (SEQ ID NO:75), BG6-D08 (SEQ ID NO:77), BG8-B03 (SEQ ID NO:73), Bgi02446 (SEQ ID NO:4), DSM9728 (SEQ ID NO:11), DSM9729 (SEQ ID NO:15), DSM9730 (SEQ ID NO:19), and DSM9731 (SEQ ID NO:23) was built using the amino acid sequences of multiple proteases listed in Tables 7-1 and 7-2, in addition to the amino acid sequences of the mature forms of the DSM 9728, DSM 9729, DSM 9730, DSM 9731 subtilisins. The sequences were entered in the Vector NTI Advance suite and a Guide Tree was created using the Neighbor Joining (NJ) method (Saitou and Nei, Mol Biol Evol, 4:406-425, 1987). The NJ method works on a matrix of distances between all pairs of sequences to be analyzed. These distances are related to the degree of divergence between the sequences. The Guide Tree is calculated after the sequences are aligned. The tree construction was calculated using the following parameters: Kimura's correction for sequence distance and ignoring positions with gaps. AlignX displays the calculated distance values in parenthesis following the molecule name displayed on the tree shown in FIG. 11.

Figure 11:
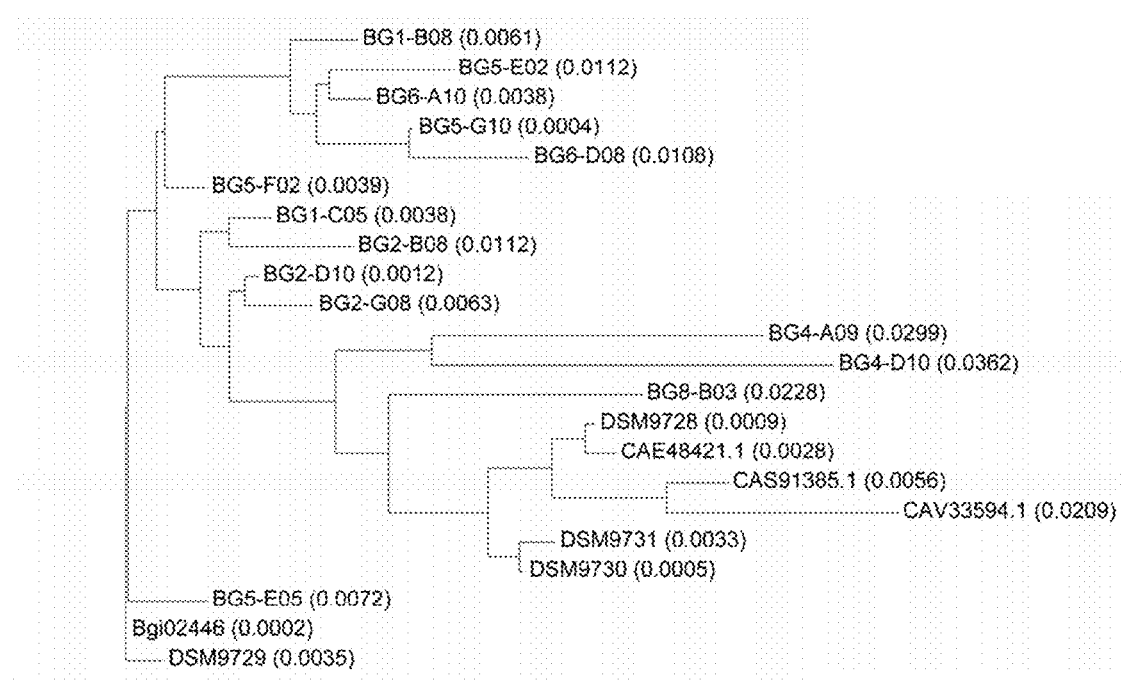
FIG. 11 provides a phylogenetic tree of the *B. gibsonii*-clade proteases.

Analysis of the sequences aligned in FIG. 10A-C show that they all contain the sequence motif described in SEQ ID NO:47. Furthermore, BG1-B08, BG1-C05, BG2-B08, BG2-D10, BG2-G08, BG4-A09, BG4-D10, BG5-E02, BG5-E05, BG5-F02, BG5-G10, BG6-A10, BG6-D08, and BG8-B03 subtilisins all cluster in the same region (as shown in FIG. 11) to form the *B. gibsonii*-clade.

We claim:

1. A recombinant polypeptide of the *Bacillus Gibsonii*-clade, wherein the recombinant polypeptide has proteolytic activity and comprises an amino acid sequence having at least 95% sequence identity to the amino acid sequence of SEQ ID NO: 79, wherein said *Bacillus Gibsonii*-clade comprises a DXGIXXHSDLXXXGGASXXXXXPTTADLNXHGTH (SEQ ID NO:47) or DXGIXXHSDLXXXGGASXXXXXXTTADLXXHGTH (SEQ ID NO:90) motif, wherein the initial D is the active site Aspartic acid residue and the penultimate H is the active site Histidine, and X is any amino acid.

2. The recombinant polypeptide of claim 1, wherein the *Bacillus Gibsonii*-clade comprises SEQ ID NO:47.

3. The recombinant polypeptide of claim 1, wherein the *Bacillus Gibsonii*-clade comprises SEQ ID NO:90.

4. The recombinant polypeptide of claim 1, wherein the polypeptide has protease activity in the presence of a surfactant.

5. The recombinant polypeptide of claim 1, where the polypeptide retains at least 50% of its maximal protease activity at a pH range of 8 to 12 or a temperature range of 50° C. to 75° C.

6. The recombinant polypeptide of claim 1, wherein the polypeptide has cleaning activity in a detergent composition.

7. The recombinant polypeptide of claim 6, wherein the detergent composition is an automatic dish washing detergent or a laundry detergent.

8. The recombinant polypeptide of claim 7, wherein the cleaning activity comprises hydrolysis of an egg yolk substrate or a substrate selected from the group consisting of blood, milk, ink and combinations thereof.

9. A composition comprising a surfactant and the recombinant polypeptide of claim 1.

10. The composition of claim 9, wherein the composition is a detergent composition.

11. The composition of claim 10, wherein said composition further comprises at least one calcium ion and/or zinc ion, at least one stabilizer, from about 0.001% to about 1.0 weight % of said recombinant polypeptide, at least one bleaching agent, at least one adjunct ingredient, and/or one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, metalloproteases, oxidases, pectate lyases, pectin acetyl esterases, pectinases, pentosanases, perhydrolase, peroxidases, phenoloxidases, phosphatases, phospholipases, phytases, polygalacturonases, proteases, pullulanases, reductases, rhamnogalacturonases, beta-glucanases, tannases, transglutaminases, xylan acetyl-esterases, xylanases, xyloglucanases, xylosidases, metalloproteases, additional serine proteases, and combinations thereof.

12. The composition of claim 9, wherein said composition is phosphate-free or contains phosphate and/or is borate-free or contains borate.

13. A method of cleaning comprising contacting a surface or an item with the composition of claim 9.

14. A polynucleotide comprising a nucleic acid sequence:
(i) encoding an amino acid sequence of SEQ ID NO:47 or 49;
(ii) encoding an amino acid sequence of SEQ ID NO:47 or 49 and further encoding an amino acid sequence having 95% identity to an amino acid sequence of SEQ ID NO: 79;
(iii) encoding an amino acid sequence of SEQ ID NO:47 or 49 and further encoding an amino acid sequence having 95% identity to an amino acid sequence of SEQ ID NO: 79;
(iv) encoding an amino acid sequence of SEQ ID NO:47 or 49 and further encoding an amino acid sequence having 95% identity to an amino acid sequence of SEQ ID NO: 79;
(v) encoding an amino acid sequence having 95% identity to an amino acid sequence of SEQ ID NO: 79;
(vi) encoding an amino acid sequence having 95% identity to an amino acid sequence of SEQ ID NO: 79;
(vii) encoding an amino acid sequence having 95% identity to an amino acid sequence of SEQ ID NO: 79;
(viii) having at least 70% identity to SEQ ID NO: 78; or
(ix) having complementarity to SEQ ID NO:1, 8, 12, 16, 20, 53, 54, 55, 56, 58, 60, 62, 64, 66, 68, 70, 72, 74, 76, 78, 80, or 82.

15. An expression vector comprising the polynucleotide of claim 14.

16. A host cell transformed with the vector of claim 15.

17. A composition comprising the polypeptide of claim 1, wherein said composition is selected from a textile processing composition, leather processing composition, feather processing composition, wound cleaning composition, and a contact lens cleaning composition.

* * * * *